US006855722B2

(12) United States Patent
Lu et al.

(10) Patent No.: US 6,855,722 B2
(45) Date of Patent: Feb. 15, 2005

(54) SUBSTITUTED INDOLES AND THEIR USE AS INTEGRIN ANTAGONISTS

(75) Inventors: Tianbo Lu, Kenneth Square, PA (US); Louis V. LaFrance, West Chester, PA (US); Thomas P. Markotan, Morgantown, PA (US); Juan J. Marugan Sanchez, Downingtown, PA (US); Victor J. Marder, Los Angeles, CA (US); David C. U'Prichard, Philadelphia, PA (US); Beth M. Anaclerio, New Castle, DE (US); Zihong Guo, Southbury, CT (US); Wenzi Pan, Exton, PA (US); Kristi A. Leonard, West Chester, PA (US); Bruce E. Tomczuk, Collegeville, PA (US)

(73) Assignee: Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 10/058,215

(22) Filed: Jan. 29, 2002

(65) Prior Publication Data

US 2002/0169200 A1 Nov. 14, 2002

Related U.S. Application Data

(60) Provisional application No. 60/264,260, filed on Jan. 29, 2001, and provisional application No. 60/324,519, filed on Sep. 26, 2001.

(51) Int. Cl.[7] .................... C07D 471/04; C07D 498/04; A61K 31/4375; A61K 31/5383; A61P 25/18
(52) U.S. Cl. ........................ 514/300; 546/122; 546/118; 546/112; 546/55; 546/277.4; 540/470; 540/553; 544/105; 544/333; 548/190; 548/300.4; 548/362.1; 548/455; 548/469
(58) Field of Search ........................... 514/300; 546/122

(56) References Cited

U.S. PATENT DOCUMENTS

| | | | |
|---|---|---|---|
| 5,223,517 A | 6/1993 | Müller et al. | 514/339 |
| 5,234,942 A | 8/1993 | Bernstein et al. | 514/415 |
| 5,290,788 A | 3/1994 | Stevens et al. | 514/314 |
| 5,741,796 A | 4/1998 | Hartman et al. | 514/300 |
| 5,744,488 A | 4/1998 | Cross et al. | 514/339 |
| 5,834,454 A | 11/1998 | Kitano et al. | 514/183 |
| 5,977,100 A | 11/1999 | Kitano et al. | 514/214 |
| 6,066,648 A | 5/2000 | Duggan et al. | 514/300 |
| 6,184,238 B1 | 2/2001 | Takano et al. | 514/339 |
| 2003/0045728 A1 | 3/2003 | Wiesner et al. | |

FOREIGN PATENT DOCUMENTS

| | | |
|---|---|---|
| EP | 0 623 607 A1 | 11/1994 |
| WO | WO 97/06791 | 2/1997 |
| WO | WO 97/23451 | 7/1997 |
| WO | WO 97/36859 | 10/1997 |
| WO | WO 97/45137 | 12/1997 |
| WO | WO 98/00395 | 1/1998 |
| WO | WO 98/13368 A1 | 4/1998 |
| WO | WO 98/14192 | 4/1998 |
| WO | WO 99/30713 A1 | 6/1999 |
| WO | WO 99/32150 A1 | 7/1999 |
| WO | WO 99/43651 A2 | 9/1999 |
| WO | WO 00/02874 | 1/2000 |
| WO | WO 00/33838 | 6/2000 |
| WO | WO 01/58893 A2 | 9/2001 |

OTHER PUBLICATIONS

Chalmers (TiPS vol. 17, pp. 166–172 Apr. 1996).*

Alfred Meijer {The Journal of Nutrition; Jun. 2003; 133, pp. 2057S–2062S}.*

Albelda, S.M., "Biology of Disease. Role of Integrins and Other Cell Adhesion Molecules in Tumor Progression and Metastasis," *Lab. Invest.* 68:4–17, The United States and Canadian Academy of Pathology, Inc. (1993).

Albelda, S.M. et al., "Integrin Distribution in Malignant Melanoma: Association of the $\beta_3$ Subunit with Tumor Progression," *Cancer Res.* 50: 6757–6764, American Association for Cancer Research (1990).

Batcho, A. et al., "Indoles From 2–Methylnitrobenzenes by Condensation With Formamide Acetals Followed by Reduction: 4–Benzyloxyindole (1 H–Indole, 4–(phenylmethoxy)–)," in *Organic Synthesis*, Saucy, G. et al., Eds., John Wiley & Sons, New York, NY, pp. 214–225 (1985).

(List continued on next page.)

*Primary Examiner*—Mark L. Berch
*Assistant Examiner*—Kahsay Habte
(74) *Attorney, Agent, or Firm*—Woodcock Washburn LLP

(57) ABSTRACT

The present invention relates to novel substituted indole compounds that are antagonists of alpha V ($\alpha v$) integrins, for example $\alpha_v\beta_3$ and $\alpha_v\beta_5$ integrins, their pharmaceutically acceptable salts, and pharmaceutical compositions thereof. The compounds may be used in the treatment of pathological conditions mediated by $\alpha_v\beta_3$ and $\alpha_v\beta_5$ integrins, including such conditions as tumor growth, metastasis, restenosis, osteoporosis, inflammation, macular degeneration, diabetic retinopathy, and rheumatoid arthritis. The compounds have the general formula:

IV

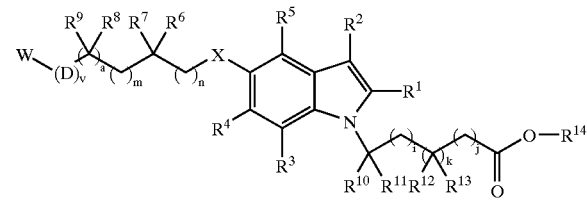

where $R^1, R^2, R^3, R^4, R^5, R^6, R^7, R^8, R^9, R^{10}, R^{11}, R^{12}, R^{13}, R^{14}$, D, X, W, a, m, n, i, j, k and v are defined herein.

56 Claims, No Drawings

OTHER PUBLICATIONS

Boudreau, N. and Rabinovitch, M., "Developmentally Regulated Changes in Extracellular Matrix in Endothelial and Smooth Muscle Cells in the Ductus Arteriosus Maybe Related to Intimal Proliferation," *Lab. Invest.* 64:187–199, The United States and Canadian Academy of Pathology, Inc. (1991).

Brocke, S. et al., "Antibodies to CD44 and integrin $\alpha_4$, but not L–selectin, prevent central nervous system inflammation and experimental encephalomyelitis by blocking secondary leukocyte recruitment." *Proc. Natl. Acad. Sci. USA* 96:6896–6901, The National Academy of Sciences (1999).

Brooks, P.C. et al., "Integrin $\alpha_v\beta_3$ Antagonists Promote Tumor Regression by Inducing Apoptosis of Angiogenic Blood Vessels," *Cell* 79:1157–1164, Cell Press (1994).

Brooks, P.C., "Integrin $\alpha v\beta 3$ : A Therapeutic Target," *DN&P* 10:456–461, Prous Science (1997).

Brooks, P.C. et al., "Antiintegrin $\alpha v\beta 3$ blocks human breast cancer growth and angiogenesis in human skin," *J. Clin. Invest.* 96:1815–1822, The American Society for Clinical Investigation, Inc. (1995).

Brooks, P.C. et al., "Requirement of Vascular Integrin $\alpha_v\beta_3$ for Angiogenesis," *Science* 264:569–571, American Association for the Advancement of Science (1994).

Brooks, P.C., "Cell adhesion molecules in angiogenesis," *Cancer Met. Rev.* 15:187–194, Kluwer Academic Publishers (1996).

Cheresh, D.A., "Structure, function and biological properties of integrin of $\alpha_v\beta_3$ on human melanoma cells," *Cancer Met. Rev. 10*: 3–10, Kluwer Academic Publishers (1991).

Choi, E.T. et al., "Inhibition of neointimal hyperplasia by blocking $\alpha_v\beta_3$ integrin with a small peptide antagonist GpenGRGDSPCA," *J. Vasc. Surg.* 19:125–134, The Society for Vascular Surgery and International Society for Cardiovascular Surgery (1994).

Corey, E.J. and Fuchs, P.L., "A Synthetic Method for Formyl → Ethynyl Conversion (RCHO → RC≡CR')," *Tetrahedron Lett.* 36:3769–3772, Pergamon Press (1972).

Enenstein, J. and Kramer, R.H., "Confocal Microscopic Analysis of Integrin Expression on the Microvasculature and its Sprouts in the Neonatal Foreskin," *J. Invest. Dermatol.* 103:381–386, The Society for Investigative Dermatology, Inc. (1994).

Fisher, J.E. et al., "Inhibition of Osteoclastic Bone Resorption In Vivo by Echistatin, an "Arginyl–Glycyl–Aspartyl" (RGD) –Containing Protein," *Endocrinology* 132:1411–1413, The Endocrine Society (1993).

Friedlander, M. et al., "Definition of Two Angiogenic Pathways by Distinct $\alpha_v$ Integrins," *Science* 270:1500–1520, American Association for the Advancement of Science (1995).

Gladson, C.L., "Expression of Integrin $\alpha v\beta 3$ in Small Blood Vessels of Glioblastoma Tumors," *J. Neuropathol. Exp. Neurol.* 55:1143–1149, The American Association of Neuropathologists (1996).

Greene, T.W. and Wuts, P.G.M., "Special –NH Protective Groups. Protection for the Amino Group: Special –NH Protective Groups," in *Protective Groups in Organic Synthesis*, 2nd edition, John Wiley and Sons, Inc., New York, pp. 267–287 and p. 331 (1991).

Greenspoon, N. et al., "Structural Analysis of Integrin Recognition and the Inhibition of Integrin–Mediated Cell Functions by Novel Nonpeptidic Surrogates of the Arg–Gly–Asp Sequence," *Biochemistry* 32:1001–1008, American Chemical Society (1993).

Hardan, I. et al., "Inhibition of Metastatic Cell Colonization in Murine Lungs and Tumor–Induced Morbidity by Non–Peptidic Arg–Gly–Asp Mimetics," *Int. J. Cancer* 55:1023–1028, Wiley–Liss, Inc. (1993).

Hendrickson, J.B. and Hussoin, Md. S., "Facile Dehydration of Activated Ketones to Alkynes," *Synthesis* 3:217–221, Thieme Medical Publishers, Inc. (1989).

Hershkoviz, R. et al., "Inhibition of $CD4^+$ T lymphocyte binding to fibronectin and immune–cell accumulation in inflammatory sites by non–peptidic mimetics of Arg–Gly–Asp," *Clin. Exp. Immunol.* 95:270–276, Blackwell Scientific Publishers (1994).

Horton, M., "Current Status Review. Vitronectin receptor: tissue specific expression or adaption to culture?," *Int. J. Exp. Pathol.* 71:741–759, Blackwell Scientific Publications (1990).

Hynes, R.O., "Integrins: Versatility, Modulation, and Signaling in Cell Adhesion," *Cell* 69:11–25, Cell Press (1992).

Juliano, R., "Signal transduction by integrins and its role in the regulation of tumor growth," *Cancer Met. Rev.* 13:25–30, Kluwer Academic Publishers (1994).

Kaul, D.K. et al., "Monoclonal antibodies to $\alpha v\beta 3$ (7E3 and LM609) inhibit sickle red blood cell–endothelium interactions induced by platelet–activating factor," *Blood* 95:368–374, The American Society of Hematology (Jan. 2000).

Ku, T.W. et al., "Direct Design of a Potent Non–Peptide Fibrinogen Receptor Antagonist Based on the Structure and Conformation of a Highly Constrained Cyclic RGD Peptide," *J. Amer. Chem. Soc.* 115:8861–8862, American Chemical Society (1993).

Marquardt, D. W., "An Algorithm for Least–Squares Estimation of Nonlinear Parameters," *J. Soc. Indust. Appl. Math.* 11:431–441, Society for Industrial and Applied Mathematics (1963).

Mitsunobu, O., "The Use of Diethyl Azodicarboxylate and Triphenylphosphine in Synthesis and Transformation of Natural Products," *Synthesis* 1:1–28, Georg Thieme Verlag (1981).

Nicosia, R.F. and Madri, J.A., "The Microvascular Extracellular Matrix. Developmental Changes During Angiogenesis in the Aortic Ring–Plasma Clot Model," *Amer. J. Pathol.* 128:78–90, American Association of Pathologists (1987).

Niiya, K. et al., "Increased Surface Expression of the Membrane Glycoprotein IIb/IIIa Complex Induced by Platelet Activation. Relationship to the Binding of Fibrinogen and Platelet Aggregation," *Blood* 70:475–483, Grune & Stratton, Inc. (1987).

Nip, J. et al.,"Coordination Expression of the Vitronectin Receptor and the Urokinase–type Plasminogen Activator Receptor in Metastatic Melanoma Cells," *J. Clin. Invest.* 95:2096–2103, The American Society for Clinical Investigation, Inc. (1995).

Okada, Y. et al., "Integrin $\alpha_v\beta_3$ Is Expressed in Selected Microvessels after Focal Cerebral Ischemia," *Amer. J. Pathol.* 149:37–44, American Society for Investigative Pathology (1996).

Relton, J.K. et al., "Inhibition of α4 Integrin Protects Against Transient Focal Cerebral Ischemia in Normotensive and Hypertensive Rats," *Stroke* 32:199–205, American Heart Association, Inc. (Jan. 2001).

Ruoslahti, E. and Giancotti, F.G., "Integrins and Tumor Cell Dissemination," *Cancer Cells* 1:119–126, Cold Spring Harbor Laboratory Press (1989).

Ruoslahti, E. and Reed, J.C., "Anchorage Dependence, Integrins, and Apoptosis," *Cell* 77:477–478, Cell Press (1994).

Savelon, L. et al., "Substituted pyrido [3,2–b] oxazin–3 (4H) –ones: synthesis and evaluation of antinociceptive activity," *Bioorganic Med. Chem.* 6:133–142, Elsevier Science Ltd. (1998).

Sato, M. et al., "Echistatin Is a Potent Inhibitor of Bone Resorption in Culture," *J. Cell Biol.* 111:1713–1723, The Rockefeller University Press (1990).

Shattil, S.J., "Function and Regulation of the $B_3$ Integrins in Hemostasis and Vascular Biology," *Thromb. Haemost.* 74:149–155, F.K. Schattauer Verlagsgesellschaft mbH (1995).

Sonogashira, K. et al., "A Convenient Synthesis of Acetylenes: Catalytic Substitutions of Acetylenic Hydrogen with Bromoalkenes, Iodoarenes, and Bromopyridines," *Tetrahedron Lett.* 50:4467–4470, Pergamon Press (1975).

Topol, E.J. et al., "Randomised trial of coronary intervention with antibody against platelet IIb/IIIa integrin for reduction of clinical restenosis: results at six months," *Lancet* 343:881–886, The Lancet Ltd. (1994).

White, J.M., "Integrins as virus receptors," *Curr. Biol.* 3:596–599, Current Biology (1993).

Yun, Z. et al., "Involvement of Integrin $\alpha_v\beta_3$ in Cell Adhesion, Motility, and Liver Metastasis of Murine RAW117 Large Cell Lymphoma," *Cancer Res.* 56:3103–3111, The American Association for Cancer Research (1996).

Chemical Abstracts English language summary of document AM2 (WO 98/00395), CAPLUS Accession No. 1998:38464.

Dennis, M.S., et al., "Binding Interactions of Kistrin With Platelet Glycoprotein IIb–IIIa: Analysis by Site–Directed Mutagenesis," *Proteins* 15:312–321, Wiley–Liss (1993).

Fabry, M.E., et al., "Second generation knockout sickle mice: the effect of HbF," *Blood* 97:410–418, American Society of Hematology (Jan. 2001).

United States Pharmacopeia/ The National Formulary for 1995, published by United States Pharmacopeial Convention, Inc., Rockville, Maryland, p. 1636 (1994).

Dialog File 351, Accession No. 14058279, Derwent WPI English language abstract for WO 01/58893 A2 (Document AM3).

* cited by examiner

SUBSTITUTED INDOLES AND THEIR USE AS INTEGRIN ANTAGONISTS

CROSS-REFERENCE TO RELATED APPLICATION

This application claims the benefit, under 35 U.S.C. § 119(e), of the earlier filing dates of U.S. provisional application Ser. No. 60/264,260, filed Jan. 29, 2001, and U.S. provisional application Ser. No. 60/324,519, filed Sep. 26, 2001. The contents of both above-referenced provisional applications are fully incorporated by reference.

BACKGROUND OF THE INVENTION

1. Field of the Invention

The present invention relates to novel substituted indole compounds that are antagonists of alpha V ($\alpha$v) integrins, for example $\alpha_v\beta_3$ and $\alpha_v\beta_5$ integrins, their pharmaceutically acceptable salts, and pharmaceutical compositions thereof.

2. Related Art

Integrins are cell surface glycoprotein receptors which bind extracellular matrix proteins and mediate cell-cell and cell-extracellular matrix interactions (generally referred to as cell adhesion events) (Hynes, R. O., *Cell* 69:11–25 (1992)). These receptors are composed of noncovalently associated alpha ($\alpha$) and beta ($\beta$) chains which combine to give a variety of heterodimeric proteins with distinct cellular and adhesive specificities (Albeda, S. M., *Lab. Invest.* 68:4–14 (1993)). Recent studies have implicated integrins in the regulation of cellular adhesion, migration, invasion, proliferation, apoptosis and gene expression (Albeda, S. M., *Lab. Invest.* 68:4–14 (1993); Juliano, R., *Cancer Met. Rev.* 13:25–30 (1994); Ruoslahti, E. and Reed, J. C., *Cell* 77:477–478 (1994); and Ruoslahti, E. and Giancotti, F. G., *Cancer Cells* 1:119–126 (1989)).

One member of the integrin family which has been shown to play a significant role in a number of pathological conditions is the integrin $\alpha_v\beta_3$, or vitronectin receptor (Brooks, P. C., *DN&P* 10(8):456–461 (1997)). This integrin binds a variety of extracellular matrix components and other ligands, including fibrin, fibrinogen, fibronectin, vitronectin, laminin, thrombospondin, and proteolyzed or denatured collagen (Cheresh, D. A., *Cancer Met. Rev.* 10:3–10 (1991) and Shattil, S. J., *Thromb. Haemost.* 74:149–155 (1995)). The two related $\alpha$v integrins, $\alpha_v\beta_5$ and $\alpha_v\beta_1$ (also vitronectin receptors), are more specific and bind vitronectin ($\alpha_v\beta_5$) or fibronectin and vitronectin ($\alpha_v\beta_1$) (Horton, M., *Int. J. Exp. Pathol.* 71:741–759 (1990)). $\alpha_v\beta_3$ and the other integrins recognize and bind to their ligands through the tripeptide sequence Arg-Gly-Asp ("RGD") (Cheresh, D. A., *Cancer Met. Rev.* 10:3–10 (1991) and Shattil, S. J., *Thromb. Haemost.* 74:149–155 (1995)) found within all the ligands mentioned above.

The $\alpha_v\beta_3$ integrin has been implicated in a number of pathological processes and conditions, including metastasis and tumor growth, pathological angiogenesis, and restenosis. For example, several studies have clearly implicated $\alpha_v\beta_3$ in the metastatic cascade (Cheresh, D. A., *Cancer Met. Rev.* 10:3–10 (1991); Nip, J. et al., *J. Clin. Invest.* 95:2096–2103 (1995); and Yun, Z., et al., *Cancer Res.* 56:3101–3111 (1996)). Vertically invasive lesions in melanomas are also commonly associated with high levels of $\alpha_v\beta_3$, whereas horizontally growing noninvasive lesions have little if any $\alpha_v\beta_3$ (Albeda, S. M., et al., *Cancer Res.* 50:6757–6764 (1990)). Moreover, Brooks et al. (in *Cell* 79:1157–1164 (1994)) have demonstrated that systemic administration of $\alpha_v\beta_3$ antagonists disrupts ongoing angiogenesis on chick chorioallantoic membrane ("CAM"), leading to the rapid regression of histologically distinct human tumors transplanted onto the CAM. These results indicate that antagonists of $\alpha_v\beta_3$ may provide a therapeutic approach for the treatment of neoplasia (solid tumor growth).

$\alpha_v\beta_3$ has also been implicated in angiogenesis, which is the development of new vessels from preexisting vessels, a process that plays a significant role in a variety of normal and pathological biological events. It has been demonstrated that $\alpha_v\beta_3$ is up-regulated in actively proliferating blood vessels undergoing angiogenesis during wound healing as well as in solid tumor growth. Also, antagonists of $\alpha_v\beta_3$ have been shown to significantly inhibit angiogenesis induced by cytokines and solid tumor fragments (Brooks, P. C., et al., *Science* 264:569–571 (1994); Enenstein, J. and Kramer, R. H., *J. Invest. Dermatol.* 103:381–386 (1994); Gladson, C. L., *J. Neuropathol. Exp. Neurol* 55:1143–1149 (1996); Okada, Y., et al., *Amer. J. Pathol.* 149:37–44 (1996); and Brooks, P. C., et al., *J. Clin. Invest.* 96:1815–1822 (1995)). Such $\alpha_v\beta_3$ antagonists would be useful for treating conditions that are associated with pathological angiogenesis, such as rheumatoid arthritis, diabetic retinopathy, macular degeneration, and psoriasis (Nicosia, R. F. and Madri, J. A., *Amer. J. Pathol.* 128:78–90 (1987); Boudreau, N. and Rabinovitch, M., *Lab. Invest.* 64:187–99 (1991); and Brooks, P. C., *Cancer Met. Rev.* 15:187–194 (1996)).

There is also evidence that $\alpha_v\beta_3$ plays a role in neointimal hyperplasia after angioplasty and restenosis. For example, peptide antagonists and monoclonal antibodies directed to both $\alpha_v\beta_3$ and the platelet receptor $\alpha II_b\beta_3$ have been shown to inhibit neointimal hyperplasia in vivo (Choi, E. T., et al., *J. Vasc. Surg.* 19:125–134 (1994); and Topol, E. J., et al., *Lancet* 343:881–886 (1994)), and recent clinical trials with a monoclonal antibody directed to both $\alpha II_b\beta_3$ and $\alpha_v\beta_3$ have resulted in significant reduction in restenosis, providing clinical evidence of the therapeutic utility of $\beta 3$ antagonists (Topol, E. J., et al., *Lancet* 343:881–886 (1994)).

It has also been reported that $\alpha_v\beta_3$ is the major integrin on osteoclasts responsible for attachment to bone. Osteoclasts cause bone resorption. When bone resorbing activity exceeds bone forming activity, the result is osteoporosis, a condition which leads to an increased number of bone fractures, incapacitation and increased mortality. Antagonists of $\alpha_v\beta_3$ have been shown to be potent antagonists of osteoclastic activity both in vitro (Sato, M., et al., *J. Cell Biol.* 111:1713–1723 (1990)) and in vivo (Fisher, J. E., et al., *Endocrinology* 132:1411–1413 (1993)).

Lastly, White (in *Current Biology* 3(9):596–599 (1993)) has reported that adenovirus uses $\alpha_v\beta_3$ for entering host cells. The $\alpha_v\beta_3$ integrin appears to be required for endocytosis of the virus particle and may be required for penetration of the viral genome into the host cell cytoplasm. Thus compounds which inhibit $\alpha_v\beta_3$ could be useful as antiviral agents.

The $\alpha_v\beta_5$ integrin has been implicated in pathological processes as well. Friedlander et al. have demonstrated that a monoclonal antibody for $\alpha_v\beta_5$ can inhibit VEGF-induced angiogenesis in rabbit cornea and chick chorioalloantoic membrane, indicating that the $\alpha_v\beta_5$ integrin plays a role in mediating growth factor-induced angiogenesis (Friedlander, M. C., et al., *Science* 270:1500–1502 (1995)). Compounds that act as $\alpha_v\beta_5$ antagonists could be used to inhibit pathological angiogenesis in tissues of the body, including ocular tissue undergoing neovascularization, inflamed tissue, solid tumors, metastases, or tissues undergoing restenosis.

Discovery of the involvement of $\alpha_v\beta_3$ and $\alpha_v\beta_5$ in such processes and pathological conditions has led to an interest in these integrins as potential therapeutic targets, as suggested in the preceding paragraphs. A number of specific antagonists of $\alpha_v\beta_3$ and $\alpha_v\beta_5$ that can block the activity of these integrins have been developed. One major group of such antagonists includes nonpeptide mimetics and organic-type compounds. For example, a number of organic non-peptidic mimetics have been developed that appear to inhibit tumor cell adhesion to a number of $\alpha_v\beta_3$ ligands, including vitronectin, fibronectin, and fibrinogen (Greenspoon, N., et al., *Biochemistry* 32:1001–1008 (1993); Ku, T. W., et al., *J. Amer. Chem. Soc.* 115:8861–8862 (1993); Hershkoviz, R., et al., *Clin. Exp. Immunol.* 95:270–276 (1994); and Hardan, L., et al., *Int. J. Cancer* 55:1023–1028 (1993)).

Additional organic compounds developed specifically as $\alpha_v\beta_3$ or $\alpha_v\beta_5$ integrin antagonists or as compounds useful in the treatment of $\alpha v$-mediated conditions have been described in several recent publications.

For example, U.S. Pat. No. 5,741,796, issued Apr. 21, 1998, discloses pyridyl and naphthyridyl compounds for inhibiting osteoclast-mediated bone resorption.

PCT Published Application WO 97/45137, published Oct. 9, 1997, discloses non-peptide sulfotyrosine derivatives, as well as cyclopeptides, fusion proteins, and monoclonal antibodies, that are useful as antagonists of $\alpha_v\beta_3$ integrin-mediated angiogenesis.

PCT Published Application WO 97/36859, published Oct. 9, 1997, discloses para-substituted phenylpropanoic acid derivatives of the general formula:

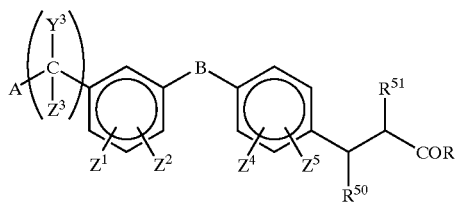

where A is:

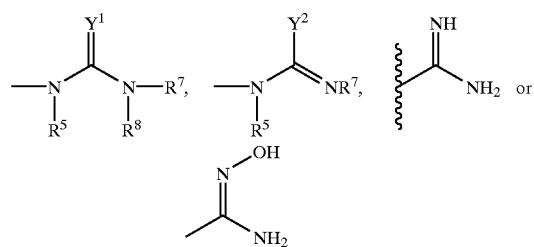

B is —CH$_2$CONH—, —CONR$^{52}$—(CH$_2$)$_p$—, —C(O)O—, —SO$_2$NH—, —CH$_2$O—, or —OCH$_2$—;

Y$^1$ is selected from the group consisting of N—R$^2$, O and S;

Y$^3$ and Z$^3$ are independently selected from the group consisting of H, alkyl, aryl, cycloalkyl and aralkyl, or Y$^3$ and Z$^3$ taken together with C form a carbonyl;

R$^{50}$ is selected from the group consisting of H, alkyl, aryl, carboxyl derivative and —CONHCH$_2$CO$_2$R$^{53}$, wherein R$^{53}$ is H or lower alkyl; and R$^{51}$ is selected from the group consisting of H, alkyl, carboxyl derivatives,

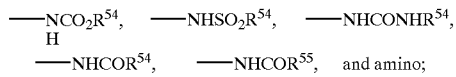

wherein R$^{54}$ is selected from the group consisting of H, alkyl, cycloalkyl, aryl, aralkyl, aralkenyl and aryl substituted by one or more alkyl or halo; and wherein R$^{55}$ is selected from the group consisting of N-substituted pyrrolidinyl, piperidinyl and morpholinyl.

The publication also discloses the use of the compounds as $\alpha_v\beta_3$ integrin antagonists.

PCT Published Application WO 97/06791, published February 1997, discloses methods for inhibition of angiogenesis in tissue using vitronectin $\alpha_v\beta_5$ antagonists.

More recently, PCT Published Application WO 97/23451, published Jul. 3, 1997, discloses tyrosine derivatives of the general formula:

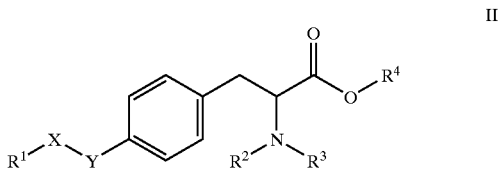

wherein

X is C$_{1-6}$alkylene or 1,4-piperidyl;

Y is absent, O, CONH or —C≡C—;

R$^1$ is H, CN, N$_3$, NH$_2$, H$_2$N—C(=NH), or H$_2$N—C(=NH)—NH, where the primary amino groups can also be provided with conventional amino protective groups;

R$^2$ and R$^3$ are independently H, A, A—SO$_2$—, Ar—SO$_2$—, camphor-10-SO$_2$—, COOA or a conventional amino protective group;

A and R$^4$ are independently H, C$_{1-10}$alkyl, or benzyl; and

Ar is phenyl or benzyl, each of which is unsubstituted or monosubstituted by CH$_3$;

and their physiologically acceptable salts.

The disclosed compounds are described as $\alpha v$-integrin antagonists (especially $\alpha_v\beta_3$ antagonists) useful in the treatment of tumors, osteoporoses, and osteolytic disorders and for suppressing angiogenesis.

PCT Published Application WO 98/00395, published Jan. 8, 1998, discloses novel tyrosine and phenylalanine derivatives as $\alpha v$ integrin and GPIIb/IIIa antagonists having the general formula:

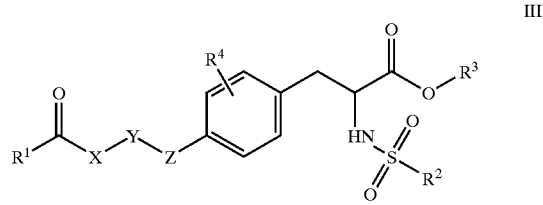

wherein

X can be, among other groups, alkyl, aryl or cycloalkyl;

Y and Z can be alkyl, O, S, NH, C(=O), CONH, NHCO, C(=S), SO$_2$NH, NHSO$_2$, CA=CA' or —C≡C—;

$R^1$ can be $H_2N-C(=NH)$ or $H_2N-(C=NH)-NH$;

$R^2$ is A, aryl or aralkyl;

$R^3$ is hydrogen or A;

$R^4$ is hydrogen, halogen, OA, NHA, NAA', —NH-Acyl, —O-Acyl, CN, $NO_2$, SA, SOA, $SO_2A$, $SO_2Ar$ or $SO_3H$; and A and A' can be hydrogen, alkyl or cycloalkyl.

The publication discloses the use of the compounds in pharmaceutical preparations for the treatment of thrombosis, infarction, coronary heart disease, tumors, arteriosclerosis, infection and inflammation.

A need continues to exist for non-peptide compounds that are potent and selective integrin antagonists, and which possess greater bioavailability or fewer side-effects than currently available integrin antagonists.

SUMMARY OF THE INVENTION

The present invention is directed to substituted indoles having Formula IV (below). Also provided is a process for preparing compounds of Formula IV. The novel compounds of the present invention exhibit inhibition of $\alpha_v\beta_3$ and $\alpha_v\beta_5$ integrin receptor binding. Also provided is a method of treating $\alpha_v\beta_3$ integrin- and $\alpha_v\beta_5$ integrin-mediated pathological conditions such as tumor growth, metastasis, osteoporosis, restenosis, inflammation, macular degeneration, diabetic retinopathy, sickle cell anemia, CNS disorders and rheumatoid arthritis in a mammal in need of such treatment comprising administering to said mammal an effective amount of a compound of Formula IV. Further provided is a pharmaceutical composition comprising a compound of Formula IV and one or more pharmaceutically acceptable carriers or diluents.

DETAILED DESCRIPTION OF THE INVENTION

The present invention is directed to compounds of Formula IV:

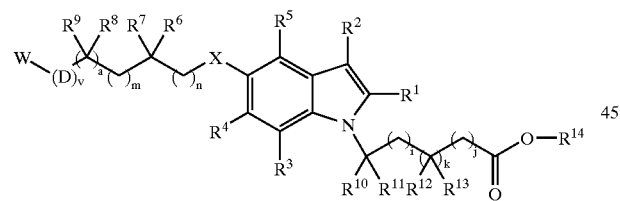

IV and pharmaceutically acceptable salts thereof; wherein $R^1$, $R^2$, $R^3$, $R^4$ and $R^5$ independently represent hydrogen, halogen, alkyl, aryl, aralkyl, heteroaryl or heteroarylalkyl;

$R^6$, $R^7$, $R^8$ and $R^9$ independently represent hydrogen, alkyl, hydroxyalkyl, aminoalkyl, monoalkylaminoalkyl, dialkylaminoalkyl, carboxyalkyl, aryl or aralkyl;

or $R^6$ and $R^7$ are taken together to form —$(CH_2)_p$—, where p is 2–8, while $R^8$ and $R^9$ are defined as above; or $R^8$ and $R^9$ are taken together to form —$(CH_2)_q$—, where q is 2–8, while $R^6$ and $R^7$ are defined as above; or $R^6$ and $R^8$ are taken together to form —$(CH_2)_r$—, while r is zero (a bond), 1 or 2, while $R^7$ and $R^9$ are defined as above;

X represents oxygen, sulfur, —$CH_2$—, —NH—, —(C=O)NH— or —NH(C=O)—;

n is from 0 to 4;

m is from 0 to 4;

a is 0 or 1;

D represents oxygen;

v is 0 or 1;

$R^{10}$, $R^{11}$, $R^{12}$ and $R^{13}$ independently represent: hydrogen; hydroxy; alkyl; alkoxy; cycloalkyl; aryl, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; alkanoyl; heteroaryl having 5–14 ring members, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; or

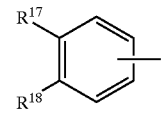

wherein $R^{17}$ and $R^{18}$ together form —$CH_2CH_2$—O—, —O—$CH_2CH_2$—, —O—$CH_2$—O— or —O—$CH_2CH_2$—O—; or $R^{10}$ and $R^{12}$ are taken together to form —$(CH_2)_s$—, wherein s is 0 (a bond) or 1 to 4, while $R^{11}$ and $R^{13}$ are as defined as above; or $R^{10}$ and $R^{12}$ are taken together to form a double bond when i is 0 and k is 1, while $R^{11}$ and $R^{13}$ are as defined above; or $R^{10}$ and $R^{11}$ are taken together to form —$(CH_2)_t$—, wherein t is 2 to 8, while $R^{12}$ and $R^{13}$ are as defined as above, or $R^{12}$ and $R^{13}$ are taken together to form —$(CH_2)_u$— wherein u is 2 to 8, while $R^{10}$ and $R^{11}$ are as defined as above;

i is from 0 to 4;

j is from 0 to 4;

k is 0 or 1;

$R^{14}$ is hydrogen or a functionality that acts as a prodrug (i.e., converts to the active species by an endogenous biological process such as an esterase, lipase, or other hydrolase), such as alkyl, aryl, aralkyl, dialkylaminoalkyl, 1-morpholinoalkyl, 1-piperidinylalkyl, pyridinylalkyl, alkoxy(alkoxy)alkoxyalkyl, or (alkoxycarbonyl)oxyethyl;

W is:

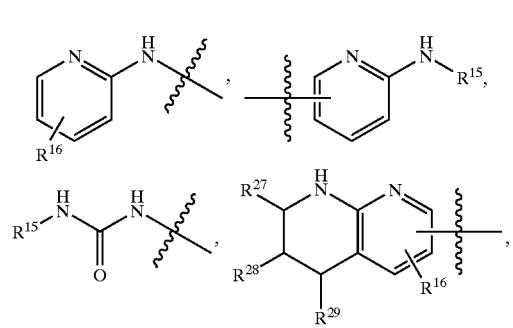

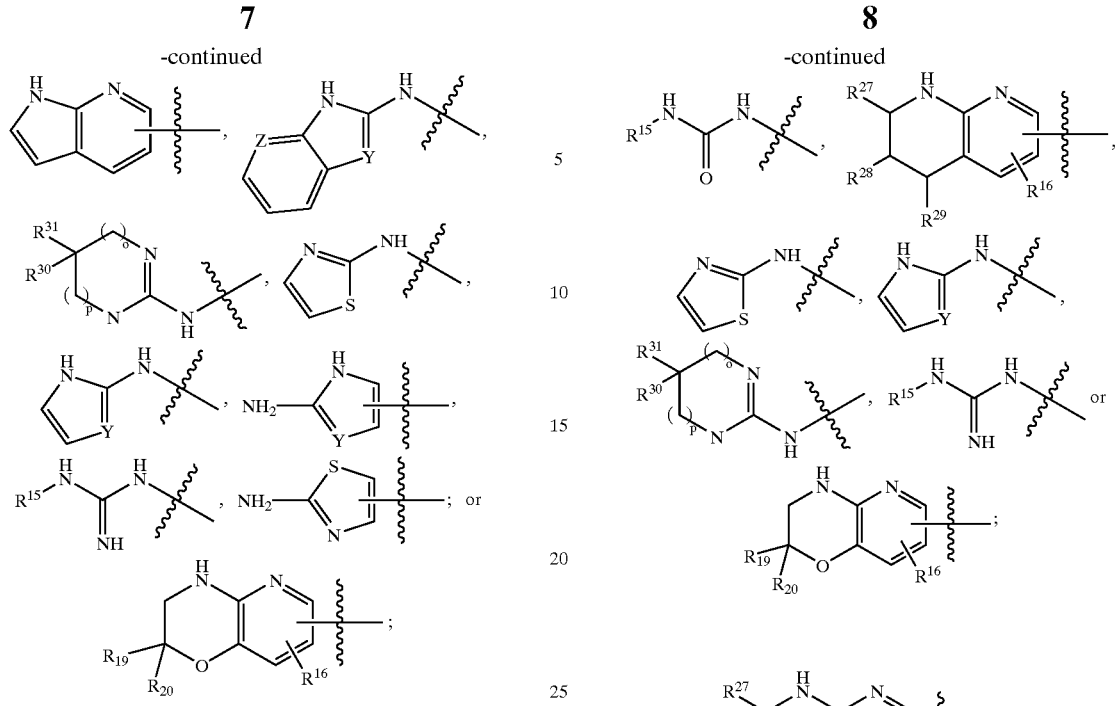

wherein:

Y is —N— or —CH—;

Z is —N— or —CH—;

$R^{15}$ is hydrogen, halogen, alkyl, aryl or arylalkyl;

$R^{16}$ is hydrogen, alkyl, haloalkyl or halogen;

$R^{19}$ and $R^{20}$ are independently hydrogen, halogen or alkyl;

$R^{27}$, $R^{28}$, $R^{29}$, $R^{30}$ and $R^{31}$ are independently hydrogen, halogen, alkyl, alkoxy or aryl; and o and p are independently 0, 1 or 2.

Where W is attached through a pyridine ring, the preferred point of attachment is either ortho or meta to the pyridine nitrogen, and more preferably ortho to the pyridine nitrogen.

Preferred compounds of the present invention are those of Formula IV, wherein $R^1$ and $R^2$ independently represent hydrogen, halogen, $(C_{1-6})$alkyl, $(C_{1-6})$alkyl$(C_{6-10})$aryl, $(C_{6-10})$ar$(C_{1-6})$alkyl, 5–14 member heteroaryl, or 5–14 member heteroaryl$(C_{1-6})$alkyl; or preferably $R^1$ and $R^2$ independently represent hydrogen, methyl, ethyl, propyl, butyl, phenyl, benzyl or phenylethyl.

Also preferred are compounds of Formula IV, wherein $R^3$, $R^4$ and $R^5$ independently represent hydrogen, $(C_{1-6})$alkyl, $(C_{6-10})$aryl, or $(C_{6-10})$ar$(C_{1-6})$alkyl, preferably, $R^3$, $R^4$ and $R^5$ are hydrogen or $(C_{1-4})$alkyl.

Preferred compounds are those of Formula IV, wherein $R^6$, $R^7$, $R^8$ and $R^9$ independently represent hydrogen or $(C_{1-4})$alkyl.

Preferred compounds are those of Formula IV, wherein X is oxygen, —CH$_2$—, —(C=O)NH— or —HN(C=O)—, more preferably, X is oxygen, —CH$_2$— or —(C=O)NH—.

Also preferred are compounds of Formula IV, wherein W is

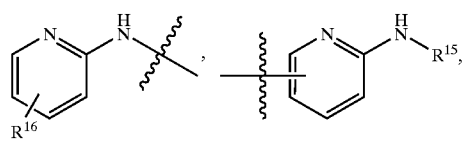

more preferably wherein, Y, $R^{15}$, $R^{16}$, $R^{19}$, $R^{20}$, $R^7$–$R^{31}$ are as defined above;

More preferably,

Y is —N— or —CH—;

$R^{15}$ is hydrogen, halogen, $(C_{1-8})$alkyl, $(C_{6-10})$aryl or $(C_{6-10})$aryl$(C_{1-8})$alkyl;

$R^{16}$ is hydrogen, $(C_{1-8})$alkyl, halo$(C_{1-8})$alkyl or halogen;

$R^{19}$ and $R^{20}$ are hydrogen, halogen or $(C_{1-8})$alkyl; and $R^{27}$, $R^{28}$, $R^{29}$, $R^{30}$ and $R^{31}$ are hydrogen, halogen, $(C_{1-8})$alkyl, $(C_{1-8})$alkoxy, $(C_{6-10})$aryl.

Further preferred compounds are those of Formula IV, wherein $R^{10}$, $R^{11}$, $R^{12}$ and $R^{13}$ independently represent hydrogen, hydroxy, $(C_{1-6})$alkyl, $(C_{3-6})$cycloalkyl, $(C_{6-10})$aryl, $(C_{6-10})$ar$(C_{1-6})$alkyl, $(C_{1-6})$aminoalkyl, mono$(C_{1-4})$alkylamino$(C_{1-6})$alkyl, di-$(C_{1-4})$alkylamino $(C_{1-6})$alkyl, carboxy$(C_{1-6})$alkyl, $(C_{1-6})$alkoxy, mono-$(C_{1-4})$alkylamino or di-$(C_{1-4})$alkylamino.

Also preferred are those compounds of Formula IV, wherein $R^{10}$ and $R^{12}$ are taken together to form —(CH$_2$)$_s$— where s is zero or 1 to 4, and $R^{11}$ and $R^{13}$ are each hydrogen.

Preferred compounds are those of Formula IV, wherein $R^{10}$ and $R^{11}$ are taken together to form —(CH$_2$)$_t$, where t is 2 to 5 and $R^{12}$ and $R^{13}$ are each hydrogen.

Preferred compounds are also those wherein $R^{12}$ and $R^{13}$ are independently,

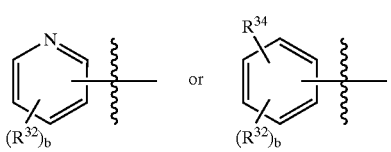

wherein:
  b is from 0 to 4;
  $R^{32}$ is halogen, $(C_{1-8})$alkyl, halo$(C_{1-8})$alkyl, $(C_{1-8})$alkoxy, $(C_{1-8})$alkoxy$(C_{1-8})$alkyl or halo$(C_{1-8})$alkoxy;
  $R^{33}$ is halogen;
  $R^{34}$ is $(C_{1-8})$alkyl, hydroxy or $(C_{1-8})$alkoxy; or
  two of $R^{32}$, or two of $R^{33}$, or one of $R^{33}$ and $R^{34}$, when attached to adjacent carbon atoms, may together form a ring, wherein the ring formed is an aliphatic, aryl or heteroaryl ring, each of which may be optionally substituted by one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; alkanoyl.

Preferred compounds of the present invention include, but are not limited to, those compounds wherein $R^{12}$ and $R^{13}$ are independently selected from:

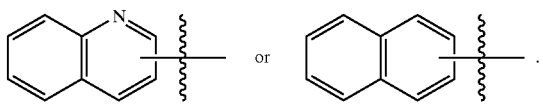

Additional preferred compounds of Formula IV, are those wherein $R^{10}$ and $R^{12}$ are taken together to form a double bond where i is 0 and k is 1, and $R^{11}$ and $R^{13}$ are each hydrogen.

Preferred compounds of the invention are also those wherein $R^{10}$ is an optionally substituted aryl or optionally substituted heteroaryl.

Additionally, preferred compounds of the invention may contain an alkenyl carboxylic acid moiety.

Further preferred compounds are those of Formula IV, wherein i and j are 0.

Preferred compounds are those of Formula IV, wherein k is 1.

Also preferred compounds are those of Formula IV, wherein $R^{14}$ is hydrogen.

Preferred compounds are those of Formula IV, wherein i and j are each zero; k is one; $R^{10}$, $R^{11}$ and $R^{12}$ are each hydrogen; and $R^{13}$ is hydrogen, $C_{1-6}$ alkyl, $C_{6-10}$ aryl or $C_{6-10}$ar$(C_{1-4})$alkyl.

Preferred compounds of the present invention are those of Formula IV wherein:
  $R^1$ is hydrogen or $(C_{1-4})$alkyl, more preferably, hydrogen or methyl;
  $R^2$, $R^3$, $R^4$, and $R^5$ are hydrogen or $(C_{1-4})$alkyl, more preferably hydrogen;
  $R^6$, $R^7$, $R^8$ and $R^9$ are preferably hydrogen or $(C_{1-4})$alkyl, more preferably hydrogen;
  X is oxygen or —$CH_2$—;
  n is 0 or 1;
  m is 0 or 1;
  $R^{10}$, $R^{11}$, $R^{12}$ and $R^{13}$ independently represent hydrogen, $(C_{1-6})$alkyl or $(C_{6-10})$ar$(C_{1-6})$alkyl; or
  one of the combination $R^{10}$ or $R^{11}$, $R^{12}$ or $R^{13}$, $R^{10}$ and $R^{12}$ are taken together to form —$(CH_2)_s$—, wherein s is 1 or 2 while the remaining $R^{10}$–$R^{13}$ are defined above;
  is 0 or 1;
  j is 0 or 1;
  k is 0 or 1;
  $R^{14}$ is hydrogen, $C_{1-6}$ alkyl or benzyl;
  W is:

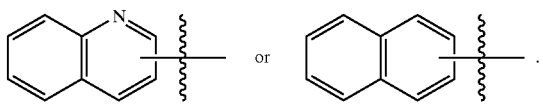

wherein:
  Y is —N— or —CH—;
  $R^{15}$ is hydrogen, halogen, $(C_{1-8})$alkyl, $(C_{6-10})$aryl or $(C_{6-10})$aryl$(C_{1-8})$alkyl;
  $R^{16}$ is hydrogen, $(C_{1-8})$alkyl, halo$(C_{1-8})$alkyl or halogen;
  $R^{19}$ and $R^{20}$ are hydrogen, halogen or $(C_{1-8})$alkyl; and
  $R^{27}$, $R^{28}$, $R^{29}$, $R^{30}$ and $R^{31}$ are hydrogen, halogen, $(C_{1-8})$alkyl, $(C_{1-8})$alkoxy, $(C_{6-10})$aryl.

Additionally preferred compounds of Formula IV are those wherein:
  X is —(C=O)NH—;
  n, m, a and v are each 0; and
  $R^6$, $R^7$, $R^{12}$ and $R^{13}$ are hydrogen.

Further preferred compounds of Formula IV are those wherein:
  X is oxygen;
  n and m are each 0;
  a and v are each 1;
  D is oxygen;
  $R^6$, $R^7$, $R^8$ and $R^9$ are hydrogen.

Preferred compounds of Formula IV are also those wherein:
  X is oxygen;
  n, m and v are each 0;
  a is 1; and
  $R^6$, $R^7$, $R^{12}$ and $R^{13}$ are hydrogen.

Further preferred compounds of Formula IV are also those wherein:

X is —$CH_2$—;

n, m and v are each 0;

a is 1; and $R^6$, $R^7$, $R^{12}$ and $R^{13}$ are hydrogen.

Examples of useful compounds of the present invention include:

3-{5-[3-(2-pyridylamino)propoxy]indolyl}propanoic acid;

3-{5-[3-(2-pyridylamino)propoxy]indolyl}acetic acid;

3-{2-methyl-5-[3-(2-pyridylamino)propoxy]indolyl}propanoic acid;

2-(trans-2-{5-[3-(2-pyridylamino)propoxy]indolyl}cyclopropyl) acetic acid;

3-(5-{2-[6-(methylamino)-2-pyridyl]ethoxy}indolyl) propanoic acid;

2-benzyl-3-{5[3-(2-pyridylamino)propoxy]indolyl}propanoic acid;

2-methyl-3-{5-[3-(2-pyridylamino)propoxy]indolyl}propanoic acid;

2-({5-[3-(2-pyridylamino)propoxy]indolyl}methyl) pentanoic acid;

2-({5-[3-(2-pyridylamino)propoxy]indolyl}methyl) octanoic acid;

3-[5-(3-{[benzylamino]carbonylamino}propoxy)indolyl] propanoic acid;

3-[5-(2-5,6,7,8-tetrahydro-[1,8]naphthyridin-2-yl-acetylamino)-indol-1-yl]-hexanoic acid;

3-(5-{2-[N-(4,5-dihydro-1H-imidazol-2yl)-aminooxy]-ethoxy}-indol-1-yl)-3-phenyl-propionic acid;

3-(5-{2-[guanidino-oxy]-ethoxy}-indol-1-yl)-3-phenyl-propionic acid;

3-{5-[2-(5,6,7,8-tetrahydro-[1,8]naphthyridin-2-yl)-ethoxy]-indol-1-yl}-hexanoic acid;

3-{5-[2-(5,6,7,8-tetrahydro-[1,8]naphthyridin-2-yl)-ethoxy]-indol-1-yl}-propionic acid;

3-phenyl-3-{5-[2-(5,6,7,8-tetrahydro-[1,8]naphthyridin-2-yl)-ethoxy]-indol-1-yl}-propionic acid;

3-phenyl-3-{5-[2-(5,6,7,8-tetrahydro-[1,8]naphthyridin-2-yl)-ethoxy]-indol-1-yl}-propionic acid;

3-(3-benzyloxy-phenyl)-3-{5-[2-(5,6,7,8-tetrahydro-[1,8]naphthyridin-2-yl)-ethoxy]-indol-1-yl}-propionic acid;

3-{5-[2-(5,6,7,8-tetrahydro-[1,8]naphthyridin-2-yl)-ethoxy]-indol-1-yl}-3-p-tolyl-propionic acid;

3-{5-[2-(5,6,7,8-tetrahydro-[1,8]naphthyridin-2-yl)-ethoxy]-indol-1-yl}-3-m-tolyl-propionic acid;

3-{5-[2-(5,6,7,8-tetrahydro-[1,8]naphthyridin-2-yl)-ethoxy]-indol-1-yl}-3-o-tolyl-propionic acid;

3-biphenyl-4-yl-3-{5-[2-(5,6,7,8-tetrahydro-[1,8] naphthyridin-2-yl)-ethoxy]-indol-1-yl}-propionic acid;

3-(3,5-dichloro-phenyl)-3-{5-[2-(5,6,7,8-tetrahydro-[1,8] naphthyridin-2-yl)-ethoxy]-indol-1-yl}-propionic acid;

3-(3,5-difluoro-phenyl)-3-{5-[2-(5,6,7,8-tetrahydro-[1,8] naphthyridin-2-yl)-ethoxy]-indol-1-yl}-propionic acid;

3-(3-cyano-phenyl)-3-{5-[2-(5,6,7,8-tetrahydro-[1,8] naphthyridin-2-yl)-ethoxy]-indol-1-yl}-propionic acid;

3-(4-cyano-phenyl)-3-{5-[2-(5,6,7,8-tetrahydro-[1,8] naphthyridin-2-yl)-ethoxy]-indol-1-yl}-propionic acid;

3-(2-methoxy-phenyl)-3-{5-[2-(5,6,7,8-tetrahydro-[1,8] naphthyridin-2-yl)-ethoxy]-indol-1-yl}-propionic acid;

3-(3-methoxy-phenyl)-3-{5-[2-(5,6,7,8-tetrahydro-[1,8] naphthyridin-2-yl)-ethoxy]-indol-1-yl}-propionic acid;

3-(4-methoxy-phenyl)-3-{5-[2-(5,6,7,8-tetrahydro-[1,8] naphthyridin-2-yl)-ethoxy]-indol-1-yl}-propionic acid;

3-quinolin-3-yl-3-{5-[2-(5,6,7,8-tetrahydro-[1,8] naphthyridin-2-yl)-ethoxy]-indol-1-yl}-propionic acid;

3-(3-chloro-phenyl)-3-{5-[2-(5,6,7,8-tetrahydro-[1,8] naphthyridin-2-yl)-ethoxy]-indol-1-yl}-propionic acid;

3-naphthalen-2-yl-3-{5-[2-(5,6,7,8-Tetrahydro-[1,8] naphthyridin-2-yl)-ethoxy]-indol-1-yl}-propionic acid;

3-(2-chloro-phenyl)-3-{5-[2-(5,6,7,8-tetrahydro-[1,8] naphthyridin-2-yl)-ethoxy]-indol-1-yl}-propionic acid;

3-naphthalen-1-yl-3-{5-[2-(5,6,7,8-Tetrahydro-[1,8] naphthyridin-2-yl)-ethoxy]-indol-1-yl}-propionic acid;

3-(4-fluoro-phenyl)-3-{5-[2-(5,6,7,8-tetrahydro-[1,8] naphthyridin-2-yl)-ethoxy]-indol-1-yl}-propionic acid;

3-{5-[2-(5,6,7,8-tetrahydro-[1,8]naphthyridin-2-yl)-ethoxy]-indol-1-yl}-3-(3-trifluoromethyl-phenyl)-propionic acid;

3-{5-[2-(5,6,7,8-tetrahydro-[1,8]naphthyridin-2-yl)-ethoxy]-indol-1-yl}-3-(4-trifluoromethyl-phenyl)-propionic acid;

3-pyridin-3-yl-3-{5-[2-(5,6,7,8-tetrahydro-[1,8] naphthyridin-2-yl)-ethoxy]-indol-1-yl}-propionic acid;

3-pyridin-2-yl-3-{5-[2-(5,6,7,8-tetrahydro-[1,8] naphthyridin-2-yl)-ethoxy]-indol-1-yl}-propionic acid;

3-pyridin-4-yl-3-{5-[2-(5,6,7,8-tetrahydro-[1,8] naphthyridin-2-yl)-ethoxy]-indol-1-yl}-acrylic acid;

3-(2,3-dihydro-benzofuran-5-yl)-3-{5-[2-(5,6,7,8-tetrahydro-[1,8]naphthyridin-2-yl)-ethoxy]-indol-1-yl}-propionic acid;

3-benzo[1,3]dioxol-5yl-3-{5-[2-(5,6,7,8-tetrahydro-[1,8] naphthyridin-2-yl)-ethoxy]-indol-1-yl}-propionic acid;

3-(5-methanesulfonyl-pyridin-3-yl)-3-{5-[2-(5,6,7,8-tetrahydro-[1,8]naphthyridin-2-yl)-ethyoxy]-indol-1-yl}-propionic acid;

3-{5-[2-(6-methylamino-pyridin-2-yl)-ethoxy]-indol-1-yl}-3-phenyl-propionic acid;

3-{5-[2-(6-methylamino-pyridin-2-yl)-ethoxy]-indol-1-yl}-3-quinolin-3-yl-propionic acid;

3-{5-[2-(6-methylamino-pyridin-2-yl)-ethoxy]-indol-1-yl}-3-pyridin-3-yl-propionic acid;

3-{5-[2-(6-methylamino-pyridin-2-yl)-ethoxy]-indol-1yl}-hexanoic acid;

3-{5-[2-(2-methyl-5,6,7,8-tetrahydro-[1,8]naphthyridin-3-yl)-ethyl]-indol-1-yl}-propionic acid;

3-{5-[3-(5,6,7,8-tetrahydro-[1,8]naphthyridin-2-yl)-propyl]-indol-1-yl}-propionic acid;

3-{5-[3-(5,6,7,8-tetrahydro-[1,8]naphthyridin-2-yl)-propyl]-indol-1-yl}-hexanoic acid;

3-phenyl-3-{5-[3-(5,6,7,8-tetrahydro-[1,8]naphthyridin-2-yl)-propyl]-indol-1-yl}-propionic acid;

3-{5-[2-(5,6,7,8-tetrahydro-[1,8]naphthyridin-2-yl)-ethoxy]-indol-1-yl}-3-[5-(2,2,2-trifluoro-ethoxy)-pyridin-3-yl]-propionic acid;

3-(5-Ethoxy-pyridin-3-yl)-3-{5-[2-(5,6,7,8-tetrahydro-[1,8] naphthyridin-2-yl)-ethoxy]-indol-1-yl}-propionic acid;

3-Pyridin-4-yl-3-{5-[2-(5,6,7,8-tetrahydro-[1,8] naphthyridin-2-yl)-ethoxy]-indol-1-yl}-propionic acid;

3-Pyridin-2-yl-3-{5-[2-(5,6,7,8-tetrahydro-[1,8] naphthyridin-2-yl)-ethoxy]-indol-1-yl}-acrylic acid;

6-(2-hydroxy-ethyl)-2,3-dihydro-pyrido[3,2-b][1,4] oxazine-4-carboxylic acid tert-butyl ester;

3-{5-[2-(6-methylamino-pyridin-2-yl)-ethoxy]-indol-1-yl}-3-quinolin-3-yl-propionic acid;

or a pharmaceutically acceptable salt, hydrate, solvate or prodrug thereof.

Particularly preferred compounds of the invention are:

3-(3-methoxy-phenyl)-3-{5-[2-(5,6,7,8-tetrahydro-[1,8] naphthyridin-2-yl)-ethoxy]-indol-1-yl}-propionic acid;

3-quinolin-3-yl-3-{5-[2-(5,6,7,8-tetrahydro-[1,8] naphthyridin-2-yl)-ethoxy]-indol-1-yl)}-propionic acid;

3-pyridin-3-yl-3-{5-[2-(5,6,7,8-tetrahydro-[1,8] naphthyridin-2-yl)-ethoxy]-indol-1-yl}-propionic acid;

3-pyridin-2-yl-3-{5-[2-(5,6,7,8-tetrahydro-[1,8] naphthyridin-2-yl)-ethoxy]-indol-1-yl}-propionic acid;

3-{5-[2-(6-methylamino-pyridin-2-yl)-ethoxy]-indol-1-yl}-3-quinolin-3-yl-propionic acid;

or a pharmaceutically acceptable salt, hydrate, solvate or prodrug thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

When any variable occurs more than one time in any constituent or in Formula IV, its definition on each occurrence is independent of its definition at every other occurrence. Also, combinations of substituents and/or variables are permissible only if such combinations result in stable compounds.

The term "alkyl" as employed herein by itself or as part of another group refers to both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aryloxy" as employed herein by itself or as part of another group refers to monocyclic or bicyclic aromatic groups containing from 6 to 12 carbons in the ring portion, preferably 6–10 carbons in the ring portion, bonded to an oxygen atom. Examples include, but are not limited to, phenoxy, naphthoxy, and the like.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4H-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "heterocycle" or "heterocyclyl" as used herein, except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, chromanyl, benzimidazolyl, thiadiazoyl, benzopyranyl, benzothiazolyl, benzo[b]thiophenyl, benzo[2,3-c]1,2,5-oxadiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "halogen" or "halo" as employed herein by itself or as part of another group refers to chlorine, bromine, fluorine or iodine with fluorine being preferred.

The term "monoalkylamino" as employed herein by itself or as part of another group refers to an amino group which is substituted with one alkyl group having from 1 to 6 carbon atoms.

The term "dialkylamino" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "haloalkyl" as employed herein refers to any of the above alkyl groups substituted by one or more chlorine, bromine, fluorine or iodine with fluorine and chlorine being preferred, such as chloromethyl, iodomethyl, trifluoromethyl, 2,2,2-trifluoroethyl, and 2-chloroethyl.

The term "haloalkoxy" as used herein refers to any of the above haloalkyl groups bonded to an oxygen atom, such as trifluromethoxy, trichloromethoxy, and the like.

The present invention is also directed to method for preparing compounds of Formula IV, comprising:
reacting a compound of Formula V:

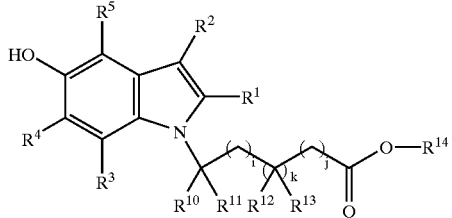

V or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i, j and k are as defined as above, with the compound of Formula VI or Formula X:

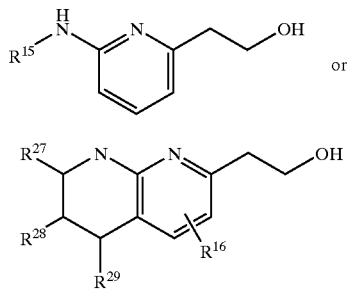

VI or

X or a salt, hydrate or solvate thereof, wherein $R^{15}$ is as defined above, to form the compound Formula IV.

The present invention is also directed to method for preparing compounds of Formula IV, comprising:
reacting a compound of Formula V:

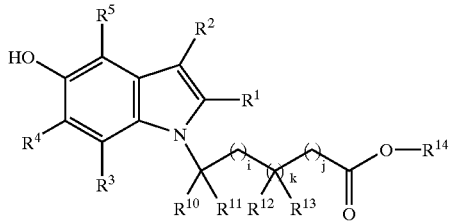

V or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i, j and k are as defined as above, with the compound of Formula IX:

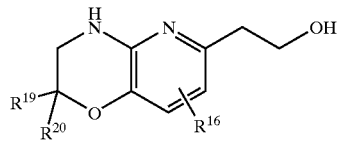

IX or a salt, hydrate or solvate thereof, wherein $R^{16}$, $R^{19}$ and $R^{20}$ are as defined above, and $R^{35}$ is alkyl, aryl, alkylaryl or arylalkyl, followed by removal of the $R^{35}$ containing protecting group to form the compound Formula IV.

The present invention is also directed to a method for preparing compounds of Formula IV, comprising reacting a compound of Formula V:

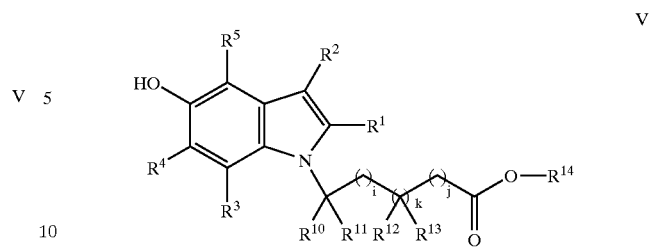

V or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i, j and k are as defined above, with the compound of Formula VII:

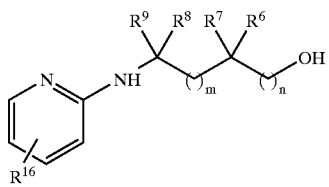

VII or a salt, hydrate or solvate thereof, wherein $R^6$, $R^7$, $R^8$, $R^9$, $R^{16}$, m and n are as defined above, to form the compound of Formula IV.

The present invention is also directed to a method for preparing compounds of Formula IV, comprising reacting a compound of Formula VIII:

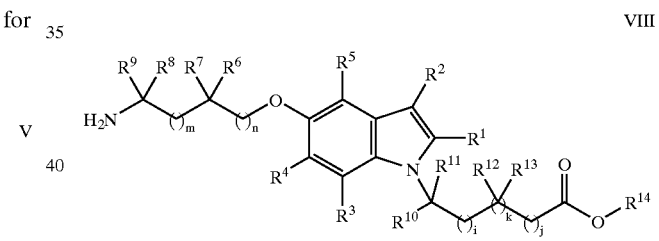

VIII or a salt, hydrate or solvate thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, i, j, k, m and n are as defined in claim 1, with $R^{15}$NCO, where $R^{15}$ is as defined in claim 1, to form a substituted indole compound of claim 1.

The compounds of the present invention may be prepared by the general procedures outlined in Schemes I–VII (below), where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{16}$, n, m, i, j, X and W are as defined above. Additional R-groups, not defined above, but used throughout the schemes below are defined as indicated below:

$R^{17}$, $R^{18}$, $R^{19}$, $R^{20}$, $R^{24}$ and $R^{25}$ are independently hydrogen, halogen or alkyl;

$R^{21}$ is trialkylsilyl or alkylorthoformate; preferably trimethylsilyl or $(C_{1-6})$alkylorthoformate;

$R^{22}$ is alkyl, aryl, heteroaryl, or an aliphatic ring system;

$R^{23}$ is a protecting group such as a trialkylsilyl, such as trimethylsilyl, triisopropylsilyl; benzyl or sulfonyl;

$R^{26}$ is hydrogen, alkyl, aryl, heteroaryl, or an aliphatic ring system;

$R^{27}$, $R^{28}$, $R^{29}$, $R^{30}$ and $R^{31}$ are independently hydrogen, halogen, alkoxyaryl or an aliphatic ring system;

$R^{30}$ and $R^{31}$ are independently hydrogen, alkyl, aryl or an aliphatic ring system;

$R^{32}$ is halogen, alkyl, haloalkyl, alkoxy, alkoxyalkyl or haloalkoxy;

$R^{33}$ is halogen, alkyl, haloalkyl, alkoxy, alkoxyalkyl or haloalkoxy, and is preferably halogen;

$R^{34}$ and $R^{35}$ are independently alkyl, hydroxy, alkoxy, aryl, alkylaryl or arylalkyl; and o and p are 0, 1 or 2.

Scheme Ia, Ib, Ic, Id and Ie outline the synthetic steps to produce compounds of the present invention where X is O, and W is

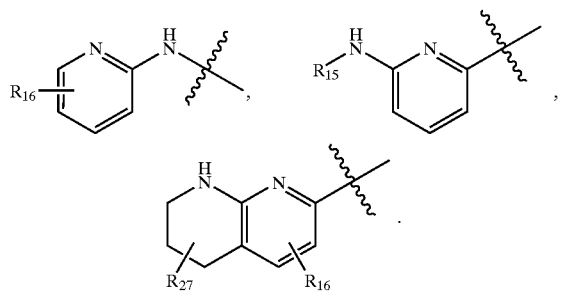

Scheme Ia

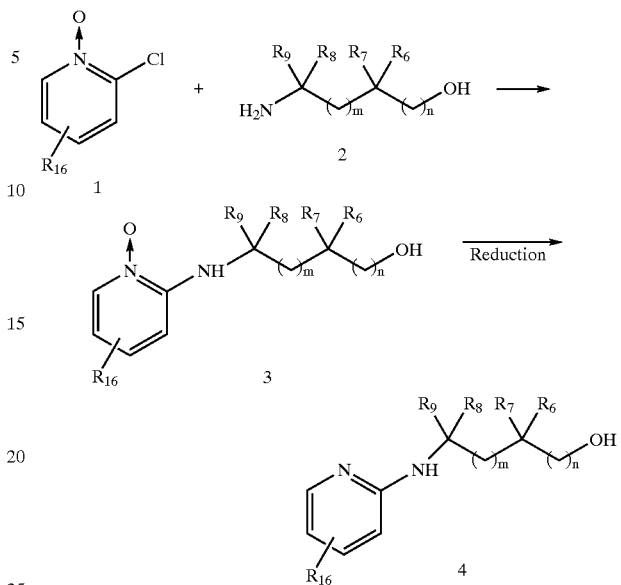

In Scheme Ia, 2-chloropyridine N-oxide derivative 1 is refluxed with aminoalkyl alcohol 2 in the presence of a base, such as sodium bicarbonate, and a suitable solvent, such as tert-amyl alcohol, to give compound 3. Compound 3 is then converted to pyridinyl aminoalkyl alcohol 4 using standard reduction conditions. Preferred conditions include treating compound 3 with cyclohexene in the presence of a catalyst, such as palladium on carbon, and a solvent, such as ethanol.

Scheme Ib

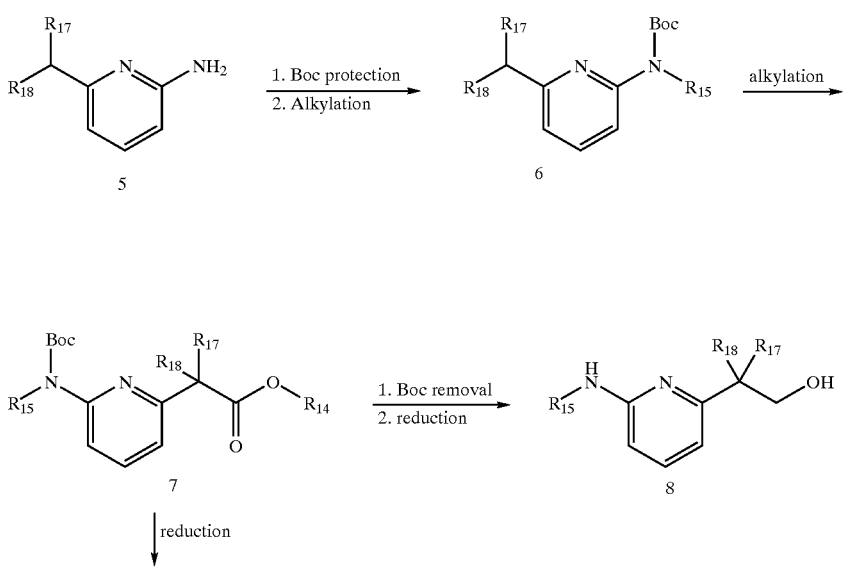

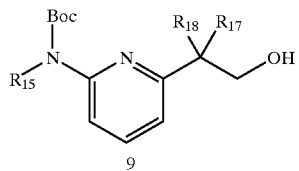
9

In Scheme Ib, a 2-amino-5-methylpyridine analogue 5 is first protected with a tert-butyloxycarbonyl (Boc) group using conditions well known in art (Greene, T. W. and Wuts, P. G. M., *Protective Groups in Organic Synthesis*, $2^{nd}$ edition, John Wiley and Sons, Inc., New York (1991)), followed by treatment with an alkyl halide, such as iodomethane, in the presence of a base, such as sodium hydride, and a solvent, such as tetrahydrofuran (THF) or dimethylformamide (DMF), to give compound 6. Converting compound 6 to compound 7 is accomplished by reacting compound 6 with a base, such as lithium diisopropylamide (LDA), and diethyl carbonate in a solvent, such as tetrahydrofuran (THF). The Boc protecting group of compound 7 is removed by standard procedures well known in the art (Greene, T. W. and Wuts, P. G. M., supra), such as trifluoroacetic acid in methylene chloride. The ester is then reduced by standard conditions, such as lithium aluminum hydride (LAH) in tetrahydrofuran (THF), to give compound 8. Alternatively, compound 7 can be treated with a reducing agent, such as lithium borohydride in a solvent such as tetrahydrofuran to give compound 9.

Scheme Ic

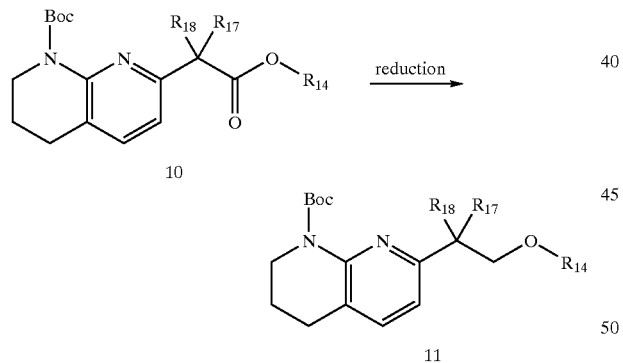

In Scheme Ic, Compound 10 (Miller, H.; Manley, P. J., PCT Int. Appl. 2000, 40 pp. WO 00/33838) is treated with a reducing agent such as lithium borohydride, in a solvent such as tetrahydrofuran, to give compound 11.

Scheme Id

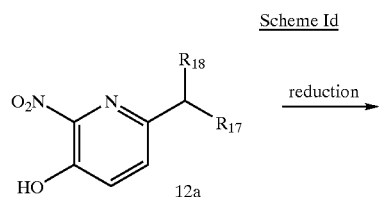

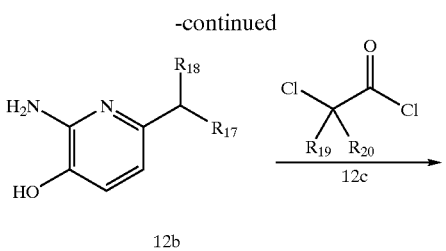

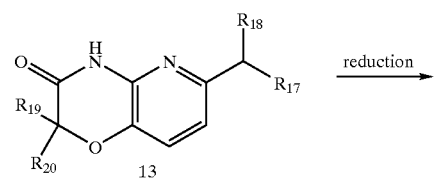

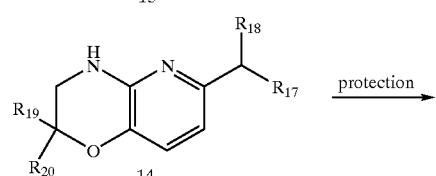

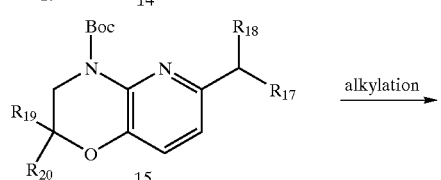

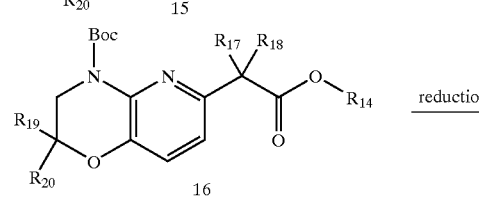

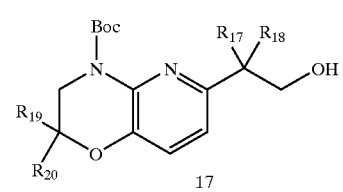

In Scheme 1d, 3-hydroxy-6-methyl-2-nitropyridine derivative 12a is reduced under suitable conditions, such as hydrogenation in the presence of palladium catalyst, with a solvent, such as ethanol, to give compound 12b. Reaction of compound 12b (L. Savelon, et.al., Biorganic and Medicinal Chemistry, 6, 133, (1998)) with 2-haloacid chloride 12c, such as chloroacetyl chloride, in the presence of base, such as sodium bicarbonate, in suitable solvents, such as water and 2-butanone, gives compound 13. Reduction of compound 13 with suitable reagent, such as lithium aluminum hydride, in a suitable solvent, such as THF, gives compound 14. Compound 14 is protected using suitable conditions, to introduce a protecting group, such as Boc, to give compound 15 (Greene, T. W. and Wuts, P. G. M., *Protective Groups in Organic Synthesis*, 2$^{nd}$ edition, John Wiley and Sons, Inc., New York (1991)). Compound 15 is alkylated under suitable conditions, such as deprotonation with base, such as LDA, followed by reaction with alkylating reagent, such as dialkylcarbonate, to produce compound 16. Reduction of compound 16 is achieved with suitable reducing reagent, such as lithium borohydride in a solvent such as tetrahydrofuran, to give compound 17.

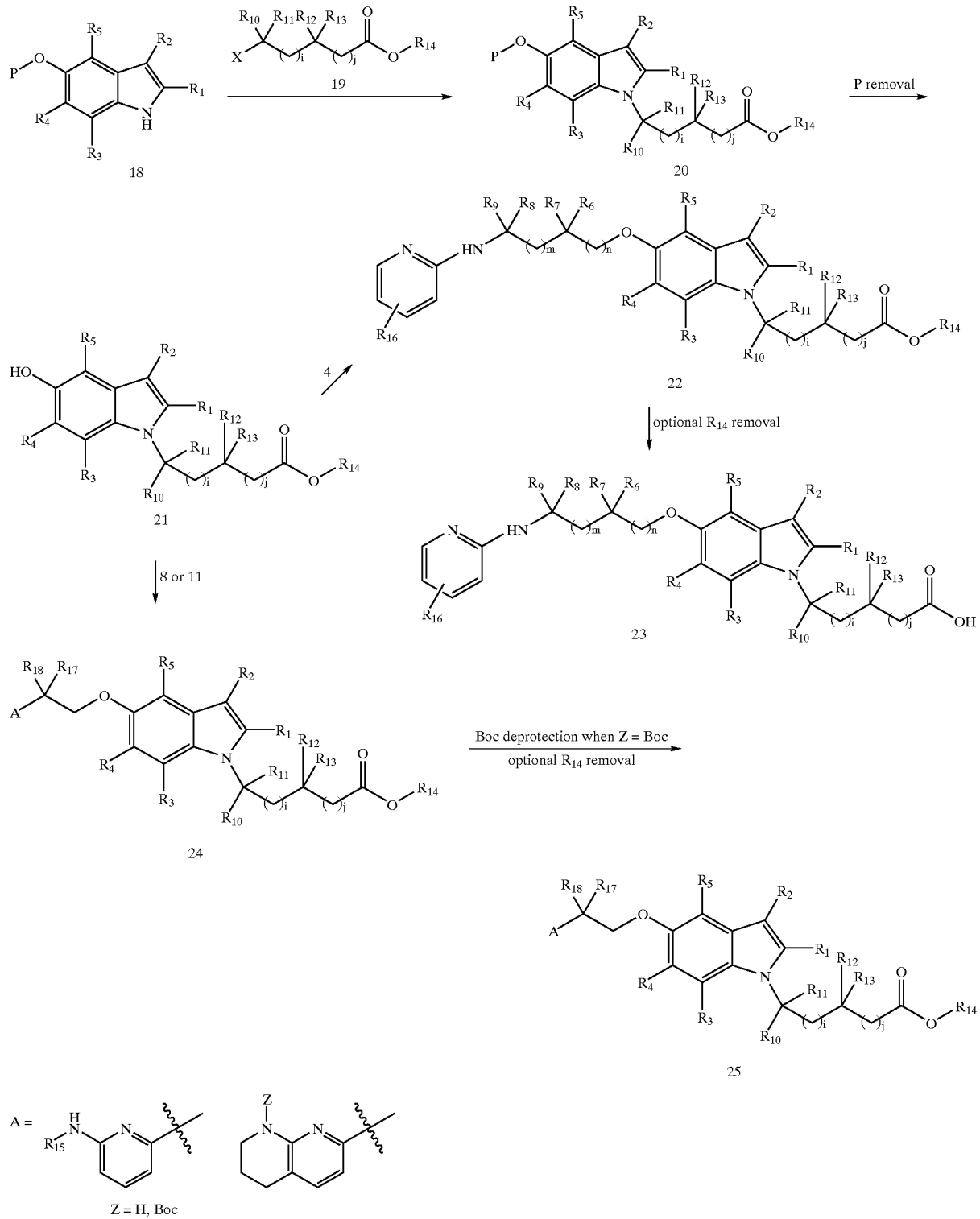

In Scheme Ie, the protected indole 18 (P is protecting group), such as 5-benzyloxyindole, is reacted with a base, such as sodium hydride, and haloalkylcarboxyl ester 19, in a suitable solvent, such as N,N-dimethylformamide (DMF), to generate compound 20. The protecting group is removed by conditions well known in the art (Greene, T. W. and Wuts, P. G. M., supra), to give compound 21. For example, deprotection of benzyl ether is achieved through catalytic hydrogenation using palladium on carbon as a catalyst in a solvent, such as ethanol or tetrahydrofuran. Compound 21 is coupled to compounds 4 using a Mitsunobu coupling procedure (Mitsunobu, O., *Synthesis*, 1 (1981)) to give compound 22. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl)dipiperidine. Compound 22 is optionally converted to compound 23 by a standard procedure, such as sodium hydroxide in a solvent, such as methanol and water. Alternatively, compound 21 is coupled to compounds 8 or 11 using a Mitsunobu coupling procedure (Mitsunobu, O., *Synthesis*, 1 (1981)) to give compound 24. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl)dipiperidine. Compound 24 is optionally deprotected when Z=Boc with standard deprotection conditions (Greene, T. W. and Wuts, P. G. M., supra), followed by and optional hydrolysis using standard conditions such as sodium hydroxide in a solvent, such as methanol and water to give compound 25.

Scheme II outlines the synthetic steps to produce compounds of the present invention where X is O, and W is

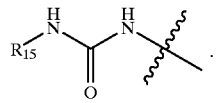

-continued

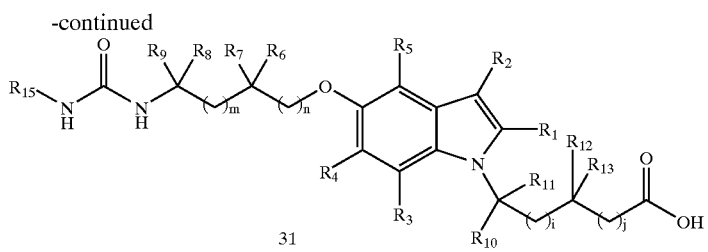

31

Compound 21 is coupled with benzyloxycarbonyl (Cbz) protected amino alcohol 26 using a Mitsunobu coupling procedure (Mitsunobu, O., *Synthesis*, 1 (1981)) to give compound 27. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine. Compound 27 is deprotected using standard deprotection conditions such as hydrogenation using palladium on carbon as a catalyst in solvents such as ethanol or tetrahydrofuran, to give compound 28. Compound 28 is treated with isocyanate analogue 29 in a solvent such as acetonitrile to give compound 30. Compound 30 is optionally converted to acid 31 by a standard hydrolysis procedure such as sodium hydroxide in a solvent, such as methanol and water.

Scheme IIIa, IIIb and IIIc outline the synthetic steps to produce compounds of the present invention where X is O, and W is

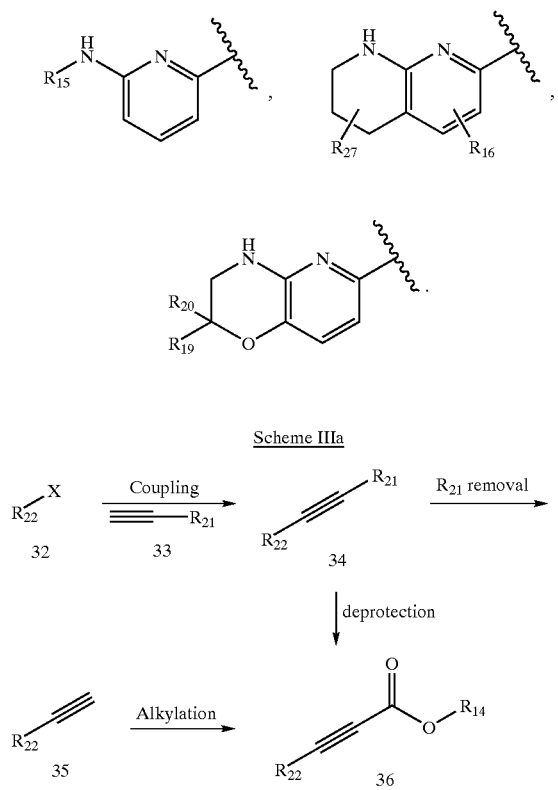

Scheme IIIa

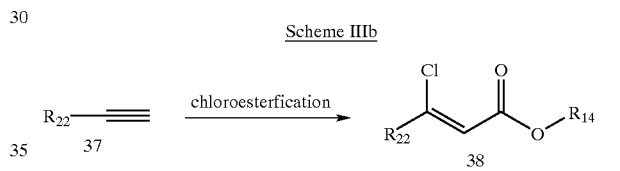

In Scheme IIIa, aryl halides 32 are reacted with protected acetylenes 33, such as trimethylsilylacetylenes or trialkyloxypropynes under cross coupling conditions with suitable reagents, such as palladium(II) and copper iodide, in the presence of base, such as triethylamine, to give protected arylacetylene compounds 34 (Sonogashira, K., Tetrahedron Lett. 1975, 50, 4467–70). Removal of the trimethylsilyl group of compound 34 is achieved under various conditions, such as tetrabutylammonium fluoride or base, to give compound 35 (Greene, T. W. and Wuts, P. G. M., *Protective Groups in Organic Synthesis*, $2^{nd}$ edition, John Wiley and Sons, Inc., New York (1991)). Treatment of compound 35 with a suitable reagent, such as alkyl haloformate, in the presence of base, such as LDA, or butyllithium, gives compound 36. Alternatively, the aryl triethoxypropyne 34 can be treated with a suitable acid, such as p-toluenesulfonic acid, to give compound 36.

Scheme IIIb

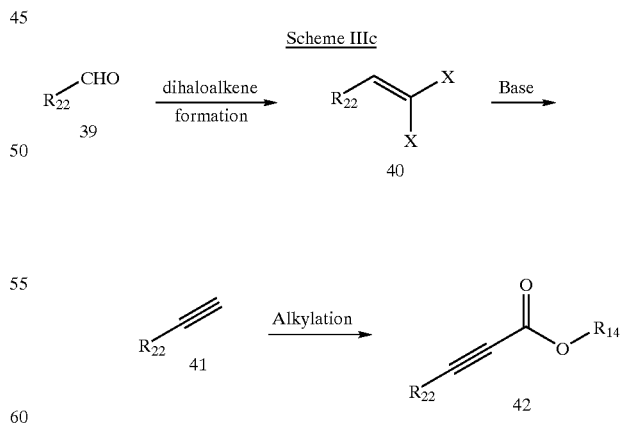

In Scheme IIIb, aliphatic acetylene 37 or aromatic acetylene 37 (synthesized using methodology describe in Scheme IIIa) is treated with alkylchloroformate in the presence of a catalyst such as carbonylchlorobis-(triphenylphosphine)-rhodium(I), in a solvent such as toluene, to give compound 38.

Scheme IIIc

In Scheme IIIc, aliphatic or aromatic aldehyde 39 is treated with suitable reagents, such carbontetrabromide and triphenylphosphine, to give compound 40. Treatment of the compound 40 with suitable base, such as n-butyllithium, gives compound 41. Reaction of compound 41 with suitable base, such as LDA, or n-butyllithium (Corey, E. J.; Fuchs, P. L., Tetrahedron Lett. (1972), (36), 3769–72), followed by alkyl haloformate, such as ethyl chloroformate, generates compound 42.

Scheme IIId

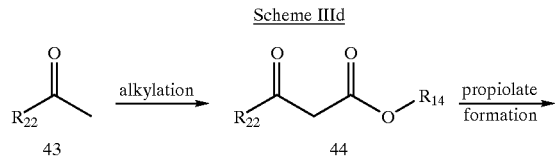

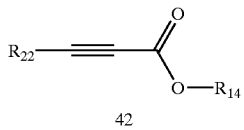

In Scheme IIId, aromatic or aliphatic ketones 43 are treated with base, such as sodium hydride, in a solvent such as tetrahydrofuran, and dialkylcarbonate or alkylchloroformate to give compound 44. Compound 44 is then treated with triphenylphophine oxide and trifluoromethanesulfonate anhydride in the presence of a base, such as triethylamine to give compound 42 (Hendrickson, J., Synthesis, 1989, 217).

Scheme IIIe

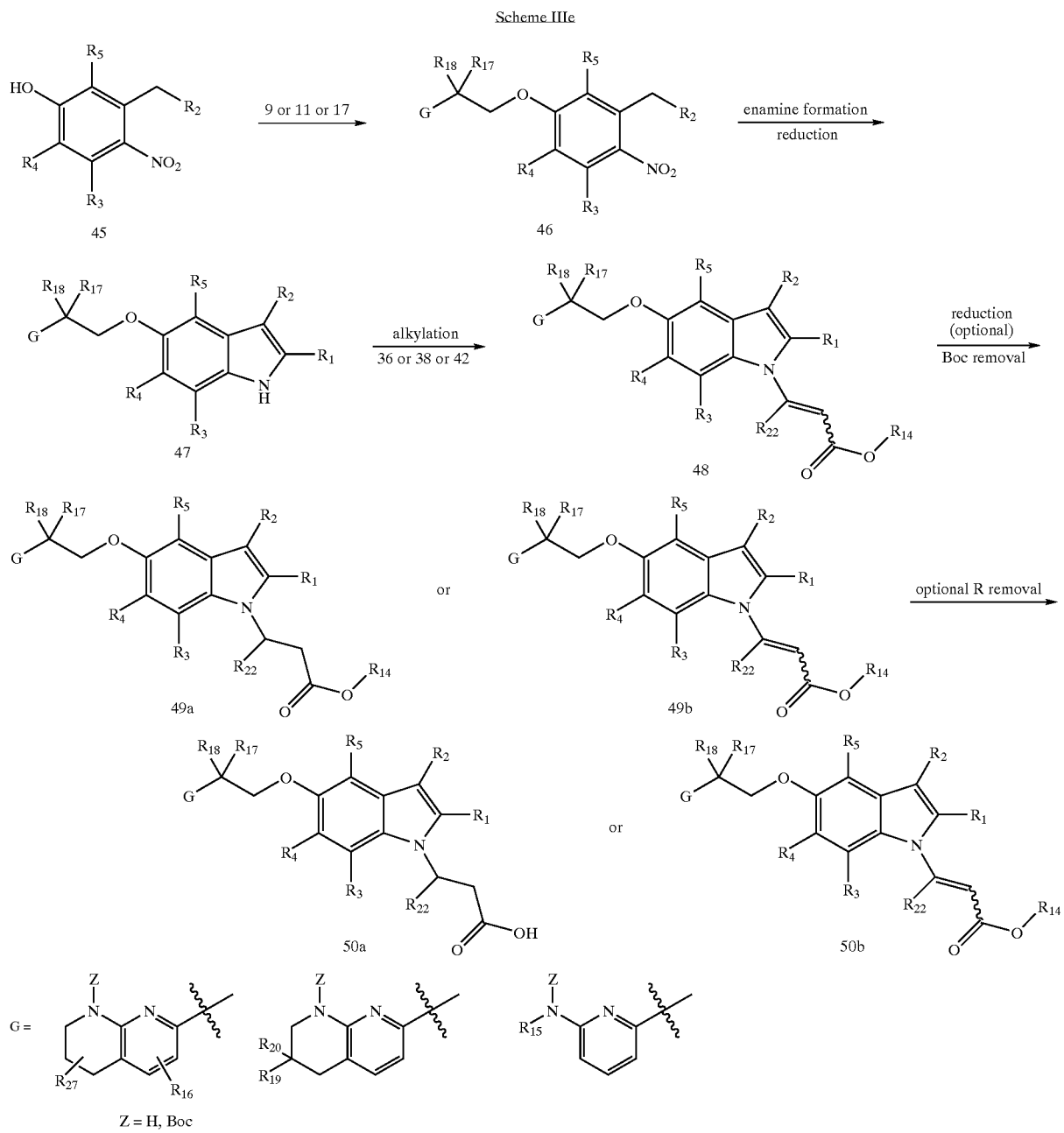

Z = H, Boc

In Scheme IIIe, compound 9 or 11 or 17 is coupled with a 3-methyl-4-nitro-phenol derivative 45 using a Mitsunobu coupling procedure (Mitsunobu, O., *Synthesis*, 1 (1981)) to give compounds 46. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine. Compound 46 can be treated with pyrrolidine and dimethoxymethyl dimethylamine to give the corresponding enamine, followed by standard reduction conditions such as hydrogenation in the presence of a catalyst, such as palladium on carbon, and a solvent such as ethanol, to give compound 47 (Batcho, A., Batcho, Andrew D.; Leimgruber, Willy., Org. Synth. 1985, 63, 214–25). Compound 47 is then reacted with an appropriate substituted propiolate 36 or 42, in the presence of a base, such as cesium fluoride or tetrabutylammonium fluoride, in a solvent such as THF or DMF, to give compound 48. Alternatively, compound 47 is treated with substituted vinylhalide ester 38 using a catalyst such as carbonylchlorobis-(triphenylphosphine)-rhodium(I) in a solvent such as toluene to give compound 48.

Compound 48 is then optionally reduced through treatment such as hydrogenation, in the presence of a catalyst, such as palladium on carbon, followed by Boc removal which can be carried out by deprotection conditions such as heating the neat compound to 180° C. to give compound 49a or 49b. Compound 49a or 49b can then optionally be hydrolyzed in the presence of a base, such as potassium hydroxide in a solvent such as methanol and water, to give compound 50a or 50b.

Scheme IVa, IVb, IVc and IVd outline the synthetic steps to produce compounds of the present invention where X is C, and W is

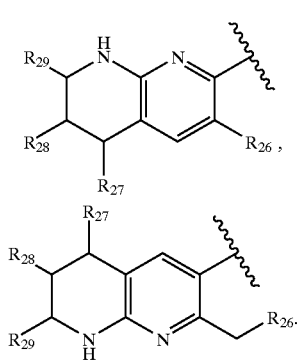

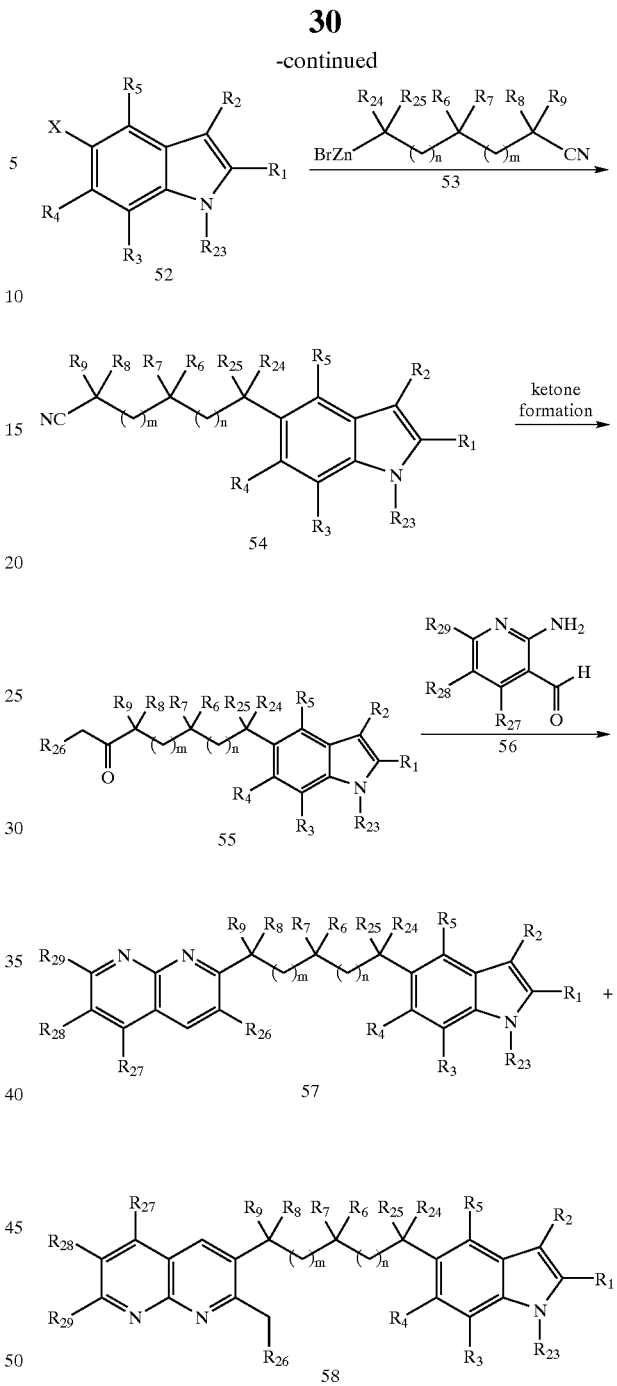

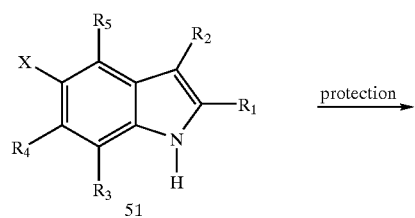

Scheme IVa

In Scheme IVa, 5-haloindole derivative 51 is protected under standard protection conditions with triisopropylsilylchloride, in the presence of a base, such as lithium hexamethyldisilazane, to give protected compound 52. Compound 52 is coupled with cyanoalkyl zinc halide 53, such as 3-cyanopropyl zinc bromide, in the presence of a catalyst, such as tetrakis(triphenylphosphine)palladium(0), to afford compound 54. Compound 54 is treated under suitable conditions, such as alkyl magnesium halides, followed by quenching with water to give compound 55. Finally, the compound 55 is condensed with substituted 2-amino-pyridine-3-carbaldehyde 56, in the presence of a base, such as L-proline, in a solvent such as ethanol, to give a mixture of compound 57 and 58.

Scheme IVb

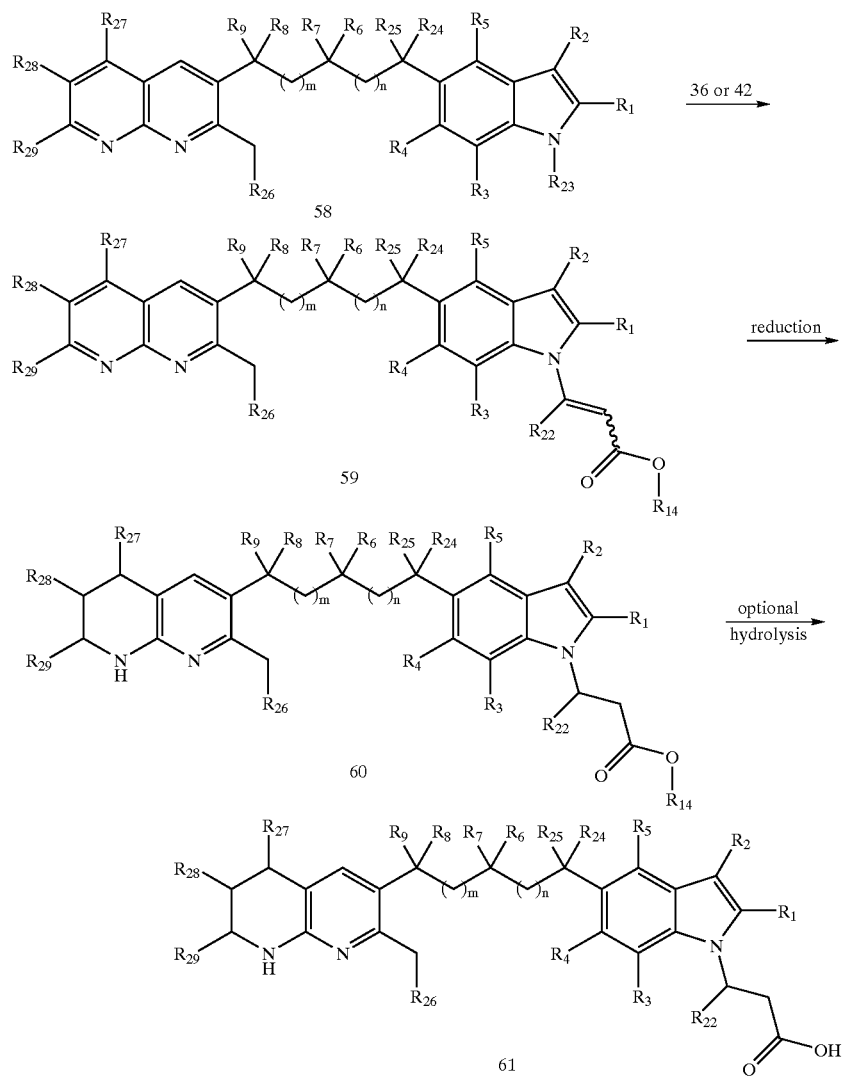

In Scheme IVb, compound 58 is treated with substituted propynoic acid ester 36 or 42, such as phenyl propynoic acid ethyl ester, in the presence of a base, such as tetrabutylammonium fluoride or cesium fluoride, in a solvent such as tetrahydrofuran, to give compound 59 as an E/Z isomeric mixture. Compound 59 is reduced under standard reduction conditions such as hydrogenation, in the presence of a catalyst, such as palladium on carbon, with a solvent, such as methanol, to give compound 60. Optional hydrolysis of compound 60 under suitable conditions, such as aqueous lithium hydroxide or sodium hydroxide, in a suitable solvent, such as methanol or THF, gives compound 61.

Scheme IVc

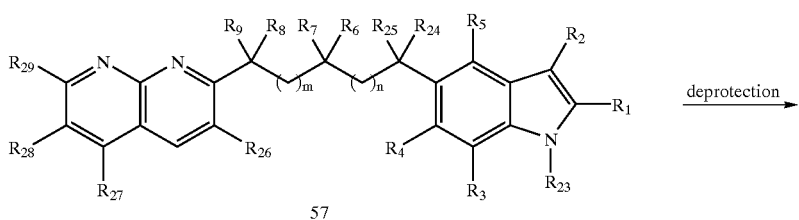

-continued

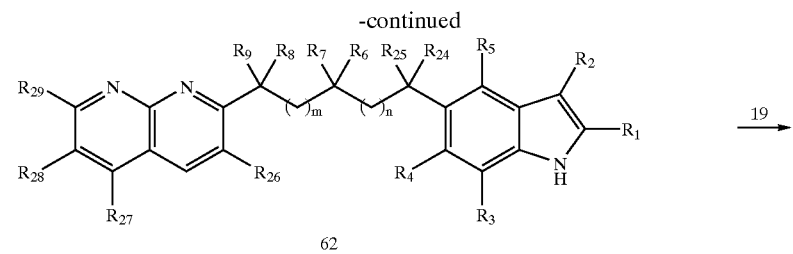
62

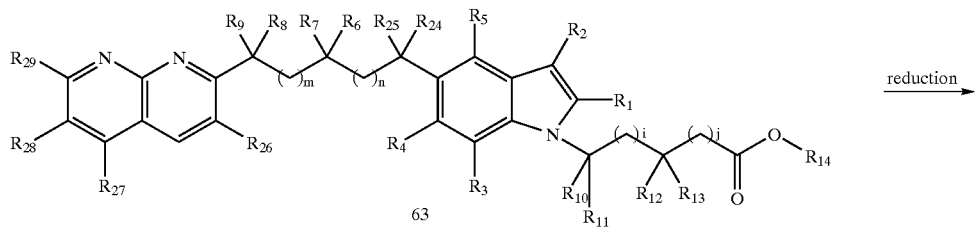
63

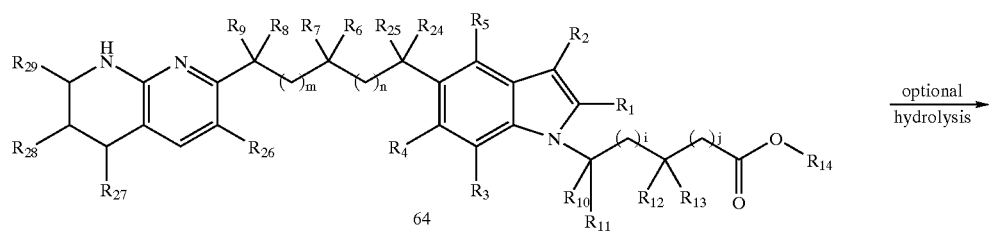
64

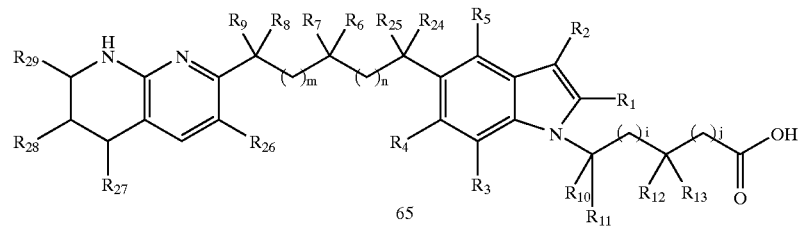
65

In Scheme IVc, compound 57 is deprotected under suitable conditions with reagents, such as tetrabutylammonium fluoride, in a solvent, such as tetrahydrofuran, to give compound 62. Compound 62 is then treated with alkyl halide 19 such as 3-bromo-propionic acid ethyl ester, in the presence of a base, such as sodium hydride, in a solvent, such as DMF, to give compound 63. Compound 63 is reduced under standard reduction conditions such as hydrogenation, in the presence of a catalyst, such as palladium on carbon, with a solvent, such as methanol or ethyl acetate, to give compound 64. Optional hydrolysis of compound 64 is done under suitable conditions, such as aqueous lithium hydroxide or sodium hydroxide, in a suitable solvent, such as methanol or THF, to give compound 65.

Scheme IVd

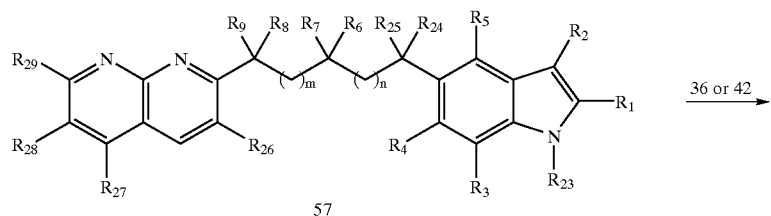
57

-continued

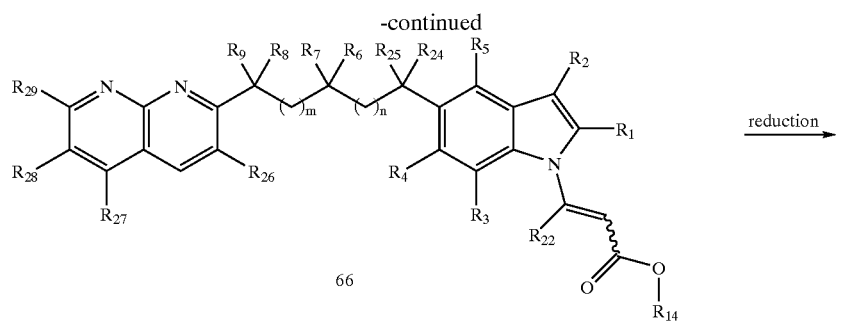
66

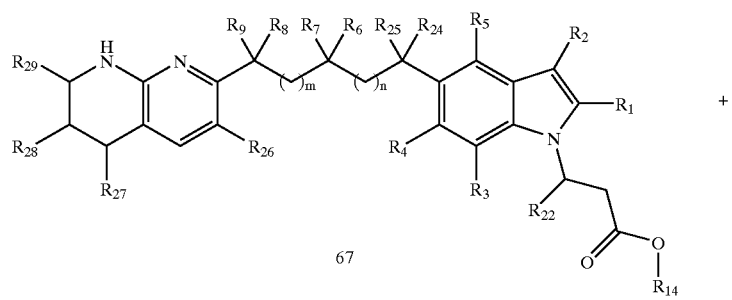
67

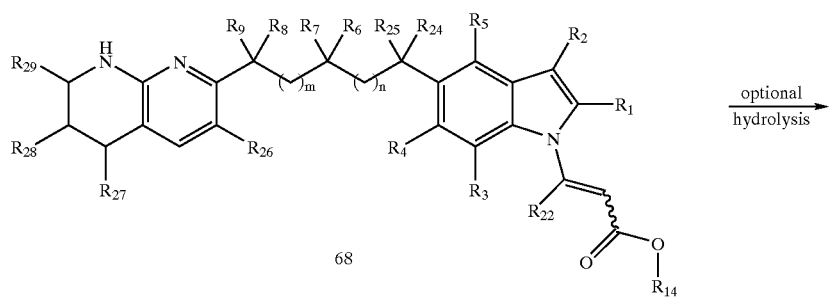
68

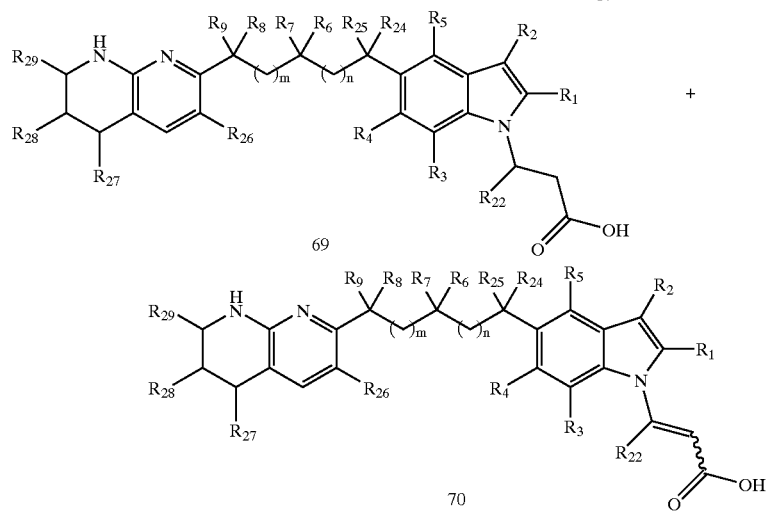
69

70

In Scheme IVd, compound 57 is treated with substituted propynoic acid ester 36 or 42, such as phenyl propynoic acid ethyl ester, in the presence of a base, such as tetrabutylammonium fluoride or cesium fluoride, in a solvent such as tetrahydrofuran, to give compound 66 as an E/Z isomeric mixture. Compound 66 is reduced under standard reduction conditions such as hydrogenation, in the presence of a catalyst, such as palladium on carbon, with a solvent, such as methanol or ethyl acetate, to give a mixture of compound 67 and 68. Without separation, optional hydrolysis of the mixture of compounds 67 and 68 under basic conditions, such as aqueous lithium hydroxide or sodium hydroxide solution in THF or methanol, to give compound 69 as the major product, with compound 70 as the minor product.

Scheme V outline the synthetic steps to produce compounds of the present invention where X is O, and W is

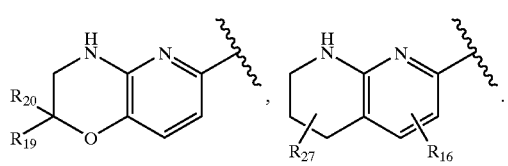

In Scheme V, protected 5-hydroxyindole compound 18 is treated with substituted propynoic acid ester 36 or 42, such as phenyl propynoic acid ethyl ester, in the presence of a base, such as tetrabutylammonium fluoride or cesium fluoride, in solvent such as tetrahydrofuran, to give compound 71 as an E/Z isomeric mixture. Compound 71 is reduced under standard reduction conditions such as hydrogenation, in the presence of a catalyst, such as palladium on carbon, with a solvent, such as methanol or ethyl acetate, to give compound 72. Compound 72 is coupled with compound 11 or 17 using a Mitsunobu coupling procedure (Mitsunobu, O., *Synthesis*, 1 (1981)) to give compound 73. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl)dipiperidine. Deprotection of compound 73 is carried out with copper (I) trifluoromethanesulfonate, in a solvent, such as DMF in toluene at 200° C. to give compound 74. Optional hydrolysis of compound 74 under basic conditions, such as aqueous lithium hydroxide or sodium hydroxide in THF or methanol, gives compound 75.

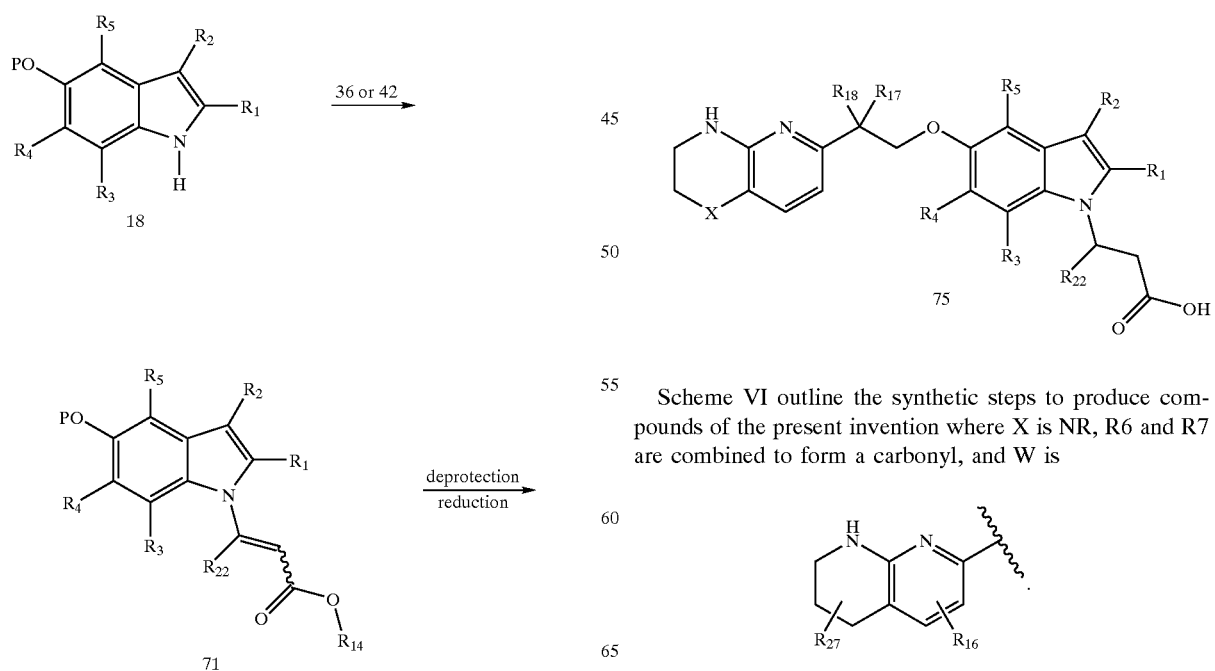

Scheme VI outline the synthetic steps to produce compounds of the present invention where X is NR, R6 and R7 are combined to form a carbonyl, and W is

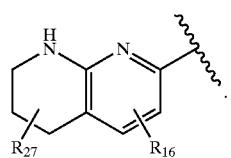

Scheme VI

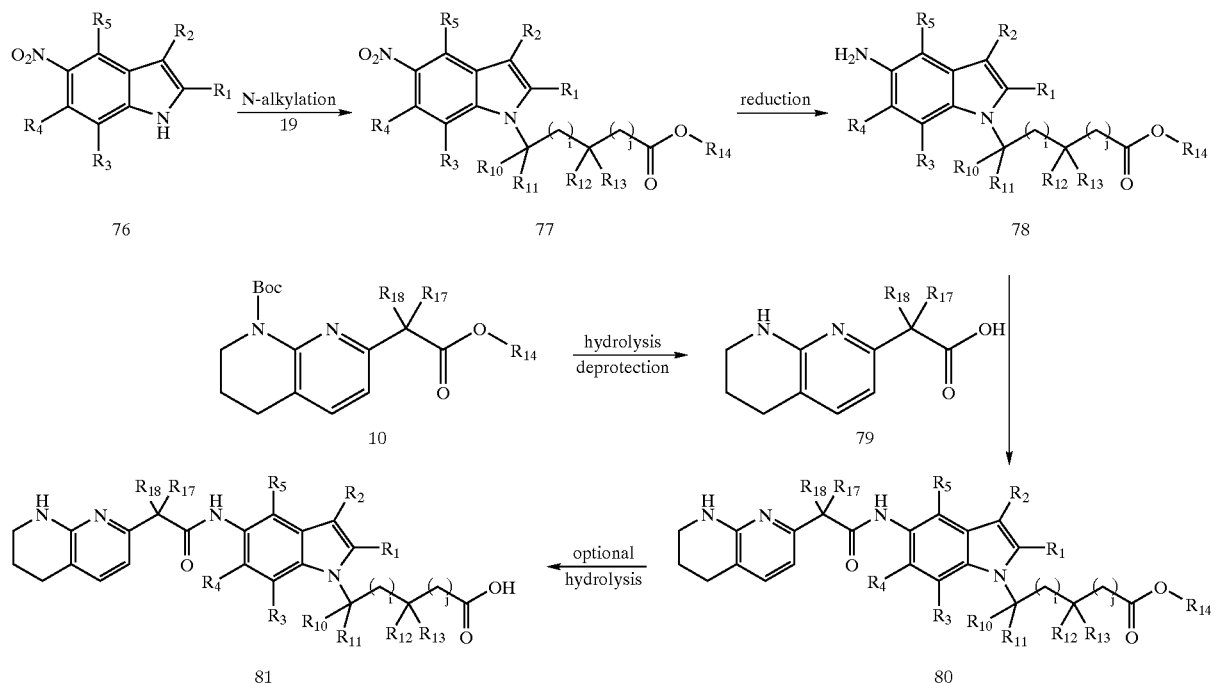

In Scheme VI, 5-nitroindole derivative 76 is treated with alkyl halides 19 in the presence of base, such as sodium hydride, to give compound 77. Compound 77 is reduced under standard conditions, such as hydrogenation with a catalyst, such as palladium on activated carbon, with a suitable solvent, such as ethanol or methanol, to compound 78. Compound 10 is hydrolyzed under suitable conditions, such as sodium hydroxide to give the free acid, followed by Boc deprotection which is carried out using standard deprotection conditions (T. W. Greene, Protective groups in organic synthesis, 1999 John Wiley & Sons, Inc.) to give compound 79. Compound 79 is then coupled with compound 78 under typical amide coupling conditions, such as benzotriazol-1-yloxy-tris(dimethylamino) phosphonium hexafluorophophate, diisopropylethylamine, and dimethylformanide, to give compound 80. Optionally, compound 80 is hydrolyzed under typical conditions, such as sodium hydroxide, with suitable solvent, such as water and methanol, to give compound 81.

Scheme VII outline the synthetic steps to produce compounds of the present invention where X is O, D is O, v is 1, and W is

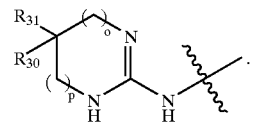

Scheme VII

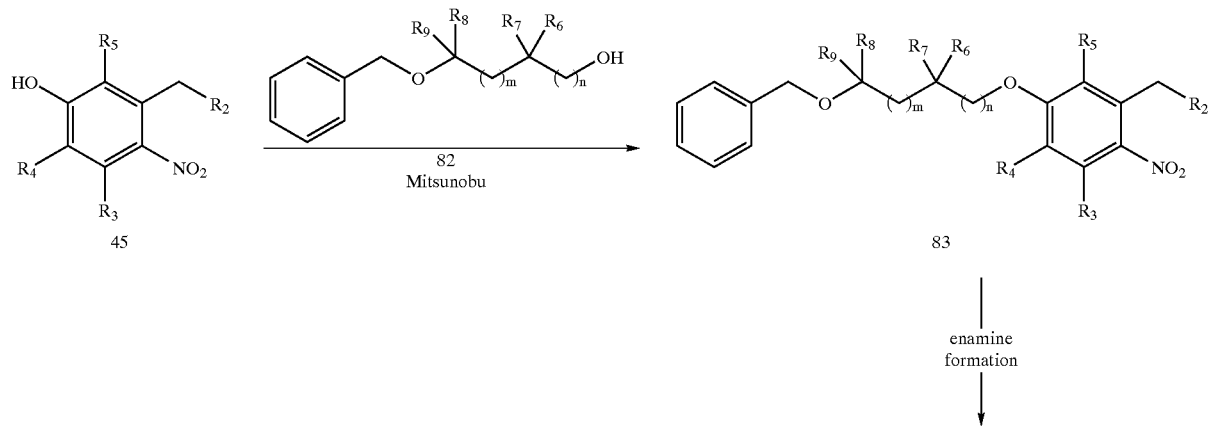

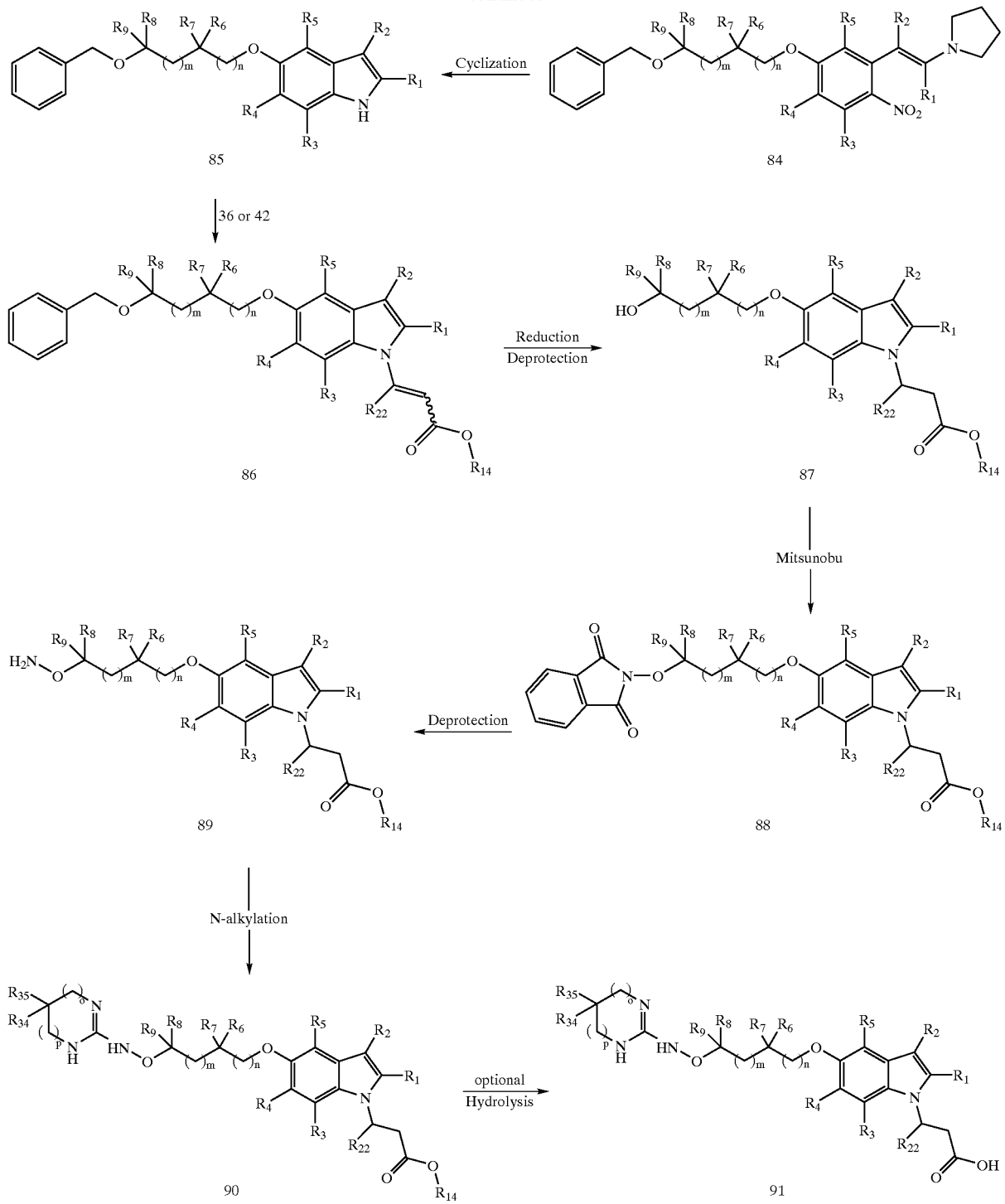

In Scheme VII, 3-methyl-4-nitrophenol derivative 45 is coupled to an aliphatic alcohol 82 using standard Mitsunobu coupling procedure (Mitsunobu, O., *Synthesis*, 1 (1981)) to give compound 83. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine. Compound 83 is treated with pyrrolidine and dimethoxymethyl dimethylamine analogues to give the corresponding enamine 84, followed by standard reduction conditions such as hydrogenation in the presence of a catalyst, such as palladium on carbon, and a solvent such as ethanol, to give compound 85 (Batcho, A., Batcho, Andrew D.; Leimgruber, Willy., Org. Synth. 1985, 63, 214–25). Compound 85 is reacted with a substituted propiolate 36 or 42, in the presence of a weak base to yield the corresponding alkene 86, as an E/Z mixture. Preferred conditions include the treatment of compound 85 with tetrabutylammonium fluoride in tetrahydrofuran. Compound 86 is deprotected and reduced using standard conditions, such as hydrogenation, using a catalyst such as palladium on carbon, in a suitable solvent, such as ethanol, to give compound 87. Compound 87 is treated with N-hydroxyphthalimide using standard Mitsunobu coupling procedure (Mitsunobu, O., *Synthesis*, 1, 1981) to give compound 88. Preferred coupling conditions include using a trialkylphosphine or triarylphosphine, such as triphenylphosphine or tri-n-butylphosphine, in a suitable solvent, such as tetrahydrofuran or methylene chloride, and an azodicarbonyl reagent, such as diethyl azodicarboxylate, diisopropyl azodicarboxylate or 1,1'-(azodicarbonyl) dipiperidine. Deprotection of compound 88 is carried out in the presence of a primary amine, preferred conditions include the use of methylamine in tetrahydrofuran, to give compound 89. Alkylation of compound 89 with a corresponding pyrazole, such as 1H-pyrazole-1-carboxamide hydrochloride or 2-(3,5-dimethylpyrazolyl)-4,5-dihydroimidazole hydrobromide in methanol gives compound 90. Optional hydrolysis of the compound 90 using lithium hydroxide in the presence of water afforded compound 91.

Compounds of the present invention can be tested for the ability to inhibit or antagonize $\alpha_v\beta_3$ or $\alpha_v\beta_5$ cell surface receptors by assays known to those of ordinary skill in the art. Such assays are described in Example 58 herein.

The present invention also provides a method of treating $\alpha_v\beta_3$ integrin- or $\alpha_v\beta_5$ integrin-mediated conditions by selectively inhibiting or antagonizing $\alpha_v\beta_3$ and $\alpha_v\beta_5$ cell surface receptors, which method comprises administering a therapeutically effective amount of a compound selected from the class of compounds depicted by Formula IV, wherein one or more compounds of Formula IV is administered in association with one or more non-toxic, pharmaceutically acceptable carriers and/or diluents and/or adjuvants and if desired other active ingredients.

More specifically, the present invention provides a method for inhibition of the $\alpha_v\beta_3$ cell surface receptor. Most preferably, the present invention provides a method for inhibiting bone resorption, treating osteoporosis, inhibiting humoral hypercalcemia of malignancy, treating Paget's disease, inhibiting tumor metastasis, inhibiting neoplasia (solid tumor growth), inhibiting angiogenesis including tumor angiogenesis, treating diabetic retinopathy, age-related macular degeneration, retinopathy of prematurity and other neo-vascular eye diseases, inhibiting arthritis, psoriasis and periodontal disease, and inhibiting smooth muscle cell migration including neointimal hyperplasia and restenosis.

The present invention also provides a method for inhibition of the $\alpha_v\beta_5$ cell surface receptor. Most preferably, the present invention provides a method for inhibiting angiogenesis associated with pathological conditions such as inflammatory disorders such as immune and non-immune inflammation, chronic articular rheumatism and psoriasis, disorders associated with inappropriate or inopportune invasion of vessels such as restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and similar cancers which require neovascularization to support tumor growth. The present invention also provides a method for treating eye diseases characterized by angiogenesis, such as diabetic retinopathy, age-related macular degeneration, presumed ocular histoplasmosis, retinopathy of prematurity, and neovascular glaucoma.

The compounds of the present invention are useful in treating cancer, including tumor growth, metastasis and angiogenesis. For example, compounds of the present invention can be employed to treat breast cancer and prostate cancer.

The compounds of the present invention are also useful in the treatment of sickle cell anemia. $\alpha_v\beta_3$ integrin has recently been implicated in the mechanism of adhesion of sickled red blood cells (RBCs) to vascular structures within the circulatory system of those suffering from sickle cell anemia. Adhesion of RBC's is responsible for the reoccurring episodes of painful vasocclusive crisis and multiple organ damage. (Kaul et al., *Blood* 95(2):368–373 (2000)). Monoclonal antibodies which bind to $\alpha_v\beta_3$ have been shown to inhibit the adhesion of sickled RBCs in the ex vivo mesocecum vasculature of the rat. By blocking $\alpha_v\beta_3$ integrin which assists in adhesion of sickled cells to vascular components, a reduction in the harmful affects of sickle cell anemia is realized.

The compounds of the present invention are also useful in the treatment of central nervous system (CNS) related disorders. Treatment of such CNS related disorders includes, but is not limited to: treating or preventing neuronal loss associated with stroke, ischemia, CNS trauma, hypoglycemia, and surgery, as well as treating neurodegenerative diseases including Alzheimer's disease, and Parkinson's disease, treating or preventing the adverse consequences of the overstimulation of the excitatory amino acids, as well as treating schizophrenia, anxiety, convulsions, chronic pain, psychosis, including anesthesia, and preventing opiate tolerance.

Studies have shown that there is a correlation between the activity of $\alpha 4$ integrin and the establishment of inflammatory lesions in the CNS. Brocke, S. et al., *Proc. Natl. Acad. Sci. USA* 96:6896–6901 (1999). Specifically, antibodies directed against CD44 and $\alpha 4$ integrin could interfere in several ways with the establishment of inflammatory lesions in the CNS and thus prevent experimental autoimmune encephalomyelitis (EAE), an inflammatory disease of the CNS similar to multiple sclerosis. Brocke at 6899.

Relton and co-workers have also shown that inhibition of $\alpha 4$ integrin activity protects the brain against ischemic brain injury, thereby implicating $\alpha 4$ integrin as a factor in acute brain injury. Relton, et al., *Stroke* 32(1):199–205 (2001).

The compounds of the present invention may be administered in an effective amount within the dosage range of about 0.01 mg/kg to about 300 mg/kg, preferably between 1.0 mg/kg to 100 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Alkaline salts can include ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such s polyethylene glycol 400, polyvinyls such as polyvinyl alcohol, povidone, cellulose derivatives such as carboxymethylcellulose, methylcellulose and hydroxypropyl methylcellulose, petroleumn derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the compounds of the present invention in the composition include alcohols such as chlorobutanol, benzalknonium chloride and EDTA, or any other appropriate preservative known to those skilled in the art.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

3-{5-[3-(2-Pyridylamino)propoxy]indolyl}propanoic acid ammonium salt

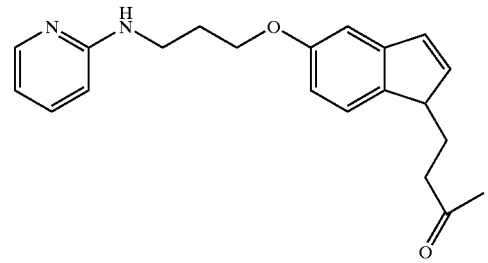

a). 2-(3-Hydroxypropyl)aminopyridine N-oxide

A mixture of 2-chloropyridine-N-oxide hydrochloride (3.32 g, 20 mmol), 3-amino-1-propanol (3.06 mL, 40 mmol), NaHCO$_3$ (8.4 g, 100 mmol) in tert-amyl alcohol (20 mL) was heated to reflux. After stirring overnight, the reaction mixture was cooled, diluted with methylene chloride (100 mL), and suction filtered to remove the insoluble materials. The filtrate was concentrated and reconcentrated from methylene chloride twice. The residue was recrystallized from ethyl acetate and hexane, collected by filtration, washed with ethyl acetate, and dried under high vacuum to give the title compound as a pale yellow solid (3.2 g, 95%). $^1$H-NMR (400 MHz, CDCl$_3$) δ 8.07 (d, J=6.5 Hz, 1H), 7.32 (br s, 1H), 7.21 (t, J=8.6 Hz, 1H), 6.64 (d, J=8.5 Hz, 1H), 6.53 (t, J=6.7 Hz, 1H), 3.75 (t, J=5.8 Hz, 2H), 3.47 (q, J=62 Hz, 2H), 1.86 (t, J=6.0 Hz, 2H).

b). 2-(3-Hydroxypropyl)aminopyridine

A mixture of 2-(3-hydroxypropyl)aminopyridine N-oxide (3.0 g, 17.9 mmol), as prepared in the preceding step, cyclohexene (10 mL, 100 mmol), and 10% palladium(0) on carbon (300 mg) in ethanol (50 mL) was heated to reflux. After two days, the reaction mixture was cooled. The catalyst was removed by filtration through Celite and the filtrate was concentrated. The residue was purified by flash column chromatography (silica gel, 5% methanol in methylene chloride) to give the title compound as a colorless oil (2.4 g, 88%). $^1$H-NMR (400 MHz, CDCl$_3$) δ 8.02 (d, J=5.0 Hz, 1H), 7.37 (t, J=7.8 Hz, 1H), 6.54 (d, J=6.0 Hz, 1H), 6.39 (t, J=8.0 Hz, 1H), 4.69 (br s, 2H), 3.65 (t, J=5.5 Hz, 2H), 3.53 (q, J=5.9 Hz, 2), 1.77 (t, J=5.6 Hz, 2H).

c). Ethyl 3-(5-benzyloxy)indolyl]propanoate

A solution of 5-benzyloxyindole (1.30 g, 5.82 mmol) was dissolved in anhydrous N,N-dimethylformamide (25 mL) under nitrogen and treated with a 60% suspension of sodium hydride in mineral oil (0.60 g, 15 mmol). After stirring 1 hour ("h") at ambient temperature, the reaction was treated with ethyl 3-bromopropionate (1.00 mL, 6.96 mmol) and stirred an additional 18 h. The reaction was then treated with additional sodium hydride (0.3 g, 7.5 mmol), stirred 2 more hours and the solvent removed in vacuo. The crude product was dissolved in methylene chloride, washed with 10% aqueous HCl, water, and brine, dried over anhydrous sodium sulfate, and filtered. The filtrate was evaporated and the residue purified by flash column chromatography (1:1 methylene chloride: ethyl acetate eluant) giving the title compound as a yellow oil (0.96 g, 51%). $^1$H NMR (400 MHz, CDCl$_3$) δ 7.47 (br d, 2H, J=7.2 Hz), 7.37 (m, 2H), 7.32 (m, 1H), 7.24 (br d, 1H, J=8.8 Hz), 7.15 (d, 1H, J=2.4 Hz), 7.10 (m, 1H), 6.96 (dd, 1H, J=8.8 Hz, 2.4 Hz), 6.38 (m, 1H), 5.09 (s, 2H), 4.44 (t, 2H, J=6.9 Hz), 4.21 (q, 2H, J=7.1 Hz), 2.92 (t, 2H, J=6.9 Hz), 1.26 (m, 3H).

d). Ethyl 3-(5-hydroxyindolyl)propanoate

A solution of the product of the preceding step (0.94 g, 2.90 mmol) and 10% palladium(0) on carbon (97 mg) in reagent ethanol (40 mL) was stirred under hydrogen at ambient pressure and temperature for 18 h. The reaction was filtered over Celite, and the evaporated filtrate purified by flash column chromatography (10% ethyl acetate in methylene chloride eluant) giving the title compound as a colorless oil (0.36 g, 53%). $^1$H NMR (400 MHz, CDCl$_3$) δ 7.18 (d, H, J=8.7 Hz), 7.10 (d, 1H, J=3.0 Hz), 7.01 (d, 1H, J=1.9 Hz), 6.78 (dd, 1H, J=8.7 Hz, 2.2 Hz), 6.34 (d, 1H, J=3.0 Hz), 4.86 (s, 1H), 4.43 (t, 2H, J=6.9 Hz), 4.22 (q, 2H, J=7.1 Hz), 2.92 (t, 2H, J=6.9 Hz), 1.27 (t, 3H, J=7.1 Hz).

e). Ethyl 3-{5-[3-(2-pyridylamino)propoxy]indolyl}propanoate

A solution of the product of the preceding step (0.35 g, 1.51 mmol) and the product of Example 1, Step b (0.24 g, 1.58 mmol) in anhydrous tetrahydrofuran (25 mL) was treated with tri-n-butylphosphine (0.43 mL, 1.72 mmol) and 1,1-(azodicarbonyl)dipiperidine (0.43 g, 1.70 mmol) at ambient temperature. After 18 h the reaction was concentrated in vacuo and the crude product purified by flash column chromatography (1:1 methylene chloride: ethyl acetate eluant) giving the title compound as a yellow oil (0.33 g, 60%). $^1$H NMR (400 MHz, CDCl$_3$) δ 8.08 (dd, 1H, J=5 Hz, 1 Hz), 7.40 (m, 1H), 7.24 (d, 1H, J=8.8 Hz), 7.11 (d, 1H, J=3.1 Hz), 7.09 (d, 1H, J=2.4 Hz), 6.89 (dd, 1H, J=8.8 Hz, 2.4 Hz), 6.55 (m, 1H), 6.41 (d, 1H, J=8.4 Hz), 6.39 (d, 1H, J=3.0 Hz), 4.76 (br m, 1H), 4.45 (t, 2H, J=6.9 Hz), 4.22 (q, 2H, J=7.1 Hz), 4.12 (m, 2H), 3.53 (dd, 2H, J=12.6 Hz, 6.5 Hz), 2.93 (t, 2H, J=6.9 Hz), 2.12 (pentet, 2H, J=6 Hz), 1.27 (m, 3H).

f). 3-{5-[3-(2-Pyridylamino)propoxy]indolyl}propanoic acid ammonium salt

The product of the preceding step (0.33 g, 0.90 mmol) was dissolved in methanol (10 mL) and treated with 1 N aqueous LiOH (2 mL) at ambient temperature. After 18 h the reaction was acidified with 10% aqueous HCl, concentrated in vacuo, and the crude product purified by flash column chromatography (15% methanol in methylene chloride eluant) giving a very hygroscopic solid. This was dissolved in a mixture of methylene chloride and methanol (saturated with ammonia gas), filtered, and the filtrate concentrated in vacuo giving the title compound as a stable, pale yellow solid (0.14 g, 42%). $^1$H NMR (400 MHz, DMSO-d$_6$): δ 7.92 (m, 1H), 7.59 (m, 1H), 7.37 (d, 1H, J=8.9 Hz), 7.28 (d, 1H, J=3.1 Hz), 7.04 (d, 1H, J=2.3 Hz), 6.78 (dd, 1H, J=8.9 Hz, 2.3 Hz), 6.75 (d, 1H, J=9.7 Hz), 6.63 (br t, 1H, J=6.3 Hz), 4.34 (t, 2H, J=6.8 Hz), 4.05 (t, 2H, J=6.2 Hz), 3.45 (dd, 2H, J=12.5 Hz, 6.6 Hz), 2.71 (t, 2H, J=6.8 Hz), 2.02 (pentet, 2H, J=6.5 Hz). Mass spectrum (LCMS, ESI pos.) Calcd. for C$_{19}$H$_{21}$N$_3$O$_3$: 339.4 (M+H). Found: 340.1.

EXAMPLE 2

3-{5-[3-(2-Pyridylamino)propoxy]indoyl}acetic acid ammonium salt

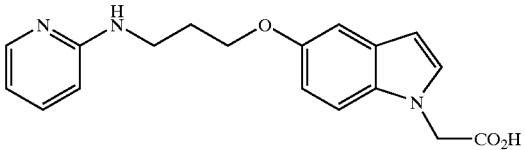

a). Methyl 2-(5-benzyloxyindolyl)acetate

5-Benzyloxyindole (0.80 g, 3.58 mmol) was dissolved in anhydrous N,N-dimethylformamide (20 mL) and treated with 60% sodium hydride in mineral oil (0.36 g, 9.00 mmol) at ambient temperature. After 2 h, ethyl bromoacetate (0.45 mL, 4.06 mmol) was added, the reaction stirred for 6 h, and additional sodium hydride (0.36 g, 9.00 mmol) was added. The reaction stirred for 3 days, the N,N-dimethylformamide was removed in vacuo, and the residue was dissolved in methylene chloride. The resulting solution washed with 10% aqueous HCl, water, and brine, dried over anhydrous sodium sulfate, and filtered. The evaporated filtrate was then dissolved in N,N-dimethylformamide (20 mL) and treated with cesium carbonate (1.57 g, 4.80 mmol) and iodomethane (0.30 mL, 3.75 mmol) at ambient temperature for 18 h. The reaction was concentrated in vacuo, the crude product dissolved in methylene chloride, and the solution washed with saturated aqueous bicarbonate, water, and brine, dried over sodium sulfate, and filtered. The evaporate filtrate then gave the title compound (0.93 g, 84%) as an oily orange solid. $^1$H NMR (400 MHz, CDCl$_3$): δ 7.46 (br d, 2H, J=7.3 Hz), 7.38 (m, 2H), 7.31 (d, 1H, J=7.2 Hz), 7.17 (d, 1H, J=2.4 Hz), 7.14 (d, 1H, J=8.8 Hz), 7.06 (d, 1H, J=3.1 Hz), 6.96 (dd, 1H, J=8.9 Hz, 2.4 Hz), 6.46 (d, 1H, J=3.1 Hz), 5.10 (s, 2H), 4.79 (s, 2H), 4.20 (q, 2H, J=7.1 Hz), 1.25 (t, 3H, J=7.1 Hz).

b). Methyl 2-(5-hydroxyindolyl)acetate

A solution of the product of the preceding step (0.92 g, 2.97 mmol) and 10% palladium(0) on carbon (94 mg) in reagent ethanol (40 mL) was stirred under hydrogen at ambient pressure and temperature for 18 h. The reaction was filtered over Celite, and the evaporated filtrate dissolved in reagent ethanol (50 mL) and hydrogenated again as above over 10% palladium(0) on carbon (170 mg) for 24 h. The reaction was again filtered over Celite, the evaporated filtrate dissolved in methylene chloride, poured over a short bed of silica gel, and eluted with 1:1 methylene chloride:ethyl acetate. The eluate was then concentrated in vacuo giving the title compound as a light brown oil (0.61 g, 93%). $^1$H NMR (400 MHz, CDCl₃): δ 7.09 (d, 1H, J=8.7 Hz), 7.06 (d, 1H, J=3.1 Hz), 7.02 (d, 1H, J=2.4 Hz), 6.78 (dd, 1H, J=8.7 Hz, 2.4 Hz), 6.42 (m, 1H), 4.79 (s, 2H), 4.21 (q, 2H, J=7.1 Hz), 1.25 (m, 3H).

c). Methyl 2-{5-[3-(2-pyridylamino)propoxy]indolyl}acetate

A solution of the product of the preceding step (0.31 g, 1.41 mmol) and the product of Example 1, Step b (0.23 g, 1.48 mmol) in anhydrous tetrahydrofuran (30 mL) was treated with tri-n-butylphosphine (0.41 mL, 1.64 mmol) and 1,1-(azodicarbonyl)dipiperidine (0.41 g, 1.63 mmol) at ambient temperature. After 18 h the reaction was concentrated in vacuo and the crude product purified by flash column chromatography (1:1 methylene chloride:ethyl acetate eluant) giving the title compound (0.24 g, 48%) as a gold oil. ¹H NMR (400 MHz, CDCl₃): δ 8.09 (m, 1H), 7.39 (ddd, 1H, J=8.3 Hz, 7.2 Hz, 1.9 Hz), 7.13 (d, 1H, J=8.9 Hz), 7.10 (d, 1H, J=2.3 Hz), 7.06 (d, 1H, J=3.1 Hz), 6.89 (dd, 1H, J=8.9 Hz, 2.3 Hz), 6.55 (ddd, 1H, J=7.1 Hz, 5.1 Hz, 0.8 Hz), 6.46 (dd, 1H, J=3.1 Hz, 0.6 Hz), 6.41 (d, 1H, J=8.4 Hz), 4.78 (m, 3H), 4.20 (q, 2H, J=7.1 Hz), 4.13 (m, 2H), 3.52 (dd, 2H, J=12.6 Hz, 6.5 Hz), 2.12 (pentet, 2H, J=6.3 Hz), 2.04 (s, 3H), 1.26 (m, 3H).

d). 2-{5-[3-(2-Pyridylamino)propoxy]indolyl}acetic acid ammonium salt

The product of the preceding step (0.23 g, 0.65 mmol) was dissolved in methanol (15 mL) and treated with 1 N aqueous LiOH (2 mL) at ambient temperature. After 3 days, the reaction was acidified with 10% aqueous HCl, concentrated in vacuo. The crude product purified by flash column chromatography (25% methanol in methylene chloride saturated with ammonia gas as eluant), the concentrated fractions treated with a few drops of 4 N HCl in dioxane, and concentrated in vacuo giving a yellow gum. This was dissolved in a mixture of methylene chloride and methanol (saturated with ammonia gas), filtered, and the filtrate concentrated in vacuo giving the title compound as a yellow solid (0.16 g, 70%). ¹H NMR (400 MHz, DMSO-d₆): δ 7.33 (m, 1H), 7.21 (d, 1H, J=2.9 Hz), 7.18 (d, 1H, J=8.8 Hz), 7.02 (d, 1H, J=2.2 Hz), 6.73 (dd, 1H, J=8.8 Hz, 2.1 Hz), 6.56 (m, 1H), 6.45 (m, 2H), 6.26 (d, 1H, J=2.8 Hz), 4.65 (s, 2H), 4.03 (t, 2H, J=6.3 Hz), 3.37 (m, 2H), 1.96 (m, 2H). Mass spectrum (LCMS, ESI pos.) Calcd. for C₁₈H₁₉N₃O₃: 326.4 (M+H). Found: 326.1.

EXAMPLE 3

3-{2-Methyl-5-[3-(2-pyridylamino)propoxy]indolyl}propanoic acid sodium salt

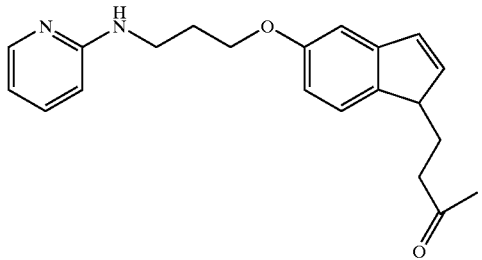

a). 3-(5-Methoxy-2-methylindolyl)propanoic acid

5-Methoxy-2-methylindole (0.50 g, 3.10 mmol) was dissolved in anhydrous N,N-dimethylformamide (25 mL) and treated with 60% sodium hydride in mineral oil (0.19 g, 4.70 mmol) at ambient temperature for 2 h. Ethyl 3-bromopropionate (0.60 mL, 4.20 mmol) was added, the reaction stirred for 3.5 h, treated with additional sodium hydride (0.20 g, 4.88 mmol), and stirred another 24 h. After concentration in vacuo, the crude product was dissolved in methylene chloride, the solution washed with dilute aqueous HCl and brine, dried over anhydrous sodium sulfate, and filtered. The evaporated filtrate was purified by flash column chromatography (1:1 hexane:ethyl acetate as eluant) giving the title compound as a yellow-orange solid (0.56 g, 77%). ¹H NMR (400 MHz, CDCl₃): δ 7.16 (d, 1H, J=8.8 Hz), 7.00 (d, 1H, J=2.4 Hz), 6.80 (dd, 1H, J=8.8 Hz, 2.4 Hz), 6.17 (s, 1H), 4.36 (t, 2H, J=7.4 Hz), 3.83 (s, 3H), 2.78 (t, 2H, J=7.4 Hz), 2.41 (s, 3H).

b). 3-(5-Hydroxy-2-methylindolyl)propanoic acid

The product of the preceding step (0.55 g, 2.36 mmol) was dissolved in anhydrous methylene chloride (25 mL) under nitrogen, cooled to −78° C., and treated with 1 N boron tribromide in methylene chloride (4.8 mL, 4.8 mmol). The reaction was allowed to slowly warm to ambient temperature over 18 h, quenched with excess water, and the phases separated. The organic phase was washed with brine, dried over sodium sulfate, filtered, and the evaporated filtrate purified by flash column chromatography (10% methanol in methylene chloride as eluant) giving the title compound as a light brown oil (0.17 g, 32%). ¹H NMR (400 MHz, CDCl₃/CD₃OD): δ 7.13 (d, 1H, J=8.7 Hz), 6.92 (d, 1H, J=2.3 Hz), 6.71 (dd, 1H, J=8.7 Hz, 2.4 Hz), 6.09 (s, 1H), 4.33 (t, 2H, J=7.5 Hz), 2.70 (t, 2H, J=7.5 Hz), 2.40 (s, 3H).

c). Methyl 3-(5-hydroxy-2-methylindolyl)propanoate

A solution of the product of the preceding step (0.16 g, 0.73 mmol), sodium bicarbonate (0.06 g, 0.75 mmol), and iodomethane (0.06 mL, 0.96 mmol) in N,N-dimethylformamide (10 mL) was stirred at ambient temperature for 3 days. Additional sodium bicarbonate (0.10 g, 1.25 mmol) and iodomethane (0.20 mL, 3.21 mmol) were added and the reaction stirred for another 24 h. The crude product was concentrated in vacuo, put onto a short bed of silica gel, eluted with 1:1 methylene chloride:ethyl acetate, and the eluate evaporated giving the title compound as a yellow oil (0.17 g, 97%).

¹H NMR (400 MHz, CDCl₃): δ 7.12 (d, 1H, J=8.7 Hz), 6.92 (d, 1H, J=2.4 Hz), 6.70 (dd, 1H, J=8.7 Hz, 2.5 Hz), 6.12 (s, 1H), 4.53 (s, 1H), 4.35 (t, 2H, J=7.4 Hz), 3.67 (s, 3H), 2.73 (t, 2H, J=7.4 Hz), 2.41 (m, 3H).

d). Methyl 3-{2-methyl-5-[3-(2-pyridylamino)propoxy]indolyl}propanoate

A solution of the product of the preceding step (0.16 g, 0.68 mmol) and the product of Example 1, step b (0.12 g, 0.82 mmol) in anhydrous tetrahydrofuran (15 mL) was treated with tri-n-butylphosphine (0.19 mL, 0.76 mmol) and 1,1-(azodicarbonyl)dipiperidine (0.20 g, 0.79 mmol) at ambient temperature. After 18 h the reaction was concentrated in vacuo and the crude product purified by flash column chromatography (1:1 methylene chloride:ethyl acetate eluant) giving the title compound as a pale yellow solid (94 mg, 48%). ¹H NMR (400 MHz, CDCl₃): δ 8.08 (dd, 1H, J=5.0 Hz, 1.1 Hz), 7.40 (m, 1H), 7.16 (d, 1H, J=8.8 Hz), 7.00 (d, 1H, J=2.4 Hz), 6.81 (t, 1H, J=8.8 Hz, 2.4 Hz), 6.55 (m, 1H), 6.41 (d, 1H, J=8.4 Hz), 6.15 (s, 1H), 4.76 (br s, 1H), 4.36 (t, 2H, J=7.4 Hz), 4.12 (t, 2H, J=5.9 Hz), 3.67 (s, 3H), 3.52 (dd, 2H, J=12.6 Hz, 6.5 Hz), 2.73 (t, 2H, J=7.4 Hz), 2.42 (s, 3H), 2.16 (pentet, 2H, J=6.2 Hz).

e). 3-{2-Methyl-5-[3-(2-pyridylamino)propoxy]indolyl}propanoic acid sodium salt

The product of the preceding step (94 mg, 0.26 mmol) was dissolved in methanol (10 mL) and treated with 1 N aqueous sodium hydroxide (1.5 mL) at ambient temperature for 18 h. The reaction was concentrated in vacuo and the crude product purified by preparative thin-layer chromatography (10% methanol in methylene chloride as eluant) giving the title compound as pale yellow solid (34 mg, 35%). $^1$H NMR (400 MHz, DMSO-$d_6$): δ 7.95 (d, 1H, J=4.3 Hz), 7.34 (m, 1H), 7.24 (d, 1H, J=8.8 Hz), 6.92 (d, 1H, J=2.2 Hz), 6.68 (dd, 1H, J=8.6 Hz, 2.0 Hz), 6.54 (m, 1H), 6.44 (m, 2H), 6.06 (s, 1H), 4.24 (br t, 2H, J=6.9 Hz), 4.01 (t, 2H, J=6.3 Hz), 3.38 (dd, 2H, J=12.5 Hz, 6.5 Hz), 2.50 (m, 2H), 2.37 (s, 3H), 1.96 (pentet, 2H, J=6.5 Hz). Mass spectrum (LCMS, ESI pos.) Calcd. for $C_{20}H_{22}N_3O_3$: 354.4 (M+H). Found: 354.2.

EXAMPLE 4

2-(trans-2-{5-[3-(2-Pyridylamino)propoxy]indolyl}cyclopropyl)acetic acid

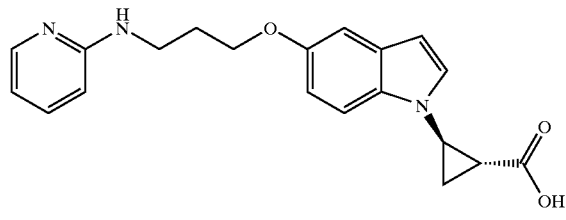

a). Ethyl 2-bromocyclopropanecarboxylate:

A mixture of vinyl bromide (50 g, 0.47 mol) and rhodium (II) acetate dimer (0.1 g, 0.2 mol) was dissolved in 20 ml of 1,2-dichloroethane. Ethyl diazoacetate (20 g, 0.18 mol) was added dropwise over a period of 30 minutes. The reaction was stirred at room temperature for 4 h, the solvent was removed under vacuum, and the residue was distilled with the help of an oil pump to obtain the title compound (14 g, 16%). $^1$H NMR (400 MHz, CDCl$_3$) δ 1.27 (t, 3H, J=7.1 Hz), 1.29 (m, 1H), 1.60 (m, 1H), 2.04 (m, 1H), 3.23 (m, 1H), 4.21 (q, 2H, J=7.1 Hz).

b). Ethyl 2-(5-benzyloxyindolyl)cyclopropanecarboxylate

To a suspension of NaH (0.355 g, 14.0 mmol) in 100 ml of dry N,N-dimethylformamide was added slowly 5-benzyloxyindole (3.0 g, 13.4 mmol). When the evolution of H$_2$ ceased, ethyl 2-bromocyclopropanecarboxylate(2.85 g, 0.0148 mol), as prepared in the preceding step, was added to the mixture and the reaction was refluxed for a period of 17 h under argon. Then the reaction was cooled down at ambient temperature and quenched carefully with water. After evaporation of the solvent under vacuum, the crude product was purified by flash chromatography on silica gel to obtain the title compound (3.45 g, 77%). $^1$H NMR (400 MHz, CDCl$_3$) δ 1.34 (t, 3H, J=7.1 Hz), 1.62 (m, 1H), 1.73 (m, 1H), 2.14 (m, 1H), 3.78 (m, 1H), 4.24 (c, 2H, J=7.1 Hz), 5.10 (s, 2H), 6.36 (dd, 1H, J=0.7, 3.2 Hz), 6.98 (dd, 1H, J=2.4, 8.8 Hz), 7.04 (d, 1H, J=3.2 Hz), 7.14 (d, 1H, J=2.4 Hz), 7.38 (m, 4H), 7.45 (m, 2H).

c). Ethyl 2-(5-hydroxyindolyl)cyclopropanecarboxylate

Ethyl 2-(5-benzyloxyindolyl)cyclopropanecarboxylate (1.75 g, 0.0052 mol), as prepared in the preceding step, was added under argon to a suspension of 10% of palladium(0) on carbon (0.50 g) in methanol (50 mL). The reaction was carried out under H$_2$ atmosphere for a period of 6 h. Filtration of the reaction over Celite and evaporation of the filtrate yielded the title compound (1.27 g, 99%). $^1$H NMR (400 MHz, CDCl$_3$) δ 1.32 (t, 3H, J=7.1 Hz), 1.60 (m, 1H), 1.72 (m, 1H ), 2.13 (m, 1H), 3.77 (m, 1H), 4.25 (q, 2H, J=7.1 Hz), 6.29 (d, 1H, J=3.0 Hz), 6.81 (d, 1H, J=8.3 Hz), 7.00 (m, 2H), 7.27 (m, 1H)

d). Ethyl 2-{5-[3-(2-pyridylamino)propoxy]indolyl}cyclopropanecarboxylate

Ethyl 2-(5-hydroxyindolyl)cyclopropanecarboxylate (0.59 g, 2.40 mmol), as prepared in the preceding step, and 3-hydropropylaminopyridine (0.37 g, 2.40 mmol), as prepared in step b of Example 1, were dissolved in tetrahydrofuran (25 mL) at ambient temperature. tri-n-Butylphosphine (0.97 g, 4.80 mL) followed by 1,1'-(azodicarbonyl)dipiperidine (1.20 g, 4.79 mmol) were added and the reaction was stirred at ambient temperature overnight. The solvent was removed under vacuum and the crude product was chromatographed on silica gel to obtain the title compound (0.38 g, 42%). $^1$H-NMR (400 MHz, CDCl$_3$) δ 1.34 (t, 3H, J=7.1 Hz), 1.69 (m, 4H), 2.12 (m, 1H), 3.51 (m, 2H), 3.78 (m, 1H), 4.12 (t, 2H, J=5.9 Hz), 4.26 (q, 2H, J=7.1 Hz), 4.80 (bs, 1H), 6.36 (dd, 1H, J=0.60, 3.1 Hz), 6.41 (d, 1H, J=8.4 Hz), 6.54 (m, 1H), 6.91 (dd, 1H, J=2.4, 8.8 Hz), 7.06 (dd, 1H, J=2.3, 9.2 Hz), 7.34 (d, 1H, J=8.8 Hz), 7.39 (m, 1H), 8.07 (m, 1H). Mass spectrum (LCMS, ESI) Calcd. for $C_{21}H_{23}N_3O_3$: 366.2 (M+H); Found: 366.3.

e). 2-(trans-2-{5-[3-(2-pyridylamino)propoxy]indolyl}cyclopropyl)acetic acid

Ethyl 2-{5-[3-(2-pyridylamino)proproxy]indolyl}cyclopropane-carboxylate (0.38 g, 1.056 mmol), as prepared in the preceding step, was dissolved in 7.5 mL of methanol. A solution of NaOH (0.13 g, 3.18 mmol) in water (2.5 mL) was added and the reaction was stirred at ambient temperature overnight. The base was then neutralized with an aqueous solution of HCl (3.18 mmol), and the solvent was evaporated under vacuum. The crude product was chromatographed on silica gel to obtain the title compound (200 mg, 57%). $^1$H NMR (400 MHz, CDCl$_3$) δ 1.66 (m, 2H), 2.00 (m, 1H), 2.16 (m, 2H), 3.58 (m, 2H), 3.72 (m, 1H), 4.12 (t, 2H, J=5.8 Hz), 6.31 (dd, 1H, J=0.7, 3.2 Hz), 6.77 (m, 1H), 6.85 (dd, 1H, J=2.3, 8.8 Hz), 6.97 (d, 1H, J=9.0 Hz), 7.06 (d, 1H, J=2.3 Hz), 7.13 (d, 1H, J=3.2 Hz), 7.33 (d, 1H, J=8.8 Hz), 7.77 (m, 2H). Mass spectrum (LCMS, ESI pos.) Calcd. for $C_{21}H_{23}N_3O_3$ 352.2 (M+H); Found: 352.2.

EXAMPLE 5

3-(5-{2-[6-(Methylamino)-2-pyridyl]ethoxy}indolyl)propanoic acid

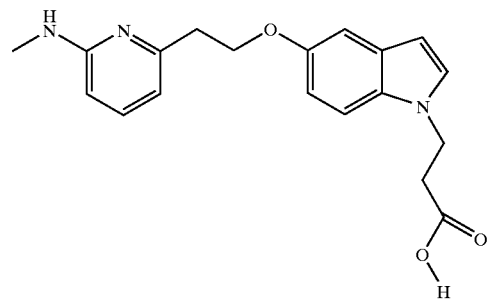

a). (tert-Butoxy)-N-[6-methyl-(2-pyridyl)]carboxamide

A mixture of 2-amino-picoline (6.0 g, 5.5 mmol) and di-tert-butyldicarbonate (13.3 g, 6.0 mmol) was heated to 60° C. overnight (16 h). The reaction was cooled and poured into saturated NH$_4$Cl (250 mL) and extracted ethyl acetate (2×250 mL). The combined organic layers were washed with brine, dried (Na$_2$SO$_4$), filtered and concentrated to give a yellow oil (crude 12.3 g) which was used directly in the next reaction.

b). (tert-Butoxy)-N-methyl-N-[6-methyl-(2-pyridyl)]carboxamide

To a suspension of NaH (2.63 g 6.6 mmol) in 200 mL of N,N-dimethylformamide at 0° C. was added a solution of (tert-butoxy)-N-[6-methyl-(2-pyridyl)]carboxamide (12.3 g, crude), as prepared in the preceding step, in 50 mL of N,N-dimethylformamide. The reaction stirred at 0° C. for 15 min then at ambient temperature for 1 h. Then iodomethane (10.22 g, 7.2 mmol) was added and the mixture was stirred at ambient temperature overnight (16 h). The reaction mixture was concentrated in vacuo, diluted with saturated $NH_4Cl$ (400 mL), and extracted with ethyl acetate (2×250 mL). The combined organic layers were washed with brine, dried ($Na_2SO_4$), filtered and concentrated. The residue was purified by flash chromatography on silica gel (10% ethyl acetate in hexane) to give the title compound as a yellow oil (7.56 g, 57%). $^1$H-NMR (400 MHz, DMSO-$d_6$) δ 7.63 (t, J=7.2 Hz, 1H), 7.37 (d, J=8.0 Hz, 1H), 6.97 (d, J=6.9 Hz, 1H), 3.27 (s, 2H), 2.42 (s, 3H), 1.45 (s, 9H).

c). Ethyl 2-{6-[(tert-butoxy)-N-methylcarbonylamino]-2-pyridyl}acetate

Lithium diisopropylamide (6.6 mmol) was prepared in tetrahydrofuran (60 mL), cooled to −78° C., and (tert-butoxy)-N-methyl-N-[6-methyl-(2-pyridyl)]carboxamide (7.56 g, 3.3 mmol), as prepared in the preceding step, was dissolved in tetrahydrofuran (100 mL) and added dropwise over 30 min. The mixture was stirred for 15 min then diethylcarbonate (6.24 g, 5.3 mmol) was added. The solution was stirred for an additional 15 min, then allowed to warm to 0° C. over 2 h. The reaction was quenched with saturated $NH_4Cl$ solution (200 mL). The mixture was allowed to warm to ambient temperature and extracted with ethyl acetate (2×100 mL). The combined organic layers were washed with brine, dried ($Na_2SO_4$), filtered and concentrated. The residue was purified by flash chromatography (silica gel, 10% ethyl acetate in hexane) to give the title compound as a yellow oil (5.51 g, 60%). $^1$H-NMR (400 MHz, DMSO-$d_6$) δ 7.71 (t, J=7.9 Hz, 1H), 7.49 (d, J=8.2 Hz, 1H), 7.07 (d, J=7.4 Hz, 1H), 4.09 (q, J=7.1 Hz, 2H), 3.78 (s, 2H), 2.54 (s, 3H), 1.46 (s, 9H), 1.18 (t, J=7.1 Hz, 3H).

d). Ethyl 2-[6-(methylamino)-2-pyridylacetate

A solution of ethyl 2-{6-[(tert-butoxy)-N-methylcarbonylamino]-2-pyridyl}acetate (5.51 g, 1.9 mmol), as prepared in the preceding step, in methylene chloride (25 mL) was stirred in an ice bath at 0° C. Trifluoroacetic acid (10 mL) was then added and the solution were allowed to warm to ambient temperature and stirred overnight (16 h). The reaction mixture was concentrated, 10% aqueous $K_2CO_3$ (300 mL) was added and the mixture was extracted with ethyl acetate (2×100 mL). The combined organic layers were washed with brine, dried ($Na_2SO_4$), filtered and concentrated to give the title compound as a bright yellow oil (3.4 g, 100%). $^1$H-NMR (400 MHz, DMSO-$d_6$) δ 7.32 (t, J=7.2 Hz, 1H), 6.40 (d, J=7.0 Hz, 1H), 6.29 (d, J=8.3 Hz, 1H), 4.07 (q, J=7.1 Hz, 2H), 3.56 (s, 2H), 2.71 (d, J=4.9 Hz, 3H), 1.17 (t, J=7.1 Hz, 3H).

e). 2-[6-(Methylamino)-2-pyridyl]ethan-1-ol

To a suspension of lithium aluminum hydride (1.8 g, 4.9 mmol) in tetrahydrofuran (50 mL) was added dropwise a solution of ethyl 2-[6-(methylamino)-2-pyridylacetate (3.5 g, 1.9 mmol), as prepared in the preceding step, in tetrahydrofuran (50 mL) at 0° C. After the addition was completed, the reaction mixture was stirred at 0° C. for 30 minutes then stirred at ambient temperature for 2 h. The reaction mixture was then cooled back to 0° C. and quenched with $H_2O$ (1.8 mL), 10% NaOH (1.8 mL) and $H_2O$ (3.0 mL) and allowed to warm back to ambient temperature. The solids were removed by filtration through Celite and washed with tetrahydrofuran (100 mL). The filtrate was dried ($Na_2SO_4$), filtered and concentrated. The residue was purified by flash chromatography on silica gel (3% methanol in methylene chloride) to give the title compound as a yellow oil (2.1 g, 70%). $^1$H-NMR (400 MHz, CDCl$_3$) δ 7.36 (t, J=7.8 Hz, 1H), 6.41 (d, J=7.2 Hz, 1H), 6.26 (d, J=8.3 Hz, 1H), 4.51 (br, s, 1H), 3.96 (t, J=5.2 Hz, 2H), 2.89 (d, J=5.1 Hz, 3H), 2.84 (t, J=5.4 Hz, 2H).

f). Methyl 3-(5-benzyloxyindolyl)propanoate

To a solution of 5-benzyloxyindole (1.15 g, 5 mmol) in N,N-dimethylformamide (40 mL) was added sodium hydride (200 mg, 5 mmol). After stirring for 30 minutes, ethyl bromopropionate (900 mg, 5.0 mmol) was added and the mixture was stirred at ambient temperature for 1 h, additional sodium hydride (100 mg, 2.5 mmol) was added. After stirring for 10 minutes, additional ethyl bromopropionate (180 mg, 1.0 mmol) was added. The mixture was stirred at ambient temperature overnight. The solvent was removed under high vacuum, the residue was dissolved in water (10 mL) and tetrahydrofuran (10 mL), NaOH (500 mg) was added and stirred for 2 h. After acidifying to pH 4–5, the mixture was extracted with methylene chloride. The methylene chloride layer was washed with brine and dried over $Na_2SO_4$. After evaporating the solvent in vacuo, the residue was purified by flash column chromatography (1–5% ethyl acetate in methylene chloride) to give 3-(5-benzyloxyindolyl)propanic acid as white solid. The solid was dissolved in N,N-dimethylformamide (20 mL), $K_2CO_3$ (1.0 g) and iodomethane (840 mg) were added and the reaction was stirred at ambient temperature for 3 h. The mixture was concentrated under high vacuum and residue was purified by flash column chromatography (methylene chloride) to give the title compound as a colorless oil (1.10 g, 71%). $^1$H-NMR (400 MHz, CDCl$_3$) δ 7.47 (d, J=7.3 Hz, 2H), 7.38 (t, J=7.3 Hz, 2H), 7.32 (d, J=7.2 Hz, 1H), 7.23 (d, J=10.2 Hz, 1H), 7.15 (d, J=2.3 Hz, 1H), 7.09 (d, J=3.1 Hz, 1H), 6.96 (dd, J=8.8, 2.5 Hz, 1H), 6.39 (d, J=3.1 Hz, 1H), 5.10 (s, 2H), 4.41 (t, J=6.9 Hz, 2H), 3.66 (s, 3H), 2.81 (t, J=6.8 Hz, 2H).

g). Methyl 3-(5-hydroxyindolyl)propanoate

A mixture of methyl 3-(5-benzyloxyindolyl)propanoate (1.1 g, 3.56 mmol), as prepared in the preceding step, 10% palladium(0) on carbon (100 mg) in ethanol was stirred under hydrogen for 3 h. The catalyst was removed by filtration, the filtrate was concentrated in vacuo and the residue was purified by flash column chromatography (1–5% ethyl acetate in methylene chloride) to give the title compound as a pale yellow oil (700 mg, 90%). $^1$H-NMR (400 M Hz, CDCl$_3$) δ 7.18 (d, J=8.8 Hz, 1H), 7.08 (d, J=3.1 Hz, 1H), 7.02 (d, J=3.2 Hz, 1), 6.77 (dd, J=8.8, 2.5 Hz, 1H), 6.34 (d, J=3.1 Hz, 1H), 4.75 (s, 1H), 4.40 (t, J=6.9 Hz, 2H), 3.66 (s, 3H), 2.81 (t, J=6.9 Hz, 2H).

h). Methyl 3-(5-{2-[6-(methylamino)-2-pyridyl]ethoxy}indolyl)propanoate

Diisopropyl azodicarboxylate (0.19 g, 0.94 mmol) was added to a solution of 2-[6-(methylamino)-2-pyridyl]ethan-1-ol (0.10 g, 0.66 mmol), as prepared in step e of Example 5, methyl 3-(5-hydroxyindolyl)propanoate (0.10 g, 0.46 mmol), as prepared in the preceding step, and triphenylphosphine (0.24 g, 0.92 mmol) in tetrahydrofuran (5.0 mL) at 0° C. in an ice bath. After stirring at ambient temperature overnight (16 h), the reaction was concentrated and the residue was purified by flash chromatography on silica gel (20%–30% ethyl acetate in hexane) to give the title compound as a yellow oil (0.023 g, 15%). $^1$H-NMR (400 M Hz, CDCl$_3$) δ 7.39 (t, J=7.3 Hz, 1H), 7.20 (d, J=8.9 Hz, 1H), 7.11

(d, J=2.3 Hz, 1H), 7.07 (d, J=3.1 Hz, 1H ), 6.87 (dd, J=2.4, 8.9 Hz, 1H), 6.56 (d, J=7.2 Hz, 1H), 6.37 (d, J=3.1 Hz, 1H), 6.24 (d, J=8.2 Hz, 1H), 4.56 (br s, 1H), 3.40 (t, J=6.9 Hz, 2H), 4.34 (t, J=7.0 Hz, 2H), 3.65 (s, 3H), 3.10 (t, J=7.0 Hz, 2H), 2.89 (d, J=4.8 Hz, 2H), 2.80 (t, J=6.9 Hz, 2H).

i). 3-(5-{2-[6-(methylamino)-2-pyridyl]ethoxy}indolyl) propanoic acid

To a solution of methyl 3-(5-{2-[6-(methylamino)-2-pyridyl]ethoxy}indolyl)propanoate (0.023 g, 0.65 mmol), as prepared in the preceding step, in methanol (3 mL) was added sodium hydroxide (0.15 g, 3.8 mmol) in H$_2$O (0.5 mL) and the reaction was stirred for 6 hours at ambient temperature. After evaporating the solvent in vacuo, the residue is taken up in H$_2$O (5 mL) and acidified to pH 4–5 with 10% HCl, extracted with a mixture of ethyl acetate and butanol (2×50 mL) and the combined organic layers were washed with brine, dried (Na$_2$SO$_4$), filtered and concentrated to give the title compound as a solid (0.018 g, 82%). $^1$H-NMR (400 M Hz, CDCl$_3$+CD$_3$OD) δ 7.52 (t, J=7.3 Hz, 1H), 7.25 (d, J=8.9 Hz, 1H), 7.14 (d, J=3.1 Hz, 1H), 7.06 (d, J=2.3 Hz, 1H), 6.81 (dd, J=8.9, 2.4 Hz, 1H), 6.60 (d, J=7.3 Hz, 1H), 6.38 (d, J=8.6 Hz, 1H), 6.33 (d, J=3.2 Hz, 1H), 4.38 (t, J=7.0 Hz, 2H), 4.24 (t, J=6.6 Hz, 2H), 3.06 (t, J=6.6 Hz, 2H), 2.89 (s, 3H), 2.77 (t, J=6.9 Hz, 2H). Mass spectrum (LCMS, ESI pos.) Calcd. for C$_{19}$H$_{21}$N$_3$O$_3$ 340.3 (M+H); Found: 340.9.

EXAMPLE 6

2-Benzyl-3-{5-[3-(2-pyridylamino)propoxy]indolyl}propanoic acid

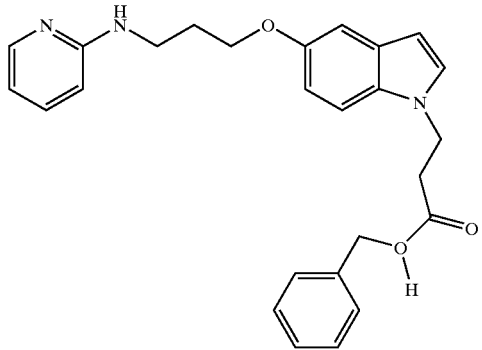

a). Methyl 3-[5(benzyloxyindolyl]-2-benzylpropanoate

Lithium diisopropylamide (0.55 mmol) was prepared in tetrahydrofuran (4.0 mL), cooled to −78° C., and treated with a solution of methyl 3-(5-benzyloxyindolyl)propanoate (0.15 g, 0.49 mmol), as prepared in the step f of Example 5, in tetrahydrofuran (4.0 mL). After stirring for 90 min at −78° C., benzyl bromide (0.08 g, 0.49 mmol) was added and the reaction mixture was allowed to was to ambient temperature slowly over 3 h. The reaction mixture was poured into saturated NH$_4$NCl (20 mL) and extracted with ethyl acetate (2×50 mL). The combined organic layers were washed with brine, dried (Na$_2$SO$_4$), filtered and concentrated. The residue was purified by flash chromatography on silica gel (8% ethyl acetate in hexane) to give the title compound as an oil (0.09 g, 50%). $^1$H-NMR (400 MHz, CDCl$_3$) δ 7.46 (d, J=7.2 Hz, 2H), 7.30 (m, 4H), 7.26 (m, 1H), 7.16 (m, 3H), 7.00 (m, 2H), 6.88 (dd, J=2.4, 8.6 Hz, 1H), 6.36 (m, 1H), 5.08 (s, 2H), 4.40 (dd, J=8.9, 13.9 Hz, 1H), 4.15 (dd, J=14.4, 5.3 Hz, 1H), 3.50 (s, 3H), 3.23, (m, 1H), 3.04 (dd, J=13.1, 7.8 Hz, 1H), 2.76 (dd, J=14.4, 7.1 Hz, 1H).

b). Methyl 3-(5-hydoxylindolyl)-2-benzylpropanoate

A mixture of methyl 3-(5-benzyloxyindolyl)-2-benzylpropanoate (0.16, 0.39 mmol), as prepared in the preceding step, 10% palladium(0) on carbon (0.02 g) in ethanol (10 mL) was stirred at ambient temperature under hydrogen (balloon) overnight (16 h). The catalyst was removed by filtration through Celite. The filtrate was concentrated to give the title compound as a light brown oil (0.12 g, 100%) which was used directly in next reaction.

c). Methyl 2-benzyl-3-{5-[2-(pyridylamino)propoxy]indolyl}propanoate 1,1'-(Azodicarbonyl)dipiperidine (0.18 g, 0.7 mmol) was added to a solution of methyl 3-(5-hydoxylindolyl)-2-benzylpropanoate (0.12 g, 0.39 mmol), as prepared in the preceding step, 2-(3-hydroxypropyl)aminopyridine (0.07 g, 0.47 mmol), as prepared instep b of Example 1, and tri-n-butylphosphine (0.14 g, 0.7 mmol) in tetrahydrofuran (6.0 mL). After stirring at ambient temperature overnight (16 h), the reaction was concentrated in vacuo and the residue purified by flash chromatography on silica gel (10%-50% ethyl acetate in hexane) to give the title compound as a yellow oil (0.064 g, 38%). $^1$H-NMR (400 MHz, CDCl$_3$) δ 8.08 (br s, 1H), 7.40 (m, 1H), 7.37 (m, 1H), 7.22 (m, 2H), 7.00 (m, 3H), 6.84 (dd, J=8.9, 2.4 Hz, 1H), 6.54 (m, 1H), 6.40 (d, J=8.4 Hz, 2H), 6.36 (d, J=3.1 Hz, 1H), 4.77 (br s, 1H), 4.40 (m, 1), 4.17 (m, 3H), 3.52 (m, 5H), 3.24 (m, 1), 3.08 (m, 1H), 2.76 (m, 1H), 2.11 (m, 2H).

d). 2-Benzyl-3-{5-[3-(2-pyridylamino)propoxy]indolyl}propanoic acid

To a solution of methyl 2-benzyl-3-{5-[2-(pyridylamino)propoxy]indolyl}propanoate (0.06 g, 0.13 mmol), as prepared in the preceding step, in methanol (3.0 mL) was added a solution of NaOH (0.1 g, 2.5 mmol) in H$_2$O (0.3 mL), and the reaction was stirred at ambient temperature overnight. After evaporating the solvent in vacuo, the residue is mixed with H$_2$O (5 mL) and acidified to pH 4–5 with 10% HCl, extracted with ethyl acetate (2×25 mL). The combined organic layers were washed with brine, dried (Na$_2$SO$_4$), filtered and concentrated. The residue was purified by flash chromatography on silica gel (4% methanol in methylene chloride) to give the title compound as an oil (0.043 g, 80%). $^1$H-NMR (400 MHz, CDCl$_3$) δ 7.66 (d, J=4.7 Hz, 1H), 7.50 (m, 1H), 7.22 (m, 3H), 7.11 (d, J=8.9 Hz, 1H), 7.04 (d, J=2.8 Hz, 1H), 6.95 (d, J=2.3 Hz, 1H), 6.71 (dd, J=8.8, 2.3 Hz, 1H), 6.50 (m, 2H), 6.24 (d, J=2.7 Hz, 1H), 4.32 (m, 1H), 4.0 (m, 1H), 3.91 (t, J=5.7 Hz, 2H), 3.28 (t, J=6.6 Hz, 2H), 3.15 (m, 1H), 2.75 (m, 1H), 1.93 (m, 2H). Mass spectrum (LCMS, ESI pos.) Calcd. for C$_{26}$H$_{27}$N$_3$O$_3$ 430.5 (M+H); Found: 430.2.

EXAMPLE 7

2-Methyl-3-{5-[3-(2-pyridylamino)propoxy]indolyl}propanoic acid

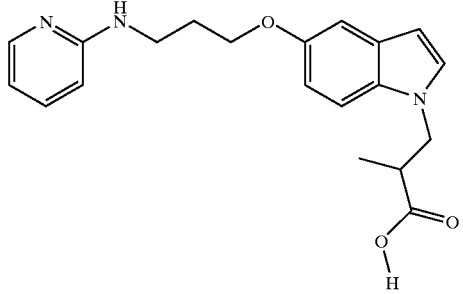

a). Methyl 2-methyl-3-(5-benzyloxyindolyl)propanoate

Lithium diisopropylamide (0.99 mmol) was prepared in tetrahydrofuran (4.0 mL), cooled to −78° C., and methyl 3-(5-benzyloxyindolyl)propanoate (0.19 g, 0.62 mmol), as prepared in step f of Example 5, was added dropwise in tetrahydrofuran (4.0 mL). After stirring for 90 min at −78° C., iodomethane (0.44 g, 3.1 mmol) was added and the reaction was allowed to warm to ambient temperature slowly over 3 h. The reaction mixture was poured into saturated NH$_4$Cl (20 mL) and extracted with ethyl acetate (2×50 mL). The combined organic layers were washed with brine, dried (Na$_2$SO$_4$), filtered and concentrated. The residue was purified by flash chromatography on silica gel (8% ethyl acetate in hexane) to give the title compound as an oil (0.18 g, 90%). $^1$H-NMR (400 MHz, CDCl$_3$) δ 7.47 (d, J=6.9 Hz, 2H), 7.39 (m, 2H), 7.33 (m, 1H), 7.24 (d, J=8.9 Hz, 1H), 7.15 (d, J=2.4 Hz, 1H), 7.04 (d, J=3.1 Hz, 1), 6.95 (dd, J=8.9, 2.5 Hz, 1H), 6.38 (d, J=3.2 Hz, 1H), 5.10 (s, 2H), 4.42 (dd, J=14.4, 7.3 Hz, 1H), 4.08 (dd, J=14.4, 7.1 Hz, 1H), 3.63 (s, 3H), 3.01 (q, J=7.1 Hz, 1H), 1.16 (d, J=7.1 Hz, 3H).

b). Methyl 3-(5-hydroxyindolyl)-2-methylpropanoate

A mixture of methyl 2-methyl-3-[5-benzyloxyindolyl]propanoate (0.18 g, 0.56 mmol), as prepared in the preceding step, 10% palladium(0) on carbon (0.018 g) in ethanol (10 mL) was stirred at ambient temperature under hydrogen (balloon) overnight (16 h). The catalyst was removed by filtration through Celite. The filtrate was concentrated to give the title compound as a light brown oil (0.11 g, 85%) which was used directly in the next reaction.

c). Methyl 2-methyl-3-{5-[3-(2-pyridylamino)propoxy]indolyl}propanoate 1,1'-(Azodicarbonyl)dipiperidine (0.13 g, 0.57 mmol) was added to the solution of methyl 3-(5-hydroxyindolyl)-2-methylpropanoate (0.062 g, 0.27 mmol), as prepared in the preceding step, 2-(3-hydroxypropyl)aminopyridine (0.06 g, 0.40 mmol), as prepared in step b of Example 1, and tri-n-butylphosphine (0.11 g, 0.53 mmol) in tetrahydrofuran (6.0 mL). After stirring at ambient temperature overnight (16 h), the reaction was concentrated and the residue was purified by flash chromatography on silica gel (10%–50% ethyl acetate in hexane) to give the title compound as a yellow oil (0.015 g, 15%). $^1$H-NMR (400 MHz, CDCl$_3$) δ 8.07 (m, 1H), 7.40 (m, 1H), 7.21 (d, J=8.9 Hz, 1H), 7.08 (d, J=2.4 Hz, 1H), 7.04 (d, J=3.1 Hz, 1H), 6.88 (dd, J=8.9, 2.4 Hz, 1H), 6.54 (m, 1H), 6.41 (m, 1H), 4.89 (br s, 1H), 4.45 (dd, J=14.2, 7.3 Hz, 1H), 4.10 (m, 4H), 3.63 (s, 3H), 5.52 (q, J=6.5 Hz, 2H), 2.13 (m, 2H), 1.66 (m, 1H), 1.52 (m, 1H), 1.16 (d, J=7.1 Hz, 3H), 0.93 (m, 3H).

d). 2-methyl-3-{5-[3-(2-pyridylamino)propoxy]indolyl}propanoic acid

To a solution of methyl 2-methyl-3-{5-[3-(2-pyridylamino)propoxy]indolyl}propanoate (0.015 g, 0.04 mmol), as prepared in the preceding step, in methanol (5.0 mL) was added a solution of NaOH (0.1 g, 2.5 mmol) in H$_2$O (0.3 mL), and the reaction was stirred at ambient temperature overnight. After evaporating the solvent in vacuo, the residue is taken up in H$_2$O (5 mL) and acidified to pH 4–5 with 10% HCl and extracted with ethyl acetate (2×15 ML). The combined organic layers were washed with brine, dried (Na$_2$SO$_4$), filtered and concentrated. The residue was purified by flash chromatography on silica gel (4% methanol in methylene chloride) to give the title compound as an oil (0.011 g, 80%). $^1$H-NMR (400 MHz, CDCl$_3$) δ 7.86 (d, J=5.6 Hz, 1H), 7.50 (m, 1H), 7.26 (d, J=8.9 Hz, 1H), 7.07 (dd, J=13.1, 2.8 Hz, 2H), 6.84 (dd, J=8.9, 2.4 Hz, 1H), 6.56 (m, 2H), 6.32 (d, J=2.0 Hz, 1H), 4.38 (dd, J=14.3, 7.0 Hz, 1H), 4.07 (t, J=5.8 Hz, 2H), 4.01 (dd, J=14.3, 7.5 Hz, 1H), 3.44 (t, J=6.7 Hz, 2H), 2.92 (q, J=7.1 Hz, 1H), 2.08 (m, 2H), 1.12 (d, J=7.1 Hz, 3H). Mass spectrum (LCMS, ESI pos.) Calcd. for C$_{20}$H$_{23}$N$_3$O$_3$ 354.3 (M+H); Found: 354.2.

EXAMPLE 8

2-({5-[3-(2-Pyridylamino)propoxy]indolyl}methyl)pentanoic acid

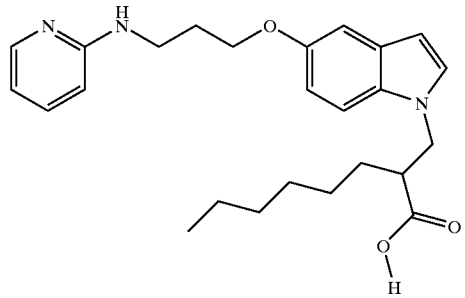

a). Methyl 2-[(5-benzyloxyindolyl)methyl]pentanoate

Lithium diisopropylamide (0.51 mmol) was prepared in tetrahydrofuran (4.0 mL), cooled to −78° C., and methyl 3-(5-benzyloxyindolyl)propanoate (0.14 g, 0.46 mmol), as prepared in step f of Example 5, was added dropwise in tetrahydrofuran (4.0 mL). After stirring for 90 min at −78° C., iodopropane (0.08 g, 0.46 mmol) was added and the reaction mixture was allowed to warm to ambient temperature slowly over 3 h. The reaction mixture was poured into saturated NH$_4$Cl (20 mL) and extracted with ethyl acetate (2×50 mL). The combined organic layers were washed with brine, dried (Na$_2$SO$_4$), filtered and concentrated. The residue was purified by flash chromatography on silica gel (8% ethyl acetate in hexane) to give the title compound as an oil (0.025 g, 16%). $^1$H-NMR (400 MHz, CDCl$_3$) δ 7.47 (m, 2H), 7.39 (m, 2H), 7.31 (m, 1H), 7.21 (d, J=8.9 Hz, 1H), 7.15 (d, J=2.4 Hz, 1H), 7.02 (d, J=3.1 Hz, 1H), 6.95 (dd, J=8.9, 2.4 Hz, 1H), 6.37 (dd, J=3.1, 0.7 Hz, 1H), 5.10 (s, 2H), 4.37 (dd, J=14.4, 8.5 Hz, 1H), 4.15 (dd, J=14.4, 6.1 Hz, 1H), 3.57 (s, 3H), 2.95 (m, 1H), 1.64 (m, 1H), 1.42 (m, 3H), 90 (t, J=7.3 Hz, 3H).

b). Methyl 2-[(5-hydroxyoxyindolyl)methylpentanoate

A mixture of methyl 2-[(5-hydroxyoxyindolyl)methyl]pentanoate (0.036 g), as prepared in the preceding step, 10% palladium(0) on carbon (0.005 g) in ethanol (5 mL) was stirred at ambient temperature under hydrogen (balloon) overnight (16 h). The catalyst was removed by filtration through Celite. The filtrate was concentrated to give the title compound as a light brown oil (0.03 g, 100%) which was used directly in the next reaction.

c). Methyl 2-({5-[3-(2-pyridylamino)propoxy]indolyl}methyl)pentanoate 1,1'-(Azodicarbonyl)dipiperidine (0.12 g, 0.48 mmol) was added to the solution of methyl 2-[(5-hydroxyindolyl)methyl]pentanoate (0.03 g, 0.12 mmol), as prepared in the preceding step, 2-(3-hydroxypropyl)aminopyridine (0.026 g, 0.17 mmol), as prepared in step b of Example 1, and tri-n-butylphosphine (0.09 g, 0.46 mmol) in tetrahydrofuran (6.0 mL). After stirring at ambient temperature overnight (16 h), the reaction was concentrated and the residue was purified by flash chromatography on silica gel (10%–50% ethyl acetate in hexane) to give the title compound as a yellow oil (0.016 g, 36%). $^1$H-NMR (400 MHz, CDCl$_3$) δ 8.08 (m, 1H), 7.20 (d, J=8.9 Hz, 1H), 7.07 (d, J=2.4 Hz, 1H), 7.02 (d, J=3.3 Hz, 1H), 6.88 (dd, J=8.9, 2.4 Hz, 1H), 6.53 (m, 1H), 6.40 (m, 2H), 4.32 (br s, 1H), 4.42 (m, 1H), 4.25 (m, 3H), 3.52 (m, 5H), 2.91 (m, 1H), 2.20 (m, 2H), 1.72 (m, 2H), 1.43 (m, 3H), 0.95 (t, J=7.2 Hz, 3H).

d). 2-({5-[(2-Pyridylamino)propoxy]indolyl}methyl)pentanoic acid

To a solution of methyl 2-({5-[3-(2-pyridylamino)propoxy]indolyl}methyl)pentanoate (0.015 g, 0.004 mmol), as prepared in the preceding step, in methanol (2.0 mL) was added a solution of NaOH (0.1 g, 2.5 mmol) in H$_2$O (0.3 mL), and the reaction was stirred at ambient temperature overnight. After evaporating the solvent in vacuo, the residue is taken up in H$_2$O (5 mL) and acidified to pH 4–5 with 10% HCl, and extracted with ethyl acetate (2×15 mL). The combined organic layers were washed with brine, dried (Na$_2$SO$_4$), filtered and concentrated. The residue was purified by flash chromatography on silica gel (4% methanol in methylene chloride) to give the title compound as an oil (0.011 g, 85%). $^1$H-NMR (400 MHz, CDCl$_3$) δ 8.28 (br s, 1H), 7.72 (d, J=4.5 Hz, 1H), 7.49 (m, 1H), 7.26 (d, J=8.9 Hz, 1H), 7.06 (d, J=3.0 Hz, 1H), 6.99 (d, J=2.3 Hz, 1H), 6.78 (dd, J=8.9, 2.4 Hz, 1H), 6.5 (m, 2H), 6.27 (d, J=2.8 Hz, 1H), 4.25 (dd, J=14.1, 8.4 Hz, 1H), 3.97 (m, 3H), 3.33 (t, J=6.6 Hz, 2H), 2.87 (br s, 1H), 1.96 (m, 2H), 1.67 (m, 1H), 1.45 (m, 3H), 0.90 (t, J=6.8 Hz, 3H). Mass spectrum (LCMS, ESI pos.) Calcd. for C$_{22}$H$_{27}$N$_3$O$_3$ 382.5 (M+H); Found: 382.2.

EXAMPLE 9

2-({5-[3-(2-Pyridylamino)propoxy]indolyl}methyl)octanoic acid

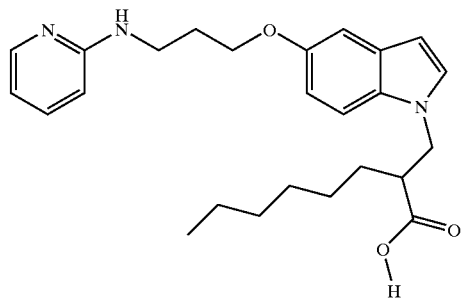

a) Methyl 2-[(5-benzylindolyl)methyloctanoate

Lithium diisopropylamide (1.3 mmol) was prepared in tetrahydrofuran (4.0 mL), cooled to −78° C., and a solution of methyl 3-(5-benzyloxyindolyl)propanoate (0.21 g, 0.7 mmol), as prepared in step f of Example 5, was added dropwise in tetrahydrofuran (4.0 mL). After stirring for 90 min at −78° C., iodohexane (0.7 g, 3.4 mmol) was added and the reaction mixture was allowed to warm to ambient temperature over 3 h. The reaction mixture was poured into saturated NH$_4$Cl (20 mL) and extracted with ethyl acetate (2×50 mL). The combined organic layers were washed with brine, dried (Na$_2$SO$_4$), filtered and concentrated. The residue was purified by flash chromatography on silica gel (8% ethyl acetate in hexane) to give the title compound as an oil (0.13 g, 50%). $^1$H-NMR (400 MHz, CDCl$_3$) 7.47 (d, J=7.0 Hz, 1H), 7.37 (m, 2H), 7.32 (m, 1H), 7.20 (d, J=8.9 Hz, 1H), 7.14 (d, J=2.4 Hz, 1H), 7.02 (d, J=3.1 Hz, 1H), 6.95 (dd, J=8.9, 2.5 Hz, 1H), 6.37 (d, J=3.1 Hz, 1H), 5.09 (s, 2H), 4.35 (dd, J=14.4, 8.5 Hz, 1H), 4.13 (dd, J=14.4, 6.1 Hz, 1H), 3.57 (s, 3H), 2.91 (m, 1H), 1.64 (m, 1H), 1.48 (m, 1H), 1.30 (m, 6H), 0.87 (t, J=6.9 Hz, 3H).

b) Methyl 2-[(5-hydroxyindolyl)methyloctanoate

A mixture of methyl 2-[(5-benzyloxyindolyl)methyloctanoate (0.15 g, 0.37 mmol), as prepared in the preceding step, 10% palladium(0) on carbon in ethanol (10 mL) was stirred at ambient temperature under hydrogen (balloon) overnight (16 h). The catalyst was removed by filtration through Celite. The filtrate was concentrated to give the title compound as a light brown oil (0.11 g, 100%) which was used directly in the next reaction.

c) Methyl 2-({[3-(2-pyridylamino)propoxy]indolyl}methyl)octanoate 1,1'-(Azodicarbonyl)dipiperidine (0.19 g, 0.75 mmol) was added to the solution of methyl 2-[(5-hydroxyindolyl)methyloctanoate (0.11 g, 0.38 mmol), as prepared in the preceding step, 2-(3-hydroxypropyl)aminopyridine (0.09 g, 0.56 mmol), as prepared in step b of Example 1, and tri-n-butylphosphine (0.13 g, 0.75 mmol) in tetrahydrofuran (6.0 mL). After stirring at ambient temperature overnight (16 h), the reaction was concentrated and the residue was purified by flash chromatography on silica gel (10%–50% ethyl acetate in hexane) to give the title compound as a yellow oil (0.04 g, 25%). $^1$H-NMR (400 MHz, CDCl$_3$) δ 8.80 (m, 1H), 7.40 (m, 1H), 7.21 (d, J=9.0 Hz, 1H), 7.08 (d, J=2.3 Hz, 1H), 7.03 (d, J=3.1 Hz, 1H), 6.88 (dd, J=9.2, 2.4 Hz, 1H), 6.55 (m, 2H), 6.40 (m, 2H), 4.81 (br s, 1H), 4.37 (dd, J=14.4, 8.5 Hz, 1H), 4.14 (m, 3H), 3.69 (s, 3H), 3.65 (m, 2H), 2.94 (m, 1H), 2.15 (m, 2H), 1.50 (m, 7H), 0.90 (m, 3H).

d) 2-({5-[3 (2-pyridylamino)propoxy]indolyl}methyl)octanoic acid

To a solution of methyl 2-({5-[3-(2-pyridylamino)propoxy]indolyl}methyl)octanoate (0.04 g, 0.09 mmol), as prepared in the preceding step, in methanol (5.0 mL) was added a solution of NaOH (0.1 g, 2.5 mmol) in H$_2$O (0.3 mL), and the reaction was stirred at ambient temperature overnight. After evaporating the solvent in vacuo, the residue is taken up in H$_2$O (5 mL) and acidified to pH 4–5 with 10% HCl, and extracted with ethyl acetate (2×15 mL). The combined organic layers were washed with brine, dried (Na$_2$SO$_4$), filtered and concentrated. The residue was purified by flash chromatography on silica gel (4% methanol in methylene chloride) to give the title compound as an oil (0.34 g, 90%). $^1$H-NMR (400 MHz, CDCl$_3$) δ 7.72 (m, 1H), 7.48 (m, 1H), 7.26 (d, 8.9 Hz, 1H), 7.02 (d, J=2.7 Hz, 2H), 6.77 (dd, J=8.9, 2.4 Hz, 1H), 6.50 (m, 2H), 6.28 (d, J=2.9 Hz, 1H), 4.27 (dd, J=14.2, 8.6 Hz, 1H), 3.99 (m, 3H), 3.32 (t, J=6.7 Hz, 2H), 2.85 (br s, 1H), 1.95 (m, 2H), 1.67 (m, 1H), 1.30 (m, 9H), 0.84 (t, J=6.6 Hz, 3H). Mass spectrum (LCMS, ESI pos.) Calcd. for C$_{25}$H$_{33}$N$_3$O$_3$ 424.2 (M+H); Found: 424.7.

EXAMPLE 10

3-[5-(3-{Benzylamino]carbonylamino}propoxy)indolyl]propanoic acid

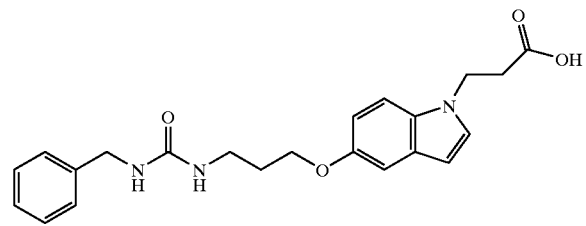

a) Methyl 3-{5-[3-(benzyloxycarbonylamino)propoxy]indolyl}propanoate 1,1'-(Azodicarbonyl)dipiperidine (370 mg, 1.5 mmol) was added to the solution of methyl 3-(5-hydroxyindolyl)propanoate (220 mg, 1.0 mmol), as prepared in step g of Example 5, 3-(benzyloxycarbonylamino)propanol (230 mg, 1.1 mmol) and tri-n-butylphosphine (305 mg, 1.5 mmol) in tetrahydrofuran (20 mL). After stirring at ambient temperature overnight, the reaction mixture was concentrated and the residue was purified by flash column chromatography on silica gel (0–2% ethyl acetate in methylene chloride) to give the title compound as an off white solid (310 mg, 76%). ¹H-NMR (400 MHz, CDCl₃) δ 7.35 (m, 5H), 7.22 (d, J=8.9 Hz, 1H), 7.09 (d, J=3.1 Hz, 1H), 7.07 (d, J=2.1 Hz, 1H), 6.86 (dd, J=8.8, 2.4 Hz, 1H), 6.38 (d, J=2.9 Hz, 1H), 5.11 (br s, 3H), 4.41 (t, J=6.8 Hz, 2H), 4.07 (t, J=5.9 Hz, 2H), 3.66 (s, 3H), 3.44 (q, J=6.3 Hz, 2H), 2.81 (t, J=6.8 Hz, 2H), 2.02 (m, 2H).

b) Methyl 3-[5-(aminopropoxy)indolyl]propanoate

A mixture of methyl 3-{5-[3-(benzyloxycarbonylamino) propoxy]indolyl}propanoate (300 mg, 0.73 mmol), as prepared in the preceding step, 10% palladium(0) on carbon (50 mg) in ethanol (20 mL) was stirred at ambient temperature under hydrogen (balloon) for 3 h. The catalyst was removed by filtration through Celite. The filtrate was concentrated to give the title compound as an off white solid (150 mg, 74%). ¹H-NMR (400 MHz, CDCl₃/CD₃OD) δ 7.25 (d, J=8.9 Hz, 1H), 7.13 (d, J=2.6 Hz, 1H), 7.08 (d, J=2.5 Hz, 1H), 6.85 (dd, J=8.9, 2.5 Hz, 1H), 6.38 (d, J=2.9 Hz, 1H), 4.43 (t, J=6.8 Hz, 2H), 4.10 (t, J=5.8 Hz, 2H), 3.66 (s, 3H), 3.01 (q, J=7.0 Hz, 2H), 2.83 (t, J=6.8 Hz, 2H), 2.04 (m, 2H).

c) Methyl 3-[5-(3-{[benzylamino]carbonylamino}propoxy) indolyl]propanoate

To the solution of methyl 3-[5-(aminopropoxy)indolyl] propanoate (140 mg, 0.5 mmol), as prepared in the preceding step, in acetonitrile (10 mL) was added benzyl isocynate (135 mg, 1.0 mmol), and the mixture was stirred at ambient temperature overnight. After evaporating the solvent in vacuo, the residue was purified by flash column chromatography on silica gel (methylene chloride to 5% ethyl acetate in methylene chloride) to give the title compound as a white solid (85 mg, 42%). ¹H-NMR (400 MHz, CDCl₃) δ 7.28 (m, 5H), 7.20 (d, J=8.9 Hz, 1H), 7.10 (d, J=2.8 Hz, 1H), 7.05 (d, J=2.5 Hz, 1H), 6.81 (dd, J=8.8, 2.5 Hz, 1H), 6.38 (d, J=2.9 Hz, 1H), 4.66 (br s, 2H), 4.41 (t, J=6.8 Hz, 2H), 4.35 (d, J=5.7 Hz, 2H), 4.06 (t, J=5.8 Hz, 2H), 3.66 (s, 3H), 3.43 (q, J=6.2 Hz, 2H), 2.81 (t, J=6.8 Hz, 2H), 1.99 (t, J=6.1, 2H).

d) 3-[5-(3-{(Benzylamino]carbonylamino}propoxy)indolyl] propanoic acid

To the solution of methyl 3-[5-(3-{[benzylamino] carbonylamino}propoxy)indolyl]propanoate (80 mg, 0.2 mmol), as prepared in the preceding step, in tetrahydrofuran (5 mL) and water (5 mL) was added sodium hydroxide (20 mg), and the reaction mixture was stirred at ambient temperature for 2 h. After evaporating the tetrahydrofuran, the aqueous solution was acidified (pH 5–6), the white solid formed was collected, washed with water and dried under high vacuum to give the title compound (65 mg, 82%). ¹H-NMR (400 MHz, DMSO₆) δ 7.21 –7.37 (m, 7H), 7.02 (d, J=2.4 Hz, 1H), 6.78 (dd, J=8.8, 2.4 Hz, 1H), 6.36 (t, J=6.0 Hz, 1H), 6.30 (d, J=2.9 Hz, 1H), 6.06 (t, J=5.7 Hz, 1H), 4.34 (t, J=6.8 Hz, 2H), 4.20 (d, J=6.0 Hz, 2H), 3.96 (t, J=6.2 Hz, 2H), 3.19 (q, J=6.4 Hz, 2H), 2.71 (t, J=6.8 Hz, 2H), 1.83 (t, J=6.5 Hz, 2H). Mass spectrum (LCMS, ESI) Calcd. for C₂₂H₂₅N₃O₄ 396.4 (M+H), found: 396.1.

EXAMPLE 11

3-[5-(2-5,6,7,8-Tetrahydro-[1,8]naphthyridin-2-yl-acetylamino)-indol-1-yl]-hexanoic acid

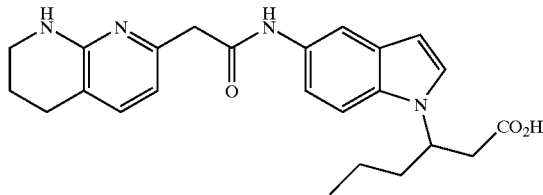

a) (5,6,7,8-Tetrahydro-[1,8]naphthyridin-2-yl)-acetic acid

To a solution of 7-ethoxycarbonylmethyl-3,4-dihydro-2H-[1,8]naphthyridine-1-carboxylic acid tert-butyl ester (1.0 g, 3.12 mmol) in methanol (10 mL) was added a solution of NaOH (0.15 g, 3.75 mmol) in H₂O (1.0 mL), and stirred at ambient temperature overnight. After evaporating the solvents, the resulting mixture was acidified to pH 3–4 with 1 N HCl, and extracted with EtOAc (3 times). The extracts were combined, washed with brine, dried over sodium sulfate, concentrated and flash chromatographed on silica gel, eluting with MeOH/DCM (1, 2.5, and 5%) to give the desired acid (0.57 g, 63% yield) as a yellow solid. The solid (0.57 g, 1.95 mmol) was dissolved DCM (5.0 mL), and TFA added (0.45 mL). After stirring at ambient temperature overnight, additional TFA (0.9 mL) was added, and the mixture stirred for 24 h. Solvents were evaporated, giving the title compound (0.60 g, quantitative yield) as a yellow solid. Mass Spectrum (LCMS, ESI) calculated for C₁₀N₁₃N₂O₂ 193.1 (M+H); found 193.2.

b) 3-(5-Nitro-indol-1-yl)-hexanoic acid ethyl ester

The title compound was synthesized from 5-nitroindole using the procedure described in Example 2, step (c), in 34% yield as an orange oil. Mass spectrum (LCMS, ESI) calculated for C₁₆H₂₁N₂O₄ 305.3 (M+H); found 305.2.

c) 3-(5-Amino-indol-1-yl)-hexanoic acid ethyl ester

A mixture of 3-(5-nitro-indol-1-yl)-hexanoic acid ethyl ester (1.49 g, 4.9 mmol), and 10% palladium on activated carbon (149 mg) in ethanol (15 mL) was hydrogenated in a hydrogen balloon for 2 days. The mixture was filtered through Celite, and the Celite was washed with methanol. The filtrate and washing were combined, concentrated, and flash chromatographed on silica gel, eluting with EtOAc/DCM (20, 30%) to afford the title compound (1.05 g, 78% yield) as dark brown oil. ¹H NMR (CDCl₃) δ 7.22 (d, 1H, J=8.7 Hz), 7.05 (d, 1H, J=3.2 Hz), 6.90 (d, 1H, J=2.3 Hz), 6.66 (dd, 1H, J=2.2, 8.7 Hz), 6.33 (d, 1H, J=3.2 Hz), 4.78–4.73 (m, 1H), 4.02–3.96 (m, 2H), 3.47 (bs, 2H), 2.87–2.74 (m, 2H), 1.94–1.87 (m, 1H), 1.84–1.77 (m, 1H), 1.27–1.09 (m, 2H), 1.08 (t, 3H, J=7.1 Hz), 0.85 (t, 3H, J=7.3 Hz).

d) 3-[5-(2-5,6,7,8-Tetrahydro-[1,8]naphthyridin-2-yl-acetylamino)-indol-1-yl]-hexanoic acid ethyl ester A solution of (5,6,7,8tetrahydro-[1,8]-naphthyridin-2-yl)-acetic acid (0.2 g, 0.65 mmol), 3-(5-amino-indol-1-yl)-hexanoic acid ethyl ester (0.19 g, 0.71 mmol), BOP (0.35 g, 0.78 mmol), and diisopropylethylamine (0.45 mL, 2.6 mmol) in DMF (2.5 mL) was stirred for 16 h. Solvents were evaporated. The resulting residue was partitioned between H₂O and EtOAc. The aqueous layer was separated and extracted once more with EtOAc. The extracts were combined, washed with H₂O, brine, dried over Na₂SO₄, concentrated, and flash chromatographed on silica gel, eluting with EtOAc/DCM (15, 30, 50, and 80%) to give the title compound (0.20 g, 67% yield) as a brown oil. Mass spectrum (LCMS, ESI) calculated for $C_{26}H_{33}N_4O_3$ 449.3 (M+H); found 449.3.

e) 3-[5-(2-5,6,7,8-Tetrahydro-[1,8]naphthyridin-2-yl-acetylamino)-indol-1-yl]-hexanoic acid To a solution of 3-[5-(2-5,6,7,8-tetrahydro-[1,8] naphthyridin-2-yl-acetylamino)-indol-1-yl]-hexanoic acid ethyl ester (50 mg, 0.12 mmol) in THF (1.0 mL) was added a solution of NaOH (18 mg, 0.45 mmol) in $H_2O$ (0.15 mL), and stirred at ambient temperature for 14 h. Solvents were evaporated. To the resulting residue was added 1N HCl until the solution reached a pH of 5. The mixture was extracted with EtOAc/DCM (9:1) several times until the aqueous layer was free from product by TLC. The extracts were combined, dried over $Na_2SO_4$, concentrated, and flash chromatographed on silica gel, eluting with MeOH/DCM (2.5, 5, and 7.5%) to afford the title compound (38 mg, 81% yield) as a pale brown solid. $^1$H NMR (CDCl$_3$) δ 7.79 (d, 1H, J=1.9 Hz), 7.57 (d, 1H, J=7.3 Hz), 7.45 (d, 1H, J=8.9 Hz,), 7.34 (d, 1H, J=3.2 Hz), 7.23 (dd, 1H, J=2.0, 8.8 Hz), 6.69 (d, 1H, J=7.3 Hz), 6.46 (d, 1H, J=3.2 Hz), 3.83 (s, 0.9H), 3.81 (s, 0.5H), 3.49 (t, 2H, J=5.6 Hz), 2.89 (d, 2H, J=7.2 Hz), 2.83 (t, 2H, J=6.1 Hz), 2.67–1.86 (m, 4H), 1.19–0.99 (m, 2H), 0.86 (t, 3H, J=7.3 Hz). Mass spectrum (LCMS, ESI) calculated for $C_{24}H_{29}N_4O_3$ 421.2 (M+H); found 421.3.

EXAMPLE 12

3-(5-{2-[N-(4,5-Dihydro-1-imidazol-2-yl)-aminooxy]-ethoxy}-indol-1-yl-3-phenyl-propionic acid

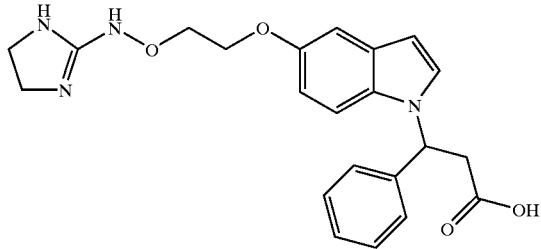

a) 5 (2-Benzyloxy-ethoxy)-2-nitro-toluene

3-Methyl-4-nitrophenol (8.75 g, 57.1 mmol), 2-benzyloxyethanol (8.70 g, 57.1 mmol) and triphenylphosphine (22.5 g, 85.1 mmol) were dissolved in tetrahydrofuran (200 mL). The mixture was placed under argon at 0° C. and stirred for 10 minutes. Diisopropylazodicarboxylate (17.3 g, 58.1 mmol) was added all at once. The reaction was stirred overnight (16 h). The solvent was removed under vacuum, and the crude mixture was purified via column chromatography to give the product with reduced diisopropylazodicarboxylate impurities. The impurities were eliminated via crystallization with hexane/ethyl acetate. The crystals were filtered and the mother liquid was concentrated under vacuum to afford the title compound (12.36 g, 75%) as oil. $^1$H NMR (CDCl$_3$), δ 8.08 (d, 1H, J=9.7 Hz), 7.31–7.38 (m, 3H), 6.82 (m, 2H), 4.65 (s, 2H), 4.23 (t, 2H, J=4.9 Hz), 3.87 Hz), 2.63 (s, 3H).

b) 5-(2-Benzyloxy-ethoxy)-1H-indole 5 (2-Benzyloxy-ethoxy)-2-nitro-toluene (12.4 g, 43.0 mmol), N-N-dimethylformamide dimethyl acetal (6.55 g, 51.6 mmol) and pyrrolidine (3.68 g, 51.6 mmol) were dissolved in N-N-dimethylformamide (25 mL). The mixture was heated to 120° C. for 16 h. The solvent was evaporated under vacuum and the crude reaction was dissolved in 70% ethyl acetate/methanol (250 mL). The reaction was placed in a Parr Hydrogenator under a hydrogen atmosphere for 16 h with 10% palladium on carbon [10% w/w] (3.00 g) at 50 psi. The reaction was filtrated over celite and the crude mixture was purified via column chromatography with silica gel eluting with hexane/ethyl acetate to give the title compound (22% yield). $^1$H NMR (CDCl$_3$) δ 7.27–7.41 (m, 6H), 7.19 (t, 1H, J=2.5 Hz), 7.13 (d, 1H, J=2.3 Hz), 6.91 (dd, 1H, J=2.5, 8.8 Hz), 6.48 (m, 1H), 4.67 (s, 2H), 4.21 (m, 2H), 3.87 (m, 2H).

c) 3-[5-(2-Benzyloxy-ethoxy)-indol-1-yl]-3-phenyl-acrylic acid ethyl ester 5-(2-Benzyloxy-ethoxy)-1H-indole (2.20 g, 8.20 mmol) and ethyl phenyl propiolate (1.72 g, 9.80 mmol) were dissolved in tetrahydrofuran (5 mL) under an argon atmosphere. Tetrabutylammonium flouride ]1M in THF] (20.5 ml, 20.5 mmol) was added at once and the reaction was heated at 70° C. for 16 hr. The reaction was extracted with a mixture of ethyl acetate and brine. The organic layer was collected, dried (Na$_2$SO$_4$), filtered and evaporated under vacuum to give a crude mixture, which was purified via column chromatography with silica gel, eluting with hexane/ethyl acetate to give the title compound (69% yield) as an E/Z isomeric mixture. $^1$H NMR (CDCl$_3$), δ 7.30–7.53 (m, 10.7H), 7.09–7.13 (m, 2H), 6.97 (d, 0.3H, J=3.2 Hz), 6.78 (m, 1H), 6.61 (d, 0.7H, J=3.9 Hz), 6.24 (s, 0.7H), 6.17 (s, 0.3H), 4.67 (s, 2H), 4.20 (m, 2H), 4.14 (c, 0.6H, J=7.2 Hz), 4.06 (c, 1.4H, J=7.2 Hz), 3.87 (m, 2H), 1.18 (t, 0.9H, J=6.9 Hz), 1.05 (t, 2.1H, J=7.2 Hz).

d) 3-[5-(2-Hydroxy-ethoxy)-indol-1-yl]-3-phenyl-propionic acid ethyl ester

3-[-5-(2-benzyloxy-ethoxy)-indol-1-yl]-3-phenyl-acrylic acid ethyl ester (2.5 g, 5.6 mmol) was dissolved in 70% ethyl acetate/methanol (50 mL) and added under an argon atmosphere to a suspension of 10% palladium on carbon [10% w/w] (3.0 g) in the same solvent (50 mL). The reaction was placed in a Parr Hydrogenator for 6 h. The reaction was filtered through celite and the solvent was evaporated under vacuum. Purification of the crude mixture via column chromatography with silica gel, eluting with hexane/ethyl acetate gave the title compound (80% yield). $^1$H NMR (CDCl$_3$), δ 7.14–7.32 (m, 7H), 6.82 (dd, 1H, J=2.3, 8.8 Hz), 6.45 (d, 1H, J=3.0 Hz), 6.07 (d, 1H, J=2.1 Hz), 6.01 (t, 1H, J=7.4 Hz), 4.03 (m, 4H), 3.91 (m, 2H), 3.27 (m, 2H), 1.06 (t, 3H, J=7.2 Hz).

e) 3-{5-[2-(1,3-Dioxo-1,3-dihydro-isoindol-2-yloxy)-ethoxy]-indol-1-yl}-3-phenyl-propionic acid ethyl ester 3-[5-(2-hydroxy-ethoxy)-indol-1yl]-3-phenyl-propionic acid ethyl ester (0.77 g, 2.10 mmol), N-hydroxyphthalimide (0.40 g, 2.40 mmol) and triphenylphosphine (0.85 g, 3.24 mmol) were dissolved in tetrahydrofuran (5 mL). The mixture was placed under an argon atmosphere at 0° C. and stirred for 10 minutes. Diisopropylazodicarboxylate (0.65 g, 3.24 mmol) was added all at once. After stirring overnight (16 h), the solvent was removed under vacuum, and the crude mixture was purified via column chromatogpraphy to afford the title compound (96% yield). $^1$H NMR (CDCl$_3$) δ 7.79 (m, 2H), 7.70 (m, 2H), 7.15–7.29 (m, 7H), 7.03 (d, 1H, J=2.3 Hz), 6.69 (dd, 1H, J=2.5, 9.0 Hz), 6.43 (d, 1H, J=3.7 Hz), 5.99 (t, 1H, J=7.7 Hz), 4.56 (m, 2H), 4.34 (m, 2H), 4.02 (c, 2H, J=7.2 Hz), 3.27 (m, 2H), 1.06 (t, 3H, J=7.2 Hz).

f) 3-[5-(2-Aminooxy-ethoxy)-indol-1yl]-3-[phenyl-propionic acid ethyl ester

3-{5-[2-(1,3-dioxo-1,3-dihydro-isoindol-2-yloxy)-ethoxy]-indol-1-yl}-3-phenyl-propionic acid ethyl ester (1.0 g, 2.0 mmol) was dissolved in tetrahydrofuran (4 mL) at room temperature. Dimethylamine ]1.0 M in THF] (10 mL, 10 mmol) was added and the reaction stirred at room temperature for 16 h. The solvent was evaporated under vacuum and the crude mixture was purified via column chromatography with silica gel to afford the title compound (73% yield). $^1$H NMR (CDCl$_3$) δ 7.15–7.28 (m, 7H), 7.08 (d, 1H, J=2.5 Hz), 6.84 (dd, 1H, J=2.3, 8.8 Hz), 6.45 (d, 1H, J=2.3 Hz), 6.00 (t, 1H, J=7.7 Hz), 4.56 (m, 2H), 4.15 (m, 2H), 4.00 (m, 4H), 3.26 (m, 2H), 1.06 (t, 3H, J=7.2 Hz).

g) 3-(5-{2-[N-(4,5-Dihydro-1H-imidazol-2-yl)-aminooxy]-ethoxy}-indol-1-yl)-3-phenyl-propionic acid ethyl ester 3-[5-(2-aminooxy-ethoxy)-indol-1yl]-3-phenyl-propionic acid ethyl ester (208 mg, 0.56 mmol) and 2-(3,5-dimethylpyrazolyl)-4,5-dihydroimidazole hydrobromide (125 mg, 0.90 mmol) were dissolved in methanol (3 mL) and stirred for 5 days. The solvent was evaporated under vacuum and the crude mixture was purified via column chromatography with silica gel, eluting with 10% methanol in dichloromethane to afford the title compound (99% yield). $^1$H NMR (CDCl$_3$) δ 7.16–7.29 (m, 7H), 7.07 (d, 1H, J=2.3 Hz), 6.80 (dd, 1H, J=2.3, 8.8 Hz), 6.47 (d, 1H, J=3.2 Hz), 6.00 (t, 1H, J=7.0 Hz), 4.24 (m, 2H), 4.17 (m, 2H), 4.03 (c, 2H, J=7.2 Hz), 3.51 (br s, 4H), 3.26 (m, 2H), 1.09 (t, 3H, J=7.2 Hz).

h). 3-(5-{2-[N-(4,5-Dihydro-1H-imidazol-2yl)-aminooxy]-ethoxy}-indol-1-yl)-3-phenyl-propionic acid 3-(5-{2-[N-(4,5-Dihydro-1H-imidazol-2yl)-aminooxy]-ethoxy}-indol-1-yl)-3-phenyl-pr acid ethyl ester (0.24 g, 0.55 mmol) was dissolved in 70% methanol/water (4 mL). Lithium hydroxide monohydratate (0.70 g, 4.67 mmol) was added and the reaction was stirred for 16 h at room temperature under an argon atmosphere. The solution was neutralized with 1.0 N HCl (4.67 mL) and the solvent was evaporated under vacuum. The crude mixture was purified via column chromatography with silica gel, eluting with 10% methanol/dichloromethane to afford the title compound (74% yield). $^1$H NMR (DMSO-d6) δ 7.68 (d, 1H, J=3.2 Hz), 7.42 (d, 1H, J=9.0 Hz), 7.20–7.34 (m, 5H), 7.05 (d, 1H, J=2.5 Hz), 6.75 (dd, 1H, J=2.5, 9.0 Hz), 6.40 (d, 1H, J=3.0 Hz), 5.96 (m, 1H), 4.16 (m, 4H), 3.59 (br s, 4H), 3.36 (m, 2H). Mass Spectrum (LCMS, ESI) calculate for C$_{22}$H$_{25}$N$_4$O$_4$ 409.2 (M+H); found 409.2.

EXAMPLE 13

3-(5-{2-[Guanidino-oxy]-ethoxy}-indol-1-yl)-3-phenyl-propionic acid

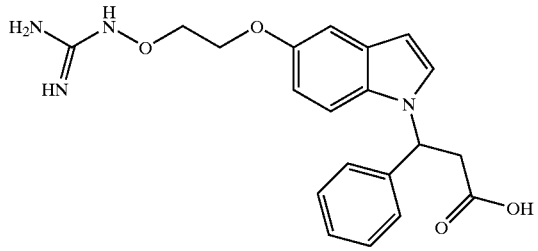

a) 3-(5-{2-[Guanidino-oxy]-ethoxy}-indol-1-yl)-3-phenyl-propionic acid ethyl ester 3-[5-(2-aminooxy-ethoxy)-indol-1-yl]-3-phenyl-propionic acid ethyl ester (0.28 g, 0.75 mmol) and 1H-pyrazole-1-carboxamide hydrochloride (0.99 g, 0.67 mmol) were dissolved in methanol (3 mL) and stirred for 5 days. The solvent was evaporated under vacuum and the crude mixture was purified via column chromatography with silica gel, eluting with 10% methanol/dichloromethane to afford the title compound (97% yield). $^1$H NMR (CDCl$_3$), δ 7.11–7.26 (m, 7H), 7.00 (d, 1H, J=2.3 Hz), 6.75 (dd, 1H, J=2.3, 8.8 Hz), 6.43 (d, 1H, J=3.2 Hz), 5.98 (t, 1H, J=7.6 Hz), 4.08 (m, 2H), 3.99 (m, 4H), 3.23 (m, 2H), 1.05 (t, 3H, J=7.2 Hz).

b) 3-(5-{2-[Guanidino-oxy]-ethoxy}-indol-1-yl)-3-phenyl-propionic acid 3-(5-{2-[guanidino-oxy]-ethoxy}-indol-1-yl)-3-phenyl-propionic acid ethyl ester (0.30 gg, 0.71 mmol) was dissolved in 70% methanol/water (4 mL) and lithium hydroxide monohydratate (0.70 g, 4.67 mmol) was added. The reaction was stirred for 16 h at room temperature under an argon atmosphere. The solution was neutralized with 1.0 N HCl (4.67 mL) and the solvent was evaporated under vacuum. The crude mixture was purified via column chromatography with silica gel, eluting with 10% methanol/dichloromethane to afford the title compound (80% yield). $^1$H NMR (CD$_3$OD-d4) δ 7.34 (d, 1H, J=3.2 Hz), 7.06–7.15 (m, 6H), 6.97 (d, 1H, J=2.3 Hz), 6.65 (dd, 1H, J=2.5, 9.0 Hz), 6.31 (d, 1H, J=3.2 Hz), 5.93 (t, 1H, J=7.0 Hz), 4.01 (m, 4H), 3.07 (m, 2H).

EXAMPLE 14

3-{5-[2-(5,6,7,8-Tetrahydro-[1,8]naphthyridin-2-yl)-ethoxy]-indol-1-yl}-hexanoic acid

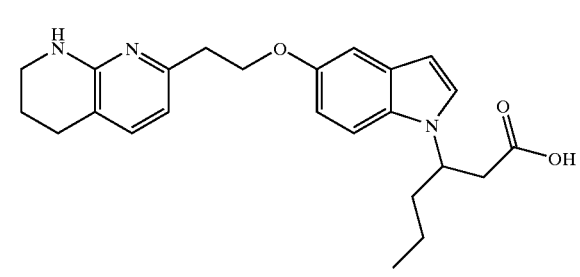

a) 3-(5-Benzyloxy-indol-1-yl)-hexanoic acid ethyl ester

A solution of 5-benzyloxyindole (5.00 g, 22.4 mmol) in DMF (20 mL) was added dropwise to a stirred solution of sodium hydride (0.91 g, 38.1 mmol) in DMF (50 mL) at 0° C. and stirred for 20 minutes. Ethyl-β-bromocaproate (5.59 g, 26.9 mmol) in DMF (20 mL) was added and the reaction was stirred at room temperature overnight. The reaction was then poured into cold H$_2$O (150 mL) and extracted with ethyl acetate (3×50 mL), dried over magnesium sulfate and concentrated. The residue was purified by flash chromatography on silica gel (40% ethyl acetate in hexane) to give the title compound as oil (40% yield). $^1$H NMR (CDCl$_3$) δ 7.47 (d, 2H, J=7.2 Hz), 7.38 (t, 2H, J=7.1 Hz), 7.32 (d, 2H, J=8.8 Hz), 7.12 (dd, 2H, J=2.4, 13.7 Hz), 6.94 (dd, 1H, J=2.4, 10.2 Hz), 6.44 (d, 1H, J=3.1 Hz), 5.09 (s, 2H), 4.79 (m, 1H), 3.98 (q, 2H, J=7.1 Hz), 2.80 (m, 2H), 1.90 (m, 2H), 1.25 (m, 2H), 1.07 (t, 3H, J=7.2 Hz), 0.86 (t, 3H, J=7.3 Hz).

b) 3-(5-Hydroxy-indol-1-yl)-hexanoic acid ethyl ester

Palladium(0) on carbon [10% w/w] (0.20 g) was added to a solution of (5-benzyloxy-indol-1-yl)-hexanoic acid ethyl ester (2.00 g, 5.47 mmol) in methanol (10 mL) under an argon atmosphere. The reaction was placed under H$_2$ atmosphere and stirred overnight. The solution was filtered through a bed of celite and concentrated. The residue was purified by flash chromatography on silica gel (10% ethyl acetate in hexane) to give the title compound as a solid (93% yield). $^1$H NMR (CDCl$_3$) δ 7.30 (d, 2H, J=8.8 Hz), 7.12 (m, 1H), 7.00 (m, 1H), 6.75 (m, 1H), 6.45 (m, 1H), 4.80 (m, 1H), 4.72 (s, 1H), 3.95 (q, 2H, J=7.2 Hz), 2.80 (m, 2H), 1.84 (m, 2H), 1.28 (m, 2H), 1.10 (t, 3H, J=7.2 Hz), 0.90 (t, 3H, J=7.2 Hz).

c) 7-{2-[1-(1-Ethoxycarbonylmethyl-butyl)-1H-indol-5-yloxy]-ethyl}-3,4-dihydro-2H-[1,8]naphthyridine-1-carboxylic acid tert-butyl ester Triphenylphosphine (0.20 g, 0.77 mmol) was added to a solution of 7-(2-hydroxy-ethyl)-3,4-dihydro-2H-[1,8]

naphthyridine-1-carboxylic acid tert-butyl ester (0.16 g, 0.58 mmol) and 3-(5-hydroxy-indol-1-yl)-hexanoic acid ethyl ester (0.10 g, 0.38 mmol) in THF (4 mL) at 0° C. Diisopropylazodicarboxylate (0.15 g, 0.77 mmol) was added dropwise and the reaction was stirred at room temperature overnight. The solution was then concentrated. The residue was purified by flash chromatography on silica gel (30% ethyl acetate in hexane) to give the title compound (13% yield). $^1$H NMR (CDCl$_3$) δ 7.30 (m, 2H), 7.09 (m, 2H), 6.96 (d, 1H, J=7.6 Hz), 6.86 (m, 1H), 6.41 (d, 1H, J=3.2 Hz), 4.78 (m, 1H), 4.39 (t, 2H, J=6.9 Hz), 3.98 (q, 2H, J=7.1 Hz), 3.75 (m, 2H), 3.21 (t, 2H, J=6.9 Hz), 2.86 (m, 2H), 2.77 (m, 2H), 1.85 (m, 4H), 1.50 (s, 9H), 1.20 (m, 2H), 1.06 (t, 3H, J=7.1 Hz), 0.85 (t, 3H, J=7.4 Hz).

d) 3-{5-[2-(5,6,7,8-Tetrahydro-[1,8]naphthyridin-2-yl)-ethoxy]-indol-1-yl}-hexanoic acid ethyl ester 7-{2-[1-(1-Ethoxycarbonylmethyl-butyl)-1H-indol-5-yloxy]-ethyl}-3,4-dihydro-2H-[1,8]naphthyridine-1-carboxylic acid tert-butyl ester (0.02 g, 0.04 mmol) was heated neat to 200° C. for 15 minutes. The residue was purified by flash chromatography on silica gel (ethyl acetate) to give the title compound (90% yield). $^1$H NMR (CDCl$_3$) δ 7.28 (m, 1H), 7.08 (m, 3H), 6.86 (m, 1H), 6.48 (d, 1H, J=8.0 Hz), 6.41 (d, 1H, J=4.0 Hz), 4.84 (s, 1H), 4.78 (m, 1H), 4.29 (t, 2H, J=4.0 Hz), 3.98 (q, 2H, J=8.0 Hz), 3.39 (m, 2H), 3.04 (t, 2H, J=8.0 Hz), 2.81 (m, 2H), 2.69 (t, 2H, J=8.0 Hz), 1.93 (m, 4H), 1.25 (m, 2H), 1.10 (t, 3H), 0.85 (t, 3H).

e) 3-{5-[2-(5,6,7,8-Tetrahydro-[1,8]naphthyridin-2-yl)-ethoxy]-indol-1-yl}-hexanoic acid Sodium hydroxide (0.01 g, 0.23 mmol) was added to a solution of 3-{5-[2-(5,6,7,8-tetrahydro-[1,8]naphthyridin-2-yl)-ethoxy]-indol-1-yl}-hexanoic acid ethyl ester (0.02 g, 0.04 mmol) in methanol/water (9/1, 1 mL) and stirred overnight. The reaction was acidified to pH 6 with 1N HCl and the crude product was extracted with ethyl acetate (3×10 mL) and concentrated. The residue was purified by flash chromatography on silica gel (10% methanol in ethyl acetate) to give the title compound (28% yield). $^1$H NMR (CDCl$_3$) δ 10.4 (bs, 1H), 7.38 (d, 1H, J=8.0 Hz), 7.21 (d, 1H, J=3.2 Hz), 7.14 (d, 1H, J=8.0 Hz), 7.00 (d, 1H, J=2.3 Hz), 6.73 (m, 1H), 6.48 (d, 1H, J=7.3 Hz), 6.32 (d, 2H, J=3.0 Hz), 4.80 (s, 1H), 4.22 (t, 2H, J=7.0 Hz), 3.47 (m, 2H), 2.95 (t, 2H, J=6.8 Hz), 2.68 (m, 4H), 1.88 (m, 4H), 1.15 (m, 2H), 0.81 (t, 3H, J=7.4 Hz). Mass Spectrum (LCMS, ESI) calculated for C$_{24}$H$_{30}$N$_3$O$_3$ 408.2 (M+H); found 408.3.

EXAMPLE 15

3-{5-[2-(5,6,7,8-Tetrahydro-[1,8]naphthyridin-2-yl)-ethoxy]-indol-1-yl}-propionic acid

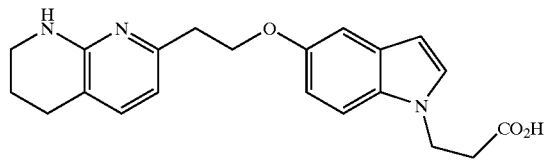

a) 7-{2-[1-(2-Ethoxycarbonyl-ethyl)-1H-indol-5-yloxy]-ethyl}-3,4-dihydro-2H-[1,8]naphthyridine-1-carboxylic acid tert-butyl ester The title compound was synthesized from 7-(2-hydroxy-ethyl)-3,4-dihydro-2H-[1,8]naphthyridine-1-carboxylic acid tert-butyl ester and ethyl 2-(5-hydroxyindolyl) propanoate using the procedure described in Example 14, step (c), in 20% yield. $^1$H NMR (CDCl$_3$) δ 7.32 (d, J=7.62 Hz, 1H), 7.21 (d, J=8.87 Hz, 1H), 7.11 (d, 1H, J=2.3 Hz), 7.08 (d, 1H, J=3.10 Hz), 6.95 (d, 1H, J=7.60 Hz), 6.88 (dd, 1H, J=2.4, 8.9 Hz), 6.37 (dd, 1H, J=0.6, 3.1 Hz), 4.42-4.36 (m, 2H), 4.11 (q, 2H, J=7.2 Hz), 3.76 (dd, 2H, J=6.0, 7.2 Hz), 3.21 (t, 2H, J=6.9 Hz), 2.79 (t, 2H, J=6.9 Hz), 2.73 (t, 2H, J=6.7 Hz), 1.92 (p, 2H, J=6.6 Hz), 1.52 (s, 9H), 1.20 (t, 3H, J=7.1 Hz).

b) 3-{5-[2-(5,6,7,8-Tetrahydro-[1,8]naphthyridin-2-yl)-ethoxy]-indol-1-yl}-propionic acid ethyl ester The title compound was synthesized from 7-{2-[1-(2-ethoxycarbonyl-ethyl)-1H-indol-5-yloxy]-ethyl}-3,4-dihydro-2H-[1,8]naphthyridine-1-carboxylic acid tert-butyl ester using the procedure described in Example 14, step (d), in 50% yield. $^1$H NMR (CDCl$_3$) δ 7.21 (d, 1H, J=8.9 Hz), 7.11–7.07 (m, 3H), 6.88 (dd, 1H, J=2.4, 8.8 Hz), 6.48 (d, 1H, J=7.3 Hz), 6.37 (dd, 1H, J=0.7, 3.1 Hz), 4.81 (bs, 1H), 4.40 (t, 2H, J=6.9 Hz), 4.30 (t, 2H, J=7.3 Hz, 2H), 4.11 (q, 2H, J=7.1 Hz), 3.42–3.38 (m, 2H), 3.42–3.38 (m, 2H), 3.04 (t, 2H, J=7.0 Hz), 2.79 (t, 2H, J=6.9 Hz), 2.70 (t, 2H, J=6.3 Hz), 1.94–1.88 (m, 2H), 1.20 (t, 3H, J=7.2 Hz). Mass spectrum (LCMS, ESI) calculated for C$_{23}$H$_{28}$N$_3$O$_3$ 394.2 (M+H); found 394.3.

c) 3-{5-[2-(5,6,7,8-Tetrahydro-[1,8]naphthyridin-2-yl)-ethoxy]-indol-1-yl}-propionic acid The title compound was synthesized from 3-{5-[2-(5,6,7,8-tetrahydro-[1,8]naphthyridin-2-yl)-ethoxy]-indol-1-yl}-propionic acid ethyl ester using the procedure described in Example 14, step (e), in 99% yield. $^1$H NMR (CDCl$_3$) δ 8.83 (bs, 1H), 7.30–7.27 (m, 1H), 7.18 (d, 1H, J=8.9 Hz), 7.16 (d, 1H, J=3.1 Hz), 7.01 (d, 1H, J=2.3 Hz), 6.77 (dd, 1H, J=2.3, 8.8 Hz), 6.50 (d, 1H, J=7.3 Hz), 6.31 (d, 1H, J=3.0 Hz), 4.33 (t, 2H, J=6.8 Hz), 4.25 (t, 2H, J=5.8 Hz), 3.42 (t, 2H, J=5.4 Hz), 3.11 (t, 2H, J=5.8 Hz), 2.76 (t, 2H, J=6.7 Hz), 2.70 (t, 2H, J=6.1 Hz), 1.87 (p, 2H, J=6.1 Hz). Mass Spectrum (LCMS, ESI) calculated for C$_{21}$N$_{24}$N$_3$O$_3$ 366.2 (M+H); found 366.3.

EXAMPLE 16

3-Phenyl-3-{5-[2-(5,6,7,8-tetrahydro-[1,8]naphthyridin-2-yl)-ethoxy]-indol-1-yl}-propionic acid

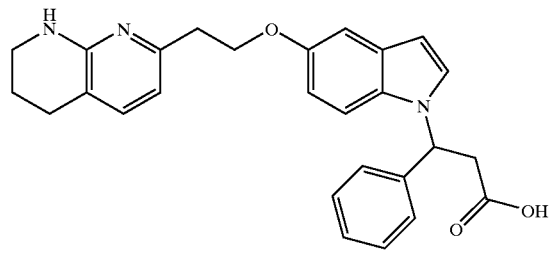

a) 7-(2-Hydroxy-ethyl)-3,4-dihydro-2H-[1,8]naphthyridine-1-carboxylic acid tert-butyl ester 7-Ethoxycarbonylmethyl-3,4-dihydro-2H-[1,8]naphthyridine-1-carboxylic acid tert-butyl ester (synthetic methodology described in Published International Patent Appl. WO 00/33838) (6.11 g, 19.0 mmol) was dissolved in tetrahydrofuran (40 mL) at room temperature. The solution was place under argon. Lithium borohydride [2M in tetrahydrofuran] (22.8 mmol, 11.43 mL) was carefully added and the reaction was refluxed overnight (16 h). The mixture was poured into a solution of saturated ammonium chloride and extracted with ethyl acetate. The organic layer was dried over Na$_2$SO$_4$, filtered, and evaporated under vacuum to give a crude mixture, which was purified via column chromatography to give 7-(2-hydroxy-ethyl)-3,4-dihydro-2H-[1,8]naphthyridine-1-carboxylic acid tert-butyl ester (49% yield). $^1$H NMR (Cl$_3$CD), δ 7.30 (d, 1H, J=7.6 Hz), 7.76 (d, 1H, J=7.6 Hz), 3.98 (m, 2H), 3.78 (m, 2H), 2.92 (m, 2H), 2.71 (m, 2H), 1.92 (m, 2H), 1.54 (s, 9H).

b) 7-[2-(3-Methyl-4-nitro-phenoxy)-ethyl]-3,4-dihydro-2H-[1,8]naphthyridine-1-carboxylic acid tert-butyl ester An ice-cooled solution of 7-(2-hydroxy-ethyl)-3,4-dihydro-2H-[1,8]naphthyridine-1-carboxylic acid tert-butyl ester (100 g, 359 mmol), 3-methyl-4-nitrophenol (45.7 g, 298 mmol), and triphenylphosphine (157 g, 597 mmol) in anhydrous THF (1.5 L) was stirred under an atmosphere of nitrogen for 15 min. To this solution was added diisopropylazodicarboxylate (118 mL, 597 mmol) over 5 minutes and the mixture was allowed to gradually warm up and stir at room temperature for 16 h. The mixture was filtered to remove the insoluble material and the filtrate was concentrated in vacuo and re-dissolved in diethyl ether (1 L) to remove most of the reduced diisopropylazodicarboxylate and triphenylphosphine oxide (125 g) by filtration. The ether solution was concentrated in vacuo to give a gum (286 g) as the crude product. The crude product was filtered through a plug of silica gel (1 Kg) using 2:1 ether/pet-ether as eluent to removed the remaining triphenylphosphine. The fractions from the plug were combined and concentrated to 1 L, which resulted in the crystallization of the title compound (91 g, 61% yield). $^1$H NMR (CDCl$_3$), δ 8.05 (d, 1H, J=8.8 Hz), 7.33 (d, 1H, J=7.6 Hz), 6.89 (d, 1H, J=7.6 Hz), 6.81 (m, 2H), 4.44 (t, 2H, J=8.00 Hz), 3.76 (m, 2H), 3.20 (t, 2H, J=8.00 Hz), 2.73 (m, 2H), 2.61 (s, 3H), 1.93 (m, 2H), 1.51 (s, 9H).

c) 7-[2-(1H-Indol-5-yloxy)-ethyl]-3,4-dihydro-2H-[1,8]naphthyridine-1-carboxylic acid tert-butyl ester Treatment of 7-[2-(3-methyl-4-nitro-phenoxy)-ethyl]-3,4-dihydro-2H-[1,8]naphthyridine-1-carboxylic acid tert-butyl ester (14.0 g, 33.9 mmol) with N,N-dimethylformamide dimethyl acetal (5.40 mL, 40.7 mmol) and pyrrolidine (3.37 mL, 40.7 mmol) in DMF (20 mL) at 75° C. gave a deep orange solution after 16 h. After that period the solvent was removed under vacuum to yield a red gum (15.5 g) corresponding with 7-{2-[4-Nitro-3-(2-pyrrolidin-1-yl-vinyl)-phenoxy]-ethyl}-3,4-dihydro-2H-[1,8]naphthyridine-1-carboxylic acid tert-butyl ester. This compound was used in the next step without further purification. 15.5 g of crude 7-{2-[4-Nitro-3-(2-pyrrolidin-1-yl-vinyl)-phenoxy]-ethyl}-3,4-dihydro-2H-[1,8]naphthyridine-1-carboxylic acid tert-butyl ester was dissolved in a 9:1 solution of EtOAc/MeOH in a Parr bottle. After evacuating and purging the solution with nitrogen, palladium on carbon [10% w/w] (1.52 g) was added and the mixture was shaken under an atmosphere of hydrogen at 50 psi overnight (16 h). The mixture was filtered through Celite and washed with methanol. The filtrate was concentrated in vacuo to afford a brown gum (15.8 g). The crude product was purified by column chromatography (SiO$_2$, 4:1 to 2:1 heptane/ethyl acetate) to give 7-[2-(1H-Indol-5-yloxy)-ethyl]-3,4-dihydro-2H-[1,8]naphthyridine-1-carboxylic acid tert-butyl ester as a gray solid contaminated with an impurity. The solid was washed with 1:1 ether/pet-ether (30 mL) to give the title compound (7.14 g, 54% yield) as a pure white solid. $^1$H NMR (CDCl$_3$) δ 7.31 (d, 1H, J=7.6 Hz), 7.26 (d, 1H, J=8.8 Hz), 7.17 (m, 1H), 7.13 (d, 1H, J=2.4 Hz), 6.96 (d, 1H, J=7.6 Hz), 6.85 (dd, 1H, J=2.4, 8.8 Hz), 6.45 (m, 1H), 4.38 (t, 2H, J=8.00 Hz), 3.76 (m, 2H,), 3.22 (t, 2H, J=8.00 Hz), 2.73 (m, 2H), 1.93 (m, 2H), 1.51 (s, 9H).

d) 7-{2-[1-(2-Ethoxycarbonyl-1-phenyl-vinyl)-1H-indol-5-yloxy]-ethyl}-3,4-dihydro-2H-[1,8]naphthyridine-1-carboxylic acid tert-butyl ester Method d1

CsF (15.2 g, 100 mmol) was added to a solution of 7-[2-(1H-indol-5-yloxy)-ethyl]-3,4-dihydro-2H-[1,8]naphthyridine-1-carboxylic acid tert-butyl ester (20.0 g, 50.8 mmol) in anhydrous DMF (50 mL). Ethyl phenylpropiolate (16.5 mL, 100 mmol) was added to the mixture at room temperature and the solution was allowed to stir under a nitrogen atmosphere at 60° C. for 4 h. The mixture was diluted with water (1 L), the crude mixture was dissolved in ethyl acetate (500 mL), washed with water, then brine, dried and concentrated under vacuum to give a yellow gum as crude product. Purification of the crude mixture on silica gel (1:1 pet-ether/ether) gave the title compound as a bright yellow solid (25.5 g, 88% yield), a mixture of E/Z isomers.

Method d2

A mixture of 7-[2-(1H-Indol-5-yloxy)-ethyl]-3,4-dihydro-2H-[1,8]naphthyridine-1-carboxylic acid tert-butyl ester (5.00 g, 12.7 mmol), phenyl-propionic acid ethyl ester (4.43 g, 25.4 mmol), and tetrabutylammonium fluoride [1.0 M in THF] (31.8 mL, 31.8 mmol) was stirred at 75° C. for 3 days. After removal of solvent, the crude reaction mixture was submitted to flash chromatography on silica gel (ethyl acetate/hexane, 1:4) to give the title compound (4.66 g, 78% yield) as an E/Z mixture. $^1$H NMR (CDCl$_3$) [E/Z mixture] δ 7.50–7.30 (m, 7H), 7.20 (m, 2H), 7.05 (m, 1H), 6.80 (m, 1H), 6.56 (m, 1H), 6.29 (s, 0.5H), 6.19 (s, 0.5H), 4.44 (m, 2H), 4.07 (q, 2H, J=6.8 Hz), 3.82 (m, 2H), 3.31 (m, 2H), 2.70 (m, 2H), 1.98 (m, 2H), 1.54 (s, 9H), 1.13 (t, 1.5H, J=7.2 Hz), 1.01 (t, 3H, J=7.2 Hz).

e) 7-{2-[1-(2-Ethoxycarbonyl-1-phenyl-ethyl)-1H-indol-5-yloxy]-ethyl}-3,4-dihydro-2H-[1,8]naphthyridine-1-carboxylic acid tert-butyl ester 10% Palladium on activated carbon (0.06 g) was added to 7-{2-[1-(2-ethoxycarbonyl-1-phenyl-vinyl)-1H-indol-5-yloxy]-ethyl}-3,4-dihydro-2H-[1,8]naphthyridine-1-carboxylic acid tert-butyl ester (0.50 g, 0.88 mmol) in methanol (10 mL) under argon. The solution was exposed to a hydrogen atmosphere (50 psi) using a Parr shaker for 24 h. The reaction was filtered through celite and washed with methanol. The filtrate was concentrated in vacuo to yield the title compound (0.48 g, 98%). $^1$H NMR (CDCl$_3$) δ 7.15–7.36 (m, 9H), 6.96 (d, 1H, J=7.6 Hz), 6.83 (dd, 1H, J=2.3, 6.6 Hz), 6.46 (d, 1H, J=3.0 Hz), 6.06 (d, 1H, J=7.6 Hz), 4.39 (m, 2H), 4.06 (q, 2H, J=7.1 Hz), 3.78 (m, 2H), 3.31–3.20 (m, 4H), 2.75 (m, 2H), 1.94 (m, 2H), 1.54 (s, 9H), 1.11 (t, 3H, J=7.1 Hz).

f) 3-Phenyl-3-{5-[2-(5,6,7,8-tetrahydro-[1,8]naphthyridin-2-yl)-ethoxy]-indol-1-yl}-propionic acid ethyl ester A solution of 7-{2-[1-(2-ethoxycarbonyl-1-phenyl-ethyl)-1H-indol-5-yloxy]-ethyl}-3,4-dihydro-2H-[1,8] naphthyridine-1-carboxylic acid tert-butyl ester (22.9 g, 40.0 mmol) in a 10:1 mixture of anhydrous toluene/DMF (220 mL) was treated with copper(I) trifluoromethanesulfonate benzene complex [30% w/w] (6.87 g) at 130° C. for 75 minutes. The mixture was cooled to room temperature, diluted with water (200 mL), extracted with dichloromethane (2×300 mL), washed with water, then brine, dried and concentrated under vacuum to give a black gum (26.0 g). Purification with silica gel (1:1 ethyl acetate/heptane) gave the title compound as an off-white solid (16.2 g, 86% yield). $^1$H NMR (CDCl$_3$) δ 7.29–6.98 (m, 10H), 6.73 (m, 1H), 6.36 (m, 1H), 5.94 (t, 1H, J=7.5 Hz), 4.69 (bs, 1H), 4.21 (t, 2H, J=7.0 Hz), 3.96 (q, 2H, J=7.1 Hz), 3.32 (m, 2H), 3.20 (m, 2H), 2.96 (t, 2H, J=7.0 Hz), 2.61 (m, 2H), 1.83 (m, 2H), 1.00 (t, 3H, J=7.2 Hz).

g) 3-Phenyl-3-{5-[2-(5,6,7,8-tetrahydro-[1,8]naphthyridin-2-yl)-ethoxy]-indol-1-yl}-propionic acid A solution of 3-phenyl-3-{5-[2-(5,6,7,8-tetrahydro-[1,8] naphthyridin-2-yl)-ethoxy]-indol-1-yl}-propionic acid ethyl ester (2.14 g, 4.49 mmol) in a 2:1:0.2 THF/MeOH/H$_2$O (67 mL) was treated with lithium hydroxide monohydrate (0.38 g, 9.00 mmol) at room temperature. The reaction was stirred for 20 h. The mixture was diluted with ethyl acetate, acidified to pH 4 (0.5 N HCl), washed with water and brine, dried and concentrated to afford a crude mixture (2.02 g), which was purified by column chromatography with silica gel (39:1 to 29:1 dichloromethane/MeOH) to give the title compound (1.31 g, 66% yield). $^1$H NMR (CDCl$_3$) δ 10.5 (s, 1H), 7.44 (d, 1H, J=3.1 Hz), 7.20–7.00 (m, 7H), 6.76 (m, 1H), 6.53 (dd, 1H, J=2.3, 6.6 Hz), 6.41 (s, 1H), 6.19 (d, 1H, J=7.3 Hz), 6.07 (dd, 1H, J=4.3, 7.1 Hz), 3.68 (m, 1H), 3.52 (m, 1H), 3.33 (m, 3H), 3.25–3.09 (m, 2H), 2.58 (m, 3H), 1.77 (m, 3H). Mass Spectrum (LCMS, ESI) calculated for C$_{27}$H$_{28}$N$_3$O$_3$ 442.2 (M+H); found 442.3.

EXAMPLE 17

3-Phenyl-3-{5-[2-(5,6,7,8-tetrahydro-[1,8]naphthyridin-2-yl)-ethoxy]-indol-1-yl}-propionic acid

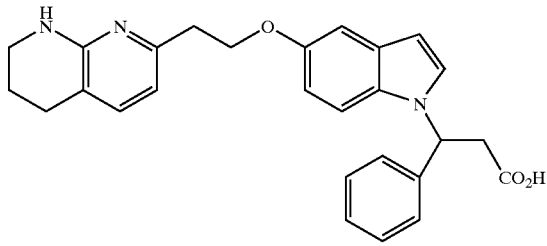

a) 3-(5-Benzyloxy-indol-1-yl)-3-phenyl-acrylic acid ethyl ester

A mixture of 5-benzyloxy-1H-indole (4.46 g, 20.0 mmol), phenyl-propionic acid ethyl ester (7.00 g, 40.0 mmol), and tetrabutylammonium fluoride [1.0 M in THF] (36.0 mL, 50.0 mmol) was stirred for 3 days. After removal of solvent, the crude reaction mixture was submitted to flash chromatography on silica gel with ethyl acetate/hexane (1:4) to give the title compound (5.42 g, 68% yield) as an E/Z isomeric mixture. Mass Spectrum (LCMS, ESI) calculated for C$_{26}$H$_{24}$NO$_3$ 398.2 (M+H); found 398.2.

b) 3-(5-Hydroxy-indol-1-yl)-3-phenyl-propionic acid ethyl ester

A mixture of 3-(5-benzyloxy-indol-1-yl)-3-phenyl-acrylic acid ethyl ester (1.94 g, 4.89 mmol) and palladium on carbon [10% w/w] (60 mg) in methanol (25 mL) was stirred under hydrogen atmosphere for 24 h. After removal of the catalyst by filtration, the crude product was purified by flash chromatography on silica gel with hexane/ethyl acetate (4:1) to give the title compound in 96% yield. $^1$H NMR (CDCl$_3$) δ 7.10–7.30 (m, 7H), 6.99 (d, J=2.4 Hz, 1H), 6.69 (dd, J=2.4 and 8.7 Hz, 1H), 6.39 (d, J=3.2 Hz, 1H), 5.99 (t, J=7.6 Hz, 1H), 5.31 (br, 1H), 4.03 (q, J=7.2 Hz, 2H), 3.26 (m, 2H), 1.08 (t, J=7.2 Hz, 3H). $^{13}$C NMR (CDCl$_3$) δ 170.4, 149.7, 139.8, 131.5, 129.3, 128.8, 127.9, 126.2, 125.8, 111.6, 110.6, 105.2, 101.4, 61.1, 56.2, 40.4, 13.9. Mass Spectrum (LCMS, ESI) calculated for C$_{19}$H$_{20}$NO$_3$ 310.1 (M+H); found 310.1.

c) 7-{2-[1-(2-Ethoxycarbonyl-1-phenyl-vinyl)-1H-indol-5-yloxy]-ethyl}-3,4-dihydro-2H-[1,8]naphthyridine-1-carboxylic acid tert-butyl ester The title compound was synthesized as an E/Z isomeric mixture from 3-(5-hydroxy-indol-1-yl)-3-phenyl-propionic acid ethyl ester using the procedure described in Example 16, step (d2), in 81% yield. Mass Spectrum (LCMS, ESI) calculated for C$_{29}$H$_{30}$N$_3$O$_3$ 468.2 (M-Boc+H); found 469.4.

d) 7-{2-[1-(2-Ethoxycarbonyl-1-phenyl-ethyl)-1H-indol-5-yloxy]-ethyl}-3,4-dihydro-2H-[1,8]naphthyridine-1-carboxylic acid tert-butyl ester The title compound was synthesized from 3-(5-hydroxy-indol-1-yl)-3-phenyl-propionic acid ethyl ester using the procedure described in Example 14, step (b), in 24% yield. $^1$H NMR (CDCl$_3$) δ 7.28 (m, 4H), 7.18 (m, 4H), 7.09 (d, J=2.9 Hz, 1H), 6.93 (d, J=7.7 Hz, 1H), 6.80 (dd, J=2.5 and 7.9 Hz 1H), 6.43 (dd, J=0.6 and 3.2 Hz, 1H), 6.00 (m, 1H), 4.35 (t, J=6.9 Hz, 2H), 4.02 (q, J=7.0 Hz, 2H), 3.75 (m, 2H), 3.26 (q, 2H), 3.19 (t, J=6.9 Hz, 2H), 2.71 (t, J=6.7 Hz, 2H), 1.92 (m, 2H), 1.51 (s, 9H), 1.08 (t, J=7.1 Hz, 3H). Mass Spectrum (LCMS, ESI) calculated for C$_{34}$H$_{40}$N$_3$O$_5$ 570.2 (M+H), found 570.0 (M+H).

e) 3-Phenyl-3-{5-[2-(5,6,7,8-tetrahydro-[1,8]naphthyridin-2-yl)-ethoxy]-indol-1-yl}-propionic acid ethyl ester The title compound was synthesized from 7-{2-[1-(2-ethoxycarbonyl-1-phenyl-ethyl)-1H-indol-5-yloxy]-ethyl}-3,4-dihydro-2H-[1,8]naphthyridine-1-carboxylic acid tert-butyl ester using the procedure described in Example 14, step (d), in 43% yield. $^1$H NMR (CDCl$_3$) δ 7.29 (m, 3H), 7.19 (m, 4H), 7.08 (m, 2H), 6.81 (dd, J=2.4 and 8.9 Hz, 1H), 6.45 (m, 2H), 6.03 (t, 1H), 4.86 (br, 1H), 4.28 (t, J=7.1 Hz, 2H), 4.06 (q, J=6.1 Hz, 2H), 3.39 (m, 2H), 3.27 (m, 2H), 3.04 (t, J=7.0 Hz, 2H), 2.68 (t, J=6.3 Hz, 2H), 1.88 (m, 2H), 1.08 (t, J=7.1 Hz, 3H). Mass Spectrum (LCMS, ESI) calculated for C$_{29}$H$_{32}$N$_3$O$_3$ 470.2 (M+H); found 470.3.

f) 3-Phenyl-3-{5-[2-(5,6,7,8-tetrahydro-[1,8]naphthyridin-2-yl)-ethoxy]-indol-1-yl}-propionic acid The title compound was synthesized from 3-phenyl-3-{5-[2-(5,6,7,8-tetrahydro-[1,8]naphthyridin-2-yl)-ethoxy]-indol-1-yl}-propionic acid ethyl ester using the procedure described in Example 14, step (e), in 51% yield. $^1$H NMR (CDCl$_3$) δ 10.59 (br, 1H), 7.08–7.27 (m, 8H), 6.84 (d, J=2.4 Hz, 1H), 6.61 (dd, J=2.4 and 8.9 Hz, 1H), 6.48 (m, 1H), 6.26 (d, J=7.3 Hz, 1H), 6.13 (dd, J=4.4 Hz, 1H), 3.59 (m, 1H), 3.17–3.42 (m, 5H), 2.40–2.64 (m, 4H), 1.84 (m, 2H). Mass Spectrum (LCMS, ESI) calculated for C$_{27}$H$_{28}$N$_3$O$_3$ 442.2 (M+H); found 442.4.

EXAMPLE 18

3-(3-Benzyloxy-phenyl)-3-{5-[2-(5,6,7,8-tetrahydro-[1,8]naphthyridin-2-yl)-ethoxy]-indol-1-yl}-propionic acid

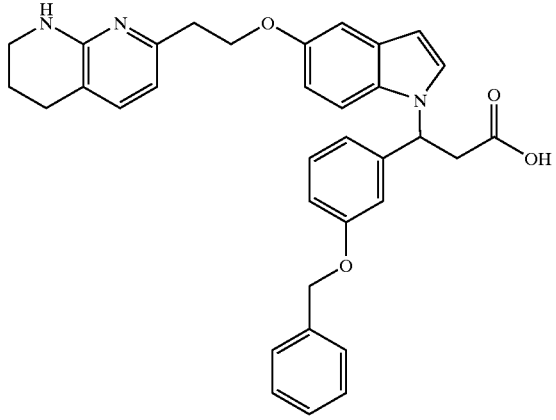

a) (3-Benzyloxy-phenylethynyl)-trimethyl-silane

To a solution of 3-benzyloxy-1-iodophenyl (8.40 g, 27.0 mmol), trimethylsilyl acetylene (4.21 mL, 29.8 mmol), copper(I) iodide (0.51 g, 2.71 mmol), and triethylamine (8.22 mL, 81.2 mmol) in dichloromethane (30 mL) was added dichlorobis(triphenylphosphine) palladium(II) (0.38 g, 5.41 mmol) portionwise over a 3 minute period, and the reaction mixture stirred overnight. The mixture was then concentrated and the resulting residue was filtered through Celite. The filtrate was concentrated, and purified via column chromatography with silica gel, eluting with dichloromethane/hexane/ethyl acetate (10/1) to give the title compound (98% yield) as pale yellow oil. $^1$H NMR (CDCl$_3$) δ 7.43–7.32 (m, 5H), 7.19 (m, 1H), 7.08 (m, 2H), 6.92 (m, 1H), 5.04 (s, 2H), 0.24 (s, 9H).

b) 3-Benzyloxy-phenylethynyl

Tetrabutylammonium fluoride [1.0 M in THF] (28.0 mL) was added dropwise at room temperature to a solution of (3-benzyloxy-phenylethynyl)-trimethyl-silane (6.40 g, 22.7 mmol) in aqueous THF (30 mL) and the reaction was stirred for 1 hour. Water (100 mL) was added and the crude product was extracted with ethyl acetate (3×50 mL), dried over magnesium sulfate and concentrated. The crude mixture was then purified via column chromatography with silica gel (10% ethyl acetate in hexane) to give the title compound (89% yield). $^1$H NMR (CDCl$_3$) δ 7.42–7.29 (m, 5H), 7.21 (m, 1H), 7.09 (m, 2H), 6.95 (m, 1H), 5.03 (s, 2H), 3.04 (s, 1H).

c) 3-(3-Benzyloxy-phenyl)-3-chloro-acrylic acid ethyl ester

A mixture of ethyl chloroformate (2.90 mL, 26.7 mmol), 3-benzyloxy-phenylethynyl (2.50 g, 8.91 mmol), and carbonylchlorobis-(triphenylphosphine)-rhodium(I) (0.03 g, 0.05 mmol) in toluene (10 ML) was heated under argon at 110° C. for 12 h. The solvent was removed under reduced pressure and the crude product was purified by chromatography on silica gel, eluting with hexane/ethyl acetate (10/1) to give the title compound (50%) as yellow oil. $^1$H NMR (CDCl$_3$) δ 7.48–7.28 (m, 8H), 7.06 (m, 1H), 6.57 (s, 1H), 5.12 (s, 2H), 4.31 (q, 2H, J=7.1 Hz), 1.37 (t, 3H, J=7.1 Hz).

d) 7-(2-{1-[1-(3-Benzyloxy-phenyl)-2-ethoxycarbonyl-vinyl]-1H-indol-5-yloxy}-ethyl)-3,4-dihydro-2H-[1,8] naphthyridine-1-carboxylic acid tert-butyl ester A solution of 7-[2-(1H-indol-5-yloxy)-ethyl]-3,4-dihydro-2H-[1,8]naphthyridine-1-carboxylic acid tert-butyl ester (0.20 g, 0.51 mmol), 7-(2-{1-[1-(3-benzyloxy-phenyl)-2-ethoxycarbonyl-vinyl]-1H-indol-5-yloxy}-ethyl)-3,4-dihydro-2H-[1,8]naphthyridine-1-carboxylic acid tert-butyl ester (0.18 g, 0.56 mmol), potassium phosphate (0.16 g, 0.77 mmol), 2-dicyclohexylphosphino-2'(N,N-dimethylamino) biphenyl (0.03 g, 0.08 mmol) and tris(dibenzylideneacetone) dipalladium(0) (0.03 mg, 0.08 mmol) in 10% DMF/toluene (3 mL) was heated at 110° C. for 6 days under argon. The reaction was cooled to room temperature and the solvent was removed under reduced pressure. The crude product was purified by column chromatography with silica gel, eluting with hexane/ethyl acetate (4/1) to give the title compound (29%) as an E/Z isomeric mixture. $^1$H NMR (CDCl$_3$) [E/Z mixture] δ 7.36–7.22 (m, 7H), 7.10 (m, 4H), 6.86 (m, 3H), 6.75 (m, 1H), 6.58 (m, 1H), 6.22 (s, 1H), 5.00 (s, 2H), 4.40 (m, 2H), 4.01 (q, 2H, J=7.2 Hz), 3.78 (m, 2H), 3.22 (m, 2H), 2.75 (m, 2H), 1.85 (m, 2H), 1.52 (s, 9H), 1.01 (t, 3H, J=6.8 Hz).

e) 7-(2-{1-[1-(3-Benzyloxy-phenyl)-2-ethoxycarbonyl-ethyl]-1H-indol-5-yloxy}-ethyl)-3,4-dihydro-2H-[1,8] naphthyridine-1-carboxylic acid tert-butyl ester Samarium(II) iodide [0.1 M in THF] (14.8 mL, 14.8 mmol) was added to a solution of 7-(2-{1-[1-(3-benzyloxy-phenyl)-2-ethoxycarbonyl-vinyl]-1H-indol-5-yloxy}-ethyl)-3,4-dihydro-2H-[1,8]naphthyridine-1-carboxylic acid tert-butyl ester (0.10 g, 0.15 mmol), hexamethylphosphoramide (0.39 mL, 2.22 mmol) and either ethanol or methanol (10 equivalents) and stirred at room temperature overnight. Saturated ammonium chloride (20 mL) was added to the reaction and the crude product was extracted with ethyl acetate (3×20 mL). The crude mixture was then purified via column chromatography in silica gel (20% ethyl acetate in hexane) to give the title compound (0.50 g, 50% yield). $^1$H NMR (CDCl$_3$) δ 7.28–7.22 (m, 5H), 7.13 (m, 4H), 7.08 (d, 1H, J=3.2 Hz), 6.86 (m, 1H), 6.79–6.69 (m, 4H), 6.35 (d, 1H, J=3.2 Hz), 5.99 (t, 1H, J=7.5 Hz), 4.98 (s, 2H), 4.29 (t, 2H, J=6.9 Hz), 3.96 (q, 2H, J=7.1 Hz), 3.68 (m, 2H), 3.18–3.10 (m, 4H), 2.66 (m, 2H), 1.85 (m, 2H), 1.45 (s, 9H), 1.01 (t, 3H, J=7.1 Hz).

f) 3-(3-Benzyloxy-phenyl)-3-{5-[2-(5,6,7,8-tetrahydro-[1,8] naphthyridin-2-yl)-ethoxy]-indol-1-yl}-propionic acid ethyl ester The title compound was synthesized from 7-(2-{f1-[1-(3-benzyloxy-phenyl)-2-ethoxycarbonyl-ethyl]-1H-indol-5-yloxy}-ethyl)-3,4-dihydro-2H-[1,8]naphthyridine-1-carboxylic acid tert-butyl ester using the procedure described in Example 16, step (f), in 43% yield. $^1$H NMR (CDCl$_3$) δ 7.36–7.32 (m, 4H), 7.17–7.07 (m, 6H), 6.77 (m, 4H), 6.43 (m, 2H), 5.99 (m, 1H), 4.96 (s, 2H), 4.90 (bs, 1H), 4.28 (m, 2H), 4.03 (q, 2H, J=7.1 Hz), 3.39 (m, 2H), 3.23 (m, 2H), 2.68 (m, 2H), 2.52 (m, 2H), 1.89 (m, 2H), 1.01 (t, 3H, J=7.1 Hz).

g) 3-(3-Benzyloxy-phenyl)-3-{5-[2-(5,6,7,8-tetrahydro-[1,8]naphthyridin-2-yl)-ethoxy]-indol-1-yl}-propionic acid A solution of 3-(3-benzyloxy-phenyl)-3-{5-[2-(5,6,7,8-tetrahydro-[1,8]naphthyridin-2-yl)-ethoxy]-indol-1-yl}-propionic acid ethyl ester (0.08 g, 0.14 mmol), lithium hydroxide (0.01 g, 0.22 mmol) and THF/methanol/water [2.0/1.0/0.2 mL] (3.2 mL) was microwave at 100° C. for 15 minutes. Saturated ammonium chloride was added (10 mL) and the product was extracted with ethyl acetate (3×10 mL). The crude product was purified via column chromatography eluting with dichloromethane: ethyl acetate (10:1) to give the title compound (25% yield) as white solid. $^1$H NMR (CDCl$_3$) δ 10.5 (bs, 1H), 7.49 (d, 1H, J=3.0 Hz), 7.39–7.22 (m, 6H), 7.16 (m, 1H), 7.08 (m, 1H), 6.80 (m, 4H), 6.60 (dd, 1H, J=2.2, 6.8 Hz), 6.46 (m, 1H), 6.26 (d, 1H, J=7.3 Hz), 6.09 (m, 1H), 5.29 (s, 2H), 3.59 (s, 1H), 3.38 (m, 3H), 3.29–3.14 (m, 2H), 2.60–2.43 (m, 5H), 1.87 (m, 2H). Mass Spectrum (LCMS, ESI) calculated for C$_{34}$H$_{34}$N$_3$O$_4$ 548.3 (M+H); found 548.4.

EXAMPLE 19

3-{5-[2-(5,6,7,8-Tetrahydro-[1,8]naphthyridin-2-yl)-ethoxy]-indol-1-yl}-3-p-tolyl-propionic acid

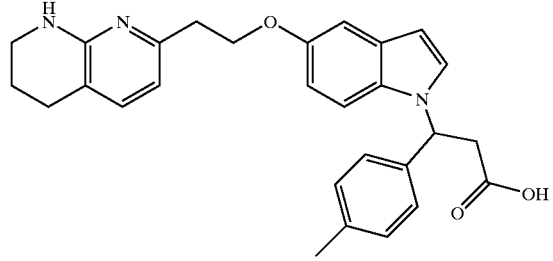

a) 1-Ethynyl-4-methyl-benzene

The title compound was synthesized from commercially available 4-iodotoluene using the procedures outlined in Example 18, step (a) and step (b), in 60% yield overall. $^1$H NMR (CDCl$_3$) δ 7.38 (d, 2H, J=2.4 Hz), 7.12 (d, 2H, J=2.4 Hz), 3.02 (s, 1H), 2.35 (s, 3H)

b) 3-Chloro-3-p-tolyl-acrylic acid ethyl ester

The title compound was synthesized from 1-ethynyl-4-methyl-benzene using the procedure outlined in Example 18, step (c), in 70% yield. ¹H NMR (CDCl₃) δ 7.58 (d, 2H, J=2.4 Hz), 7.21 (d, 2H, J=2.4 Hz), 6.52 (s, 1H), 4.27 (m, 2H), 2.39 (s, 3H), 1.33 (t, 3H, J=7.2 Hz).

c) 7-{2-[l1-(2-Ethoxycarbonyl-1-p-tolyl-vinyl)-1H-indol-5-yloxy]-ethyl}-3,4-dihydro-2H-[1,8]naphthyridine-1-carboxylic acid tert-butyl ester The title compound was synthesized from 3-chloro-3-p-tolyl-acrylic acid ethyl ester and 7-[2-(1H-indol-5-yloxy)-ethyl]-3,4-dihydro-2H-[1,8]naphthyridine-1-carboxylic acid tert-butyl ester using the procedure outlined in Example 18, step (d), in a 36% yield of E/Z isomeric mixture. ¹H NMR (CDCl₃) [E/Z mixture] δ 7.33 (m, 1.4H), 7.17 (m, 4.6H), 6.96 (m, 1.6H), 6.74 (m, 2.4H), 6.57 (d, 0.8H, J=0.8 Hz), 6.50 (d, 0.2H, J=0.8 Hz), 6.20 (s, 0.8H), 6.11 (s, 0.2H), 4.39 (t, 2H, J=8.0), 4.01 (m, 2H), 3.78 (t, 2H, J=4.0), 3.22 (t, 2H, J=8.0), 2.75 (t, 2H, J=8.0), 2.44 (s, 0.6H), 2.40 (s, 2.4H), 1.94 (m, 2H), 1.53 (s, 9H), 1.05 (t, 3H, J=8.0 Hz).

d) 7-{2-[1-(2-Ethoxycarbonyl-1p-tolyl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-p-tolyl-vinyl)-1H-indol-5-yloxy]-ethyl}-3,4-dihydro-2H-[1,8]naphthyridine-1-carboxylic acid tert-butyl ester using the procedure outlined in Example 18, step (e). Transesterification occurred during the reduction, resulting in a 1:4 mixture of ethyl and methyl esters, in a 60% yield. ¹H NMR (CDCl₃) δ 7.30 (d, 1H, J=7.2 Hz), 7.18 (m, 2H), 7.10 (m, 5H), 6.94 (d, 1H, J=7.6 Hz), 6.80 (dd, 1H, J=2.4, 7.6 Hz), 6.41 (d, 1H, J=3.2 Hz), 5.98 (t, 1H, J=7.6 Hz), 4.35 (t, 2H, J=6.8 Hz), 4.13 (m, 0.4H, ethyl ester), 3.77 (m, 2H), 3.59 (s, 2.4H, methyl ester), 3.27 (m, 2H), 3.20 (t, 2H, J=6.8 Hz), 2.72 (t, 2H, J=6.8 Hz), 2.31, (s, 3H), 1.95 (m, 2H), 1.49 (s, 9H), 1.11 (t, 0.6H, J=7.2 Hz, ethyl ester).

e) 3-{5-[2-(5,6,7,8-Tetrahydro-[1,8]naphthyridin-2-yl)-ethoxy]-indol-1-yl}-3-p-tolyl-propionic acid ethyl ester The title compound was synthesized from 7-{2-[1-(2-Ethoxycarbonyl-1-p-tolyl-ethyl)-1H-indol-5-yloxy]-ethyl}-3,4-dihydro-2H-[1,8]naphthyridine-1-carboxylic acid tert-butyl ester using the procedure outlined in Example 16, step (f), in a 78% yield of a 1:1 mixture of ethyl and methyl esters. ¹H NMR (CDCl₃) δ 7.16 (m, 3H), 7.08 (m, 5H), 6.81 (dd, 1H, J=2.4, 9.6 Hz), 6.48 (d, 1H, J=8.0 Hz), 6.43 (d, 1H, J=4.0 Hz), 5.98 (t, 1H, J=8.0 Hz), 5.17 (s, 1H), 4.27 (t, 2H, J=8.0 Hz), 4.03 (m, 1H, ethyl ester), 3.59 (s, 1.5H, methyl ester) 3.39 (m, 2H), 3.25 (m, 2H), 3.07 (t, 2H, J=8.0 Hz), 2.69 (t, 2H, J=6.8 Hz), 2.29 (s, 3H), 1.90 (m, 2H), 1.10 (t, 1.5H, J=7.2 Hz, ethyl ester).

f) 3-{5-[2-(5,6,7,8-Tetrahydro-[1,8]naphthyridin-2-yl)-ethoxy]-indol-1-yl}-3-p-tolyl-propionic acid The title compound was synthesized from 3-{5-[2-(5,6,7,8-tetrahydro-[1,8]naphthyridin-2-yl)-ethoxy]-indol-1-yl}-3-p-tolyl-propionic acid ethyl ester using the procedure outlined in Example 18, step (g), in 23% yield. ¹H NMR (DMSO-d₆) δ 7.62 (d, 1H, J=3.2 Hz), 7.35 (d, 1H, J=9.0 Hz), 7.20 (d, 2H, J=8.1 Hz), 7.06 (m, 3H), 7.01 (d, 1H, J=4.0 Hz), 6.69 (dd, 1H, J=2.4, 6.5 Hz), 6.36 (m, 3H), 5.89 (m, 1H), 4.19 (t, 2H, J=6.9 Hz), 3.25 (m, 4H) 2.86 (t, 2H, J=6.9 Hz), 2.60 (t, 2H, J=6.1 Hz), 2.21 (s, 3H), 1.74 (m, 2H). Mass Spectrum (LCMS, ESI) calculated for C₂₈H₃₀N₃O₃: 456.2 (M+H); found 456.3.

EXAMPLE 20

3-{5-[2-(5,6,7,8-Tetrahydro-[1,8]naphthyridin-2-yl)-ethoxy]-indol-1-yl}-3-m-tolyl-propionic acid

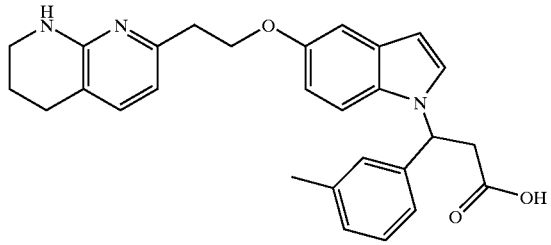

a) 1-Ethynyl-3-methyl-benzene

The title compound was synthesized from commercially available 3-iodotoluene using the procedures outlined in Example 18, step (a) and step (b), in 37% yield overall. ¹H NMR (CDCl₃) δ 7.32 (m, 2H), 7.18 (m, 2H), 3.03 (s, 1H), 2.32 (s, 3H).

b) 3-Chloro-3-m-tolyl-acrylic acid ethyl ester

The title compound was synthesized from 1-ethynyl-3-methyl-benzene using the procedure outlined in Example 18, step (c), in 70% yield. ¹H NMR (CDCl₃) δ 7.48 (m, 2H), 7.29 (m, 2H), 6.53 (s, 1H), 4.27 (m, J=8.0 Hz), 2.39 (s, 3H), 1.34 (t, 3H, J=7.2 Hz).

c) 7-{2-[1-(2-Ethoxycarbonyl-1-m-tolyl-vinyl)-1H-indol-5-yloxy]-ethyl}-3,4-dihydro-2H-[1,8]naphthyridine-1-carboxylic acid tert-butyl ester The title compound was synthesized from 3-chloro-3-m-tolyl-acrylic acid ethyl ester and 7-[2-(1H-indol-5-yloxy)-ethyl]-3,4-dihydro-2H-[1,8]naphthyridine-1-carboxylic acid tert-butyl ester using the procedure outlined in Example 18, step (d), in a 40% yield as an E/Z isomeric mixture. ¹H NMR (CDCl₃) δ 7.19 (m, 2.2H), 7.04 (m, 2.6H), 6.96 (m, 1.6H), 6.86 (m, 1.6H), 6.66 (m, 2H), 6.48 (d, 0.8H, J=0.8 Hz), 6.40 (d, 0.2H, J=0.8 Hz), 6.11 (s, 0.8H), 6.04 (s, 0.2H), 4.30 (m, 2H), 3.93 (m, 2H), 3.68 (m, 2H), 3.13 (t, 2H, J=6.4), 2.65 (t, 2H, J=6.4 Hz), 2.24 (s, 3H), 1.85 (m, 2H), 1.43 (s, 9H), 0.94 (t, 3H, J=6.8 Hz).

d) 7-{2-[1-(2-Ethoxycarbonyl-1-p-tolyl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-m-tolyl-vinyl)-1H-indol-5-yloxy]-ethyl}-3,4-dihydro-2H-[1,8]naphthyridine-1-carboxylic acid tert-butyl ester using the procedure outlined in Example 18, step (e). Transesterification occurred during the reduction, resulting in a 2:3 mixture of ethyl and methyl esters, in a 58% yield. ¹H NMR (CDCl₃) δ 7.31 (d, 1H, J=4.4 Hz), 7.21 (m, 3H), 7.05 (m, 5H), 6.83 (dd, 1H, J=2.4, 9.6 Hz), 6.48 (d, 1H, J=3.2 Hz), 5.99 (t, 1H, J=7.6 Hz), 4.37 (t, 2H, J=7.0 Hz), 4.05 (m, 0.8H, ethyl ester), 3.77 (m, 2H), 3.60 (s, 1.8H, methyl ester) 3.28 (m, 2H), 3.21 (t, 2H, J=6.8 Hz), 2.74 (t, 2H, J=6.8 Hz), 2.29 (s, 3H), 1.93 (m, 2H), 1.52 (s, 9H), 1.10 (t, 1.2H, J=7.2 Hz, ethyl ester).

e) 3-{5-[2-(5,6,7,8-Tetrahydro-[1,8]naphthyridin-2-yl)-ethoxy]-indol-1-yl}-3-m-tolyl-propionic acid ethyl ester The title compound was synthesized from 7-{2-[1-(2-ethoxycarbonyl-1-p-tolyl-ethyl)-1H-indol-5-yloxy]-ethyl}-3,4-dihydro-2H-[1,8]naphthyridine-1-carboxylic acid tert-butyl ester using the procedure described in Example 16, step (f), in a 75% yield of a 1:1 mixture of ethyl and methyl ester. ¹H NMR (CDCl₃) δ 7.19 (m, 4H), 7.05 (m, 5H), 6.81 (dd, 1H, J=2.4, 9.6 Hz), 6.48 (d, 1H, J=8.0 Hz), 6.43 (d, 1H, J=3.2 Hz), 5.97 (t, 1H, J=8.0 Hz), 5.30 (s, 1H), 4.29 (t, 2H, J=8.0 Hz), 4.05 (m, 1H, ethyl ester), 3.59 (s, 1.5H, methyl ester) 3.39 (t, 2H, J=8.0 Hz), 3.25 (m, 2H), 3.04 (t, 2H, J=8.0 Hz), 2.69 (t, 2H, J=6.8 Hz), 2.28 (s, 3H), 1.90 (m, 2H), 1.08 (t, 1.5H, J=8.0 Hz, ethyl ester)

f) 3-{5-[2-(5,6,7,8-Tetrahydro-[1,8]naphthyridin-2-yl)-ethoxy]-indol-1-yl}-3-m-tolyl-propionic acid The title compound synthesized from 3-{5-[2-(5,6,7,8-tetrahydro-[1,8]naphthyridin-2-yl)-ethoxy]-indol-1-yl}-3-m-tolyl-propionic acid ethyl ester using the procedure described in Example 18, step (g), in 37% yield. $^1$H NMR (CDCl$_3$) δ 10.39 (s, 1H), 7.43 (d, 1H, J=4.0 Hz), 7.20 (d, 1H, J=8.0 Hz), 7.05 (m, 2H), 6.90 (m, 3H), 6.77 (d, 1H, J=4.0 Hz), 6.54 (dd, 1H, J=4.0, 8.0 Hz), 6.40 (d, 1H, J=4.0 Hz), 6.19 (d, 1H, J=8.0 Hz), 6.02 (dd, 1H, J=4.0, 8.0 Hz), 3.25 (m, 6H) 2.45 (m, 4H), 2.19 (m, 3H), 1.76 (m, 2H). Mass Spectrum (LCMS, ESI) calculated for $C_{28}H_{30}N_3O_3$: 456.2 (M+H); found 456.3.

EXAMPLE 21

3-{5-[2-(5,6,7,8-Tetrahydro-[1,8]naphthyridin-2-yl)-ethoxy]-indol-1-yl}-3-o-tolyl-propionic acid

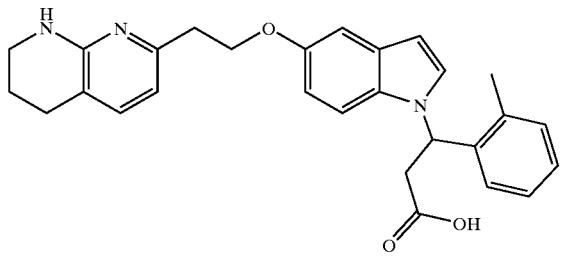

a) 1-Ethynyl-2-methyl-benzene

The title compound was synthesized from commercially available 2-iodotoluene using the procedures outlined in Example 18, step (a) and step (b), in 45% yield overall. $^1$H NMR (CDCl$_3$) δ 7.45 (m, 1H), 7.24 (m, 2H), 7.13 (m, 1H), 3.26 (s, 1H), 2.45 (s, 3H).

b) 3-Chloro-3-o-tolyl-acrylic acid ethyl ester

The title compound was synthesized from 1-ethynyl-2-methyl-benzene using the procedure outlined in Example 18, step (c), in 70% yield. $^1$H NMR (CDCl$_3$) δ 7.25 (m, 5H), 6.17 (s, 1H), 4.27 (m, 2H), 2.40 (s, 3H), 1.34 (t, 3H, J=7.2 Hz).

c) 7-{2-[1-(2-Ethoxycarbonyl-1-o-tolyl-vinyl)-1H-indol-5-yloxy]-ethyl}-3,4-dihydro-2H-[1,8]naphthyridine-1-carboxylic acid tert-butyl ester The title compound was synthesized from 3-chloro-3-o-tolyl-acrylic acid ethyl ester and 7-[2-(2H-indol-5-yloxy)-ethyl]-3,4-dihydro-2H-[1,8]naphthyridine-1-carboxylic acid tert-butyl ester using the procedure outlined in Example 18, step (d), in a 35% yield of an E/Z isomeric mixture. $^1$H NMR (CDCl$_3$) δ 7.46 (m, 0.6H), 7.30 (m, 4.8H), 7.10 (m, 1.6H), 7.03 (d, 0.6H, J=3.6 Hz), 6.94 (m, 1H), 6.85 (m, 0.4H), 6.70 (m, 1H), 6.53 (d, 0.8H, J=2.8 Hz), 6.47 (d, 0.2H, J=2.8 Hz), 6.30 (s, 0.2H), 5.82 (s, 0.8H), 4.39 (m, 2H), 4.10 (m, 2H), 3.78 (m, 2H), 3.22 (t, 2H, J=6.8), 2.75 (t, 2H, J=6.8), 2.07 (s, 2.4H), 2.02 (s, 0.6H), 1.94 (m, 2H), 1.53 (s, 9H), 1.05 (m, 3H).

d) 7-{2-[1-(2-Ethoxycarbonyl-1-o-tolyl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-o-tolyl-vinyl)-1H-indol-5-yloxy]-ethyl}-3,4-dihydro-2H-[1,8]naphthyridine-1-carboxylic acid tert-butyl ester using the procedure described in Example 18, step (e). Transesterification occurred during the reduction, resulting in a 4:1 mixture of ethyl and methyl ester in a 72% yield. $^1$H NMR (CDCl$_3$) δ 7.25 (m, 7H), 7.15 (d, 1H, J=2.4 Hz), 7.05 (m, 2H), 6.85 (dd, 1H, J=2.4, 9.6 Hz), 6.39 (d, 1H, J=3.2 Hz), 5.99 (t, 1H, J=7.6 Hz), 4.38 (t, 2H, J=7.0 Hz), 4.03 (m, 1.6H, ethyl ester), 3.77 (m, 2H), 3.60 (s, 0.6H, methyl ester), 3.21 (m, 4H), 2.74 (t, 2H, J=6.8 Hz), 2.40 (s, 3H), 1.93 (m, 2H), 1.53 (s, 9H), 1.10 (t, 2.4H, J=7.2 Hz, ethyl ester).

e) 3-{5-[2-(5,6,7,8-Tetrahydro-[1,8]naphthyridin-2-yl)-ethoxy]-indol-1-yl}-3-p-tolyl-propionic acid ethyl ester The title compound was synthesized from 7-{2-[1-(2-ethoxycarbonyl-1-o-tolyl-ethyl)-1H-indol-5-yloxy]-ethyl}-3,4-dihydro-2H-[1,8]naphthyridine-1-carboxylic acid tert-butyl ester using the procedure described in Example 16, step (f), in a 75% yield of a 1:1 mixture of ethyl and methyl esters. $^1$H NMR (CDCl$_3$) δ 7.17 (m, 5H), 7.05 (m, 2H), 6.94 (d, 1H, J=3.2 Hz), 6.81 (dd, 1H, J=2.4, 6.4 Hz), 6.46 (d, 1H, J=7.6 Hz), 6.34 (d, 1H, J=3.2 Hz), 6.13 (t, 1H, J=7.2 Hz), 4.91 (s, 1H), 4.26 (t, 2H, J=6.8 Hz), 4.10 (m, 1H ethyl ester), 3.56 (s, 1.5H, methyl ester), 3.38 (m, 2H), 3.17 (t, 2H, J=7.2 Hz), 3.08 (t, 2H, J=1.2 Hz), 2.67 (t, 2H, J=6.8 Hz), 2.20 (s, 3H), 1.88 (m, 2H), 1.07 (t, 1.5H, J=7.2 Hz).

f) 3-{5-[2-(5,6,7,8-Tetrahydro-[1,8]naphthyridin-2-yl)-ethoxy]-indol-1-yl}-3-o-tolyl-propionic acid The title compound was synthesized from 3-{5-[2-(5,6,7,8-tetrahydro-[1,8]naphthyridin-2-yl)-ethoxy]-indol-1-yl}-3-p-tolyl-propionic acid ethyl ester using the procedure outlined in Example 18, step (g), in 30% yield. $^1$H NMR (DMSO-d$_6$) δ 7.49 (d, 1H, J=3.2 Hz), 7.33 (s, 1H), 7.14 (m, 5H), 7.05 (d, 1H, J=2.4 Hz), 6.69 (dd, 1H, J=2.4, 6.5 Hz), 6.55 (d, 1H, J=6.8 Hz), 6.38 (d, 1H, J=3.2 Hz), 6.06 (m, 1H), 4.21 (t, 2H, J=6.5 Hz), 3.21 (m, 4H), 2.99 (t, 2H, J=6.0 Hz), 2.67 (t, 2H, J=6.0 Hz), 2.34 (s, 3H), 1.77 (m, 2H), Mass Spectrum (LCMS, ESI) calculated for $C_{28}H_{30}N_3O_3$: 456.2 (M+H); found 456.3.

EXAMPLE 22

3-Biphenyl-4-yl-3-{5-[2-(5,6,7,8-tetrahydro-[1,8] naphthyridin-2-yl)-ethoxy]-indol-1-yl}-propionic acid

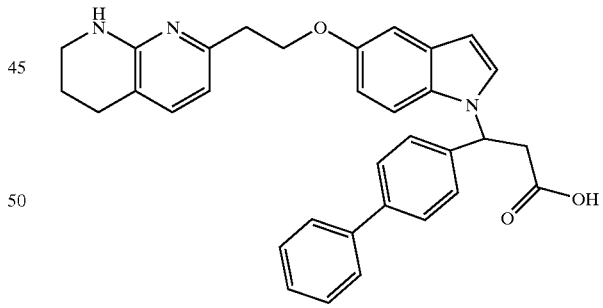

a) 3-Biphenyl-4-yl-3-chloro-acrylic acid ethyl ester

The title compound was synthesized from the commercially available 4-ethynyl-biphenyl using the procedure described in Example, 18 step (c), in 22% yield. $^1$H NMR (Cl$_3$CD), δ: 7.76 (m, 2H), 7.61 (m, 5H), 7.45 (m, 2H), 6.60 (s, 1H), 4.29 (c, 2H, J=8.0 Hz), 1.34 (t, 3H, J=7.2 Hz).

b) 7-{2-[1-(1-Biphenyl-4-yl-2-ethoxycarbonyl-vinyl)-1H-indol-5-yloxy]-ethyl}-3,4-dihydro-2H-[1,8]naphthyridine-1-carboxylic acid tert-butyl ester The title compound was synthesized from 7-[2-(1H-indol-5-yloxy)-ethyl]-3,4-dihydro-2H-[1,8]naphthyridine-1-carboxylic acid tert-butyl ester and 3-biphenyl-4-yl-3- chloro-acrylic acid ethyl ester using the procedure described in Example 18, step (d), in an 8% yield as a mixture of E/Z isomers.

$^1$H NMR (Cl$_3$CD), δ: 7.65 (m, 2H), 7.59 (m, 3H), 7.46 (m, 4H), 7.37 (m, 0.35H), 7.32 (d, 1H, J=7.6 Hz), 7.12 (d, 0.65H, J=2.5 Hz), 7.09 (m, 1H), 6.99 (d, 0.35H, J=3.5 Hz), 6.95 (d, 0.65H, J=7.6 Hz), 6.94 (d, 0.35H, J=7.6 Hz), 6.80 (d, 0.65H, J=9.0 Hz), 6.78 (dd, 0.35H, J=2.5, 9.0 Hz), 6.72 (dd, 0.65H, J=2.3, 8.8 Hz), 6.59 (d, 0.65H, J=3.5 Hz), 6.51 (d, 0.35H, J=3.2 Hz), 6.27 (s, 0.65H), 6.16 (s, 0.35H), 4.38 (m, 2H), 4.12 (c, 1.3H, J=8.0 Hz), 4.00 (c, 0.7H, J=8.0 Hz), 3.76 (m, 2H), 2.73 (t, 2H, J=8 Hz), 3.21 (m, 2H), 1.92 (m, 2H), 1.52 (m, 9H), 1.28 (t, 1.95H, J=8.0 Hz), 1.18 (t, 1.05H, J=8.0 Hz).

c) 7-{2-[1-(1-Biphenyl-4-yl-2-ethoxycarbonyl-ethyl)-1H-indol-5-yloxy]-ethyl}-3,4-dihydro-2H-[1,8]naphthyridine-1-carboxylic acid tert-butyl ester.

The title compound was synthesized from 7-{2-[1-(1-biphenyl-4-yl-2-ethoxycarbonyl-vinyl)-1H-indol-5-yloxy]-ethyl}-3,4-dihydro-2H-[1,8]naphthyridine-1-carboxylic acid tert-butyl ester using the procedure described in Example 18, step (e), in 59% yield. $^1$H NMR (Cl$_3$CD), δ: 7.43 (m, 4H), 7.33 (m, 2H), 7.25 (m, 2H), 7.15 (m, 4H), 7.02 (d, 1H, J=2.3 Hz), 6.88 (d, 1H, J=7.4 Hz), 6.76 (dd, 1H, J=2.5, 9.0 Hz), 6.38 (d, 1H, J=3.2 Hz), 5.98 (t, 1H, J=7.4 Hz), 4.29 (m, 2H), 3.98 (c, 2H, J=7.2 Hz), 3.36 (m, 2H), 3.68 (m, 2H), 3.13 (m, 2H), 2.65 (m, 2H), 1.92 (m, 2H), 1.44 (s, 9H), 1.18 (t, 3H, J=7.2 Hz).

d) 3-Biphenyl-4-yl-3-{5-[2-(5,6,7,8-tetrahydro-[1,8]naphthyridin-2-yl)-ethoxy]-indol-1-yl}-propionic acid ethyl ester The title compound was synthesized from 7-{2-[1-(1-biphenyl-4-yl-2-ethoxycarbonyl-ethyl)-1H-indol-5-yloxy]-ethyl}-3,4-dihydro-2H-[1,8]naphthyridine-1-carboxylic acid tert-butyl ester using the procedure described in Example 16, step (f), in 43% yield. $^1$H NMR (Cl$_3$CD), δ: 7.44 (m, 4H), 7.34 (m, 3H), 7.26 (m, 1H), 7.16 (m, 4H), 7.02 (d, 1H, J=2.1 Hz), 6.73 (dd, 1H, J=2.3, 8.8 Hz), 6.41 (d, 1H, J=3.0 Hz), 5.98 (t, 1H, J=7.7 Hz), 4.23 (t, 2H, J=6.0 Hz), 3.98 (c, 2H, J=6.92 Hz), 3.68 (m, 2H), 3.37 (m, 2H) 3.05 (t, 2H, J=6.3 Hz), 2.64 (t, 2H, J=6.3 Hz), 1.83 (m, 2H), 1.03 (t, 3H, J=6.9 Hz).

e) 3-Biphenyl-4-yl-3-{5-[2-(5,6,7,8-tetrahydro-[1,8] naphthyridin-2-yl)-ethoxy]-indol-1-yl}-propionic acid The title compound was synthesized from 3-biphenyl-4-yl-3-{5-[2-(5,6,7,8-tetrahydro-[1,8]naphthyridin-2-yl)-ethoxy]-indol-1-yl}-propionic acid ethyl ester using the procedure described in Example 18, step (g), in 83% yield. $^1$H NMR (Cl$_3$CD), δ: 7.45 (m, 3H), 7.39 (m, 2H), 7.32 (m, 2H), 7.24 (m, 2H), 7.15 (d, 1H, J=8.3 Hz), 7.02 (d, 1H, J=7.2 Hz), 6.80 (d, 1H, J=2.3 Hz), 6.57 (dd, 1H, J=2.3, 8.8 Hz), 6.44 (m, 1H), 6.19 (d, 1H, J=7.4 Hz), 6.11 (m, 1H), 3.54 (m, 2H), 3.32 (m, 2H), 3.18 (m, 2H), 2.55 (m, 4H), 1.76 (m, 2H). Mass Spectrum (LCMS, ESI) calculate for C$_{33}$H$_{32}$N$_3$O$_3$: 518.2, (M+1); found: 518.4.

EXAMPLE 23

3-(3,5-Dichloro-phenyl)-3-{5-[2-(5,6,7,8-tetrahydro-[1,8]naphthyridin-2-yl)-ethoxy]-indol-1-yl}-propionic acid

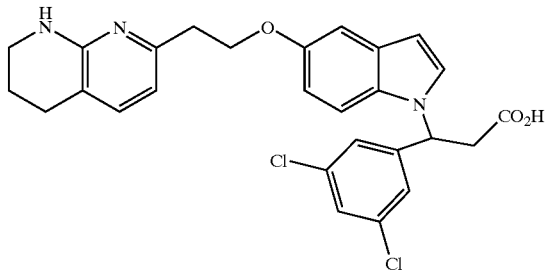

a) (3,5-Dichloro-phenylethynyl)-trimethyl-silane

The title compound was synthesized from 1,3-dichloro-5-iodo-benzene using the procedure described in Example 18, step (a), in 98% yield. $^1$H NMR (CDCl$_3$) δ 7.34–7.33 (m, 2H), 7.31–7.29 (m, 1H), 0.24 (s, 9H).

b) 1,3-Dichloro-5-ethynyl-benzene

To a solution of (3,5-dichloro-phenylethynyl)-trimethyl-silane (1.97 g, 8.1 mmol) in methanol (40 mL) was added a solution of potassium hydroxide (6.8 mg, 0.12 mmol) in H$_2$O (0.24 mL). After stirring at ambient temperature for 40 minutes, the reaction mixture was diluted with water (40 mL), and extracted with hexane until the extracting solvent showing no product by TLC. The combined organic layer was dried over MgSO$_4$, and concentrated to give the title compound (1.21 g, 87% yield) as a white solid. $^1$H NMR (CDCl$_3$) δ 7.37–7.34 (m, 3H), 3.15 (s, 1H).

c) (3,5-Dichloro-phenyl)-propynoic acid ethyl ester

To a solution of diisopropylamine (0.23 mL) in THF (0.6 mL) at −78° C. was added a solution of n-butyllithium (0.46 mL, 2.0 M in hexane). The mixture was stirred at −78° C. for 20 minutes, 0° C for 15 min., and cooled to −78° C. To this mixture was added a solution of 1,3-dichloro-5-ethynyl-benzene (136 mg, 0.80 mmol) in THF (1.0 mL) over 2 minutes. After stirring at −78° C. for 1 h, a solution of ethyl chloroformate (0.09 mL) in THF (0.2 mL) was added, and stirred for 1 h at −78° C. The reaction was quenched with saturated ammonium chloride, warmed up to ambient temperature, and extracted with ethyl acetate. The extract was dried over Na$_2$SO$_4$, concentrated, and flash chromatographed on silica gel, eluting with hexane to give the title compound (0.16 g, 87% yield) as a yellow oil. $^1$H NMR (CDCl$_3$) δ 7.47–7.44 (m, 3H), 4.31 (q, 2H, J=7.2 Hz), 1.36 (t, 3H, J=7.2 Hz).

d) 7-(2-{1-[1-(3,5-Dichloro-phenyl)-2-ethoxycarbonyl-vinyl]-1H-indol-5-yloxy}-ethyl)-3,4-dihydro-2H-[1,8] naphthyridine-1-carboxylic acid tert-butyl ester The title compound was synthesized from (3,5-dichloro-phenyl)-propynoic acid ethyl ester using the procedure described in Example 16, step (d1), in 43% yield as a mixture of E/Z isomers. $^1$H NMR (CDCl$_3$) δ 7.49–7.43 (m, 1H), 7.32 (d, 1H, J=7.6 Hz), 7.27 (d, 1H, J=1.9 Hz), 7.18–7.15 (m, 1H), 7.10–7.00 (m, 1H), 6.96–6.93 (m, 1H), 6.85 (d, 1H, J=3.5 Hz), 6.83–6.76 (m, 1H), 6.59 (d, 0.2H, J=3.4 Hz), 6.52 (d, 0.8H, J=3.5 Hz), 6.20 (s, 0.2H), 6.19 (s, 0.8H), 4.41–4.36 (m, 2H), 4.12 (q, 2H, J=7.1 Hz), 3.76 (t, 2H, J=5.6 Hz), 3.21 (t, 2H, J=6.8 Hz), 2.74 (t, 2H, J=6.6 Hz), 1.96–1.90 (m, 2H), 1.52 (s, 9H), 1.26 (t, 3H, J=7.2 Hz).

e) 7-(2-{1-[f1-(3,5-Dichloro-phenyl)-2-ethoxycarbonyl-ethyl]-1H-indol-5-yloxy}-ethyl)-3,4-dihydro-2H-[1,8] naphthyridine-1-carboxylic acid tert-butyl ester The title compound was synthesized from 7-(2-{1-[1-(3,5-dichloro-phenyl)-2-ethoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 75% yield. $^1$H NMR (CDCl$_3$) δ 7.31 (d, 1H, J=7.6 Hz), 7.25–7.24 (m, 2H), 7.17–7.10 (m, 3H), 7.04–7.03 (m, 2H), 6.94 (d, 1H, J=7.6 Hz), 6.84 (dd, 1H, J=2.4, 8.9 Hz), 6.48 (d, 1H, J=3.2Hz), 5.93 (t, 1H, J=7.5 Hz), 4.37 (t, 2H, J=6.9 Hz), 4.10–4.04 (m, 2H), 3.76 (t, 2H, J=6.0 Hz)3.30–3.16 (m, 4H), 2.73 (t, 2H, J=6.6 Hz), 1.92 (p, 2H, J=6.6 Hz), 1.50 (s, 9H), 1.12 (t, 3H, J=7.1 Hz).

f) 3-(3,5-Dichloro-phenyl)-3-{5-[2-(5,6,7,8-tetrahydro-[1,8]naphthyridin-2-yl)-ethoxy]-indol-1-yl}-propionic acid The title compound was synthesized from 7-(2-{1-[1-(3,5-dichloro-phenyl)-2-ethoxycarbonyl-ethyl]-1H-indol-5-yloxy}-ethyl)-3,4-dihydro-2H-[1,8]naphthyridine-1-carboxylic acid tert-butyl ester in two steps using the procedures described in Example 16, step (f), and Example 18, step (e), in 41% yield. $^1$H NMR (CDCl$_3$) δ 10.35 (bs, 1H), 7.44 (d, 1H, J=3.2 Hz), 7.19–7.11 (m, 3H), 7.04–7.02 (m, 2H), 6.87 (d, 1H, J=2.2 Hz), 6.63 (dd, 1H, J=2.2, 8.9 Hz), 6.49 (d, 1H, J=3.0 Hz), 6.29 (d, 1H, J=7.3 Hz), 6.05 (dd, 1H, J=4.8, 10.5 Hz), 3.73–3.67 (m, 1H), 3.56–3.51 (m, 1H), 3.48–3.37 (m, 2H), 3.26–3.08 (m, 2H), 2.70–2.53 (m, 4H), 1.85–1.82 (m, 2H). Mass Spectrum (LCMS, ESI) calculated for C$_{27}$H$_{25}$Cl$_2$N$_3$O$_3$ 510.1 (M+H); found 510.4.

EXAMPLE 24

3-(3,5-Difluoro-phenyl)-3-{5-[2-(5,6,7,8-tetrahydro-[1,8]naphthyridin-2-yl)-ethoxy]-indol-1-yl}-propionic acid

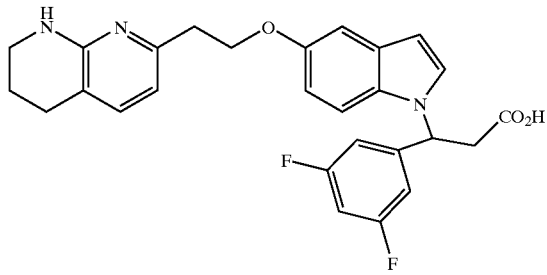

a) (3,5-Difluoro-phenylethynyl)-trimethyl-silane

The title compound was synthesized from 1,3-difluoro-5-bromobenzene using the procedure described in Example 18, step (a), in 96% yield. $^1$H NMR (CDCl$_3$) δ 7.02–6.93 (m, 2H), 6.80–6.74 (m, 1H), 0.25 (s, 9H).

b) 1-Ethynyl-3,5-difluoro-benzene

The title compound was synthesized from (3,5-difluoro-phenylethynyl)-trimethyl-silane using the procedure described in Example 23, step (b), in 79% yield. $^1$H NMR (CDCl$_3$) δ 7.04–6.97 (m, 2H), 6.85–6.80 (m, 1H), 3.14 (s, 1H).

c) (3,5-Difluoro-phenyl)-propynoic acid ethyl ester

The title compound was synthesized from 1-ethynyl-3,5-difluoro-benzene using the procedure described in Example 23, step (c), in 69% yield. $^1$H NMR (CDCl$_3$) δ 7.13–7.07 (m, 2H), 6.92 (tt, 1H, J=2.3, 8.8 Hz), 4.31 (q, 2H, J=7.2 Hz), 1.36 (t, 3H, J=7.2 Hz).

d) 7-(2-{1-[1-(3,5-Difluoro-phenyl)-2-ethoxycarbonyl-vinyl]-1H-indol-5-yloxy}-ethyl)-3,4-dihydro-2H-[1,8]naphthyridine-1-carboxylic acid tert-butyl ester The title compound was synthesized from (3,5-difluoro-phenyl)-propynoic acid ethyl ester using the procedure described in Example 16, step (d1), in 47% yield, as a mixture of E/Z isomers. $^1$H NMR (CDCl$_3$) δ 7.33–7.31 (m, 1H), 7.13–7.08 (m, 1H), 7.02 (d, 1H, J=3.3 Hz), 6.95–6.80 (m, 4H), 6.75–6.74 (m, 2H), 6.58 (d, 0.54H, J=3.4 Hz), 6.52 (dd, 0.46H, J=0.6, 3.5 Hz), 6.23 (s, 0.54H), 6.18 (s, 0.46H), 4.41–4.36 (m, 2H), 4.00 (q, 2H, J=7.1 Hz), 3.76 (t, 2H, J=6.0 Hz), 3.21 (t, 2H, J=6.9 Hz), 2.73 (t, 2H, J=6.6 Hz), 1.96–1.89 (m, 2H), 1.52 (s, 9H), 1.02 (t, 3H, J=7.1 Hz).

e) 7-(2-{1-[1-(3,5-Difluoro-phenyl)-2-methoxycarbonyl-ethyl]-1H-indol-5-yloxy}-ethyl)-3,4-dihydro-2H-[1,8]naphthyridine-1-carboxylic acid tert-butyl ester The title compound was synthesized from 7-(2-{1-[1-(3,5-difluoro-phenyl)-2-ethoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 71% yield. $^1$H NMR (CDCl$_3$) δ 7.30 (d, 1H, J=7.6 Hz), 7.25–7.10 (m, 3H), 6.94–6.92 (m, 1H), 6.84–6.82 (m, 1H), 6.70–6.65 (m, 3H), 6.47 (d, 1H, J=3.3 Hz), 5.96 (t, 1H, J=7.9 Hz), 4.38–4.35 (m, 2H), 3.76–3.74 (m, 2H), 3.63 (s, 3H), 3.33–3.18 (m, 4H), 2.74–2.70 (m, 2H), 1.95–1.88 m, 2H), 1.51 (s, 9H).

f) 3-(3,5-Difluoro-phenyl)-3-{5-[2-(5,6,7,8-tetrahydro-[1,8]naphthyridin-2-yl)-ethoxy]-indol-1-yl}-propionic acid methyl ester The title compound was synthesized from 7-(2-{1-[1-(3,5-difluoro-phenyl)-2-ethoxycarbonyl-ethyl]-1H-indol-5-yloxy}-ethyl)-3,4-dihydro-2H-[1,8]naphthyridine-1-carboxylic acid tert-butyl ester using the procedure described in Example 16, step (f), in 95% yield. Mass Spectrum (LCMS, ESI) calculated for C$_{28}$H$_{28}$F$_2$N$_3$O$_3$ 492.2 (M+H); found 492.4.

g) 3-(3,5-Difluoro-phenyl)-3-{5-[2-(5,6,7,8-tetrahydro-[1,8]naphthyridin-2-yl)-ethoxy]-indol-1-yl}-propionic acid The title compound was synthesized from 3-(3,5-difluoro-phenyl)-3-{5-[2-(5,6,7,8-tetrahydro-[1,8]naphthyridin-2-yl)-ethoxy]-indol-1-yl}-propionic acid ethyl ester using the procedure described in Example 18, step (g), in 80% yield. $^1$H NMR (DMSO-d$_6$) δ 7.72 (d, 1H, J=3.3 Hz), 7.48 (d, 1H, J=8.9 Hz), 7.21 (d, 1H, J=7.0 Hz), 7.12–7.08 (m, 3H), 7.04 (d, 1H, J=2.3 Hz), 6.72 (dd, 1H, J=2.4, 8.9 Hz), 6.46 (d, 1H, J=7.5 Hz), 6.41 (d, 1H, J=3.3 Hz), 6.00 (dd, 1H, J=5.6, 9.3 Hz), 4.21 (t, 2H, J=6.8 Hz), 3.50–3.28 (m, 4H), 2.94 (t, 2H, J=6.4 Hz), 2.64 (t, 2H, J=5.9 Hz), 1.76 (p, 2H, J=5.8 Hz). Mass Spectrum (LCMS, ESI) calculated for C$_{27}$H$_{26}$F$_2$N$_3$O$_3$ 478.2 (M+H); found 478.3.

EXAMPLE 25

3-(3-Cyano-phenyl)-3-{5-[2-(5,6,7,8-tetrahydro-[1,8]naphthyridin-2-yl)-ethoxy]-indol-1-yl}-propionic acid

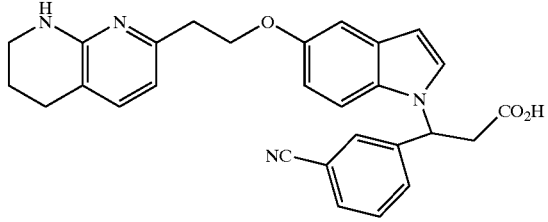

a) 3-Trimethylsilanylethynyl-benzonitrile

The title compound was synthesized from 3-bromobenzonitrile using the procedure described in Example 18, step (a), in 99% yield. $^1$H NMR (CDCl$_3$) δ 7.74 (dt, 1H, J=0.6, 6.3 Hz), 7.68–7.65 (m, 1H), 7.60–7.65 (m, 1H), 7.44–7.40 (m, 1H), 0.26 (s, 9H).

b) 3-Ethynyl-benzonitrile

The title compound was synthesized from 3-trimethylsilanylethynyl-benzonitrile using the procedure described in Example 23, step (b), in 90% yield. $^1$H NMR (CDCl$_3$) δ 7.77 (t, 1H, J=1.4 Hz), 7.70 (td, 1H, J=1.3, 7.8 Hz), 7.63 (td, 1H, J=1.4, 7.8 Hz), 7.45 (dt, 1H, J=0.4, 7.9 Hz), 3.19 (s, 1H).

c) (3-Cyano-phenyl)-propynoic acid ethyl ester

The title compound was synthesized from 3-ethynyl-benzonitrile using the procedure described in Example 23, step (c), in 80% yield. $^1$H NMR (CDCl$_3$) δ 6.87–6.86 (m, 1H), 7.80 (td, 1H, J=1.3, 7.9 Hz), 7.73 (td, 1H, J=1.3, 7.9 Hz), 7.53 (t, 1H, J=7.9 Hz), 4.32 (q, 2H, J=7.2 Hz), 1.37 (t, 3H, J=7.2 Hz).

d) 7-(2-{1-[1-(3-Cyano-phenyl)-2-ethoxycarbonyl-vinyl]-1H-indol-5-yloxy}-ethyl)-3,4-dihydro-2H-[1,8]naphthyridine-1-carboxylic acid tert-butyl ester The title compound was synthesized from (3-cyanophenyl)propynoic acid ethyl ester using the procedure described in Example 16, step (c1), in 71% yield as a mixture of E/Z isomers. $^1$H NMR (CDCl$_3$) δ 7.79–7.48 (m, 4H), 7.33–7.31 (m, 1H), 7.13–7.10 (m, 1H), 7.06–7.02 (m, 1H), 6.94 (dd, 1H, J=2.3, 7.6 Hz), 6.84–6.79 (m, 1H), 6.75–6.66 (m, 1H), 6.60 (dd, 0.56H, J=0.6, 3.3 Hz), 6.53 (dd, 0.44H, J=0.5, 3.5 Hz), 6.23 (s, 0.6H), 6.22 (s, 0.4H), 4.41–4.36 (m, 2H), 4.11 (q, 0.9H, J=7.1 Hz), 4.03 (q, 1.1H, J=7.1 Hz), 3.78–3.75 (m, 2H), 3.21 (t, 2H, J=6.9 Hz), 2.73 (t, 2H, J=6.7 Hz), 1.92 (p, 2H, J=6.6 Hz), 1.52 (s, 9H), 1.20 (t, 1.3H, J=7.1 Hz), 1.04 (t, 1.7H, J=7.2 Hz).

e) 7-(2-{1-[1-(3-Cyano-phenyl)-2-ethoxycarbonyl-ethyl]-1H-indol-5-yloxy}-ethyl)-3,4-dihydro-2H-[1,8]naphthyridine-1-carboxylic acid tert-butyl ester The title compound was synthesized from 7-(2-{1-[1-(3-cyano-phenyl)-2-ethoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 80% yield as a mixture of ethyl and methyl esters. $^1$H NMR (CDCl$_3$) δ 7.56–7.53 (m, 1H), 7.45–7.30 (m, 4H), 7.18–7.17 (m, 1H), 7.11–7.08 (m, 2H), 6.94 (d, 1H, J=7.6 Hz), 6.82 (dd, 1H, J=2.4, 8.9 Hz), 6.49 (d, 1H, J=3.2 Hz), 6.02 (t, 1H, J=7.5 Hz), 4.36 (t, 2H, J=6.9 Hz), 4.08 (q, 0.52H, J=7.1 Hz), 3.77–3.74 (m, 2H), 3.65 (s, 2.2H), 3.36–3.18 (m, 4H), 2.73 (t, 2H, J=6.6 Hz), 1.95–1.87 (m, 2H), 1.52 (s, 9H), 1.12 (t, 0.8H, J=7.1 Hz).

f) 3-(3-Cyano-phenyl)-3-{5-[2-(5,6,7,8-tetrahydro-[1,8]naphthyridin-2-yl)-ethoxy]-indol-1-yl}-propionic acid ethyl ester The title compound was synthesized from 3-(3-cyano-phenyl)-3-{5-[2-(5,6,7,8-tetrahydro-[1,8]naphthyridin-2-yl)-ethoxy]-indol-1-yl}-propionic acid ethyl ester using the procedure described in Example 16, step (e), in 50% yield as a white solid. $^1$H NMR (CDCl$_3$) δ 7.56–7.53 (m, 1H), 7.45–7.34 (m, 3H), 7.17 (t, 1H, J=3.0 Hz), 7.10–7.08 (m, 3H), 6.82 (dd, 1H, J=2.4, 8.9 Hz), 6.49–6.46 (m, 2H), 6.02 (t, 1H, J=7.5 Hz), 5.04 (bs, 1H), 4.28 (t, 2H, J=6.8 Hz), 4.07 (q, 0.6H, J=6.2 Hz), 3.63 (s, 2.1H), 3.42–3.39 (m, 2H), 3.35–3.22 (m, 4H), 3.03 (t, 2H, J=6.9 Hz), 2.69 (t, 2H, J=6.3 Hz), 1.93–1.87 (m, 2H), 1.12 (t, 0.9H, J=7.1 Hz). Mass Spectrum (LCMS, ESI) calculated for C$_{29}$H$_{29}$N$_4$O$_3$ 481.2 (methyl ester, M+H); found 481.4. Calculated for C$_{30}$H$_{31}$N$_4$O$_3$ 495.2 (ethyl ester, M+H); found 495.3.

The title compound was synthesized from 7-(2-{1-[1-(3-cyano-phenyl)-2-ethoxycarbonyl-ethyl]-1H-indol-5-yloxy}-ethyl)-3,4-dihydro-2H-[1,8]naphthyridine-1-carboxylic acid tert-butyl ester using the procedure described in Example 18, step (g), in 50% yield as a pale yellow solid. $^1$H NMR (CDCl$_3$) δ 9.72 (bs, 1H), 7.47 (d, 1H, J=6.5 Hz), 7.38–7.30 (m, 4H), 7.19 (d, 1H, J=7.3 Hz), 7.11 (d, 1H, J=8.9 Hz), 6.89 (bs, 1H), 6.64 (d, 1H, J=8.7 Hz), 6.48 (d, 1H, J=2.5 Hz), 6.35 (d, 1H, J=7.3 Hz), 6.09 (dd, 1H, J=5.5, 9.5 Hz), 3.85–3.68 (m, 2H), 3.38–3.35 (m, 2H), 3.29–3.13 (m, 2H), 2.79–2.83 (m, 4H), 1.87–1.81 (m, 2H). Mass Spectrum (LCMS, ESI) calculated for C$_{28}$H$_{28}$N$_4$O$_3$ 467.2 (M+H); found 467.3.

EXAMPLE 26

3-(4-Cyano-phenyl)-3-{5-[2-(5,6,7,8-tetrahydro-[1,8]naphthyridin-2-yl)-ethoxy]-indol-1-yl}-propionic acid

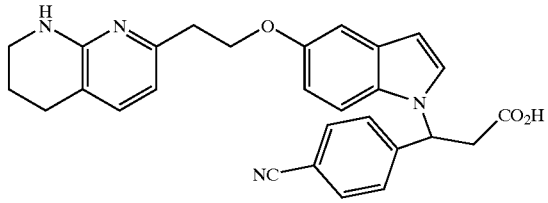

a) 4-Trimethylsilanylethynyl-benzonitrile

The title compound was synthesized from 4-benzobenzonitrile using the procedure described in Example 18, step (a), in 80% yield. $^1$H NMR (CDCl$_3$) δ 7.60–7.58 (m, 2H), 7.54–7.52 (m, 2H), 0.26 (s, 9H).

b) 4-Ethynyl-benzonitrile

The title compound was synthesized from 4-trimethylsilanylethynyl-benzonitrile using the procedure described in Example 23, step (b), in 75% yield. $^1$H NMR (CDCl$_3$) δ 7.64–7.61 (m, 2H), 7.59–7.56 (m, 2H), 3.30 (s, 1H).

c) (4-Cyano-phenyl)-propynoic acid ethyl ester

The title compound was synthesized from 4-ethynyl-benzonitrile using the procedure described in Example 23, step (c), in 59% yield. The crude product was used in the next reaction without further purification.

d) 7-(2-{1-[1-(4-Cyano-phenyl)-2-ethoxycarbonyl-vinyl]-1H-indol-5-yloxy}-ethyl)-3,4-dihydro-2H-[1,8]naphthyridine-1-carboxylic acid tert-butyl ester The title compound was synthesized from (4-cyano-phenyl)-propynoic acid ethyl ester using the procedure described in Example 16, step (c1), in 78% yield as a mixture of E/Z isomers. $^1$H NMR (CDCl$_3$) δ 7.74–7.64 (m, 2H), 7.51 (d, 1H, J=8.3 Hz), 7.39–7.37 (m, 1H), 7.32 (d, 1H, J=7.6 Hz), 7.12–7.09 (m, 1H), 7.05–7.03 (m, 1H), 6.94 (d, 1H, J=7.6 Hz), 6.84–6.65 (m, 2H), 6.59 (d, 0.6H, J=3.3 Hz), 6.52 (d, 0.4H, J=3.5 Hz), 6.27 (s, 0.6H), 6.23 (s, 0.4H), 4.40–4.35 (m, 2H), 4.11 (q, 0.8H, J=7.1 Hz), 4.03 (q, 1.2H, J=7.1 Hz), 3.76 (t, 2H, J=6.0 Hz), 3.20 (t, 2H, J=6.9 Hz), 2.73 (t, 2H, J=6.7 Hz), 1.93 (p, 2H, J=6.6 Hz), 1.52 (s, 9H), 1.20 (t, 1.2H, J=7.1 Hz), 1.04 (t, 1.8H, J=7.1 Hz).

e) 3-(4-Cyano-phenyl)-3-{5-[2-(5,6,7,8-tetrahydro-[1,8]naphthyridin-2-yl)-ethoxy]-indol-1-yl}-propionic acid methyl ester The title compound was synthesized from 7-(2-{1-[1-(4-cyano-phenyl)-2-ethoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 45% yield. $^1$H NMR (CDCl$_3$) δ 7.58–7.55 (m, 2H), 7.37 (d, 1H, J=3.2 Hz), 7.32–7.29 (m, 1H), 7.26–7.11 (m, 2H), 7.03 (d, 1H, J=2.3 Hz), 6.73–6.69 (m, 1H), 6.46–6.43 (m, 2H), 6.09–6.05 (m, 1H), 4.19 (t, 2H, J=6.8 Hz), 3.56 (s, 3H), 3.41–3.33 (m, 4H), 2.94 (t, 2H, J=7.0 Hz), 2.66 (t, 2H, J=6.2 Hz), 1.83 (p, 2H, J=6.3 Hz). Mass Spectrum (LCMS, ESI) calculated for $C_{29}H_{29}N_4O_3$ 481.2 (M+H); found 481.4.

f) 3-(4-Cyano-phenyl)-3-{5-[2-(5,6,7,8-tetrahydro-[1,8]naphthyridin-2-yl)-ethoxy]-indol-1-yl}-propionic acid The title compound was synthesized from 3-(4-cyano-phenyl)-3-{5-[2-(5,6,7,8-tetrahydro-[1,8]naphthyridin-2-yl)-ethoxy]-indol-1-yl}-propionic acid methyl ester using the procedure described in Example 18, step (g), in 43% yield. $^1$H NMR (CDCl$_3$) δ 10.38 (s, 1H), 7.52–7.44 (m, 3H), 7.20–7.10 (m, 4H), 6.87 (s, 1H, J=2.3 Hz), 6.62 (dd, 1H, J=2.3, 8.9 Hz), 6.48 (d, 1H, J=3.1 Hz), 6.30 (d, 1H, J=7.3 Hz), 6.14 (dd, 1H, J=5.1, 10.2 Hz), 3.75–3.70 (m, 1H), 3.60–3.55 (m, 1H), 3.39 (bt, 2H, J=5.1 Hz), 3.28–3.12 (m, 2H), 2.74–2.58 (m, 4H), 1.87–1.82 (m, 2H). Mass Spectrum (LCMS, ESI) calculated for $C_{28}H_{27}N_4O_3$ 467.2 (M+H); found 467.3.

EXAMPLE 27

3-(2-Methoxy-phenyl)-3-{5-[2-(5,6,7,8-tetrahydro-[1,8]naphthyridin-2-yl)-ethoxy]-indol-1-yl}-propionic acid

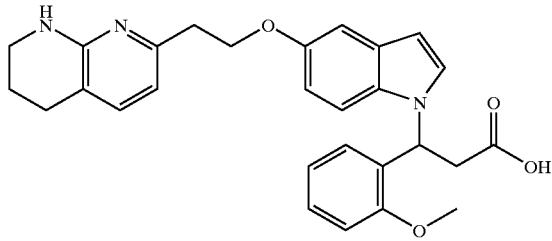

a) (2-Methoxy-phenylethynyl)trimethyl-silane

The title compound was synthesized from commercially available 1-iodo-2-methoxy-benzene using the procedure described in Example 18, step (a), in 98% yield. $^1$H NMR (CDCl$_3$) δ 7.60 (dd, 1H, J=1.8, 5.8 Hz), 7.43 (m, 1H), 7.04 (m, 2H), 4.03 (s, 3H), 0.34 (s, 9H).

b) 2-Methoxy-phenylethynyl

The title compound was synthesized from (2-methoxy-phenylethynyl)-trimethyl-silane using the procedure described in Example 18, step (b), in 63% yield. $^1$H NMR (CDCl$_3$) δ 7.46 (dd, 1H, J=1.6, 6.0 Hz), 7.30 (m, 1H), 6.90 (m, 2H), 3.89 (s, 3H), 3.30 (s, 1H).

c) (2-Methoxy-phenyl)-propynoic acid ethyl ester

The title compound was synthesized from 2-methoxy-phenylethynyl using the procedure described in Example 23, step (c), in 71% yield. $^1$H NMR (CDCl$_3$) δ 7.27 (m, 1H), 7.16 (m, 1H), 7.09 (m, 1H), 6.98 (m, 1H), 4.28 (q, 2H, J=7.2 Hz), 3.79 (s, 3H), 1.25 (t, 3H, J=7.2 Hz).

d) 7-(2-{1-[2-Ethoxycarbonyl-1-(2-methoxy-phenyl)-vinyl]-1H-indol-5-yloxy}-ethyl)-3,4-dihydro-2H-[1,8]naphthyridine-1-carboxylic acid tert-butyl ester The title compound was synthesized from (2-methoxy-phenyl)-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 16, step (d1), in a 80% yield as an E/Z isomeric mixture. $^1$H NMR (CDCl$_3$) [E/Z mixture] δ 7.45 (m, 1H), 7.28–6.95 (m, 4H), 6.85–6.60 (m, 4H), 6.49 (m, 2H), 6.25 (s, 1H), 4.39 (m, 2H), 4.09 (q, 2H, J=7.2 Hz), 3.68 (s, 2H), 3.58 (s, 1H), 3.80 (m, 2H), 3.20 (m, 2H), 2.70 (m, 2H), 1.89 (m, 2H), 1.50 (s, 9H), 1.25 (t, 3H, J=6.8 Hz). Mass Spectrum (LCMS, ESI) calculated for $C_{30}H_{32}N_3O_4$ 498.2 (M-Boc+H); found 498.4.

e) 7-(2-{1-[2-Ethoxycarbonyl-1-(2-methoxy-phenyl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-ethoxycarbonyl-1-(2-methoxy-phenyl)-vinyl]-1H-indol-5-yloxy}-ethyl)-3,4-dihydro-2H-[1,8]naphthyridine-1-carboxylic acid tert-butyl ester using the procedure described in Example 18, step (e), in 44% yield. $^1$H NMR (CDCl$_3$) δ 7.34–7.21 (m, 4H), 7.14 (m, 2H), 6.99–6.80 (m, 4H), 6.45 (m, 1H), 6.36 (m, 1H), 4.37 (m, 2H), 4.04 (q, 2H, J=7.1 Hz), 3.87 (s, 3H), 3.78 (m, 2H), 3.23 (m, 4H), 2.74 (m, 2H), 1.94 (m, 2H), 1.54 (s, 9H), 1.08 (t, 3H, J=7.1 Hz).

f) 3-(2-Methoxy-phenyl)-3-{5-[2-(5,6,7,8-tetrahydro-[1,8]naphthyridin-2-yl)-ethoxy]-indol-1-yl}-propionic acid ethyl ester The title compound was synthesized from 7-(2-{1-[2-ethoxycarbonyl-1-(2-methoxy-phenyl)-ethyl]-1H-indol-5-yloxy}-ethyl)-3,4-dihydro-2H-[1,8]naphthyridine-1-carboxylic acid tert-butyl ester using the procedure described in Example 16, step (f), in 84% yield. $^1$H NMR (CDCl$_3$) δ 7.25–7.18 (m, 3H), 7.10 (m, 2H), 6.90–6.81 (m, 4H), 6.44 (m, 2H), 6.38 (m, 1H), 5.10 (bs, 1H), 4.25 (m, 2H), 4.11 (q, 2H, J=7.2 Hz), 3.84 (s, 3H), 3.41 (m, 2H), 3.24 (m, 2H), 3.22 (m, 2H), 2.65 (m, 2H), 1.89 (m, 2H), 1.21 (t, 3H, J=7.2 Hz).

g) 3-(2-Methoxy-phenyl)-3-{5-[2-(5,6,7,8-tetrahydro-[1,8]naphthyridin-2-yl)-ethoxy]-indol-1-yl}-propionic acid The title compound was synthesized from 3-(2-methoxy-phenyl)-3-{5-[2-(5,6,7,8-tetrahydro-[1,8]naphthyridin-2-yl)-ethoxy]-indol-1-yl}-propionic acid ethyl ester using the procedure described in Example 18, step (g), in 14% yield. $^1$H NMR (CDCl$_3$/CD$_3$OD) δ 7.57 (m, 1H), 7.27–7.14 (m, 3H), 6.90 (d, 1H, J=8.4 Hz), 6.80 (m, 3H), 6.60 (dd, 1H, J=2.4, 6.4 Hz), 6.46 (m, 2H), 6.29 (d, 1H, J=7.6 Hz), 3.93 (s, 3H), 3.54 (m, 2H), 3.45 (m, 2H), 3.36–3.12 (m, 4H), 2.66 (m, 2H), 1.86 (m, 2H); Mass Spectrum (LCMS, ESI) calculated for $C_{28}H_{30}N_3O_4$ 472.2 (M+H); found 472.3.

EXAMPLE 28

3-(3-Methoxy-phenyl)-3-{5-[2-(5,6,7,8-tetrahydro-[1,8]naphthyridin-2-yl)-ethoxy]-indol-1-yl}-propionic acid

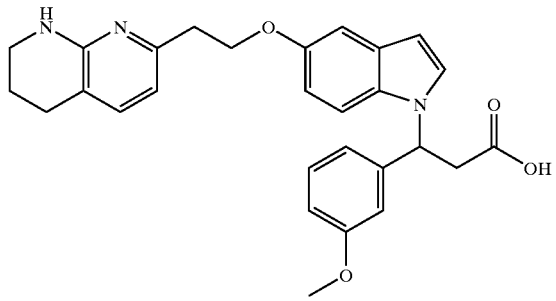

a) (3-Methoxy-phenylethynyl)-trimethyl-silane

The title compound was synthesized from commercially available 1-iodo-3-methoxy-benzene using the procedure described in Example 18, step (a), in 98% yield. $^1$H NMR (CDCl$_3$) δ 7.23 (t, 1H, J=7.8 Hz), 7.08 (dt, 1H, J=1.2, 7.6 Hz), 7.02 (m, 1H), 6.89 (m, 1H), 3.82 (s, 3H), 0.28 (s, 9H).

b) 3-Methoxy-phenylethynyl

The title compound was synthesized from (3-methoxy-phenylethynyl)-trimethyl-silane using the procedure described in Example 18, step (b), in 74% yield. $^1$H NMR (CDCl$_3$) δ 7.25 (t, 1H, J=7.9 Hz), 7.12 (d, 1H, J=1.0 Hz), 7.04 (m, 1H), 6.93 (m, 1H), 3.82 (s, 3H), 3.09 (s, 1H).

c) (3-Methoxy-phenyl)-propynoic acid ethyl ester

The title compound was synthesized from 3-methoxy-phenylethynyl using the procedure described in Example 23, step (c), in 87% yield. ¹H NMR (CDCl₃) δ 7.26 (t, 1H, J=8.0 Hz), 7.18 (m, 1H), 7.08 (m, 1H), 6.98 (m, 1H), 4.30 (q, 2H, J=7.2 Hz), 3.79 (s, 3H), 1.35 (t, 3H, J=7.2 Hz).

d) 7-(2-{1-[2-Ethoxycarbonyl-1-(3-methoxy-phenyl)-vinyl]-1H-indol-5-yloxy}-ethyl)-3,4-dihydro-2H-[1,8]naphthyridine-1-carboxylic acid tert-butyl ester The title compound was synthesized from (3-methoxy-phenyl)-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 16, step (d1), in a 90% yield as an E/Z isomeric mixture. ¹H NMR (CDCl₃) [E/Z mixture] δ 7.45–6.68 (m, 9H), 6.49 (m, 2H), 6.23 (s, 1H), 4.37 (m, 2H), 4.13 (q, 2H, J=7.2 Hz), 3.76 (t, 2H, J=5.2 Hz), 3.68 (s, 2.1H), 3.58 (s, 0.9H), 3.20 (m, 2H), 2.73 (t, 2H, J=6.8 Hz), 1.90 (m, 2H), 1.51 (s, 9H), 1.26 (t, 2.1H, J=7.2 Hz), 1.13 (t, 0.9H, J=7.2 Hz). Mass Spectrum (LCMS, ESI) calculated for C₃₀H₃₂N₃O₄ 498.2 (M-Boc+1); found 498.4.

e) 7-(2-{1-[2-Ethoxycarbonyl-1-(3-methoxy-phenyl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-ethoxycarbonyl-1-(3-methoxy-phenyl)-vinyl]-1H-indol-5-yloxy}-ethyl)-3,4-dihydro-2H-[1,8]naphthyridine-1-carboxylic acid tert-butyl ester using the procedure described in Example 18, step (e), in 38% yield. ¹H NMR (CDCl₃) δ 7.32 (d, 1H, J=7.6 Hz), 7.22 (m, 3H), 7.10 (d, 1H, J=2.4 Hz), 6.96 (d, 1H, J=7.6 Hz), 6.80 (m, 3H), 6.71 (m, 1H), 6.45 (d, 1H, J=3.2 Hz), 5.99 (t, 1H, J=7.5 Hz), 4.38 (t, 2H, J=9.6 Hz), 4.07 (q, 2H, J=7.2 Hz), 3.77 (m, 2H), 3.74 (s, 3H), 3.33–3.20 (m, 4H), 2.75 (t, 2H, J=6.6 Hz), 1.93 (m, 2H), 1.53 (s, 9H), 1.12 (t, 3H, J=7.1 Hz). Mass Spectrum (LCMS, ESI) calculated for C₃₀H₃₄N₃O₄ 500.3 (M-Boc+1); found 500.4.

f) 3-(3-Methoxy-phenyl)-3-{5-[2-(5,6,7,8-tetrahydro-[1,8]naphthyridin-2-yl)-ethoxy]-indol-1-yl}-propionic acid ethyl ester The title compound was synthesized from 7-(2-{1-[2-ethoxycarbonyl-1-(3-methoxy-phenyl)-ethyl]-1H-indol-5-yloxy}-ethyl)-3,4-dihydro-2H-[1,8]naphthyridine-1-carboxylic acid tert-butyl ester using the procedure described in Example 16, step (f), in 78% yield. ¹H NMR (CDCl₃) δ 7.21 (m, 3H), 7.05 (m, 2H), 6.80 (m, 4H), 6.45 (m, 2H), 6.00 (t, 1H, J=8.0 Hz), 4.86 (bs, 1H), 4.30 (t, 2H, J=8.0 Hz), 4.05 (q, 2H, J=8.0 Hz), 3.80 (s, 3H), 3.43 (m, 2H), 3.27 (m, 2H), 3.08 (m, 2H), 2.72 (m, 2H), 1.94 (m, 2H), 1.10 (t, 3H, J=8.0 Hz).

g) 3-(3-Methoxy-phenyl)-3-{5-[2-(5,6,7,8-tetrahydro-[1,8]naphthyridin-2-yl)-ethoxy]-indol-1-yl}-propionic acid The title compound was synthesized from 3-(3-methoxy-phenyl)-3-{5-[2-(5,6,7,8-tetrahydro-[1,8]naphthyridin-2-yl)-ethoxy]-indol-1-yl}-propionic acid ethyl ester using the procedure described in Example 18, step (g), in 22% yield. ¹H NMR (CDCl₃) δ 10.5 (bs, 1H), 7.50 (d, 1H, J=3.2 Hz), 7.26 (m, 1H), 7.15 (m, 1H), 7.07 (m, 1H), 6.82 (d, 1H, J=2.3 Hz), 6.72 (m, 3H), 6.60 (dd, 1H, J=2.3, 6.5 Hz), 6.46 (dd, 1H, J=3.0 Hz), 6.24 (d, 1H, J=7.3 Hz), 6.09 (m, 1H), 3.70 (s, 3H), 3.57 (m, 1H), 3.46–3.15 (m, 6H), 2.59 (m, 3H), 2.446 (m, 1H), 1.81 (m, 2H). Mass Spectrum (LCMS, ESI) calculated for C₂₈H₃₀N₃O₄ 472.2 (M+H); found 472.3.

EXAMPLE 29

3-(4-Methoxy-phenyl)-3-{5-[2-(5,6,7,8-tetrahydro-[1,8]naphthyridin-2-yl)-ethoxy]-indol-1-yl}-propionic acid

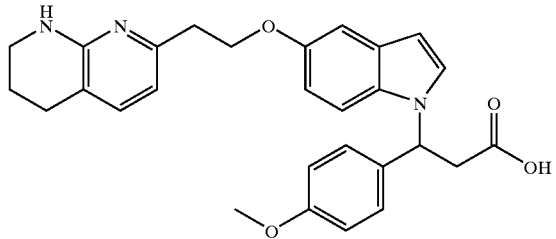

a) (4-Methoxy-phenylethynyl)-trimethyl-silane

The title compound was synthesized from commercially available 1-iodo-4-methoxy-benzene using the procedure described in Example 18, step (a), in 95% yield. ¹H NMR (CDCl₃) δ 7.43 (d, 2H, J=4.6 Hz), 6.83 (d, 2H, J=4.6 Hz), 3.82 (s, 3H), 0.26 (s, 9H).

b) 4-Methoxy-phenylethynyl

The title compound was synthesized from (4-methoxy-phenylethynyl)-trimethyl-silane using the procedure described in Example 18, step (b), in 88% yield. ¹H NMR (CDCl₃) δ 7.46 (d, 2H, J=4.9 Hz), 6.87 (d, 2H, J=4.9 Hz), 3.83 (s, 3H), 3.02 (s, 1H).

c) (4-Methoxy-phenyl)-propynoic acid ethyl ester

The title compound was synthesized from 4-methoxy-phenylethynyl using the procedure described in Example 23, step (c), in 69% yield. ¹H NMR (CDCl₃) δ 7.53 (d, 2H, J=8.8 Hz), 6.87 (d, 2H, J=8.8 Hz), 4.28 (q, 2H, J=7.2 Hz), 3.82 (s, 3H), 1.34 (t, 3H, J=7.2 Hz).

d) 7-(2-{1-[2-Ethoxycarbonyl-1-(4-methoxy-phenyl)-vinyl]-1H-indol-5-yloxy}-ethyl)-3,4-dihydro-2H-[1,8]naphthyridine-1-carboxylic acid tert-butyl ester The title compound was synthesized from (4-methoxy-phenyl)-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 16, step (d1), in a 88% yield as an E/Z isomeric mixture. ¹H NMR (CDCl₃) [E/Z mixture] δ 7.32 (m, 2H), 7.21 (m, 1H), 7.11–6.85 (m, 6H), 6.70 (m, 1H), 6.50 (m, 1H), 6.13 (s, 0.5H), 6.03 (s, 0.5H), 4.40 (m, 2H) 4.10 (q, 2H, J=7.2 Hz), 3.86 (s, 1.5H), 3.83 (s, 1H), 3.76 (t, 2H, J=5.2 Hz), 3.70 (t, 2H, J=6.0 Hz), 3.20 (t, 2H, J=6.8 Hz), 2.70 (t, 2H, J=6.8 Hz, J=6.8 Hz), 1.90 (m, 2H), 1.49 (s, 9H), 1.23 (t, 1.5H, J=7.2 Hz), 1.18 (t, 1.5H, J=7.2 Hz). Mass Spectrum (LCMS, ESI) calculated for C₃₀H₃₂N₃O₄ 498.2 (M-Boc+H); found 498.4.

e) 7-(2-{1-[2-Ethoxycarbonyl-1-(4-methoxy-phenyl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-ethoxycarbonyl-1-(4-methoxy-phenyl)-vinyl]-1H-indol-5-yloxy}-ethyl)-3,4-dihydro-2H-[1,8]naphthyridine-1-carboxylic acid tert-butyl ester using the procedure described in Example 18, step (e), in 37% yield. ¹H NMR (CDCl₃) δ 7.24–7.00 (m, 6H), 6.87–6.73 (m, 4H), 6.33 (d, 1H, J=2.8 Hz), 5.89 (m, 1H), 4.28 (t, 2H, J=6.8 Hz), 3.96 (q, 2H, J=7.2 Hz), 3.68 (m, 5H), 3.16 (m, 4H), 2.73 (m, 2H), 1.85 (m, 2H), 1.44 (s, 9H), 1.02 (t, 3H, J=7.2 Hz).

f) 3-(4-Methoxy-phenyl)-3-{5-[2-(5,6,7,8-tetrahydro-[1,8]naphthyridin-2-yl)-ethoxy]-indol-1-yl}-propionic acid ethyl ester The title compound was synthesized from 7-(2-{1-[2-ethoxycarbonyl-1-(4-methoxy-phenyl)-ethyl]-1H-indol-5- yloxy}-ethyl)-3,4-dihydro-2H-[1,8]naphthyridine-1-carboxylic acid tert-butyl ester using the procedure described in Example 16, step (f), in 80% yield. ¹H NMR (CDCl₃) δ 7.28–7.08 (m, 6H), 6.83 (m, 4H), 6.43 (d, 1H, J=2.8 Hz), 5.97 (m, 1H), 4.89 (bs, 1H), 4.28 (m, 2H), 4.05 (q, 2H, J=7.2 Hz), 3.77 (s, 3H), 3.41 (m, 2H), 3.26 (m, 2H), 3.04 (m, 2H), 2.66 (m, 2H), 1.91 (m, 2H), 1.11 (t, 3H, J=7.2 Hz).

g) 3-(4-Methoxy-phenyl)-3-{5-[2-(5,6,7,8-tetrahydro-[1,8]naphthyridin-2-yl)-ethoxy]-indol-1-yl}-propionic acid The title compound was synthesized from 3-(4-methoxy-phenyl)-3-{5-[2-(5,6,7,8-tetrahydro-[1,8]naphthyridin-2-yl)-ethoxy]-indol-1-yl}-propionic acid ethyl ester using the procedure described in Example 18, step (g), in 15% yield. ¹H NMR (CDCl₃) δ 10.6 (bs, 1H), 7.47 (d, 1H, J=3.2 Hz), 7.28 (d, 1H, J=8.9 Hz), 7.08 (m, 3H), 6.84 (d, 1H, J=2.3 Hz), 6.76 (d, 2H, J=8.8 Hz), 6.61 (dd, 1H, J=2.4, 6.5 Hz), 6.46 (m, 1H), 6.25 (d, 1H, J=7.3 Hz), 6.08 (m, 1H), 3.73 (s, 3H), 3.59 (m, 1H), 3.40 (m, 3H), 3.29–3.13 (m, 2H), 2.60 (m, 4H), 2.46 (m, 1H), 1.85 (m, 2H). Mass Spectrum (LCMS, ESI) calculated for $C_{28}H_{30}N_3O_4$ 472.2 (M-Boc+H); found 472.3.

EXAMPLE 30

3-Quinolin-3-yl-3-{5-[2-(5,6,7,8-tetrahydro-[1,8]naphthyridin-2-yl)-ethoxy]-indol-1-yl}-propionic acid

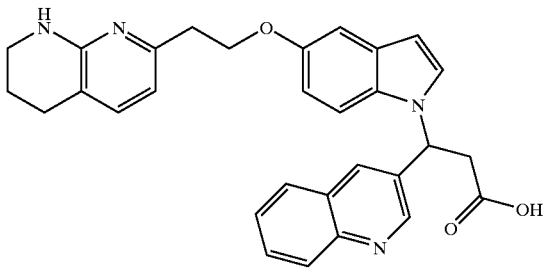

a) 3-Ethynyl-quinoline

The title compound was synthesized from 3-bromoquinoline using the procedures described in Example 18, step (a) and step (b), in 68% yield. ¹H NMR Cl₃CD, δ: 3.28 (s, 1H), 7.60 (m, 1H), 7.74 (m, 1H), 7.80 (m, 1H), 8.09 (d, 1H, J=8.8 Hz), 8.29 (d, 1H, J=2.0 Hz), 8.95 (d, 1H, J=2.0 Hz).

b) Quinolin-3-yl-propynoic acid ethyl ester

The title compound was synthesized from 3-ethynyl-quinoline using the procedure described in Example 23, step (c), in 34% yield. ¹H NMR Cl₃CD, δ: 1.38 (t, 3H, J=7.2 Hz), 4.34 (c, 2H, J=7.2 Hz), 7.60 (m, 1H), 7.80 (m, 2H), 8.11 (d, 1H, J=8.4 Hz), 8.40 (d, 1H, J=2.0 Hz), 8.99 (d, 1H, J=2.0 Hz).

c) 7-{2-[1-2-Ethoxycarbonyl-1-quinolin-3-yl-vinyl]-1H-indol-5-yloxy]-ethyl}-3,4-dihydro-2H-[1,8]naphthyridine-1-carboxylic acid tert-butyl ester The title compound was synthesized from quinolin-3-yl-propynoic acid ethyl ester and 7-[2-(1H-indol-5-yloxy)-ethyl]-3,4-dihydro-2H-[1,8]naphthyridine-1-carboxylic acid tert-butyl ester using the procedure described in Example 16, step (d1), in 81% yield as an E/Z isomeric mixture. ¹H NMR (CDCl₃) δ 8.90 (m, 1H), 8.14 (m, 1.3H), 8.04 (m, 0.7H), 7.79 (m, 2H), 7.58 (m, 1H), 7.30 (d, 1H, J=7.6 Hz), 7.13 (m, 2H), 6.93 (m, 1.3H), 6.75 (m, 1.7H), 6.63 (d, 0.7H, J=3.2 Hz), 6.53 (d, 0.3H, J=3.2 Hz), 6.38 (s, 0.7H), 6.32 (s, 0.3H), 4.38 (m, 2H), 4.05 (m, 2H), 3.75 (t, 2H, J=6.4 Hz), 3.19 (t, 2H, J=6.4 Hz), 2.72 (t, 2H, J=6.4 Hz), 1.91 (m, 2H), 1.51 (s, 9H), 1.13 (t, 0.9H, J=7.0 Hz), 1.05 (t, 2.1H, J=7.0 Hz).

d) 7-{2-[1-(2-Ethoxycarbonyl-1-quinolin-3-yl-ethyl)-1H-indol-5-yloxy]-ethyl}-3,4-dihydro-2H-[1,8]naphthyridine-1-carboxylic acid tert-butyl ester The title compound was synthesized from 7-{2-[1-2-ethoxycarbonyl-1-quinolin-3-yl-vinyl)-1H-indol-5-yloxy]-ethyl}-3,4-dihydro-2H-[1,8]naphthyridine-1-carboxylic acid tert-butyl ester using the procedure described in Example 18, step (e), in 17% yield. ¹H NMR (CDCl₃) δ 8.81 (d, 1H, J=4.4 Hz), 8.07 (d, 1H, J=2.1 Hz), 7.88 (d, 1H, J=2.4 Hz), 7.10 (m, 2H), 7.54 (m, 1H), 7.25 (m, 3H), 7.11 (d, 1H, J=2.0 Hz), 6.94 (d, 1H, J=7.6 Hz), 6.82 (dd, 1H, J=2.4, 6.4 Hz), 6.50 (d, 1H, J=3.2 Hz), 6.24 (t, 1H, J=7.6 Hz), 4.37 (t, 2H J=6.8 Hz), 4.10 (m, 2H), 3.76 (m, 2H), 3.40 (t, 2H, J=7.6 Hz), 3.20 (t, 2H, J=6.8 Hz), 2.73 (t, 2H, J=6.8 Hz), 1.92 (m, 2H), 1.51 (s, 9H), 1.13 (t, 3H, J=6.8 Hz).

e) 3-Quinolin-3-yl-3-{5-[2-(5,6,7,8-tetrahydro-[1,8]naphthyridin-2-yl)-ethoxy]-indol-1-yl}-propionic acid ethyl ester The title compound was synthesized from 7-{2-[1-(2-ethoxycarbonyl-1-quinolin-3-yl-ethyl)-1H-indol-5-yloxy]-ethyl}-3,4-dihydro-2H-[1,8]naphthyridine-1-carboxylic acid tert-butyl ester using the procedure described in Example 16, step (f), in 60% yield. ¹H NMR (CDCl₃) δ 8.83 (d, 1H, J=2.0 Hz), 8.08 (d, 1H, J=8.8 Hz), 7.88 (d, 1H, J=2.0 Hz), 7.71 (m, 2H), 7.54 (m, 1H), 7.23 (m, 2H), 7.10 (m, 2H), 6.84 (dd, 1H, J=2.4, 6.4 Hz), 6.49 (m, 2H), 6.24 (t, 1H, J=3.2 Hz), 4.95 (s, 1H), 4.29 (t, 2H, J=6.8 Hz), 4.08 (m, 2H), 3.41 (m, 4H), 3.05 (t, 2H, J=6.4 Hz), 2.70 (t, 2H, J=6.0 Hz 1.92 (m, 2H), 1.13 (t, 3H, J=7.2 Hz).

f) 3-Quinolin-3-yl-3-{5-[2-(5,6,7,8-tetrahydro-[1,8]naphthyridin-2-yl)-ethoxy]-indol-1-yl}-propionic acid The title compound was synthesized from 3-quinolin-3-yl-3-{5-[2-(5,6,7,8-tetrahydro-[1,8]naphthyridin-2-yl)-ethoxy]-indol-1-yl}-propionic acid ethyl ester using the procedure described in Example 18, step (g), in 21% yield. ¹H NMR (CDCl₃) δ 10.21 (bs, 1H), 8.87 (d, 1H, J=2.4 Hz), 8.04 (d, 1H, J=8.8 Hz), 7.78 (d, 1H, J=1.6 Hz), 7.67 (m, 2H), 7.50 (m, 2H), 7.13 (d, 2H, J=7.6 Hz), 6.91 (d, 1H, J=2.4 Hz), 6.54 (dd, 1H, J=0.8, 8.8 Hz), 6.52 (d, 1H, J=2.8 Hz), 6.30 (m, 2H), 3.71 (m, 2H), 3.37 (m, 4H), 2.65 (m, 4H), 1.82 (m, 2H). Mass Spectrum (LCMS, ESI) calculated for $C_{30}H_{29}N_4O_3$: 493.2 (M+H), found: 493.3.

EXAMPLE 31

3-(3-Chloro-phenyl)-3-{5-[2-(5,6,7,8-tetrahydro-[1,8]naphthyridin-2-yl)-ethoxy]-indol-1-yl}-propionic acid

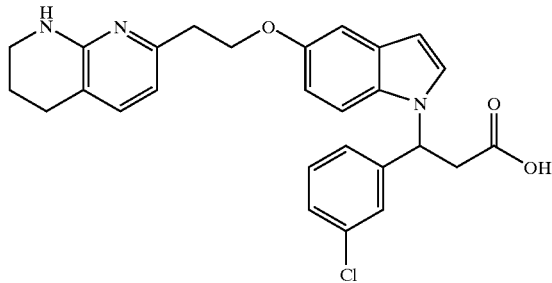

a) (3-Chloro-phenylethynyl)-trimethyl-silane

The title compound was synthesized from commercially available 1-iodo-3-chloro-benzene using the procedure described in Example 18, step (a), in 98% yield. ¹H NMR (CDCl₃) δ 7.48 (t, 1H, J=1.8 Hz), 7.36 (dt, 1H, J=1.4, 7.5 Hz), 7.30 (m, 1H), 7.26 (m, 1H), 0.28 (s, 9H).

b) 3-Chloro-phenylethynyl

The title compound was synthesized from (3-chloro-phenylethynyl)-trimethyl-silane using the procedure described in Example 23, step (b), in 98% yield. $^1$H NMR (CDCl$_3$) δ 7.48 (m, 1H), 7.38 (m, 2H), 7.25 (m, 1H), 3.11 (s, 1H).

c) (3-Chloro-phenyl)-propynoic acid ethyl ester

The title compound was synthesized from 4-chloro-phenylethynyl using the procedure described in Example 23, step (c), in 52% yield. $^1$H NMR (CDCl$_3$) δ 7.61 (m, 1H), 7.41 (m, 2H), 7.25 (m, 1H), 4.32 (q, 2H), 1.31 (t, 3H).

d) 7-(2-{1-[1-(3-Chloro-phenyl)-2-ethoxycarbonyl-vinyl]-1H-indol-5-yloxy}-ethyl)-3,4-dihydro-2H-[1,8]naphthyridine-1-carboxylic acid tert-butyl ester The title compound was synthesized from (3-chloro-phenyl)-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 16, step (d1), in 90% yield as an E/Z isomeric mixture. $^1$H NMR (CDCl$_3$) [E/Z mixture] δ 7.36–7.24 (m, 2H), 7.14–7.6.70 (m, 8H), 6.56 (s, 0.5H), 6.48 (m, 0.5H), 6.21 (s, 0.5H), 6.14 (s, 0.5H), 4.37 (m, 2H), 4.12 (q, 2H, J=6.8 Hz), 3.76 (m, 2H), 3.20 (t, 2H, J=6.8 Hz), 2.73 (t, 2H, J=6.8 Hz), 1.92 (m, 2H), 1.52 (s, 9H), 1.26 (t, 3H, J=7.2 Hz). Mass Spectrum (LCMS, ESI) calculated for C$_{29}$H$_{29}$ClN$_3$O$_3$ 502.2 (M-Boc+1); found 502.4.

e) 7-(2-{1-[1-(3-Chloro-phenyl)-2-ethoxycarbonyl-ethyl]-1H-indol-5-yloxy}-ethyl)-3,4-dihydro-2H-[1,8]naphthyridine-1-carboxylic acid tert-butyl ester The title compound was synthesized from 7-(2-{1-[1-(3-chloro-phenyl)-2-ethoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 86% yield. $^1$H NMR (CDCl$_3$) δ 7.23–7.01 (m, 7H), 6.94 (m, 1H), 6.85 (d, 1H, J=7.6 Hz), 6.75 (dd, 1H, J=2.4, 6.5 Hz), 6.37 (d, 1H, J=4.0 Hz), 5.89 (t, 1H, J=7.5 Hz), 4.28 (q, 2H, J=6.9 Hz), 3.98 (q, 2H, J=7.1 Hz), 3.67 (m, 2H), 3.14 (m, 4H), 2.64 (t, 2H, J=6.6 Hz), 1.83 (m, 2H), 1.43 (s, 9H), 1.02 (t, 3H, J=7.1 Hz). Mass Spectrum (LCMS, ESI) calculated for C$_{29}$H$_{31}$ClN$_3$O$_3$ 504.2 (M-Boc+H); found 504.4.

f) 3-(3-Chloro-phenyl)-3-{5-[2-(5,6,7,8-tetrahydro-[1,8]naphthyridin-2-yl)-ethoxy]-indol-1-yl}-propionic acid ethyl ester The title compound was synthesized from 7-(2-{1-[1-(3-Chloro-phenyl)-2-ethoxycarbonyl-ethyl]-1H-indol-5-yloxy}-ethyl)-3,4-dihydro-2H-[1,8]naphthyridine-1-carboxylic acid tert-butyl ester using the procedure described in Example 16, step (f), in 63% yield. $^1$H NMR (CDCl$_3$) δ 7.26–7.00 (m, 8H), 6.82 (dd, 1H, J=2.4, 6.4 Hz), 6.46 (m, 1H), 5.97 (t, 1H, J=7.6 Hz), 4.85 (bs, 1H), 4.30 (t, 2H, J=7.2 Hz), 4.06 (q, 2H, J=7.2 Hz), 3.39 (m, 2H), 3.31–3.18 (m, 2H), 3.03 (t, 1H, J=6.8 Hz), 2.68 (t, 2H, J=6.4 Hz), 1.89 (m, 2H), 1.10 (t, 3H, J=7.2 Hz).

g) 3-(3-Chloro-phenyl)-3-{5-[2-(5,6,7,8-tetrahydro-[1,8]naphthyridin-2-yl)-ethoxy]-indol-1-yl}-propionic acid The title compound was synthesized from 3-(3-chloro-phenyl)-3-{5-[2-(5,6,7,8-tetrahydro-[1,8]naphthyridin-2-yl)-ethoxy]-indol-1-yl}-propionic acid ethyl ester using the procedure described in Example 18, step (g), in 30% yield. $^1$H NMR (CDCl$_3$/CD$_3$OD) δ 7.24 (d, 1H, J=3.2 Hz), 7.13 (d, 1H, J=7.3 Hz), 7.03 (m, 4H), 6.85 (m, 2H), 6.60 (m, 1H), 6.33 (m, 2H), 5.85 (m, 1H), 3.30–3.21 (m, 4H), 3.00 (m, 2H), 2.81 (m, 2H), 2.57 (m, 2H), 1.76 (m, 2H). Mass Spectrum (LCMS, ESI) calculated for C$_{27}$H$_{27}$ClN$_3$O 476.2 (M+H); found 476.9.

EXAMPLE 32

3-Naphthalen-2-yl-3-{5-[2-(5,6,7,8-Tetrahydro-[1,8]naphthyridin-2-yl)-ethoxy]-indol-1-yl}-propionic acid

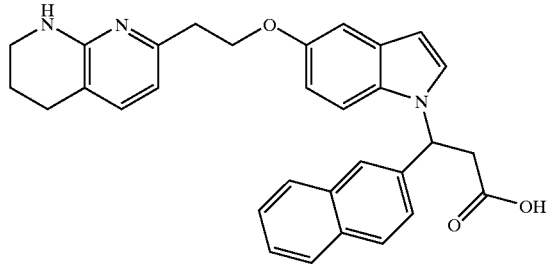

a) 3-Naphthalen-2-yl-3-oxo-propionic acid ethyl ester

Diethylcarbonate (3.90 mL, 33.0 mmol) was added to a slurry of sodium hydride (1.30 g, 33.0 mmol) in toluene (100 mL) at room temperature under Ar. A solution of 2-acetophenone (5.00 g, 29.0 mmol) in toluene (30 mL) was added immediately and the mixture was heated at reflux for 2 hours. After cooling to room temperature, the mixture was poured over ice/water and extracted with ethyl acetate. The organic extracts were dried over magnesium sulfate and the solvent was removed under reduced pressure. The crude product was purified over silica (2.5% ethyl acetate/hexanes) to give the title compound (4.45 g, 55%, 3:1 mixture of keto/enol form) as clear oil. $^1$H NMR (CDCl$_3$) δ 12.69 (s, 0.25H, enol), 8.46 (d, 0.75H, J=0.8 Hz), 8.37 (d, 0.25H, J=0.8 Hz), 7.98 (m, 2H), 7.88 (m, 3H), 7.78 (m, 0.25H), 7.57 (m, 2.75H), 5.82 (s, 0.25H, enol), 4.27 (m, 2H), 4.13 (s, 1.5H, keto) 1.36 (t, 0.75H, J=8.0 Hz), 1.27 (t, 1.25H, J=8.0 Hz).

b) Naphthalene-2-yl-propynoic acid ethyl ester

Triflic anhydride (2.9 mL, 17 mmol) was added dropwise to a solution of triphenylphosphine oxide (4.8 g, 17 mmol) in 1,2-dichloroethane (40 mL) at 0° C. The resulting suspension was stirred for 15 minutes, followed by the dropwise addition of a solution of 3-naphthalen-2-yl-3-oxo-propionic acid ethyl ester (3.2 g, 12 mmol) in 1,2-dichloroethane (40 mL). After the addition was complete, triethylamine (4.0 mL, 29 mmol) was added and the reaction mixture was heated at reflux for 1 hr. The solution was cooled to room temperature, washed with water, and dried (MgSO$_4$). The solvent was removed under reduced pressure, and the product was purified via column chromatography with silica eluting with hexane/ethyl acetate (9/1) to yield naphthalene-2-yl-propynoic acid ethyl ester (1.15 g, 37% yield) as a yellow oil. $^1$H NMR (CDCl$_3$) δ 8.25 (s, 1H), 7.95 (m, 3H), 7.66 (m, 3H), 4.46 (m, 2H), 1.51 (t, 3H, J=8.0 Hz).

c) 7-{2-[1-(2-Ethoxycarbonyl-1-naphthalen-2-yl-vinyl)-1H-indol-5-yloxy]-ethyl}-3,4-dihydro-2H-[1,8]naphthyridine-1-carboxylic acid tert-butyl ester The title compound was synthesized from naphthalene-2-yl-propynoic acid ethyl ester and 7-[2-(1H-indol-5-yloxy)-ethyl]-3,4-dihydro-2H-[1,8]naphthyridine-1-carboxylic acid tert-butyl ester using the procedure described in Example 16, step (d1), in 88% yield as an E/Z isomeric mixture. $^1$H NMR (CDCl$_3$) δ 7.85 (m, 4H), 7.50 (m, 2.6H), 7.33 (m, 1.6H), 7.12 (m, 1.8H), 6.95 (m, 1.4H), 6.74 (m, 1.6H), 6.61 (d, 0.6H, J=0.4 Hz), 6.50 (d, 0.4H, J=0.4 Hz), 6.35 (s, 0.6H), 6.23 (s, 0.4 Hz), 4.36 (t, 2H, J=8.0 Hz), 4.05 (m, 2H), 3.76 (m, 2H), 3.20 (t, 2H, J=8.0), 2.73 (t, 2H, J=8.0 Hz), m, 2H), 1.51 (s, 9H), 1.07 (m, 3H).

d) 7-{2-[1-(2-Ethoxycarbonyl-1-naphthalen-2-yl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-naphthalen-2-yl-vinyl)-1H-indol-5-yloxy]-ethyl}-3,4-dihydro-2H-[1,8]naphthyridine-1-carboxylic acid tert-butyl ester using the procedure described in Example 18, step (e), in 80% yield. $^1$H NMR (CDCl$_3$) δ 7.76 (m, 3H), 7.67 (s, 1H), 7.45 (m, 2H), 7.29 (d, 1H, J=7.6 Hz), 7.23 (m, 3H), 7.09 (d, 1H, J=2.4 Hz), 6.92 (d, 2H, J=8.0 Hz), 6.80 (dd, 1H, J=2.4, 6.4 Hz), 6.18 (t, 1H, J=7.6 Hz), 4.35 (t, 2H, J=7.2 Hz), 4.08 (m, 2H), 3.75 (m, 2H), 3.36 (m, 2H), 3.19 (t, 2H, J=6.8 Hz), 2.71 (t, 2H, J=6.8 Hz), 1.91 (m, 2H), 1.50 (s, 9H), 1.10 (t, 3H, J=6.8 Hz).

e) 3-Naphthalen-2-yl-3-{5-[2-(5,6,7,8-Tetrahydro-[1,8]naphthyridin-2-yl)-ethoxy]-indol-1-yl}-propionic acid ethyl ester The title compound was synthesized from 7-{2-[1-(2-ethoxycarbonyl-1-naphthalen-2-yl-vinyl)-1H-indol-5-yloxy]-ethyl}-3,4-dihydro-2H-[1,8]naphthyridine-1-carboxylic acid tert-butyl ester using the procedure described in Example 16, step (f), in 71% yield. $^1$H NMR (CDCl$_3$) δ 7.76 (m, 3H), 7.67 (s, 1H), 7.46 (m, 2H), 7.23 (m, 3H), 7.08 (m, 2H), 6.80 (dd, 1H, J=2.4, 6.4 Hz), 6.45 (m, 2H), 6.17 (t, 1H, J=Hz), 5.07 (s, 1H), 4.27 (t, 2H, J=6.8 Hz), 4.05 (m, 2H), 3.38 (m, 4H), 3.05 (t, 2H, J=6.8 Hz), 2.67 (t, 2H, J=6.4 Hz 1.88 (m, 2H), 1.09 (t, 3H, J=7.2 Hz).

f) 3-Naphthalen-2-yl-3-{5-[2-(5,6,7,8-Tetrahydro-[1,8]naphthyridin-2-yl)-ethoxy]-indol-1-yl}-propionic acid The title compound was synthesized from 3-naphthalen-2-yl-3-{5-[2-(5,6,7,8-tetrahydro-[1,8]naphthyridin-2-yl)-ethoxy]-indol-1-yl}-propionic acid ethyl ester using the procedure described in Example 18, step (g), in 34% yield. $^1$H NMR (DMSO-d$_6$) δ 7.90 (s, 1H), 7.84 (m, 3H), 7.71 (d, 1H, J=3.2 Hz), 7.47 (m, 4H), 7.02 (m, 2H), 6.68 (dd, 1H, J=2.4, 6.4 Hz), 6.39 (d, 1H, J=2.8 Hz), 6.34 (d, 1H, J=7.2 Hz), 6.31 (s, 1H), 6.10 (m, 1H), 4.18 (t, 2H, J=6.8 Hz), 3.59 (m, 2H), 3.23 (m, 2H), 2.85 (t, 2H, J=6.8 Hz), 2.50 (t, 2H, J=2.0 Hz), 1.75 (m, 2H). Mass Spectrum (LCMS, ESI) calculated for C$_{31}$H$_{30}$N$_3$O$_3$: 492.2 (M+H), found: 492.3.

EXAMPLE 33

3-(2-Chloro-phenyl)-3-{5-[2-(5,6,7,8-tetrahydro-[1,8]naphthyridin-2-yl)-ethoxy]-indol-1-yl}-propionic acid

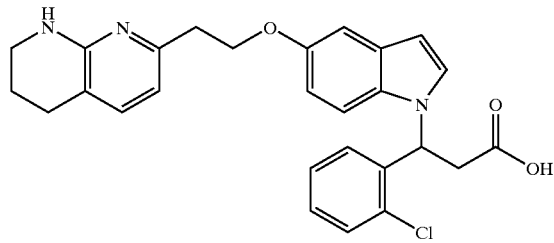

a) (2-Chloro-phenyl)-propynoic acid methyl ester

The title compound was synthesized from commercially available 3-(2-chloro-phenyl)-3-oxo-propionic acid methyl ester using the procedure described in Example 32, step (b), in 71% yield. $^1$H NMR (CDCl$_3$) δ 7.53 (dd, 1H, J=1.6, 6.0 Hz), 7.36 (m, 1H), 7.30 (dt, 1H, J=1.6, 5.7 Hz), 7.19 (dt, 1H, J=1.3, 6.4 Hz), 3.78 (s, 3H).

b) 7-(2-{1-[1-(2-Chloro-phenyl)-2-methoxycarbonyl-vinyl]-1H-indol-5-yloxy}-ethyl)-3,4dihydro-2H-[1,8]naphthyridine-1-carboxylic acid tert-butyl ester The title compound was synthesized from (2-chloro-phenyl)-propynoic acid methyl ester and 7-[2-(1H-Indol-5-yloxy)-ethyl]-3,4-dihydro-2H-[1,8]naphthyridine-1-carboxylic acid tert-butyl ester using the procedure described in Example 16, step (d1), in 43% yield as an E/Z isomeric mixture. $^1$H NMR (CDCl$_3$) [E/Z mixture] δ 7.54–7.30 (m, 6H), 7.18 (m, 1H), 6.95 (m, 1H), 6.83 (m, 1H), 6.68–6.50 (m, 2H), 6.35 (s, 0.33H), 5.95 (s, 0.67H), 4.39 (m, 2H), 3.78 (m, 2H), 3.64 (s, 3H), 3.22 (m, 2H), 2.73 (m, 2H), 1.92 (m, 2H) 1.52 (s, 9H). Mass Spectrum (LCMS, ESI) calculated for C$_{28}$H$_{27}$ClN$_3$O$_3$ 488.2 (M-Boc+H); found 488.4.

c) 7-(2-{1-[1-(2-Chloro-phenyl)-2-methoxycarbonyl-ethyl]-1H-indol-5-yloxy}-ethyl)-3,4-dihydro-2H-[1,8]naphthyridine-1-carboxylic acid tert-butyl ester The title compound was synthesized from 7-(2-{1-[1-(2-chloro-phenyl)-2-methoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 85% yield. $^1$H NMR (CDCl$_3$) δ 7.41–7.25 (m, 3H), 7.22–6.79 (m, 7H), 6.50 (m, 1H), 6.40 (m, 1H), 4.37 (t, 2H, J=7.2 Hz), 3.76 (m, 2H), 3.61 (s, 3H), 3.20 (m, 4H), 2.75 (m, 2H), 1.94 (m, 2H), 1.50 (s, 9H).

d) 3-(2-Chloro-phenyl)-3-{5-[2-(5,6,7,8-tetrahydro-[1,8]naphthyridin-2-yl)-ethoxy]-indol-1-yl}-propionic acid methyl ester The title compound was synthesized from 7-(2-{1-[1-(2-chloro-phenyl)-2-methoxycarbonyl-ethyl]-1H-indol-5-yloxy}-ethyl)-3,4-dihydro-2H-[1,8]naphthyridine-1-carboxylic acid tert-butyl ester using the procedure described in Example 16, step (f), in 45% yield. $^1$H NMR (CDCl$_3$) δ 7.31 (m, 1H), 7.20–7.00 (m, 6H), 6.83 (dd, 1H, J=1.7, 6.0 Hz), 6.74 (dd, 1H, J=1.7, 6.0 Hz), 6.39 (m, 2H), 6.32 (m, 1H), 4.82 (s, 1H), 4.21 (m, 2H), 3.54 (s, 3H), 3.32 (m, 2H), 3.17 (m, 2H), 2.95 (m, 2H), 2.62 (m, 2H), 1.82 (m, 2H).

e) 3-(2-Chloro-phenyl)-3-{5-[2-(5,6,7,8-tetrahydro-[1,8]naphthyridin-2-yl)-ethoxy]-indol-1-yl}-propionic acid The title compound was synthesized from 3-(2-chloro-phenyl)-3-{5-[2-(5,6,7,8-tetrahydro-[1,8]naphthyridin-2-yl)-ethoxy]-indol-1-yl}-propionic acid methyl ester using the procedure described in Example 18, step (g), in 33% yield. $^1$H NMR (CDCl$_3$) δ 10.4 (bs, 1H), 7.60 (d, 1H, J=2.8 Hz), 7.37 (dd, 1H, J=1.2, 6.8 Hz), 7.18–7.04 (m, 4H), 6.85 (dd, 1H, J=1.4, 6.3 Hz), 6.78 (d, 1H, J=2.3 Hz), 6.59 (dd, 1H, J=2.2, 6.7 Hz), 6.49 (m, 2H), 6.23 (d, 1H, J=7.2 Hz), 3.42 (m, 3H), 3.39–3.08 (m, 4H), 2.62 (t, 2H, J=6.2 Hz), 2.51 (m, 1H), 3.35 (m, 1H), 1.82 (m, 2H). Mass Spectrum (LCMS, ESI) calculated for C$_{27}$H$_{27}$ClN$_3$O$_3$ 476.2 (M+H); found: 476.31.

EXAMPLE 34

3-Naphthalen-1-yl-3-{5-[2-(5,6,7,8-Tetrahydro-[1,8]naphthyridin-2-yl)-ethoxy]-indol-1-yl}-propionic acid

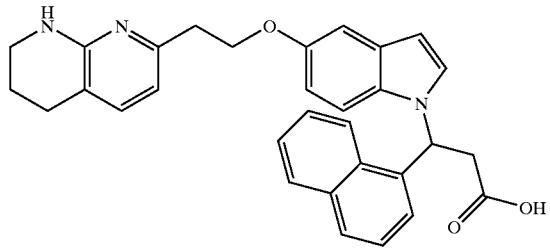

a) 3-Naphthalen-1-yl-3-oxo-propionic acid ethyl ester

The title compound was synthesized from commercially available 1-acetonapthrone using the procedure described in Example 32, step (a), in 25% yield as a 3:1 mixture of keto/enol tautomers. $^1$H NMR (CDCl$_3$) δ 12.73 (s, 0.25H, enol), 8.75 (dd, 0.75H, J=4.0, 8.0 Hz, keto), 8.36 (dd, 0.25H, J=4.0, 8.0 Hz, enol), 8.03 (d, 0.75H, J=8.0 Hz), 7.90 (m, 2.75H), 7.64 (m, 1.5H), 7.54 (m, 3H), 5.50 (s, 0.25H, enol), 4.32 (m, 0.5H), 4.20 (m, 1.5H) 4.11 (s, 1.5H, keto), 1.36 (t, 0.75H, J=8.0 Hz), 1.21 (t, 1.25, J=8.0 Hz).

b) Naphthalene-1-yl-propynoic acid ethyl ester

The title compound was synthesized from 3-naphthalen-1-yl-3-oxo-propionic acid ethyl ester using the procedure described in Example 32, step (b), in 25% yield. $^1$H NMR (CDCl$_3$) δ 8.35 (dd, 1H, J=0.4, 1.4 Hz), 7.95 (d, 1H, J=8.0 Hz), 7.86 (m, 2H), 7.61 (m, 2H), 7.46 (m, 1H), 4.36 (m, 2H), 1.41 (t, 3H, J=8.0 Hz).

c) 7-{2-[1-(2-Ethoxycarbonyl-1-naphthalen-1-yl-vinyl)-1H-indol-5-yloxy]-ethyl}-3,4-dihydro-2H-[1,8]naphthyridine-1-carboxylic acid tert-butyl ester The title compound was synthesized from naphthalene-1-yl-propynoic acid ethyl ester and 7-[2-(1H-indol-5-yloxy)-ethyl]-3,4-dihydro-2H-[1,8]naphthyridine-1-carboxylic acid tert-butyl ester using the procedure described in Example 16, step (d1), in 37% yield as an E/Z isomeric mixture. $^1$H NMR (CDCl$_3$) δ 8.32 (m, 1H), 7.85 (m, 2H), 7.47 (m, 3H), 7.27 (m, 2.5H), 6.95 (m, 3H), 6.72 (m, 1.5H), 6.58 (m, 0.5H), 6.35 (m, 1.5H), 4.27 (m, 2H), 4.03 (m, 2H), 3.69 (m, 2H), 3.14 (m, 2H), 2.67 (m, 2H), 1.86 (m, 2H), 1.45 (s, 9H), 1.18 (m, 3H).

d) 7-{2-[1-(2-Ethoxycarbonyl-1-naphthalen-1-yl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-naphthalen-1-yl-vinyl)-1H-indol-5-yloxy]-ethyl}-3,4-dihydro-2H-[1,8]naphthyridine-1-carboxylic acid tert-butyl ester using the procedure described in Example 18, step (e), in 23% yield. $^1$H NMR (CDCl$_3$) δ 8.04 (m, 1H), 7.88 (m, 1H), 7.81 (d, 1H, J=8.4 Hz), 7.50 (m, 2H), 7.40 (t, 1H, J=7.6 Hz), 7.28 (m, 4H), 7.10 (d, 1H, J=2.4 Hz), 6.96 (t, 1H, J=7.6 Hz), 6.83 (m, 2H), 6.40 (d, 1H, J=8.0 Hz), 4.35 (t, 2H, J=8.0 Hz), 4.06 (m, 2H), 3.77 (m, 2H), 3.36 (m, 2H), 3.21 (t, 2H, J=8.0 Hz), 2.74 (t, 2H, J=8.0 Hz), 1.92 (m, 2H), 1.50 (s, 9H), 1.11 (t, 3H, J=8.0 Hz).

e) 3-Naphthalen-1-yl-3-{5-[2-(5,6,7,8-Tetrahydro-[1,8]naphthyridin-2-yl)-ethoxy]-indol-1-yl}-propionic acid ethyl ester The title compound was synthesized from 7-{2-[1-(2-ethoxycarbonyl-1-naphthalen-1-yl-ethyl)-1H-indol-5-yloxy]-ethyl}-3,4-dihydro-2H-[1,8]naphthyridine-1-carboxylic acid tert-butyl ester using the procedure described in Example 16, step (f), in 90% yield. $^1$H NMR (CDCl$_3$) δ 8.02 (m, 1H), 7.89 (m, 1H), 7.81 (d, 1H, J=8.0 Hz), 7.50 (m, 2H), 7.39 (t, 1H, J=7.6 Hz), 7.28 (m, 2H), 7.10 (m, 3H), 6.85 (m, 2H), 6.48 (m, 1H), 6.41 (d, 1H, J=3.2 Hz), 4.92 (s, 1H), 4.30 (t, 2H, J=7.2 Hz), 4.07 (m, 2H), 3.37 (m, 4H), 3.05 (t, 2H, J=6.4 Hz), 2.68 (t, 2H, J=6.4 Hz), 1.88 (m, 2H), 1.09 (t, 3H, J=7.2 Hz).

f) 3-Naphthalen-1-yl-3-{5-[2-(5,6,7,8-Tetrahydro-[1,8]naphthyridin-2-yl)-ethoxy]-indol-1-yl}-propionic acid The title compound was synthesized from 3-naphthalen-1-yl-3-{5-[2-(5,6,7,8-Tetrahydro-[1,8]naphthyridin-2-yl)-ethoxy]-indol-1-yl}-propionic acid ethyl ester using the procedure described in Example 18, step (g), in 52% yield. $^1$H NMR (DMSO-d$_6$) δ 8.17 (d, 1H, J=8.4 Hz), 7.96 (m, 1H), 7.88 (d, 1H, J=8.0 Hz), 7.55 (m, 3H), 7.45 (t, 1H, J=7.2 Hz), 7.30 (m, 2H), 7.03 (m 2H), 6.68 (m, 2H), 6.36 (m, 2H), 6.31 (s, 1H), 4.19 (t, 2H, J=7.2 Hz), 3.60 (m, 2H) 3.24 (m, 2H), 2.86 (t, 2H, J=7.2 Hz), 2.60 (t, 2H, J=6.4 Hz), 1.74 (m, 2H). Mass Spectrum (LCMS, ESI) calculated for C$_{31}$H$_{30}$N$_3$O$_3$: 492.2 (M+H), found: 492.3.

EXAMPLE 35

3-(4-Fluoro-phenyl)-3-{5-[2-(5,6,7,8-tetrahydro-[1,8]naphthyridin-2-yl)-ethoxy]-indol-1-yl}-propionic acid

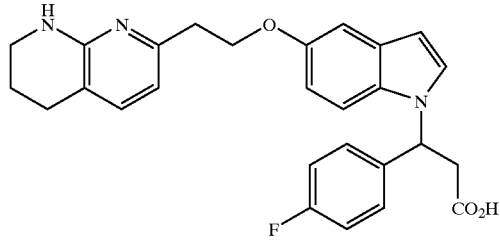

a) (4-Fluoro-phenyl)-propynoic acid methyl ester

The title compound was synthesized from 3-(4-fluoro-phenyl)-3-oxo-propionic acid methyl ester using the procedure described in Example 32, step (b), in 91% yield. $^1$H NMR (CDCl$_3$) δ 7.59 (m, 2H), 7.08 (m, 2H), 3.84 (s, 3H).

b) 7-(2-{1-[1-(4-Fluoro-phenyl)-2-methoxycarbonyl-vinyl]-1H-indol-5-yloxy}-ethyl)-3,4-dihydro-2H-[1,8]naphthyridine-1-carboxylic acid tert-butyl ester The title compound was synthesized from (4-fluoro-phenyl)-propynoic acid methyl ester and 7-[2-(1H-Indol-5-yloxy)-ethyl]-3,4-dihydro-2H-[1,8]naphthyridine-1-carboxylic acid tert-butyl ester using the procedure described in Example 17, step (a), in 73% yield as an E/Z isomeric mixture. $^1$H NMR (CDCl$_3$) [E/Z mixture] δ 7.43 (m, 1H), 7.30 (m, 2H), 7.00–7.20 (m, 3), 6.94 (m, 1H), 6.50–6.90 (m, 3H), 6.12 (s, 1H), 4.36 (m, 2H), 3.75 (m, 2H), 3.7 and 3.6 (s, 3H), 3.20 (m, 2H), 2.75 (m, 2H), 1.90 (m, 2H), 1.50 (s, 9H). Mass Spectrum (LCMS, ESI) calculated for C$_{33}$H$_{35}$FN$_3$O$_5$ 572.3 (M+H); found 472.3 (M-Boc+H).

c) 7-(2-{1-[1-(4-Fluoro-phenyl)-2-methoxycarbonyl-ethyl]-1H-indol-5-yloxy}-ethyl)-3,4-dihydro-2H-[1,8]naphthyridine-1-carboxylic acid tert-butyl ester The title compound was synthesized from 7-(2-{1-[1-(4-fluoro-phenyl)-2-methoxycarbonyl-vinyl]-1H-indol-5-yloxy}-ethyl)-3,4-dihydro-2H-[1,8]naphthyridine-1-carboxylic acid tert-butyl ester using the procedure described in Example 18, step (e), in 57% yield. $^1$H NMR (CDCl$_3$) δ 7.34 (d, 1H), 7.15 (m, 4H), 6.95 (m, 4H), 6.80 (d, 1H), 6.45 (d, 1H), 6.00 (t, 1H), 4.40 (t, 2H), 7.50 (t, 2H), 3.60 (s, 3H), 3.15–3.30 (m, 4H), 2.72 (t, 2H), 1.90 (m, 2H), 1.50 (s, 9H). Mass Spectrum (LCMS, ESI) calculated for C$_{33}$H$_{37}$FN$_3$O$_5$ 574.3 (M+H); found 474.2 (M-Boc+H).

d) 3-(4-Fluoro-phenyl)-3-{5-[2-(5,6,7,8-tetrahydro-[1,8]naphthyridin-2-yl)-ethoxy]-indol-1-yl}-propionic acid methyl ester The title compound was synthesized from 7-(2-{1-[1-(4-fluoro-phenyl)-2-methoxycarbonyl-ethyl]-1H-indol-5-yloxy}-ethyl)-3,4-dihydro-2H-[1,8]naphthyridine-1-carboxylic acid tert-butyl ester using the procedure described in Example 16, step (f), in 83% yield. $^1$H NMR (CDCl$_3$) δ 7.04 (m, 4H), 6.86 (m, 2H), 6.87 (t, 2H), 6.75 (dd, J=2.4 and 8.9 Hz, 1H), 6.36 (m, 2H), 5.90 (t, 1H), 4.91 (br, 1H), 4.20 (t, J=7.0 Hz, 2H), 3.53 (s, 3H), 3.3 (m, 2H), 3.20 (m, 2H), 2.95 (t, J=7.0 Hz, 2H), 2.60 (t, 2H), 1.82 (m, 2H). Mass Spectrum (LCMS, ESI) calculated for C$_{28}$H$_{29}$FN$_3$O$_3$ 474.2 (M+H); found 474.3.

e) 3-(4-Fluoro-phenyl)-3-{5-[2-(5,6,7,8-tetrahydro-[1,8]naphthyridin-2-yl)-ethoxy]-indol-1-yl}-propionic acid The title compound was synthesized from 3-(4-fluoro-phenyl)-3-{5-[2-(5,6,7,8-tetrahydro-[1,8]naphthyridin-2-yl)-ethoxy]-indol-1-yl}-propionic acid methyl ester using the procedure described in Example 16, step (g), in 64% yield. $^1$H NMR (CDCl$_3$) δ 10.47 (br, 1H), 10.39 (d, J=3.2 Hz, 1H), 7.15 (d, J=8.9 Hz, 1H), 7.04 (m, 3H), 6.83 (m, 3H), 6.54 (q, 1H), 6.39 (d, J=3.0 Hz, 1H), 6.20 (d, J=7.2 Hz), 6.02 (q, 1H), 3.57 (br, 1H), 3.40 (br, 1H), 3.31 (t, J=5.3 Hz, 2H), 3.05–3.18 (m, 2H), 2.43–2.58 (m, 4H), 1.76 (m, 2H). Mass Spectrum (LCMS, ESI) calculated for C$_{27}$H$_{27}$FN$_3$O$_3$ 460.2 (M+H); found 460.2.

EXAMPLE 36

3-{5-[2-(5,6,7,8-Tetrahydro-[1,8]naphthyridin-2-yl)-ethoxy]-indol-1-yl}-3-(3-trifluoromethyl-phenyl)-propionic acid

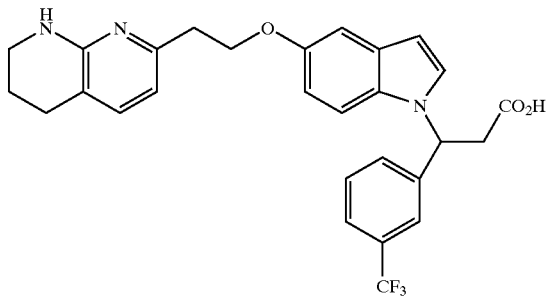

a) (3-Trifluoromethyl-phenyl)-propynoic acid methyl ester

The title compound was synthesized from commercially available 3-oxo-3-(3-trifluoromethyl-phenyl)-propionic acid methyl ester using the procedure described in Example 32, step (b), in 100% yield. $^1$H NMR (CDCl$_3$) δ 7.84 (s, 1H), 7.75 (q, 1H), 7.50 (t, 1H), 3.90 (s, 3H).

b) 7-(2-{1-[2-Methoxycarbonyl-1-(3-trifluoromethyl-phenyl)-vinyl]-1H-indol-5-yloxy}-ethyl)-3,4-dihydro-2H-[1,8]naphthyridine-1-carboxylic acid tert-butyl ester The title compound was synthesized from (3-trifluoromethyl-phenyl)-propynoic acid methyl ester using the procedure described in Example 16, step (d2), in 47% yield. $^1$H NMR (CDCl$_3$) δ 7.77 (m, 1H), 7.67 (s, 1H), 7.60 (m, 2H), 7.34 (d, J=7.7 Hz, 1H), 7.13 (m, 2H), 6.96 (d, J=7.6 Hz, 1H), 6.85 (m, 2H), 6.54 (dd, J=3.5 and 0.6 Hz, 1H), 6.26 (s, 1H), 4.41 (m, 2H), 3.78 (m, 2H), 3.67 (s, 3H), 3.23 (t, J=6.8 Hz, 2H), 2.76(t, J=6.7 Hz, 2H), 1.94 (m, 2H), 1.54 (s, 9H). Mass Spectrum (LCMS, ESI) calculated for C$_{34}$H$_{35}$F$_3$N$_3$O$_5$ 622.3 (M+H); found: 522.4 (M-Boc+H).

c) 7-(2-{1-[2-Methoxycarbonyl-1-(3-trifluoromethyl-phenyl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-methoxycarbonyl-1-(3-trifluoromethyl-phenyl)-vinyl]-1H-indol-5-yloxy}-ethyl)-3,4-dihydro-2H-[1,8]naphthyridine-1-carboxylic acid tert-butyl ester using the procedure described in Example 18, step (e), in 70% yield. $^1$H NMR (CDCl$_3$) δ 7.45 (m, 3H), 7.23 (m, 1H), 7.17 (m, 1H), 7.10 (m, 1H), 7.06 (m, 1H), 6.87 (m, 1H), 6.75 (m, 1H), 6.40 (m, 1H), 5.97 (t, J=7.5 Hz, 1H), 4.28 (m, 2H), 3.72 (m, 2H), 3.54 (s, 3H), 3.07–3.29 (m, 4H), 2.66 (m, 2H), 1.84 (m, 2H), 1.45 (s, 9H). Mass Spectrum (LCMS, ESI) calculated for C$_{34}$H$_{37}$F$_3$N$_3$O$_5$ 624.3 (M+H); found: 524.4 (M-Boc+H).

d) 3-{5-[2-(5,6,7,8-Tetrahydro-[1,8]naphthyridin-2-yl)-ethoxy]-indol-1-yl}-3-(3-trifluoromethyl-phenyl)-propionic acid methyl ester The title compound was synthesized from 7-(2-{1-[2-methoxycarbonyl-1-(3-trifluoromethyl-phenyl)-ethyl]-1H-indol-5-yloxy}-ethyl)-3,4-dihydro-2H-[1,8]naphthyridine-1-carboxylic acid tert-butyl ester using the procedure described in Example 16, step (f), in 37% yield. $^1$H NMR (CDCl$_3$) δ 7.43 (m, 2H), 7.32 (t, J=7.8 Hz, 1H), 7.19 (m, 1H), 7.01–7.13 (m, 3H), 6.75 (dd, J=2.3 and 8.9 Hz, 1H), 6.39 (m, 2H), 5.98 (m, 1H), 4.22 (m, 2H), 3.54 (s, 3H), 3.16–3.40 (m, 4H), 2.96 (m, 2H), 2.62 (t, J=6.2 Hz, 2H), 1.82 (m, 2H). Mass Spectrum (LCMS, ESI) calculated for C$_{29}$H$_{29}$F$_3$N$_3$O$_3$ 524.2 (M+H); found 524.4.

e) 3-{5-[2-(5,6,7,8-Tetrahydro-[1,8]naphthyridin-2-yl)-ethoxy]-indol-1-yl}-3-(3-trifluoromethyl-phenyl)-propionic acid The title compound was synthesized from 3-{5-[2-(5,6,7,8-tetrahydro-[1,8]naphthyridin-2-yl)-ethoxy]-indol-1-yl}-3-(3-trifluoromethyl-phenyl)-propionic acid methyl ester using the procedure described in Example 16, step (g), in 55% yield. $^1$H NMR (CDCl$_3$) δ 10.5 (br, 1H), 7.48 (m, 3H), 7.35 (t, J=7.6 Hz, 1H), 7.25 (m, 3H), 7.15 (dd, J=7.0 and 8.5 Hz, 1H), 6.88 (d, J=2.2 Hz, 1H), 6.63 (dd, J=2.2 and 8.9 Hz, 1H), 6.50 (s, 1H), 6.30 (d, J=7.3 Hz, 1H), 6.18 (q, 1H), 3.73 (m, 1H), 3.55 (m, 1H), 3.40 (m, 2H), 3.13–3.31 (m, 2H), 2.76 (m, 4H), 1.85 (m, 2H). Mass Spectrum (LCMS, ESI) calculated for C$_{28}$H$_{27}$F$_3$N$_3$O$_3$ 510.2 (M+H); found 510.3 (M$^+$+1, 100%).

EXAMPLE 37

3-{5-[2-(5,6,7,8-Tetrahydro-[1,8]naphthyridin-2-yl)-ethoxy]-indol-1-yl}-3-(4-trifluoromethyl-phenyl)-propionic acid

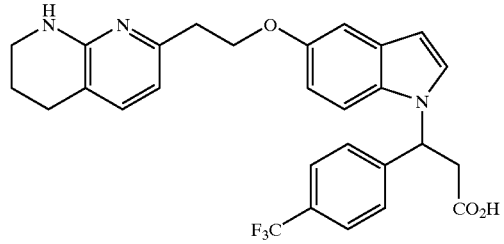

a) (4-Trifluoromethyl-phenyl)-propynoic acid methyl ester

The title compound was synthesized from commercial available 3-oxo-3-(4-trifluoromethyl-phenyl)-propionic acid methyl ester using the procedure described in Example 32, step (b), in 84% yield. $^1$H NMR (CDCl$_3$) δ 7.70 (m, 4H), 3.85 (s, 3H).

b) 7-(2-{1-[2-Methoxycarbonyl-1-(4-trifluoromethyl-phenyl)-vinyl]-1H-indol-5-yloxy}-ethyl)-3,4-dihydro-2H-[1,8]naphthyridine-1-carboxylic acid tert-butyl ester The title compound was synthesized from (4-trifluoromethyl-phenyl)-propynoic acid methyl ester using the procedure described in Example 16, step (d2), in 62% yield as an E/Z isomeric mixture. $^1$H NMR (CDCl$_3$) [E/Z mixture] δ 7.62 (d, J=8.1 Hz, 1H), 7.54 (d, J=8.2 Hz, 1H), 7.44 (d, J=7.8 Hz, 1H), 7.33 (m, 1H), 7.23 (m, 1H), 7.05 (m, 2H), 6.88 (m, 1H), 6.75 (m, 1H), 6.53 (m, 1H), 6.17 (s, 1H), 4.31 (m, 2H), 3.69 (m, 2H), 3.53 (s, 3H), 3.13 (m, 2H), 2.66 (t, J=6.6 Hz, 2H), 1.85 (m, 2H), 1.44 (s, 9H). Mass Spectrum (LCMS, ESI) calculated for C$_{34}$H$_{35}$F$_3$N$_3$O$_5$ 622.3 (M+H); found: 522.4 (M−Boc+H).

c) 7-(2-{1-[2-Methoxycarbonyl-1-(4-trifluoromethyl-phenyl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-methoxycarbonyl-1-(4-trifluoromethyl-phenyl)-vinyl]-1H-indol-5-yloxy}-ethyl)-3,4-dihydro-2H-[1,8]naphthyridine-1-carboxylic acid tert-butyl ester using the procedure described in Example 18, step (e), in 36% yield, and was used directly in the next reaction without purification.

d) 3-{5-[2-(5,6,7,8-Tetrahydro-[1,8]naphthyridin-2-yl)-ethoxy]-indol-1-yl}-3-(4-trifluoromethyl-phenyl)-propionic acid methyl ester The title compound was synthesized from 7-(2-{1-[2-methoxycarbonyl-1-(4-trifluoromethyl-phenyl)-ethyl]-1H-indol-5-yloxy}-ethyl)-3,4-dihydro-2H-[1,8]naphthyridine-1-carboxylic acid tert-butyl ester using the procedure described in Example 16, step (f), in 33% yield. $^1$H NMR (CDCl$_3$) δ 7.60 (d, 2H), 7.30 (d, 2H), 7.15 (d, 1H), 7.10 (m, 3H), 6.83 (m, 1H), 6.50 (m, 2H), 6.08 (t, 1H), 5.15 (br, 1H), 4.33 (t, 2H), 3.60 (s, 3H), 3.25–3.45 (m, 4H), 3.10 (m, 2H), 2.75 (m, 2H), 1.90 (m, 2H). Mass Spectrum (LCMS, ESI) calculated for C$_{29}$H$_{29}$F$_3$N$_3$O$_3$ 524.2 (M+H); found: 524.4.

e) 3-{5-[2-(5,6,7,8-Tetrahydro-[1,8]naphthyridin-2-yl)-ethoxy]-indol-1-yl}-3-(4-trifluoromethyl-phenyl)-propionic acid The title compound was synthesized from 3-{5-[2-(5,6,7,8-tetrahydro-[1,8]naphthyridin-2-yl)-ethoxy]-indol-1-yl}-3-(4-trifluoromethyl-phenyl)-propionic acid methyl ester using the procedure described in Example 16, step (g), in 67% yield. $^1$H NMR (CDCl$_3$) δ 10.60 (br, 1H), 7.40 (d, J=8.0 Hz, 3H), 7.15 (d, J=8.1 Hz, 2H), 7.08 (m, 2H), 6.81 (d, J=1.9 Hz, 1H), 6.56 (dd, J=2.3 and 8.9 Hz, 1H), 6.40 (s, 1H), 6.37 (m, 1H), 6.08 (m, 1H), 3.65 (m, 1H), 6.45 (br, 3H), 6.1–6.3 (m, 2H), 2.60 (m, 4H), 1.85 (m, 2H). Mass Spectrum (LCMS, ESI) calculated for C$_{28}$H$_{27}$F$_3$N$_3$O$_3$ 510.2 (M+H); found 510.3.

EXAMPLE 38

3-Pyridin-3-yl-3-{5-[2-(5,6,7,8-tetrahydro-[1,8]naphthyridin-2-yl)-ethoxy]-indol-1-yl}-propionic acid

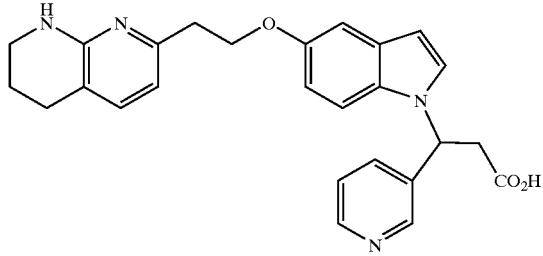

a) Pyridin-3-yl-propynoic acid methyl ester

The title compound was synthesized from 3-oxo-3-pyridin-3-yl-propionic acid methyl ester using the procedure described in Example 32, step (b), in 80% yield. $^1$H NMR (CDCl$_3$) δ 8.80 (dd, J=0.7 and 2.0 Hz, 1H), 8.66 (dd, J=1.7 and 4.9 Hz, 1H), 7.88 (m, 1H), 7.36 (m, 1H), 3.86 (s, 3H).

b) 7-{2-[1-(2-Methoxycarbonyl-1-pyridin-3-yl-vinyl)-1H-indol-5-yloxy]-ethyl}-3,4-dihydro-2H-[1,8]naphthyridine-1-carboxylic acid tert-butyl ester The title compound was synthesized from pyridin-3-yl-propynoic acid methyl ester using the procedure described in Example 17, step (a), in 78% yield as an E/Z isomeric mixture. Mass Spectrum (LCMS, ESI) calculated for C$_{32}$H$_{35}$N$_4$O$_5$ 555.3 (M+H); found 455.4 (M-Boc+H).

c) 7-{2-[1-(2-Methoxycarbonyl-1-pyridin-3-yl-ethyl)-1H-indol-5-yloxy]-ethyl}-3,4-dihydro-2H-[1,8]naphthyridine-1-carboxylic acid tert-butyl ester The title compound was synthesized 7-{2-[1-(2-methoxycarbonyl-1-pyridin-3-yl-vinyl)-1H-indol-5-yloxy]-ethyl}-3,4-dihydro-2H-[1,8]naphthyridine-1-carboxylic acid tert-butyl ester using the procedure described in Example 17, step (b), in 45% yield. $^1$H NMR (CDCl$_3$) δ 8.47 (s, 1H), 8.42 (m, 1H), 7.28 (d, J=8.0 Hz, 1H), 7.22 (J=7.6 Hz, 1H), 7.02–7.13 (m, 4H), 6.86 (d, J=7.6 Hz, 1H), 6.74 (d, J=8.8 Hz, 1H), 6.39 (d, J=2.1 Hz, 1H), 5.96 (t, J=7.6 Hz, 1H), 4.28 (m, 2H), 3.67 (t, 2H), 3.54 (s, 3H), 3.24 (m, 2H), 3.12 (m, 2H), 2.65 (t, J=6.5 Hz, 2H), 1.84 (m, 2H), 1.43 (s, 9H). Mass Spectrum (LCMS, ESI) calculated for C$_{32}$H$_{37}$N$_4$O$_5$ 557.3 (M+H); found 457.4 (M-Boc+H), 557.1.

d) 3-Pyridin-3-yl-3-{5-[2-(5,6,7,8-tetrahydro-[1,8]naphthyridin-2-yl)-ethoxy]-indol-1-yl}-propionic acid methyl ester The title compound was synthesized from 7-{2-[1-(2-methoxycarbonyl-1-pyridin-3-yl-ethyl)-1H-indol-5-yloxy]-ethyl}-3,4-dihydro-2H-[1,8]naphthyridine-1-carboxylic acid tert-butyl ester using the procedure described in Example 16, step (f), in 26% yield. $^1$H NMR (CDCl$_3$) δ 8.43–8.47 (br, 2H), 7.29 (d, J=8.0 Hz, 1H), 7.00–7.14 (m, 5H), 6.73 (dd, J=2.4 and 8.9 Hz, 1H), 6.41 (d, J=7.1 Hz, 2H), 5.96 (t, J=7.6 Hz, 1H), 5.37 (br, 1H), 4.19 (t, J=6.7 Hz, 2H), 3.54 (s, 3H), 3.33 (m, 2H), 3.24 (m, 2H), 2.97 (t, J=6.7 Hz, 2H), 2.62 (t, J=6.3 Hz, 2H), 1.82 (m, 2H). Mass Spectrum (LCMS, ESI) calculated for C$_{27}$H$_{29}$N$_4$O$_3$ 457.2 (M+H); found 457.4.

e) 3-Pyridin-3-yl-3-{5-[2-(5,6,7,8-tetrahydro-[1,8]naphthyridin-2-yl)-ethoxy]-indol-1-yl}-propionic acid The title compound was synthesized from 3-pyridin-3-yl-3-{5-[2-(5,6,7,8-tetrahydro-[1,8]naphthyridin-2-yl)-ethoxy]-indol-1-yl}-propionic acid methyl ester using the procedure described in Example 14, step (e), in 36% yield. $^1$H NMR (CDCl$_3$) δ 10.50 (br, 1H), 8.57 (d, 1H), 8.42 (d, 1H), 7.50 (1H), 7.35 (d, 1H), 7.20 (m, 2H), 6.95 (d, 1H), 6.88 (s, 1H), 6.60 (d, 1H), 6.50 (s, 1H), 6.28 (d, 1H), 6.22 (m, 1H), 5.10 (br, 1H), 3.70 (m, 1H), 3.50 (m, 1H), 3.45 (m, 2H), 3.10–3.30 (m, 2H), 2.60 (m, 2H), 2.50 (m, 2H), 1.85 (m, 2H). Mass Spectrum (LCMS, ESI) calculated for C$_{26}$H$_{27}$N$_4$O$_3$ 443.2 (M+H); found 443.3.

EXAMPLE 39

3-Pyridin-2-yl-3-{5-[2-(5,6,7,8-tetrahydro-[1,8]naphthyridin-2-yl)-ethoxy]-indol-1-yl}-propionic acid

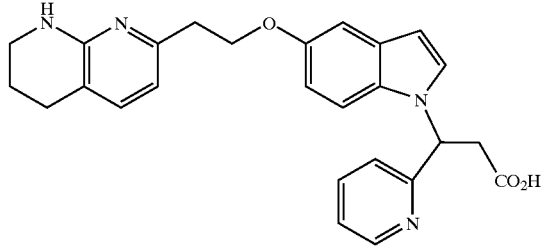

a) Pyridin-2-yl-propynoic acid ethyl ester

The title compound was synthesized from commercially available 3-oxo-3-pyridin-2-yl-propionic acid methyl ester using the procedure described in Example 32, step (b), in 76% yield. $^1$H NMR (CDCl$_3$) δ 8.66 (d, J=4.8 Hz, 1H), 7.73 (m, 1H), 7.59 (d, J=7.8 Hz, 1H), 7.36 (m, 1H), 4.31 (q, J=7.1 Hz, 2H), 1.35 (t, J=7.1 Hz, 3H).

b) 7-{2-[1-(2-Ethoxycarbonyl-1-pyridin-2-yl-vinyl)-1H-indol-5-yloxy]-ethyl}-3,4-dihydro-2H-[1,8]naphthyridine-1-carboxylic acid tert-butyl ester The title compound was synthesized from pyridin-2-yl-propynoic acid ethyl ester using the procedure described in Example 17, step (a), in 90% yield as an E/Z isomeric mixture. Mass Spectrum (LCMS, ESI) calculated for C$_{33}$H$_{37}$N$_4$O$_5$ 569.3 (M+H); found 469.3 (M-Boc+H).

c) 7-{2-[1-(2-Methoxycarbonyl-1-pyridin-2-yl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-pyridin-2-yl-vinyl)-1H-indol-5-yloxy]-ethyl}-3,4-dihydro-2H-[1,8]naphthyridine-1-carboxylic acid tert-butyl ester using the procedure described in Example 18, step (e), in 90% yield. Transesterification occurred during the reduction, resulting in a mixture of ethyl and methyl esters. $^1$H NMR (CDCl$_3$) δ 8.49 (br, 2H), 7.30 (m, 2H), 7.15 (d, J=3.2 Hz, 1H), 7.06 (m, 1H), 6.98 (m, 2H), 6.93 (m, 1H), 6.80 (d, J=2.4 Hz, 1H), 6.47 (d, J=3.3 Hz, 1H), 5.99 (t, 7.5 Hz, 1H), 4.34 (t, J=6.9 Hz, 2H), 3.73 (t, J=6.0 Hz, 2H), 3.61 (s, 3H), 3.25 (m, 2H), 3.18 (m, 2H), 2.70 (m, 2H), 1.91 (m, 2H), 1.49 (s, 9H). Mass Spectrum (LCMS, ESI) calculated for C$_{32}$H$_{36}$N$_4$O$_5$ 557.3 (M+H); found 457.4 (M-Boc+H), 557.0.

d) 3-Pyridin-2-yl-3-{5-[2-(5,6,7,8-tetrahydro-[1,8]naphthyridin-2-yl)-ethoxy]-indol-1-yl}-propionic acid methyl ester The title compound was synthesized from 7-{2-[1-(2-methoxycarbonyl-1-pyridin-2-yl-ethyl)-1H-indol-5-yloxy]-ethyl}-3,4-dihydro-2H-[1,8]naphthyridine-1-carboxylic acid tert-butyl ester using the procedure described in Example 16, step (f), in 58% yield. Mass Spectrum (LCMS, ESI) calculated for C$_{27}$H$_{29}$N$_4$O$_3$ 457.2 (M+H); found 457.4.

e) 3-Pyridin-2-yl-3-{5-[2-(5,6,7,8-tetrahydro-[1,8]naphthyridin-2-yl)-ethoxy]-indol-1-yl}-propionic acid The title compound was synthesized from 3-pyridin-2-yl-3-{5-[2-(5,6,7,8-tetrahydro-[1,8]naphthyridin-2-yl)-ethoxy]-indol-1-yl}-propionic acid methyl ester using the procedure described in Example 16, step (g), in 14% yield. $^1$H NMR (CDCl$_3$) δ 10.29 (br, 1H), 8.41 (br, 1H), 7.35 (d, J=2.8 Hz, 1H), 6.92–7.17 (m, 3H), 6.81 (d, J=2.0 Hz, 1H), 6.55 (dd, J=2.0 and 8.8 Hz, 1H), 6.43 (d, J=2.8 Hz, 1H), 6.26 (m, 1H), 6.02 (br, 1H), 3.66 (br, 1H), 3.58 (m, 1H), 3.34 (m, 2H), 3.13 (m, 2H), 2.59 (m, 4H), 1.81 (m, 2H). Mass Spectrum (LCMS, ESI) calculated for C$_{26}$H$_{27}$N$_4$O$_3$ 443.2 (M+H); found 443.3.

EXAMPLE 40

3-Pyridin-4-yl-3-{5-[2-(5,6,7,8-tetrahydro-[1,8]naphthyridin-2-yl)-ethoxy]-indol-1-yl}-acrylic acid

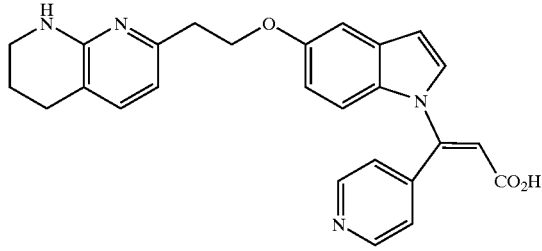

a) Pyridin-4-yl-propynoic acid ethyl ester

The title compound was synthesized from commercially available 3-oxo-3-pyridin-4-yl-propionic acid ethyl ester using the procedure described in Example 32, step (b), in 65% yield. $^1$H NMR (CDCl$_3$) δ 8.67 (dd, J=1.5 and 4.5 Hz, 2H), 7.42 (dd, J=1.5 and 4.5, 2H), 4.33 (q, J=7.2 Hz, 2H), 1.37 (t, J=7.2 Hz, 3H).

b) 7-{2-[1-(2-Ethoxycarbonyl-1-pyridin-4-yl-vinyl)-1H-indol-5-yloxy]-ethyl}-3,4-dihydro-2H-[1,8]naphthyridine-1-carboxylic acid tert-butyl ester The title compound was synthesized from pyridin-4-yl-propynoic acid ethyl ester using the procedure described in Example 17, step (a), in 90% yield as an E/Z isomeric mixture. Mass Spectrum (LCMS, ESI) calculated for C$_{33}$H$_{35}$N$_4$O$_5$ 569.3 (M+H); found 469.4 (M-Boc+H).

c) 7-{2-[1-(2-Ethoxycarbonyl-1-pyridin-4-yl-ethyl)-1H-indol-5-yloxy]-ethyl}-3,4-dihydro-2H-[1,8]naphthyridine-1-carboxylic acid tert-butyl ester The title compound was synthesized from 7-{2-[1-(2-ethoxycarbonyl-1-pyridin4-yl-vinyl)-1H-indol-5-yloxy]-ethyl}-3,4-dihydro-2H-[1,8]naphthyridine-1-carboxylic acid tert-butyl ester using the procedure described in Example 14, step (b), in 26% yield. Mass Spectrum (LCMS, ESI) calculated for C$_{33}$H$_{39}$N$_4$O$_5$ 571.3 (M+H); found 471.4 (M-Boc+H).

d) 3-Pyridin-4-yl-3-{5-[2-(5,6,7,8-tetrahydro-[1,8]naphthyridin-2-yl)-ethoxy]-indol-1-yl}-acrylic acid ethyl ester The title compound was synthesized from 7-{2-[1-(2-ethoxycarbonyl-1-pyridin4-yl-ethyl)-1H-indol-5-yloxy]-ethyl}-3,4-dihydro-2H-[1,8]naphthyridine-1-carboxylic acid tert-butyl ester using the procedure described in Example 16, step (f), in 77% yield as an E/Z isomeric mixture. Mass Spectrum (LCMS, ESI) calculated for C$_{28}$H$_{29}$N$_4$O$_3$ 469.2 (M+H); found 469.4.

e) 3-Pyridin-4-yl-3-{5-[2-(5,6,7,8-tetrahydro-[1,8]naphthyridin-2-yl)-ethoxy]-indol-1-yl}-acrylic acid The title compound was synthesized from 3-pyridin-4-yl-3-{5-[2-(5,6,7,8-tetrahydro-[1,8]naphthyridin-2-yl)-ethoxy]-indol-1-yl}-acrylic acid ethyl ester using the procedure described in Example 14, step (e), in 23% yield as a single isomer. $^1$H NMR (CDCl$_3$) δ 10.48 (br, 1H), 8.48 (d, J=5.6 Hz, 2H), 7.15 (d, J=3.2, 1H), 7.08 (d, J=7.3 Hz, 1H), 7.03 (d, J=5.9, 2H), 6.88 (d, 8.9 Hz, 1H), 6.73 (m, 2H), 6.59 (d, 2.2 Hz, 1H), 6.57 (d, J=2.2 Hz, 1H), 6.51 (d, J=3.0 Hz, 1H), 6.25 (d, J=7.3 Hz, 1H), 3.48 (br, 2H), 3.35 (br, 2H), 2.59 (m, 2H), 2.44 (br, 2H), 1.80 (m, 2H). Mass Spectrum (LCMS, ESI) calculated for C$_{26}$H$_{25}$N$_4$O$_3$ 441.19 (M+H); found 441.3.

EXAMPLE 41

3-(2,3-Dihydro-benzofuran-5-yl)-3-{5-[2-(5,6,7,8-tetrahydro-[1,8]naphthyridin-2-yl)-ethoxy]-indol-1-yl}-propionic acid

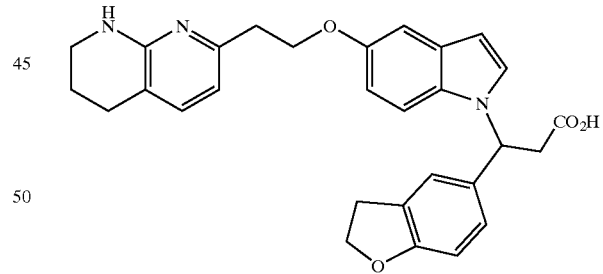

a) 3-(2,3-Dihydro-benzofuran-5-yl)-3-oxo-propionic acid ethyl ester

The title compound was synthesized from 1-(2,3-dihydro-benzofuran-5-yl)-ethanone using the procedure described in Example 32, step (a), in 47% yield. $^1$H NMR (CDCl$_3$) 7.85 (d, 1H, J=1.4 Hz), 7.78 (dd, 1H, J=1.9, 8.4 Hz), 6.81 (d, 1H, J=8.4 Hz), 4.67 (t, 2H, J=8.8 Hz), 4.21 (q, 2H, J=7.2 Hz), 3.92 (s, 2H), 3.26 (t, 2H, J=8.7 Hz,), 1.26 (t, 3H, J=7.1 Hz). Mass Spectrum (LCMS, ESI) calculated for C$_{13}$H$_{15}$O$_4$ 235.1 (M+H); found 235.2.

b) (2,3-Dihydro-benzofuran-5-yl)-propynoic acid ethyl ester

The title compound was synthesized from 3-(2,3-dihydro-benzofuran-5-yl)-3-oxo-propionic acid ethyl ester using the procedure described in Example 32, step (b), in 65% yield. $^1$H NMR (CDCl$_3$) δ 7.42–7.38 (m, 2H), 6.77–6.74 (m, 1H), 4.62 (t, 2H, J=8.9 H), 4.28 (q, 2H, J=7.2 Hz), 3.21 (t,2H), J=8.9 Hz), 1.35 (t, 3H, J=7.1 Hz).

c) 7-(2-{1-[1-(2,3-Dihydro-benzofuran-5-yl)-2-ethoxycarbonyl-vinyl]-1H-indol-5-yloxy}-ethyl)-3,4-dihydro-2H-[1,8]naphthyridine-1-carboxylic acid tert-butyl ester The title compound was synthesized from (2,3-dihydro-benzofuran-5-yl)-propynoic acid ethyl ester and 7-[2-(1H-indol-5-yloxy)-ethyl]-3,4-dihydro-2H-[1,8]naphthyridine-1-carboxylic acid tert-butyl ester using the procedure described in Example 16, step (c1), in 52% yield as an E/Z mixture. $^1$H NMR (CDCl$_3$) δ 7.31 (d, 1H, J=7.6 Hz), 7.18–7.01 (m, 4H), 6.94 (dd, 1H, J=3.5, 7.6 Hz), 6.82–6.71 (m, 3H), 6.56–6.48 (m, 1H), 6.10 (s, 0.6H), 6.00 (s, 0.4H), 4.62 (q, 2H, J=8.8 Hz), 4.39–4.35 (m, 2H), 4.13 (q, 0.8H, J=7.1 Hz), 3.98 (q, 1.2H, J=7.1 Hz), 3.76 (t, 2H, J=5.9 Hz), 3.23–3.14 (m, 4H), 2.73 (t, 2H, J=6.64 Hz), 1.95–1.89 (m, 2H), 1.52 (s, 9H), 1.21 (t, 1.2H, J=7.1 Hz), 1.00 (t, 1.8 Hz, J=7.1 Hz).

The titled compound is prepared using the procedures described in Example 18, step (e), followed by Example 16, step (e), and Example 18, step (g).

EXAMPLE 42

3-Benzo[1,3]dioxol-5-yl-3-{5-[2-(5,6,7,8-tetrahydro-[1,8]naphthyridin-2-yl)-ethoxy]-indol-1-yl}-propionic acid

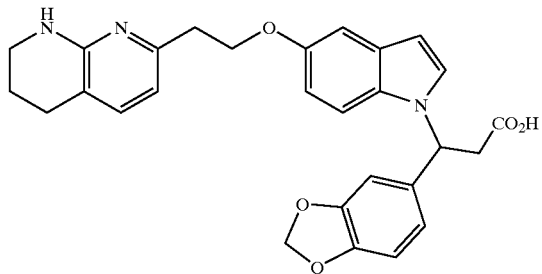

a) 5-(2,2-Dibromo-vinyl)-benzo[1,3]dioxole

To a solution of piperonal (4.5 g, 30 mmol) and triphenylphosphine (24 g, 90 mmol) in DCM (120 mL) in an ice-water bath was added a solution of carbontetrabromide (15 g, 45 mmol) over a 10 minutes period. After the addition completed, the ice-water bath was removed, the reaction stirred at ambient temperature for 2 h, and then quenched with saturated NaHCO$_3$. Aqueous was separated, and extracted with dichloromethane (2 times). The organic layers were combined, dried over Na$_2$SO$_4$, filtered, and concentrated to give a redish colored residue, that was filtered through a short path silica gel plug, eluting with DCM/hexane (10% to 20%). Concentration of the filtrate gave the title compound (6.5 g, 74% yield) as a pale yellow liquid. $^1$H NMR (CDCl$_3$) δ 7.36 (s, 1H), 7.18 (d, 1H, J=1.6 Hz), 6.95 (dd, 1H, J=1.5, 8.1 Hz), 6.79 (d, 1H, J=8.1 Hz), 5.99 (s, 2H).

b) 5-Ethynyl-benzo[1,3]dioxole

To a solution of 5-(2,2-dibromo-vinyl)-benzo[1,3]dioxole (1.47 g, 5.0 mmol) in THF (10 mL) at −78° C. was added 2.0 M solution of n-butyllithium (5.5 mL, in cyclohexane) over 5 minutes period. After the addition completed, the reaction was stirred for 1 h, and then quenched with saturated NH$_4$Cl. The mixture was allowed to warm up to room temperature. THF was removed. The aqueous was extracted with ethyl acetate. The organic layer was washed with water, brine, dried over Na$_2$SO$_4$, concentrated, and flash chromatographed on silica gel, eluting with DCM/hexane (5 to 10%) to give the title compound (0.64 g, 95% yield) as an orange oil. $^1$H NMR (CDCl$_3$) δ 7.02 (dd, 1H, J=1.6, 8.1 Hz), 6.93 (d, 1H, J=1.6 Hz), 6.75 (d, 1H, J=8.0 Hz), 5.98 (s, 2H), 2.97 (s, 1H).

c) Benzo[1,3]dioxol-5-yl-propynoic acid ethyl ester

The title compound was synthesized from 5-ethynyl-benzo[1,3]dioxole and 7-[2-(1H-indol-5-yloxy)-ethyl]-3,4-dihydro-2H-[1,8]naphthyridine-1-carboxylic acid tert-butyl ester using the procedure described in Example 23, step (c), in 54% yield. $^1$H NMR (CDCl$_3$) δ 7.16 (dd, 1H, J=1.6, 8.1 Hz), 7.00 (d, 1H, J=1.6 Hz,), 6.80 (d, 1H, J=8.1 Hz,), 6.02 (s, 2H), 4.29 (q, 2H, J=7.2 Hz,), 1.35 (t, 3H, J=7.2 Hz).

d) 7-{2-[1-(1-Benzo[1,3]dioxol-5-yl-2-ethoxycarbonyl-vinyl)-1H-indol-5-yloxy]-ethyl}-3,4-dihydro-2H-[1,8]naphthyridine-1-carboxylic acid tert-butyl ester The title compound was synthesized from benzo[1,3]dioxol-5-yl-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 16, step (c1), in 39% yield as an E/Z mixture. $^1$H NMR (CDCl$_3$) δ 7.32 (d, 1H, J=7.6 Hz), 7.10–7.04 (m, 2H), 7.00–6.90 (m, 2H), 6.85–6.71 (m, 4H), 6.56–6.49 (m, 1H), 6.10 (s, 0.6H), 6.04 (s, 0.4H), 6.03 (s, 0.8H), 6.00 (s, 1.2H), 4.40–4.35 (m, 2H), 4.13 (q, 0.8H, J=7.1 Hz), 3.98 (q, 1.2H, J=7.1 Hz), 3.76 (t, 2H, J=5.9 Hz), 3.20 (t, 2H, 6.8 Hz), 2.73 (t, 2H, 6.7 Hz), 1.95–1.89 (m, 2H), 1.519 (s, 5.4H), 1.516 (s, 3.6 H), 1.22 (t, 1.2H, J=7.1 Hz), 1.01 (t, 1.8H, J=7.1 Hz). Mass Spectrum (LCMS, ESI) calculated for C$_{30}$H$_{29}$N$_3$O$_5$ 512.3 (M-Boc +1); found 512.3.

e) 7-{2-[1-(1-Benzo[1,3]dioxol-5-yl-2-ethoxycarbonyl-ethyl)-1H-indol-5-yloxy]-ethyl}-3,4-dihydro-2H-[1,8]naphthyridine-1-carboxylic acid tert-butyl ester The title compound was synthesized from 7-{2-[1-(1-Benzo[1,3]dioxol-5-yl-2-ethoxycarbonyl-vinyl)-1H-indol-5-yloxy]-ethyl}-3,4-dihydro-2H-[1,8]naphthyridine-1-carboxylic acid tert-butyl ester using the procedure described in Example 18, step (e), in 89% yield as a yellow oil. $^1$H NMR (CDCl$_3$) δ 7.30 (d, 1H, J=7.6 Hz), 7.21–7.16 (m, 2H), 7.08 (d, 1H, J=2.4 Hz), 6.94 (d, 1H, J=7.6 Hz), 6.82 (dd, 1H, J=2.4, 8.9 Hz), 6.73–6.68 (m, 2H), 6.62 (d, 1H, J=0.7 Hz), 6.42 (d, 1H, J=3.2 Hz), 5.90–5.89 (m, 2H), 4.36 (t, 2H, J=6.9 Hz), 4.04 (q, 2H, J=7.1 Hz), 3.75 (t, 2H, J=6.0 Hz), 3.24–3.15 (m, 4H), 2.72 (t, 2H, J=6.6 Hz), 1.95–1.89 (m, 2H), 1.51 (s, 9H), 1.10 (t, 2H, J=7.1 Hz).

f) 3-Benzo[1,3]dioxol-5-yl-3-{5-[2-(5,6,7,8-tetrahydro-[1,8]naphthyridin-2-yl)-ethoxy]-indol-1-yl}-propionic acid ethyl ester The title compound was synthesized from 7-{2-[1-(1-benzo[1,3]dioxol-5-yl-2-ethoxycarbonyl-ethyl)-1H-indol-5-yloxy]-ethyl}-3,4-dihydro-2H-[1,8]naphthyridine-1-carboxylic acid tert-butyl ester using the procedure described in Example 16, step (e), in 53% yield as a yellow oil. $^1$H NMR (CDCl$_3$) δ 7.20–7.15 (m, 2H), 7.09–7.07 (m, 2H), 6.82 (dd, 1H, J=2.4, 9.1 Hz), 6.73–6.68 (m, 2H), 6.62 (bs, 1H), 6.47 (d, 1H, J=7.2 Hz), 6.42 (d, 1H, J=3.0 Hz), 5.92–5.88 (m, 3H), 4.92 (bs, 1H), 4.28 (t, 2H, J=7.0 Hz), 4.04 (q, 2H, J=7.1 Hz), 3.41–3.38 (m, 2H), 3.28–3.15 (m, 2H), 3.03 (t, 2H, J=7.0 Hz), 2.69 (t, 2H, J=6.3 Hz), 1.93–1.87 (m, 2H), 1.10 (t, 3H, J=7.1 Hz).

g) 3-Benzo[1,3]dioxol-5-yl-3-{5-[2-(5,6,7,8-tetrahydro-[1,8]naphthyridin-2-yl)-ethoxy]-indol-1-yl}-propionic acid.

The title compound was synthesized from 3-benzo[1,3]dioxol-5-yl-3-{5-[2-(5,6,7,8-tetrahydro-[1,8]naphthyridin-2-yl)-ethoxy]-indol-1-yl}-propionic acid ethyl ester using the procedure described in Example 18, step (g), in 87% yield as a yellow oil. ¹H NMR (CDCl₃) δ 10.46 (bs, 1H), 7.45 (d, 1H, J=3.2 Hz), 7.26–7.24 (m, 1H), 7.08 (d, 1H, J=7.3 Hz), 6.83 (d, 1H, J=2.3 Hz), 6.69–6.60 (m, 4H), 6.45 (d, 1H, 3.1 Hz), 6.26 (d, 1H, 7.3 Hz), 6.03 (dd, 1H, J=4.6, 11.1 Hz), 5.88–5.86 (m, 2H), 3.65–3.60 (m, 1H), 3.74–3.42 (m, 1H), 3.38–3.35 (m, 2H), 3.28–3.10 (m, 2H), 2.59–2.43 (m, 4H), 1.84–1.80 (m, 2H). Mass Spectrum (LCMS, ESI) calculated for $C_{28}H_{28}N_3O_5$ 486.2 (M+H); found 486.3.

EXAMPLE 43

3-(5-Methanesulfonyl-pyridin-3-yl)-3-{5-[2-(5,6,7,8-tetrahydro-[1,8]naphthyridin-2-yl)-ethyoxy]-indol-1-yl}-propionic acid

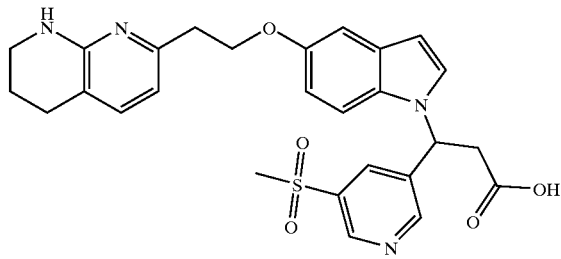

a) Trimethyl-triethoxyprop-1-ynyl-silane

Boron trifluoride diethyl etherate (36.0 mL, 280 mmol) was added to diethyl ether (50 mL) under argon. The mixture was transferred to a dropping funnel and added dropwise under argon to a solution of tetraethyl orthocarbonate (40.0 g, 208 mmol) in diethyl ether (100 mL) at 0° C. After the addition was complete, the mixture was stirred for 5 min and then cooled to −78° C. In a separate reaction flask, n-butyllithium (166 mL, 2.5 M solution in hexanes, 416 mmol) was added dropwise to a solution of trimethylsilyl acetylene (59.0 mL, 416 mmol) in diethyl ether (200 mL) at 0° C. under argon. After stirring for 1 h at 0° C., the solution was cooled to −78° C. This solution was added via cannula to the triethoxycarbenium tetrafluoroborate formed previously. The mixture was stirred at −78° C. for 1 h before being warming to room temperature. Saturated aqueous potassium carbonate was added and mixture was extracted with diethyl ether. The organic extracts were dried with magnesium sulfate and the solvent was removed under reduced pressure to give the title compound (50.0 g, 100% yield) as yellow oil. ¹H NMR (CDCl₃) δ 3.68(q, 6H, J=7.2 Hz), 1.23 (t, 9H, J=7.2 Hz), 0.20, (s, 9H).

b) 3,3,3-Triethoxypropyne

A solution of sodium hydroxide (0.14 g, 3.60 mmol) in water (50 mL) was added to a solution of trimethyl-triethoxyprop-1-ynyl-silane (50.0 g, 208 mmol) in ethanol (250 mL). After stirring for 1 hour at room temperature, water was added and the mixture was extracted with ethyl acetate. The organic extracts were dried with magnesium sulfate and the solvent was removed under reduced pressure to give the title compound (20.0 g, 52% yield) as yellow oil. ¹H NMR (CDCl₃) δ 3.70 (q, 6H, J=8.0 Hz), 2.56 (s, 1H) 1.24 (t, 9H, J=8.0 Hz).

c) 3-Bromo-5-methylsulfanyl-pyridine

Sodium thiomethoxide (1.6 g, 23 mmol) was added to a solution of 3,5-dibromopyridine (5 g, 21 mmol) in DMF (25 mL). After stirring overnight at room temperature, the reaction mixture was diluted with ethyl acetate and washed several times with brine. The extracts were dried over magnesium sulfate and the solvent was removed under reduced pressure. The crude material was chromatographed on silica (10% ethyl acetate/hexanes) to give the title compound (3.8 g, 89% yield) as a clear oil.

d) 3-Bromo-5-methanesulfonyl-pyridine

MCPBA (9.2 g, 38 mmol) was added slowly to a solution of 3-bromo-5-methylsulfanyl-pyridine (3.8 g, 19 mmol) in dichloromethane (50 mL). After stirring for 30 minutes, the reaction was diluted with dichloromethane and quenched carefully with 1N NaOH. The product was extracted with dichloromethane and dried over magnesium sulfate. The solvent was removed under reduced pressure to give title compound (2.7 g, 82% yield) as a white solid.

e) 3-Methanesulfonyl-5-triethoxyprop-1-ynyl-pyridine

A solution of 3-bromo-5-methanesulfonyl-pyridine (1.00 g, 4.20 mmol), 3,3,3-triethoxypropyne (1.75 g, 9.4 mmol), dichlorobis(triphenylphospine)palladium(II) (0.15 g, 0.21 mmol), copper(I)iodide (0.08 g, 0.42 mmol), triethylamine (1.80 mL, 12.7 mmol) and dichloromethane (40 mL) was heated at reflux for 48 h. The mixture was cooled to room temperature and the solvent was removed under reduced pressure. The crude product was chromatographed on silica (30% ethyl acetate/hexanes) to give the title compound (1.2 g, 87% yield) as yellow solid. ¹H NMR (CDCl₃) δ 9.08(d, 1H, J=2.4 Hz), 8.91 (d, 1H J=2.0), 8.28 (t, 1H, J=2.0 Hz), 3.75 (q, 6H, J=7.2), 3.13 (s, 3H), 1.29 (t, 9H, J=7.2).

f) (5-Methanesulfonyl-pyridin-3-yl)-propynoic acid ethyl ester p-Toluenesulfonic acid monohydrate (1.39 g, 0.73 mmol) was added to a solution of 3-methanesulfonyl-5-triethoxyprop-1-ynyl-pyridine (1.20 g, 3.70 mmol) in toluene (40 mL). After stirring overnight at room temperature, the solvent was removed under reduced pressure. The crude product was chromatographed on silica (30% ethyl acetate/hexanes) to give the title compound (0.55 g, 53% yield) as a white solid. ¹H NMR (CDCl₃) δ 9.17 (d, 1H, J=2.4 Hz), 9.03 (d, 1H, J=2.0), 8.40 (t, 1H, J=2.0 Hz), 4.35 (q, 6H, J=8.0), 3.14 (s, 3H), 1.38 (t, 9H, J=8.0).

g) 7-(2-{1-[2-Ethoxycarbonyl-1-(5-methanesulfonyl-pyridin-3-yl)-vinyl]-1H-indol-5-yloxy}-ethyl)-3,4-dihydro-2H-[1,8]naphthyridine-1-carboxylic acid tert-butyl ester The title compound was synthesized from (5-methanesulfonyl-pyridin-3-yl)-propynoic acid ethyl ester and 7-[2-(1H-indol-5-yloxy)-ethyl]-3,4-dihydro-2H-[1,8] naphthyridine-1-carboxylic acid tert-butyl ester using the procedure described in Example 16, step (d1), in 80% yield. Mass Spectrum (LCMS, ESI) calculated for $C_{29}H_{31}N_4O_5S$: 547.2 (M-Boc+H); found 547.3 (-Boc).

h) 7-(2-{1-[2-Ethoxycarbonyl-1-(5-methanesulfonyl-pyridin-3-yl)-ethyl]-1H-indol-5-yloxy}-ethyl)-3,4-dihyrdo-2H-[1,8]naphthyridine-1-carboxylic acid tert-butyl ester The title compound was synthesized from 7-(2-{1-[2-ethoxycarbonyl-1-(5-methanesulfonyl-pyridin-3-yl)-vinyl]-1H-indol-5-yloxy}-ethyl)-3,4-dihydro-2H-[1,8] naphthyridine-1-carboxylic acid tert-butyl ester using the procedure described in Example 18, step (e), in 25% yield. ¹H NMR (CDCl₃) δ 9.03 (d, 1H, J=2.0 Hz), 8.71 (d, 1H, J=2.0 Hz), 7.97 (t, 1H, J=2.0 Hz), 7.30 (m, 2H), 7.20 (d, 1H, J=3.6 Hz), 6.84 (dd, 1H, J=1.6, 6.8 Hz), 6.93 (m, 2H), 6.52 (d, 1H, J=3.2 Hz), 6.12 (t, 1H, J=3.2 Hz).

i) 3-(5-Methanesulfonyl-pyridin-3-yl)-3-{5-[2-(5,6,7,8-tetrahydro-[1,8]naphthyridin-2-yl)-ethoxy]-indol-1-yl}propionic acid ethyl ester The title compound was synthesized from 7-(2-{1-[2-ethoxycarbonyl-1-(5-methanesulfonyl-pyridin-3-yl)-ethyl]-1H-indol-5-yloxy}-ethyl)-3,4-dihyrdo-2H-[1,8] naphthyridine-1-carboxylic acid tert-butyl ester using the procedure described in Example 16, step (f), in 32% yield. ¹H NMR (CD₃OD) δ 8.96 (s, 1H), 8.67 (s, 1H), 8.16 (s, 1H), 7.96 (s, 1H), 7.49 (d, 1H, J=2.8 Hz), 7.43 (d, 1H, J=7.2 Hz), 7.29 (d, 1H, J=8.8), 7.06 (d, 1H, J=2.0 Hz), 6.76 (dd, 1H, J=2.4, 6.4 Hz), 6.63 (d, 1H, J=7.6 Hz), 6.48 (d, 1H, J=2.8 Hz), 6.40 (t, 1H, J=3.2 Hz), 4.24 (t, 2H, J=6.0 Hz), 4.01 (m, 2H), 3.51 (m, 2H), 3.42 (t, 2H, J=5.6 Hz), 3.06 (t, 2H, J=6.0 Hz), 2.97 (s, 3H), 2.74 (t, 2H, J=6.0 Hz), 1.99 (m, 2H), 1.05 (t, 3H, J=6.8 Hz).

j) Methanesulfonyl-pyridin-3-yl)-3-{5-[2-(5,6,7,8-tetrahydro-[1,8]naphthyridin-2-yl)-ethoxy]-indol-1-yl}-propionic acid The title compound was synthesized from 3-(5-Methanesulfonyl-pyridin-3-yl)-3-{5-[2-(5,6,7,8-tetrahydro-[1,8]naphthyridin-2-yl)-ethoxy]-indol-1-yl}propionic acid ethyl ester using the procedure described in Example 18, step (g), in 30% yield. $^1$H NMR (CDCl$_3$) δ 10.50 (s, 1H), 8.91 (s, 1H), 8.61 (s, 1H), 7.89 (s, 1H), 7.37 (d, 1H, J=2.8 Hz), 7.10 (d, 1H, J=7.6 Hz), 7.01 (d, 1H, J=8.8 Hz), 6.83 (d, 1H, J=1.6 Hz), 6.55 (d, 1H, J=8.8 Hz), 6.43 (d, H, J=2.8 Hz), 6.25 (d, 1H, J=7.6 Hz), 6.14 (t, 1H, J=7.2 Hz), 3.74 (m, 2H), 3.34 (m, 2H), 3.23 (m, 2H), 3.10 (m, 2H), 2.93 (s, 3H), 2.59 (t, 2H, J=6.0 Hz), 1.78 (m, 2H). Mass Spectrum (LCMS, ESI) calculated for C$_{27}$H$_{29}$N$_4$O$_3$S: 521.2 (M+H); found 521.3.

EXAMPLE 44

3-{5-[2-(6-Methylamino-pyridin-2-yl)-ethoxy]-indol-1-yl}-3-phenyl-propionic acid

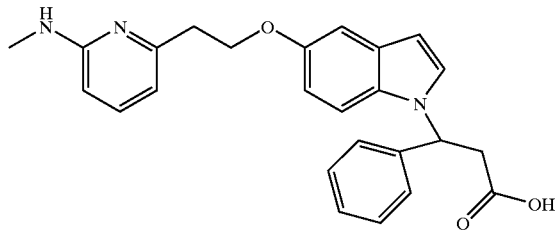

a) [6-(2-Hydroxy-ethyl)-pyridin-2-yl]-methyl-carbamic acid tert-butyl ester

The title compound was synthesized from [6-(tert-butoxycarbonyl-methyl-amino)-pyridin-2-yl]-acetic acid ethyl ester (synthetic methodology described in WO 98/14192) using the procedure described in Example 16, step (a), in 80% yield. $^1$H NMR (Cl$_3$CD), δ: 7.55 (m, 2H), 6.85 (dd, 1H, J=1.1, 6.7 Hz), 4.00 (m, 2H), 3.37 (s, 3H), 2.97 (m, 2H), 1.53 (s, 9H).

b) Methyl-{6-[2-(3-methyl-4-nitro-phenoxy)-ethyl]-pyridin-2-yl}-carbamic acid tert-butyl ester.

The title compound was synthesized from [6-(2-hydroxy-ethyl)-pyridin-2-yl]-methyl-carbamic acid tert-butyl ester and the commercially available 3-methyl-4-nitro-phenol using the procedure described in Example 16, step (b), in 81% yield. $^1$H NMR (Cl$_3$CD), δ: 1.52 (s, 9H), 2.62 (s, 3H), 3.21 (t, 2H, J=8.00 Hz), 3.36 (s, 3H), 4.44 (t, 2H, J=8.00 Hz), 6.80 (m, 2H), 6.94 (dd, 1H, J=2.4, 5.6 Hz), 7.55 (m, 2H), 8.05 (d, 1H, J=8.8 Hz).

c) {6-[2-(1H-Indol-5-yloxy)-ethyl]-pyridin-2-yl}-methyl-carbamic acid tert-butyl ester The title compound was synthesized from methyl-{6-[2-(3-methyl-4-nitro-phenoxy)-ethyl]-pyridin-2-yl}-carbamic acid tert-butyl ester using the procedure described in Example 16, step (c), in 48% yield. H$^1$ NMR (Cl$_3$CD), δ: 8.09 (1H, br s), 7.55 (m, 1H), 7.49 (d, 1H, J=7.8 Hz), 7.26 (d, 1H, J=8.7 Hz), 7.17 (m, 1H), 7.14 (d, 1H, J=2.4 Hz), 6.98 (d, 1H, J=7.3 Hz), 6.85 (dd, 1H, J=2.4, 6.8 Hz), 6.80 (m, 2H), 6.46 (t, 2H, J=6.8 Hz), 4.39 (t, 2H, J=6.8 Hz), 3.39 (s, 3H), 3.22 (t, 2H, J=6.8 Hz), 1.51 (s, 9H).

d) 3-(5-{2-[6-(tert-Butoxycarbonyl-methyl-amino)-pyridin-2-yl]-ethoxy}-indol-1-yl)-3-phenyl-acrylic acid ethyl ester The title compound was synthesized from {6-[2-(1H-indol-5-yloxy)-ethyl]-pyridin-2-yl}-methyl-carbamic acid tert-butyl ester and the commercially available phenyl propynoic acid ethyl ester using the procedure described in Example 16, step (d1), in 81% yield as an E/Z isomeric mixture. H$^1$ NMR (Cl$_3$CD), δ: 7.57–7.53 (m, 1H), 7.52–7.46 (m, 1.5H), 7.44 (m, 1H), 7.41–7.34 (m, 2.5H), 7.29 (m, 1H), 7.12 (d, 0.5H, J=2.1 Hz), 7.07 (m, 1.5H), 6.97 (m, 1.5H), 6.76 (m, 1H), 6.70 (m, 0.5H), 6.59 (d, 0.5H, J=3.2 Hz), 6.51 (d, 0.5H, J=3.5 Hz), 6.22 (s, 0.5H), 6.15 (s, 0.5H), 4.38 (m, 2H), 4.09 (c, 1.5H, J=7.0 Hz), 4.01 (c, 1.5H, J=7.2 Hz), 3.39 (m, 3H), 3.21 (m, 2H), 1.52 (s, 9H), 1.16 (t, 1.5H, J=7.2 Hz), 1.03 (t, 1.5H, J=7.0 Hz).

e) 3-(5-{2-[6-(tert-Butoxycarbonyl-methyl-amino)-pyridin-2-yl]-ethoxy}-indol-1-yl)-3-phenyl-propionic acid ethyl ester The title compound was synthesized from 3-(5-{2-[6-(tert-butoxycarbonyl-methyl-amino)-pyridin-2-yl]-ethoxy}-indol-1-yl)-3-phenyl-acrylic acid ethyl ester using the procedure described in Example 16, step (e), in 97% yield. H$^1$ NMR (Cl$_3$CD), δ: 7.54 (m, 1H) 7.48 (d, 1H, J=7.2 Hz), 7.29–7.16 (m, 7H), 7.10 (d, 1H, J=2.4 Hz), 6.97 (dd, 1H, J=0.8, 7.2 Hz), 6.80 (dd, 1H, J=2.4, 9.2 Hz), 6.45 (dd, 1H, J=0.8, 3.6 Hz), 6.02 (t, 1H, J=7.6 Hz), 4.37 (t, 2H, J=8.0 Hz), 4.04 (c, 2H, J=8.0 Hz), 3.38 (s, 3H), 3.27 (m, 2H), 3.20 (t, 2H, J=8.0 Hz), 1.51 (s, 9H), 1.10 (t, 3H, J=8.0 Hz).

f) 3-{5-[2-(6-Methylamino-pyridin-2-yl)-ethoxy]-indol-1-yl}-3-phenyl-propionic acid ethyl ester The title compound was synthesized from 3-(5-{2-[6-(tert-butoxycarbonyl-methyl-amino)-pyridin-2-yl]-ethoxy}-indol-1-yl)-3-phenyl-propionic acid ethyl ester using the procedure described in Example 16, step (f), in 73% yield. H$^1$ NMR (Cl$_3$CD), δ: 7.40 (m, 1H) 7.30–7.25 (m, 3H), 7.20–7.16 (m, 4H), 7.10 (d, 1H, J=2.4 Hz), 6.81 (dd, 1H, J=2.4, 8.9 Hz), 6.56 (d, 1H, J=7.2 Hz), 6.44 (d, 1H, J=3.2 Hz), 6.24 (d, 1H, J=8.2 Hz), 6.01 (t, 1H, J=7.6 Hz), 4.55 (br s, 1H), 4.32 (t, 2H, J=8.0 Hz), 4.03 (c, 2H, J=8.0 Hz), 3.26 (m, 1H), 3.09 (t, 3H, J=8.0 Hz), 2.89 (s, 3H), 1.08 (t, 3H, J=8.0 Hz).

g) 3-{5-[2-(6-Methylamino-pyridin-2-yl)-ethoxy]-indol-1-yl}-3-phenyl-propionic acid.

The title compound was synthesized from 3-{5-[2-(6-methylamino-pyridin-2-yl)-ethoxy]-indol-1-yl}-3-phenyl-propionic acid ethyl ester using the procedure described in Example 16, step (g), in 66% yield. H$^1$ NMR (DMSO-d6), δ: 7.66 (m, 1H), 7.39–7.19 (m, 7H), 7.04 (d, 1H, J=2.4 Hz), 6.70 (dd, 1H, J=2.4, 9.2 Hz), 6.43 (d, 1H, J=6.8 Hz), 6.35 (m, 2H), 6.25 (d, 1H, J=8.0 Hz), 5.94 (m, 1H), 4.25 (t, 2H, J=8.0 Hz), 3.39 (m, 1H), 2.94 (t, 3H, J=8.0 Hz), 2.74 (m, 3H).

Mass Spectrum (LCMS, ESI) calculated for $C_{25}H_{26}N_3O_3$ 416.2, (M+1); found: 416.3.

EXAMPLE 45

3-{5-[2-(6-Methylamino-pyridin-2-yl)-ethoxy]-indol-1-yl}-3-quinolin-3-yl-propionic acid

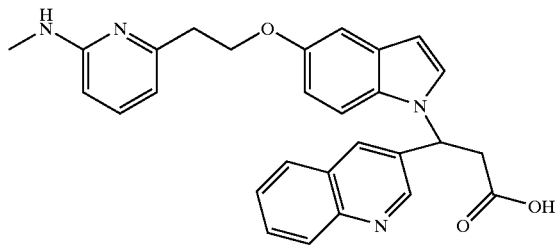

a) 3-Ethynyl-quinoline

The title compound was synthesized from the commercially available 3-bromo quinoline using the procedures described in Example 18, step (a) and step (b), in 68% yield. $H^1$ NMR ($Cl_3CD$), δ: 8.95 (d, 1H, J=2.0 Hz), 8.29 (d, 1H, J=2.0 Hz), 8.09 (d, 1H, J=8.8 Hz), 7.80 (m, 1H), 7.74 (m, 1H), 7.60 (m, 1H), 3.28 (s, 1H).

b) Quinolin-3-yl-propynoic acid ethyl ester.

The title compound was synthesized from 3-ethynyl-quinoline using the procedure described in Example 23, step (c), in 34% yield. $H^1$ NMR ($Cl_3CD$), δ: 8.99 (d, 1H, J=2.0 Hz), 8.40 (d, 1H, J=2.0 Hz), 8.11 (d, 1H, J=8.4 Hz), 7.80 (m, 2H), 7.60 (m, 1H), 4.34 (q, 2H, J=7.2 Hz), 1.38 (t, 3H, J=7.2 Hz).

c) 3-(5-{2-[6-(tert-Butoxycarbonyl-methyl-amino)-pyridin-2-yl]-ethoxy}-indol-1-yl)-3-quinolin-3-yl-acrylic acid ethyl ester.

The title compound was synthesized from {6-[2-(1H-indol-5-yloxy)-ethyl]-pyridin-2-yl}-methyl-carbamic acid tert-butyl ester and quinolin-3-yl-propynoic acid ethyl ester, using the procedure described in Example 16, step (d1), in 48% yield, as an E/Z isomeric mixture. $H^1$ NMR ($Cl_3CD$), δ: 8.91 (d, 0.3H, J=2.1 Hz), 8.88 (d, 0.3H, J=2.3 Hz), 8.17 (d, 0.7H, J=8.8 Hz), 8.14–8.11 (m, 1H), 7.97 (d, 0.3H, J=2.0 Hz), 7.82–7.74 (m, 2H), 7.60 (m, 1H), 7.53 (m, 1H), 7.49 (m, 1H), 7.17 (m, 1H), 7.11 (m, 1H), 6.92–6.97 (m, 2H), 6.78 (dd, 0.7H, J=2.5, 9.0 Hz), 6.70 (dd, 0.3H, J=2.5, 9.0 Hz), 6.64 (d, 0.3H, J=3.2 Hz), 6.55 (d, 0.7H, J=3.5 Hz), 6.39 (s, 0.3H), 6.32 (s, 0.7H), 4.39 (m, 2H), 4.10 (q, 1.4H, J=7.2 Hz), 4.04 (q, 0.6H, J=7.2 Hz), 1.39 (s, 0.9H), 1.38 (s, 2.1H), 3.21 (m, 2H), 1.51 (s, 9H), 1.14 (t, 2.1H, J=7.2 Hz), 1.05 (t, 0.9H, J=7.2 Hz).

d) 3-(5-{2-[6-(tert-Butoxycarbonyl-methyl-amino)-pyridin-2-yl]-ethoxy}-indol-1-yl)-3-quinolin-3-yl-propionic acid ethyl ester The title compound was synthesized from 3-(5-{2-[6-(tert-butoxycarbonyl-methyl-amino)-pyridin-2-yl]-ethoxy}-indol-1-yl)-3-quinolin-3-yl-acrylic acid ethyl ester using the procedure described in Example 18, step (d), in 53% yield. $H^1$ NMR ($Cl_3CD$), δ: 8.88 (m, 1H), 8.06 (d, 1H, J=8.6 Hz), 7.87 (m, 1H), 7.72 (m, 1H), 7.68 (m, 2H), 7.55–7.47 (m, 3H), 7.24 (m, 2H), 7.11 (d, 1H, J=2.3 Hz), 6.95 (d, 1H, J=7.2 Hz), 6.81 (dd, 1H, J=2.3, 8.8 Hz), 6.51 (d, 1H, J=3.2 Hz), 6.23 (t, 1H, J=7.4 Hz), 4.36 (t, 2H, J=6.7 Hz), 4.07 (q, 2H, J=7.2 Hz), 3.38 (m, 5H), 3.19 (t, 2H, J=6.7 Hz), 1.51 (s, 9H), 1.11 (t, 3H, J=7.2 Hz).

e) 3-{5-[2-(6-Methylamino-pyridin-2-yl)-ethoxy]-indol-1-yl}-3-quinolin-3-yl-propionic acid ethyl ester The title compound was synthesized from 3-(5-{2-[6-(tert-butoxycarbonyl-methyl-amino)-pyridin-2-yl]-ethoxy}-indol-1-yl)-3-quinolin-3-yl-propionic acid ethyl ester using the procedure described in Example 16, step (f), in 20% yield. $H^1$ NMR ($Cl_3CD$), δ: 8.83 (d, 1H, J=2.3 Hz), 8.08 (d, 1H, J=8.4 Hz), 7.89 (m, 1H), 7.75 (m, 1H), 7.71 (m, 1H), 7.55 (m, 1H), 7.40 (m, 1H), 7.24 (d, 1H, J=3.2 Hz), 7.23 (m, 1H), 7.14 (d, 1H, J=2.3 Hz), 6.84 (dd, 1H, J=2.5, 9.0 Hz), 6.57 (d, 1H, J=7.2 Hz), 6.52 (d, 1H, J=3.2 Hz), 6.25 (m, 2H), 4.52 (br s, 1H), 4.35 (t, 2H, J=6.9 Hz), 4.10 (q, 2H, J=7.2 Hz), 3.43 (m, 2H), 3.10 (t, 2H, J=6.9 Hz), 2.91 (m, 3H), 1.14 (t, 3H, J=7.2 Hz).

f) 3-{5-[2-(6-Methylamino-pyridin-2-yl)-ethoxy]-indol-1-yl}-3-quinolin-3-yl-propionic acid The title compound was synthesized from 3-{5-[2-(6-methylamino-pyridin-2-yl)-ethoxy]-indol-1-yl}-3-quinolin-3-yl-propionic acid ethyl ester using the procedure described in Example 18, step (g), in 60% yield. $H^1$ NMR (DMSO-d6) δ: 8.91 (d, 1H, J=2.3 Hz), 8.33 (d, 1H, J=2.0 Hz), 7.96 (d, 1H, J=8.6 Hz), 7.90 (m, 1H), 7.77 (d, 1H, J=3.2 Hz), 7.59 (m, 1H), 7.72 (m, 1H) 7.52 (d, 1H, J=9.0 Hz), 7.28 (m, 1H), 7.06 (d, 1H, J=2.5 Hz), 6.71 (dd, 1H, J=2.3, 8.8 Hz), 6.43 (m, 2H), 6.33(m, 1H), 6.25 (d, 1H, J=8.6 Hz), 6.21 (m, 1H), 4.25 (t, 2H, J=6.7 Hz), 3.56 (m, 2H), 2.93 (t, 2H, J=6.7 Hz), 2.73 (m, 3H). Mass Spectrum (LCMS, ESI) calculated for $C_{28}H_{27}N_4O_3$ 467.2, (M+1); found: 467.2.

EXAMPLE 46

3-{5-[2-(6-Methylamino-pyridin-2-yl)-ethoxy]-indol-1-yl}-3-pyridin-3-yl-propionic acid

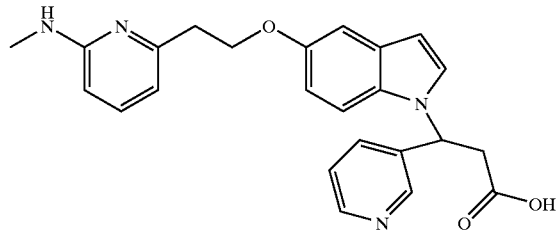

a) 3-(5-{2-[6-(tert-Butoxycarbonyl-methyl-amino)-pyridin-2-yl]-ethoxy}-indol-1-yl)-3-pyridin-3-yl-acrylic acid methyl ester The title compound was synthesized from {6-[2-(1H-indol-5-yloxy)-ethyl]-pyridin-2-yl}-methyl-carbamic acid tert-butyl ester and pyridin-3-yl-propynoic acid methyl ester, using the procedure described in Example 16, step (d1), in a 96% yield, as an E/Z isomeric mixture. $^1$H NMR ($Cl_3CD$), δ: 8.74–8.64 (m, 2H), 7.68 (m, 0.4), 7.57–7.48 (m, 2H), 7.45 (m, 0.6H), 7.38 (m, 0.4H), 7.28 (m, 0.6H), 7.13 (m, 1H), 7.08 (m, 1H), 6.96 (d, 1H, J=7.0 Hz), 6.88 (d, 0.4H, J=3.5 Hz), 6.80–6.66 (m, 1.6H), 6.61 (d, 0.6H, J=3.2 Hz), 6.54 (d, 0.4H, J=3.5 Hz), 6.26 (s, 0.4H), 6.24 (s, 0.6H), 4.39 (m, 2H), 3.67 (s, 1.2H), 3.61 (s, 1.8H), 3.39 (m, 3H), 3.20 (m, 2H), 1.51 (s, 9H).

b) 3-(5-{2-[6-(tert-Butoxycarbonyl-methyl-amino)-pyridin-2-yl]-ethoxy}-indol-1-yl)-3-pyridin-3-yl-propionic acid methyl ester The title compound was synthesized from 3-(5-{2-[6-(tert-butoxycarbonyl-methyl-amino)-pyridin-2-yl]-ethoxy}-indol-1-yl)-3-pyridin-3-yl-acrylic acid methyl ester using the procedure described in Example 16, step (e), in 53% yield. $^1$H NMR ($Cl_3CD$), δ: 8.55 (d, 1H, J=2.3 Hz), 8.51 (dd, 1H, J=1.6, 8.5 Hz), 7.52 (m, 2H), 7.21–7.15 (m, 3H), 7.37 (m, 1H), 7.10 (d, 1H, J=2.3 Hz), 6.96 (dd, 1H, J=0.6, 7.1 Hz), 6.81 (dd, 1H, J=2.4, 8.9 Hz), 6.48 (d, 1H, J=3.1 Hz), 6.04 (t, 1H, J=7.6 Hz), 4.36 (t, 2H, J=8.0 Hz), 3.62 (s, 3H), 3.38 (s, 3H), 3.31 (m, 2H), 3.19 (t, 2H, J=8.0 Hz), 1.51 (s, 9H).

c) 3-{5-[2-(6-Methylamino-pyridin-2-yl)-ethoxy]-indol-1-yl}-3-pyridin-3-yl-propionic acid methyl ester The title compound was synthesized from 3-(5-{2-[6-(tert-butoxycarbonyl-methyl-amino)-pyridin-2-yl]-ethoxy}-indol-1-yl)-3-pyridin-3-yl-propionic acid methyl ester using the procedure described in Example 16, step (f), in 55% yield. $^1$H NMR (Cl$_3$CD), δ: 8.55 (d, 1H, J=2.3 Hz), 8.51 (dd, 1H, J=1.5, 4.8 Hz), 7.37 (m, 2H), 7.18 (m, 3H), 7.10 (d, 1H, J=2.4 Hz), 6.82 (dd, 1H, J=2.4, 8.9 Hz), 6.55 (d, 1H, J=7.2 Hz), 6.47 (d, 1H, J=2.9 Hz), 6.23 (d, 1H, J=8.2 Hz), 6.04 (t, 1H, J=7.5 Hz), 4.54 (br s, 1H), 4.33 (t, 2H, J=8.0 Hz), 3.62 (s, 3H), 3.31 (m, 2H), 3.09 (t, 2H, J=8.0 Hz), 2.89 (m, 3H).

d) 3-{5-[2-(6-Methylamino-pyridin-2-yl)-ethoxy]-indol-1-yl}-3-pyridin-3-yl-propionic acid The title compound was synthesized from 3-{5-[2-(6-methylamino-pyridin-2-yl)-ethoxy]-indol-1-yl}-3-pyridin-3-yl-propionic acid methyl ester using the procedure described in Example 16, step (g), in 42% yield. $^1$H NMR (DMSO-d6) δ: 8.62 (br s, 1H), 8.44 (br s, 1H), 7.71 (m, 2H), 7.46 (d, 1H, J=8.9 Hz), 7.29 (m, 2H), 7.05 (d, 1H, J=2.3Hz), 6.71 (dd, 1H, J=2.3, 8.9 Hz), 6.43 (d, 1H, J=7.1 Hz), 6.39 (d, 1H, J=3.1 Hz) 6.35 (m, 1H), 6.25 (d, 1H, J=8.2 Hz), 4.25 (t, 2H, J=8.0 Hz), 6.02 (m, 1H), 3.49 (m, 2H), 2.93 (t, 2H, J=8.0 Hz), 2.74 (m, 3H). Mass Spectrum (LCMS, ESI) calculated for C$_{25}$H$_{25}$N$_4$O$_3$ 417.2, (M+1); found: 417.3.

EXAMPLE 47

3-{5-[2-(6-Methylamino-pyridin-2-yl)-ethoxy]-indol-1-yl}-hexanoic acid

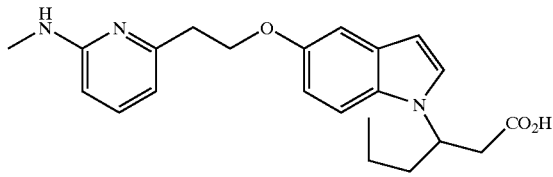

a) 3-{5-[2-(6-Methylamino-pyridin-2-yl)-ethoxy]-indol-1-yl}-hexanoic acid ethyl ester The title compound was synthesized from 2-(6-methylamino-pyridin-2-yl)-ethanol and 3-(5-hydroxy-indol-1-yl)-hexanoic acid ethyl ester using the procedure described in Example 14, step (c), in 25% yield. The crude product was used in the next step without further purification.

b) 3-{5-[2-(6-Methylamino-pyridin-2-yl)-ethoxy]-indol-1-yl}-hexanoic acid

The title compound was synthesized from 3-{5-[2-(6-methylamino-pyridin-2-yl)-ethoxy]-indol-1-yl}-hexanoic acid ethyl ester using the procedure described in Example 14, step (e), in 51% yield. $^1$H NMR (CDCl$_3$) δ 7.50 (dd, 1H, J=7.4, 8.8 Hz), 7.38 (d, 1H, J=9.0 Hz), 7.21 (d, 1H, J=3.2 Hz), 6.91 (d, 1H, J=2.4 Hz), 6.69 (dd, 1H, J=2.4, 8.9 Hz), 6.49 (d, 1H, J=7.3 Hz), 6.43 (d, 1H, J=3.1 Hz), 6.33 (d, 1H, J=8.7 Hz), 4.92–2.84 (m, 1H), 3.93–3.88 (m, 1H), 3.79–3.75 (m, 1H), 2.92–2.66 (m, 7H), 1.87–1.77 (m, 2H), 1.26–1.14 (m, 1H), 1.13–1.01 (m, 1H), 0.84 (t, 3H, J=7.2 Hz). Mass spectrum (LCMS, ESI) calculated for C$_{22}$H$_{28}$N$_3$O$_3$ 382.2 (M+H); found 382.3.

EXAMPLE 48

3-{5-[2-(2-Methyl-5,6,7,8-tetrahydro-[1,8]naphthyridin-3-yl)-ethyl]-indol-1-yl}-propionic acid

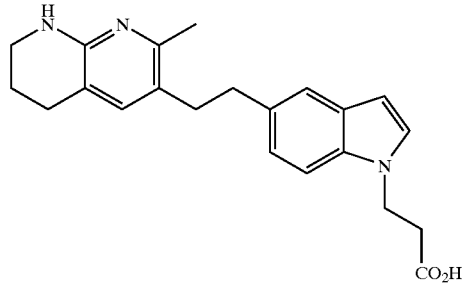

a) 4-(1H-Indol-5-yl)-butyronitrile

A mixture of 5-bromoindole (0.25 g, 1.25 mmol) and tetrakis(triphenylphosphine)palladium(0) (0.10 g, 0.12 mmol) was stirred under a nitrogen atmosphere for 10 minutes. 3-cyanopropyl zinc bromide [0.5 M in THF] (5.0 mL, 2.50 mmol) was added to the mixture and heated in the microwave at 100° C. for 15 minutes. The solvent was removed and the crude mixture was purified via column chromatography with silica gel, eluting with hexane/ethyl acetate (4/1) to afford the title compound in 63% yield. $^1$H NMR (CDCl$_3$) δ 8.22 (br, 1H), 7.43 (s, 1H), 7.31 (d, J=8.3 Hz, 1H), 7.18 (s, 1H), 7.00 (d, J=8.3 Hz, 1H), 6.49 (s, 1H), 2.86 (t, J=7.3 Hz, 2H), 2.28 (t, J=7.2 Hz, 2H), 2.02 (m, 2H). Mass Spectrum (LCMS, ESI) calculated for C$_{12}$H$_{13}$N$_2$ 185.1 (M+H); found 185.1.

b) 5-Bromo-1-triisopropylsilanyl-1H-indole

Lithium hexamethyldisilazane [1.0 M] (44.7 mL, 44.4 mmol) was added to a solution of 5-bromo-1H-indole (7.30 g, 37.0 mmol) in tetrahydrofuran (50 mL) at room temperature. After stirring for 5 minutes, triisopropylsilyl chloride (8.62 g, 44.4 mmol) was added to reaction mixture and stirred for 30 minutes. Water was added to quench the reaction and the solvent was removed under reduced pressure to give the crude mixture, which was purified via column chromatography on silica gel (9:1 Hexane/ethyl acetate) to give the title compound in 92% yield. $^1$H NMR (CDCl$_3$) δ 7.74 (d, J=1.8, 1H), 7.36 (d, J=8.8 Hz, 1H), 7.22 (m, 2H), 6.55 (d, J=3.1 Hz, 1H), 1.65 (m, 3H), 1.12 (d, J=7.5 Hz, 18H).

c) 4-(1-Triisopropylsilanyl-1H-indol-5-yl)-butyronitrile

Method c1

A mixture of 5-bromo-1-triisopropylsilanyl-1H-indole (4.30 g, 12.2 mmol), tetrakis(triphenylphosphine)-palladium (0) (1.41 g, 1.22 mmol), and 3-cyanopropyl zinc bromide [0.5 M in THF] (50 mL, 24.4 mmol) was heated at 70° C. overnight. The reaction was cooled and 1.0 N HCl (50 mL) was added. The crude product was extracted with methylene chloride (3×30 mL), and the combined organic layers were washed with water, brine, and then dried over Na$_2$SO$_4$. Removal of solvent gave a crude mixture which was purified via column chromatography, eluting with hexane/ethyl acetate (9/1) to give the title compound (64% yield).

Method c2

Lithium hexamethyldisiazane [1.0 M] (0.90 mL, 0.90 mmol) was added dropwise to a solution of 4-(1H-indol-5-yl)-butyronitrile (0.15 g, 0.82 mmol) in THF (2 mL) at −78° C. under nitrogen. After 5 minutes, triisopropylsilyl chloride (0.40 mL, 0.90 mmol) was added and the reaction was warmed to room temperature and stirred for an additional 4 h. Water was added to quench the reaction and the solvent was removed under reduced pressure. The crude mixture was purified via column chromatography with silica gel, eluting with hexane/ethyl acetate (4/1) to give the title compound (95% yield). $^1$H NMR (CDCl$_3$) δ 7.45 (d, 2H), 7.25 (m, 1H), 6.90 (m, 1H), 6.55 (m, 1H), 2.86 (t, 2H), 2.30 (t, 2H), 2.06 (m, 2H), 1.67 (m, 3H), 1.10 (d, 18H).

d) 5-(1-Triisopropylsilanyl-1H-indol-5-yl)-pentan-2-one

Methyl magnesium iodide [3 M in ether] (12.0 mL, 36.0 mmol) was added to a solution of 4-(1H-indol-5-yl)-butyronitrile (6.14 g, 18.0 mmol) in ether (50 mL) at 78° C. After addition, the reaction mixture was warmed to room temperature and stirred for 2 days. The reaction was quenched with a saturated ammonium chloride and the crude product was extracted with dichloromethane. The solvent was removed under reduced pressure and the crude mixture was purified via column chromatography with silica gel, eluting with hexane/ethyl acetate (4/1) to give the title compound (86% yield). $^1$H NMR (CDCl$_3$) δ 7.41 (m, 2H), 7.21 (m, 1H), 6.95 (dd, J=1.9, 8.5 Hz, 1H), 6.55 (dd, J=0.6, 2.2 Hz, 1H), 2.69 (t, J=7.5 Hz, 2H), 2.43 (t, J=7.4 Hz, 2H), 2.09 (s, 3H), 1.96 (m, 2H), 1.71 (, 3H), 1.13 (d, J=7.6 Hz, 9H). $^{13}$C NMR (CDCl$_3$) δ 209.1, 139.3, 132.6, 131.5, 131.3, 122.2, 119.8, 113.6, 104.3, 42.9, 34.9, 29.6, 29.9, 25.7, 18.1, 12.7.

e) 2-[3-(1-Triisopropylsilanyl-1H-indol-5-yl)-propyl]-[1,8]naphthyridine and 2-Methyl-3-[2-(1-triisopropylsilanyl-1H-indol-5-yl)-ethyl]-[1,8]naphthyridine A mixture of 5-(1-triisopropylsilanyl-1H-indol-5-yl)-pentan-2-one (1.10 g, 3.07 mmol), 2-amino-pyridine-3-carbaldehyde (0.37 g, 3.07 mmol), and L-proline (0.18 g, 1.53 mmol) in ethanol (15 mL) was heated at reflux for 24 h. The solvent was removed under reduced pressure to give a crude mixture which was purified via column chromatography, eluting with hexane/ethyl acetate (1/2) to give the two title compounds in a 2:1 ratio.

2-[3-(1-Triisopropylsilanyl-1H-indol-5-yl)-propyl]-[1,8]naphthyridine (major isomer, 56% yield): $^1$H NMR (CDCl$_3$) δ 9.08 (dd, J=2.0, 4.3 Hz, 1H), 8.13 (dd, J=1.9, 8.0 Hz, 1H), 8.06 (d, J=8.3 Hz, 1H), 7.37–7.45 (m, 4H), 7.21 (d, J=3.2 Hz, 1H), 7.01 (dd, J=1.8 and 8.5, 1H), 6.54 (dd, J=0.6, 2.4 Hz, 1H), 3.11 (t, J=7.7 Hz, 2H), 2.83 (t, J=7.6 Hz, 2H), 2.28 (m, 2H), 1.69 (m, 3H), 1.13 (d, J=7.5 Hz, 18H). $^{13}$C NMR (CDCl$_3$) δ 166.6, 155.8, 152.9, 139.2, 136.7, 136.5, 133.1, 131.5, 131.1, 122.4, 122.3, 121.1, 120.8, 119.7, 113.5, 104.3, 38.8, 35.5, 31.4, 17.9, 12.6. Mass Spectrum (LCMS, ESI) calculated for C$_{28}$H$_{38}$N$_3$Si 444.3 (M+H); found 444.4.

2-Methyl-3-[2-(1-triisopropylsilanyl-1H-indol-5-yl)-ethyl]-[1,8]naphthyridine (minor isomer, 24% yield): $^1$H NMR (CDCl$_3$) δ 9.01 (dd, J=1.9, 3.2 Hz, 1H), 8.04 (dd, J=1.9, 8.1 Hz, 1H), 7.80 (s, 1H), 7.37–7.47 (m, 4H), 6.95 (dd, J=1.6, 8.4 Hz, 1H), 6.56 (d, J=3.1 Hz, 1H), 3.07–3.18 (m, 4H), 2.81 (s, 3H), 1.57–1.73 (m, 3H), 1.14 (d, J=7.6 Hz, 18H). $^{13}$C NMR (CDCl$_3$) δ 162.4, 154.5, 152.2, 139.4, 135.9, 135.1, 135.0, 131.9, 131.5, 131.4, 122.0, 121.3, 121.1, 119.6, 113.6, 104.2, 35.7, 35.1, 23.5, 17.9, 12.6. Mass Spectrum (LCMS, ESI) calculated for C$_{28}$H$_{38}$N$_3$Si 444.23 (M+H); found 444.4.

f) 3-{5-[2-(2-Methyl-[1,8]naphthyridin-3-yl)-ethyl]-indol-1-yl}-acrylic acid methyl ester A mixture of 2-methyl-3-[2-(1-triisopropylsilanyl-1H-indol-5-yl)-ethyl]-[1,8]naphthyridine (0.25 g, 0.74 mmol), propynoic acid methyl ester (0.07 g, 0.84 mmol), and tetrabutylammonium fluoride [1.0 M] (2.23 mL, 2.23 mmol) was stirred at room temperature overnight. The solvent was removed under reduced pressure to give a crude mixture which was purified via column chromatography with silica gel, eluting with methylene chloride/methanol (95/5) to give the title compound (66% yield) as an E/Z isomeric mixture. $^1$H NMR (CDCl$_3$) δ 9.00 (m, 1H), 8.23 (s, 1H), 8.08 (m, 1H), 7.80 (m, 1H), 7.50 (d, 1H). Mass Spectrum (LCMS, ESI) calculated for C$_{22}$H$_{22}$N$_3$O$_2$ 372.2 (M+H); found 372.2.

g) 3-{5-[2-(2-Methyl-5,6,7,8-tetrahydro-[1,8]naphthyridin-3-yl)-ethyl]-indol-1-yl}-propionic acid methyl ester 3-{5-[2-(2-Methyl-[1,8]naphthyridin-3-yl)-ethyl]-indol-1-yl}-acrylic acid methyl ester (230 mg, 6.1 mmol) was stirred in methanol (5 mL) under a hydrogen atmosphere in the presence of 10% palladium on carbon (10% w/w) (20 mg) for 3 days. After removal of solvent, the crude product was purified by flash chromatography on silica gel with methylene chloride/methanol (95/5) to give the title product (14 mg, 6% yield). $^1$H NMR (CDCl$_3$) δ 7.40 (1H), 7.33 (1H), 7.23 (1H), 7.10 (1H), 7.00 (d, 1H), 6.65 (br, 1H), 6.45 (1H), 4.45 (t, 2H), 3.67 (s, 3H), 3.40 (br, 2H), 2.85 (4H), 2.30 (s, 3H), 2.70 (m, 2H), 1.90 (m, 2H). Mass Spectrum (LCMS, ESI) calculated for C$_{23}$H$_{28}$N$_3$O$_2$ 378.2 (M+H); found 378.3.

h) 3-{5-[2-(2-Methyl-5,6,7,8-tetrahydro-[1,8]naphthyridin-3-yl)-ethyl]-indol-1-yl}-propionic acid The title compound was synthesized from 3-{5-[2-(2-methyl-5,6,7,8-tetrahydro-[1,8]naphthyridin-3-yl)-ethyl]-indol-1-yl}-propionic acid methyl ester using the procedure described in Example 14, step (e), in 56% yield. $^1$H NMR (CDCl$_3$) δ 7.34 (d, J=8.2 Hz, 1H), 7.25 (m, 1H), 7.20 (m, 2H), 6.86 (m, 1H), 6.28 (d, J=2.8 Hz, 1H), 4.43 (t, J=7.0 Hz, 2H), 3.39 (m, 2H), 2.85 (t, J=3.8 Hz, 2H), 2.79 (t, J=6.7 Hz, 2H), 2.68 (m, 4H), 1.97 (s, 3H), 1.88 (m, 2H). Mass Spectrum (LCMS, ESI) calculated for C$_{22}$H$_{26}$N$_3$O$_2$ 364.2 (M+H); found 364.3.

EXAMPLE 49

3-{5-[3-(5,6,7,8-Tetrahydro-[1,8]naphthyridin-2-yl)-propyl]-indol-1-yl}-propionic acid

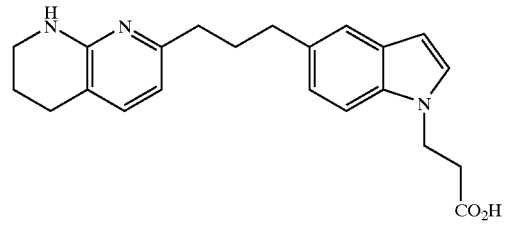

a) 2-[3-(1H-Indol-5-yl)-propyl]-[1,8]naphthyridine

Tetrabutylammonium fluoride [1.0 M in THF] (5.10 mL, 5.10 mmol) was added to a solution of 2-[3-(1-triisopropylsilanyl-1H-indol-5-yl)-propyl]-[1,8] naphthyridine (1.14 g, 2.57 mmol) in THF (20 mL) at room temperature and stirred for 1 h. The solvent was removed and the resulting crude product was purified via column chromatography on silica gel, eluting with ethyl acetate/hexane (2/1) to give the title product (100% yield). $^1$H NMR (CDCl$_3$) δ 9.08 (dd, J=2.0, 4.3 Hz, 1H), 8.28 (br, 1H), 8.14 (dd, J=2.0, 8.1, 1H), 8.07 (d, J=8.4 Hz, 1H), 7.45 (m, 2H), 7.36 (d, J=8.3, 1H), 731 (d, J=8.3 Hz, 1H), 7.18 (t, J=2.8 Hz, 1H), 7.05 (dd, J=1.6, 8.3 Hz, 1H), 6.47 (m, 1H), 3.10 (t, J=7.8 Hz, 2H), 2.84 (t, J=7.7 Hz, 2H), 2.28 (m, 2H). Mass Spectrum (LCMS, ESI) calculated for C$_{19}$H$_{18}$N$_3$ 288.2 (M+H); found 288.2.

b) 3-[5-(3-[1,8]Naphthyridin-2-yl-propyl)-indol-1-yl]-acrylic acid methyl ester

The title compound was synthesized from 2-[3-(1H-indol-5-yl)-propyl]-[1,8]naphthyridine using the procedure described in Example 17, step (a), in 78% yield as an E/Z c) 3-[5-(3-[1,8]Naphthyridin-2-yl-propyl)-indol-1-yl]-propionic acid ethyl ester To a solution of 2-[3-(1H-indol-5-yl)-propyl]-[1,8]naphthyridine (0.180 g, 0.627 mmol) in DMF (2 mL) was added sodium hydride (24.0 mg. 1.00 mmol) at 0° C. The reaction mixture was warmed to room temperature and stirred for 2 h. After cooling to 0° C., 3-chloro-propionic acid ethyl ester (85.0 mg, 0.63 mmol) was added and stirred overnight at room temperature. Ice water was added and the resulting mixture was extracted with methylene chloride. The combined organic layers were washed with water and brine, and dried over $Na_2SO_4$. Chromatography of the crude product on silica gel (methylene chloride/methanol, 95:5) gave the title product (0.11 g, 45% yield). $^1$H NMR (CDCl$_3$) δ 9.08 (d, 1H), 8.13 (d, 1H), 8.08 (d, 1H), 7.30–7.50 (m, 4H), 7.10 (m, 2M), 6.40 (dd, 1H), 4.40 (t, 2H), 4.10 (m, 2H), 3.10 (t, 2H), 2.80 (m, 4H), 2.25 (m, 2H), 1.20 (q, 3H).

d) 3-{5-[3-(5,6,7,8-Tetrahydro-[1,8]naphthyridin-2-yl)-propyl]-indol-1-yl}-propionic acid ethyl (and methyl) esters 3-[5-(3-[1,8]Naphthyridin-2-yl-propyl)-indol-1-yl]-propionic acid ethyl ester (0.11 g, 0.29 mmol) in methanol (5 mL) was stirred under hydrogen in the presence of 10% palladium on carbon (30.0 mg) for 24 h. After removal of solvent, the crude product was used in next reaction without further purification.

For ethyl ester: $^1$H NMR (CDCl$_3$) δ 7.42 (s, 1H), 7.24 (d, J=8.2 Hz, 2H), 7.05 (m, 2H), 6.39 (d, J=2.9, 1H), 6.34 (d, J=7.4 Hz, 1H), 4.90 (br, 1H), 4.41 (t, J=6.8 Hz, 2H), 4.11 (m, 4H), 3.37 (m, 2H), 2.58–2.80 (m, 6H), 2.03 (m, 2H), 1.88 (m, 2H), 1.29 (m, 3H).

For methyl ester: Mass Spectrum (LCMS, ESI) calculated for $C_{23}H_{28}N_3O_2$ 378.3 (M+H); found 378.3.

e) 3-{5-[3-(5,6,7,8-Tetrahydro-[1,8]naphthyridin-2-yl)-propyl]-indol-1-yl}-propionic acid A mixture of 3-{5-[3-(5,6,7,8-tetrahydro-[1,8]naphthyridin-2-yl)-propyl]-indol-1-yl}-propionic acid ethyl (or methyl) esters (0.10 g, 0.26 mmol) and sodium hydroxide (0.06 g, 1.58 mmol) in tetrahydrofuran/water (7.5 mL, 3:1) was stirred at room temperature for 3 days. After neutralizing with 1.0 N HCl, the crude product was extracted with ethyl acetate and purified via column chromatography (methylene chloride/methanol) (95:5) to give the title compound as a white solid (49% yield). $^1$H NMR (CDCl$_3$) δ 13.97 (br, 1H), 8.98 (br, 1H), 7.38 (d, J=7.3 Hz, 1H), 7.34 (d, J=1.1 Hz, 1H), 7.18 (m, 1H), 7.02 (dd, J=1.6 and 8.4 Hz, 1H), 6.44 (d, J=7.4 Hz, 1H), 6.36 (dd, J=0.6, 4.0 Hz, 1H), 4.39 (t, J=6.7 Hz, 2H), 3.38 (m, 2H), 2.79 (m, 6H), 1.99 (m, 4H), 1.83 (m, 2H). Mass Spectrum (LCMS, ESI) calculated for $C_{22}H_{26}N_3O_2$ 364.2 (M+H); found 364.3.

isomeric mixture. Mass Spectrum (LCMS, ESI) calculated for $C_{23}H_{22}N_3O_2$ 372.2 (M+H); found 372.3.

EXAMPLE 50

3-{5-[3-(5,6,7,8-Tetrahydro-[1,8]naphthyridin-2-yl)-propyl]-indol-1-yl}-hexanoic acid

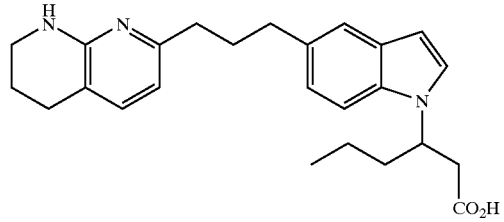

a) 3-[5-(3-[1,8]Naphthyridin-2-yl-propyl)-indol-1-yl]-hexanoic acid ethyl ester

To a solution of 2-[3-(1H-indol-5-yl)-propyl]-[1,8]naphthyridine (0.18 g, 0.62 mmol) in DMF (2 mL) was added sodium hydride (30.0 mg, 1.24 mmol) at room temperature. After stirring for 15 minutes, 3-bromo-hexanoic acid ethyl ester (276 mg, 1.24 mmol) was added. The reaction mixture was stirred overnight and quenched with water. The crude product was extracted with methylene chloride, washed with brine, and purified via column chromatography with silica gel (ethyl acetate/hexane:1:1), to give the title product (17% yield). $^1$H NMR (CDCl$_3$) δ 9.08 (dd, J=1.7, 4.0 Hz, 1H), 8.14 (m, 1H), 8.06 (m, 1H), 7.32–7.44 (m, 4H), 7.05–7.12 (m, 2H), 6.45 (d, J=3.2 Hz, 1H), 4.81 (m, 1H), 3.99 (m, 2H), 3.08 (m, 2H), 2.83 (m, 4H), 2.22 (m, 2H), 1.90 (m, 2H), 1.20 (m, 2H), 1.07 (m, 3H), 0.87 (m, 3H). Mass Spectrum (LCMS, ESI) calculated for $C_{27}H_{32}N_3O_2$ 430.3 (M+H); found 430.3.

b) 3-{5-[3-(5,6,7,8-Tetrahydro-[1,8]naphthyridin-2-yl)-propyl]-indol-1-yl}-hexanoic acid ethyl ester A mixture of 3-[5-(3-[1,8]naphthyridin-2-yl-propyl)-indol-1-yl]-hexanoic acid ethyl ester (100 mg, 0.665 mmol) and 10% palladium on carbon (30 mg) in methanol (5 mL) was stirred under hydrogen for 2 days. The reaction solution was filtered through celite and dried to give the crude product, which was purified via column chromatography eluting with hexane/ethyl acetate (4/1), to give the title compound (80% yield). $^1$H NMR (CDCl$_3$) δ 7.39 (d, J=0.9 Hz, 1H), 7.31 (d, J=8.5 Hz, 1H), 7.02–7.10 (m, 3H), 6.44 (dd, J=3.6, 6.3 Hz, 1H), 6.33 (d, J=7.3 Hz, 1H), 5.60 (br, 1H), 4.82 (m, 1H), 3.97 (q, 2H), 3.35 (t, 2H), 2.60–2.80 (m, 8H), 1.80–2.10 (m, 6H), 1.20 (m, 2H), 1.11 (m, 3H), 0.87 (m, 3H). Mass Spectrum (LCMS, ESI) calculated for $C_{27}H_{36}N_3O_2$ 434.3 (M+H); found 434.4.

c) 3-{5-[3-(5,6,7,8-Tetrahydro-[1,8]naphthyridin-2-yl)-propyl]-indol-1-yl}-hexanoic acid A mixture of 3-{5-[3-(5,6,7,8-tetrahydro-[1,8]naphthyridin-2-yl)-propyl]-indol-1-yl}-hexanoic acid ethyl ester (83.0 mg, 0.218 mmol) and NaOH (52.0 mg, 1.31 mmol) in THF/H$_2$O (3:1) was stirred at room temperature for 2 days. Aqueous HCl solution (1 N) was added to adjust the pH to 4–5. The crude product was extracted with ethyl acetate, and the combined organic layers were washed with brine and dried over $Na_2SO_4$. Removal of solvent gave the crude product, which was purified via column chromatography, eluting with 5% methanol in methylene chloride, to give the title compound (65% yield). $^1$H NMR (CDCl$_3$) δ 9.35 (br, 1H), 7.42 (d, J=8.1 Hz, 1H) 7.27 (m, H), 7.16–7.20 (m, 2H), 6.95 (d, J=7.9 Hz, 1H), 6.40 (d, J=2.5 Hz, 1H), 6.22 (d, J=7.2 Hz, 1H), 4.91 (br, 1H), 3.40 (m, 2H), 2.56–2.82 (m, 10H), 1.84–2.05 (m, 6H), 0.86 (m, 3H). Mass Spectrum (LCMS, ESI) calculated for $C_{25}H_{32}N_3O_2$ 406.3 (M+H); found 406.4.

EXAMPLE 51

3-Phenyl-3-{5-[3-(5,6,7,8-tetrahydro-[1,8]naphthyridin-2-yl)-propyl]-indol-1-yl}-propionic acid

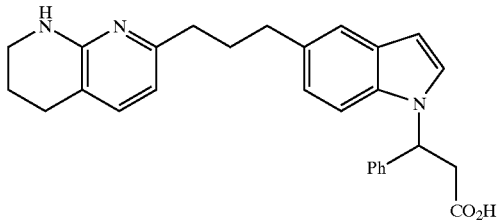

a) 3-[5-(3-[1,8]Naphthyridin-2-yl-propyl)-indol-1-yl]-3-phenyl-acrylic acid ethyl ester A mixture of 2-[3-(1-triisopropylsilanyl-1H-indol-5-yl)-propyl]-[1,8]naphthyridine (125 mg, 0.282 mmol), phenyl-propynoic acid ethyl ester (98.0 mg, 0.563 mmol), and tetrabutylammonium fluoride [1.0 M] 0.85 mL, 0.85 mmol) in THF (3 mL) was stirred for 24 h. After removal of the solvent, the crude reaction mixture was purified via column chromatography on silica gel with ethyl acetate/hexane (2:1) to give the title product as an E/Z isomeric mixture in 64% yield. Mass Spectrum (LCMS, ESI) calculated for $C_{30}H_{28}N_3O_2$ 462.2 (M+H); found 462.3.

b). 3-Phenyl-3-{5-[3-(5,6,7,8-tetrahydro-[1,8]naphthyridin-2-yl)-propyl]-indol-1-yl}-propionic acid ethyl ester 3-[5-(3-[1,8]Naphthyridin-2-yl-propyl)-indol-1-yl]-3-phenyl-acrylic acid ethyl ester (30.0 mg, 0.484 mmol) in methanol (2 mL) was stirred under hydrogen in the presence of 10% palladium on carbon (15.0 mg) at room temperature for 3 days. Then, the reaction mixture was filtered through celite and purified via column chromatography on silica gel (methylene chloride/methanol) (95/5) to give the title product as yellow oil (20.0 mg, 66% yield). $^1$H NMR (CDCl$_3$) δ 8.2 (d, 1H), 8.0 (m, 1H), 7.45 (m, 2H), 7.27 (m, 2H), 6.9–7.2 (m, 4H), 6.5 (1H), 6.3 (1H), 6.20 (m, 1H), 6.10 (m, 1H), 4.15 (m, 2H), 3.4 (m, 2H), 3.3 (m, 4H), 2.6 (m, 4H), 2.1 (m, 2H), 1.89 (m, 2H). Mass Spectrum (LCMS, ESI) calculated for $C_{30}H_{34}N_3O_2$ 468.27 (M+H); found 468.3.

c) 3-Phenyl-3-{5-[3-(5,6,7,8-tetrahydro-[1,8]naphthyridin-2-yl)-propyl]-indol-1-yl}-propionic acid A mixture of 3-phenyl-3-{5-[3-(5,6,7,8-tetrahydro-[1,8]naphthyridin-2-yl)-propyl]-indol-1-yl}-propionic acid ethyl ester (0.020 g, 0.04 mmol) and sodium hydroxide (0.01 g, 0.25 mmol) in THF/H$_2$O [1/0.3] (1.3 mL) was stirred at 50° C. for 24 h. The reaction mixture was neutralized with 1.0 N HCl to pH 5 and extracted with ethyl acetate. After removal of solvent, the crude product was purified via column chromatography, eluting with methylene chloride/methanol (95/5) to give the title compound (15% yield) as white solid. $^1$H NMR (CDCl$_3$) δ 10.76 (br, 1H), 8.16 (br, 1H), 7.57 (br, 1H), 7.10–7.45 (m, 8H), 7.03 (m, 1H), 6.95 (m, 2H), 6.18 (m, 1H), 3.38 (m, 2H), 3.21 (m, 2H), 2.61 (m, 2H), 2.43 (m, 2H), 2.03 (m, 2H), 1.82 (m 2H), 1.70 (m, 2H). Mass Spectrum (LCMS, ESI) calculated for $C_{28}H_{30}N_3O_2$ 440.2 (M+H); found 440.3.

d) 3-Phenyl-3-{5-[3-(5,6,7,8-tetrahydro-[1,8]naphthyridin-2-yl)-propyl]-indol-1-yl}-acrylic acid The title compound was synthesized from 3-[5-(3-[1,8]naphthyridin-2-yl-propyl)-indol-1-yl]-3-phenyl-acrylic acid ethyl ester using the procedures described in Example 50, step (b) (isolated as a minor product) and step (c), in 10% yield as an E/Z isomeric mixture. $^1$H NMR (CDCl$_3$) δ 7.10–7.35 (m, 7H), 7.00 (m, 1H), 6.92 (d, J=3.3 Hz, 1H), 6.46 (d, J=3.3 Hz, 1H), 6.31 (s, 1H), 6.22 (d, J=7.3 Hz, 1H), 6.13 (m, 1H), 3.37 (m, 2H), 2.64 (m, 2H), 2.56 (m, 2H), 2.47 (m, 2H), 2.04 (m, 2H), 1.84 (m, 2H). Mass Spectrum (LCMS, ESI) calculated for $C_{28}H_{28}N_3O_2$ 437.3 (M+H); found: 438.4.

EXAMPLE 52

3-{5-[2-(5,6,7,8-Tetrahydro-[1,8]naphthyridin-2-yl)-ethoxy]-indol-1-yl}-3-[5-(2,2,2-trifluoro-ethoxy)-pyridin-3-yl]-propionic acid

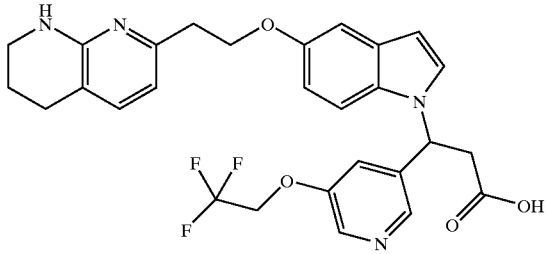

a) 3-Bromo-5-(2,2,2-trifluoro-ethoxy)-pyridine

To a slurry of sodium hydride (60% dispersion in mineral oil, 0.54 g, 14 mmol) in DMF (15 mL) was added commercially available 2,2,2-trifluoroethanol (0.97 mL, 14 mmol) at room temperature. After stirring for 15 minutes, a solution of 3,5-dibromopyridine (3.2 g, 14 mmol) in 5 mL of DMF was added dropwise. The reaction mixture was heated overnight at 70° C. After cooling to room temperature, the reaction was diluted with water and extracted with ethyl acetate. The extracts were dried over magnesium sulfate and the solvent was removed under reduced pressure. The crude product was chromatographed on silica (5% ethyl acetate/hexanes) to give the title compound (1.6 g, 46% yield) as clear oil. $^1$H NMR (CDCl$_3$) δ 8.42 (d, 1H, J=1.7 Hz), 8.32 (d, 1H, J=2.5 Hz), 7.46 (m, 1H), 4.42 (m, 2H).

b) 3-Triethoxyprop-1-ynyl-5-(2,2,2-trifluor-ethoxy)-pyridine

The title compound was synthesized from 3-bromo-5-(2,2,2-trifluoro-ethoxy)-pyridine and 3,3,3-triethoxypropyne using the procedure described in Example 43, step (e), in 46% yield. $^1$H NMR (CDCl$_3$) δ 8.44 (bs, 1H), 8.35 (bs, 1H), 7.34 (m, 1H), 4.40 (q, 2H, J=7.9 Hz), 3.76 (q, 6H, J=7.1 Hz), 1.28 (t, 9H, J=7.1 Hz).

c) [5-(2,2,2-Trifluoro-ethoxy)-pyridin-3-yl]-propynoic acid ethyl ester

The title compound was synthesized from 3-triethoxyprop-1-ynyl-5-(2,2,2-trifluor-ethoxy)-pyridine using the procedure described in Example 43, step (f), in 100% yield. $^1$H NMR (CDCl$_3$) δ 8.55 (bs, 1H), 8.48 (bs, 1H), 7.43 (m, 1H), 4.43 (q, 2H, J=7.9 Hz), 4.33 (q, 2H, J=7.2 Hz), 1.38 (t, 3H, J=7.2 Hz).

d) 7-[2-(1-{2-Ethoxycarbonyl-1-[5-(2,2,2-trifluoro-ethoxy)-pyridin-3-yl]-vinyl}-1H-indol-5-yloxy)-ethyl]-3,4-dihydro-2H-[1,8]naphthyrdine-1-carboxylic acid tert-butyl ester The title compound was synthesized from 7-[2-(1H-indol-5-yloxy)-ethyl]-3,4-dihydro-2H-[1,8]naphthyridine-1-carboxylic acid tert-butyl ester and [5-(2,2,2-trifluoroethoxy)-pyridin-3-yl]-propynoic acid ethyl ester using the procedure described in Example 16, step (d1), in 79% yield as an E/Z isomeric mixture. $^1$H NMR (CDCl$_3$) δ 8.47 (d, 0.33 H, J=2.6 Hz), 8.42 (d, 0.67H, J=2.6 Hz), 8.36 (bs, 1H), 7.31 (d, 1H, J=7.8 Hz), 7.23 (m, 0.33H), 7.16 (d, 0.33H, J=9.1 Hz), 7.12 (m, 0.67H), 7.09 (d, 0.33H, J=2.6 Hz), 7.02 (d, 0.67H, J=3.3 Hz), 6.99 (m, 0.67H), 6.93 (d, 1H, J=7.8 Hz), 6.83 (m, 1H), 6.74 (m, 0.67H), 6.59 (d, 0.67H, J=3.3 Hz), 6.52 (dd, 0.67H, J=0.48, 2.8 Hz), 6.26 (s, 0.33H), 6.25 (s, 0.67H), 4.35 (m, 4H), 4.11 (m, 2H), 3.75 (m, 2H), 3.20 (m, 2H), 2.73 (t, 2H, J=6.5 Hz), 1.92 (m, 2H), 1.52 (s, 9H), 1.19 (t, 1H, J=7.0 Hz), 1.03 (t, 2H, J=7.2 Hz).

e) 7-[2-(1-{2-Ethoxycarbonyl-1-[5-(2,2,2-trifluoro-ethoxy)-pyridin-3-yl]-ethyl}-1H-indol-5-yloxy)-ethyl-3,4-dihydro-2H-[1,8]naphthyridine-1-carboxylic acid tert-butyl ester The title compound was synthesized from 7-[2-(1-{2-ethoxycarbonyl-1-[5-(2,2,2-trifluoro-ethoxy)-pyridin-3-yl]-vinyl}-1H-indol-5-yloxy)-ethyl]-3,4-dihydro-2H-[1,8]naphthyrdine-1-carboxylic acid tert-butyl ester using the procedure described in Example 18, step (e), in 59% yield. $^1$H NMR (CDCl$_3$) δ 8.27 (bs, 1H), 8.23 (bs, 1H), 7.30 (d, 1H, J=7.6 Hz), 7.16 (m, 2H), 7.09 (d, 1H, J=2.3 Hz), 6.92 (m, 2H), 6.82 (dd, 1H, J=2.3, 6.5 Hz), 6.47 (d, 1H, J=3.3 Hz), 6.02 (t, 1H, J=7.4 Hz), 4.35 (t, 2H, J=7.0 Hz), 4.09 (m, 4H), 3.74 (m, 2H), 3.18 (t, 2H, J=7.0 Hz), 2.71 (t, 2H, J=6.5 Hz), 1.91 (m, 2H), 1.50 (s, 9H), 1.11 (t, 3H, J=7.0 Hz).

f) 3-{5-[2-(5,6,7,8-Tetrahydro-[1,8]naphthyridin-2-yl)-ethoxy]-indol-1-yl}-3-[5-(2,2,2-trifluoro-ethoxy)-pyridin-3-yl]-propionic acid ethyl ester The title compound was synthesized from 7-[2-(1-{2-ethoxycarbonyl-1-[5-(2,2,2-trifluoro-ethoxy)-pyridin-3-yl]-ethyl}-1H-indol-5-yloxy)-ethyl-3,4-dihydro-2H-[1,8]naphthyridine-1-carboxylic acid tert-butyl ester using the procedure described in Example 16, step (f), in 71% yield. $^1$H NMR (CDCl$_3$) δ 8.26 (bs, 1H), 8.24 (bs, 1H), 7.13 (m, 4H), 6.92 (m, 1H), 6.81 (dd, 1H, J=2.3, 6.5 Hz), 6.48 (m, 2H), 6.03 (t, 1H, J=7.4 Hz), 5.35 (bs, 1H), 4.27 (m, 4H), 4.06 (m, 2H), 3.34 (m, 2H), 3.28 (t, 2H, J=9.0 Hz), 3.05 (t, 2H, J=6.7 Hz), 2.68 (t, 2H, J=6.2 Hz), 1.88 (m, 2H), 1.12 (t, 3H, J=7.2 Hz).

g) 3-{5-[2-(5,6,7,8-Tetrahydro-[1,8]naphthyridin-2-yl)-ethoxy]-indol-1-yl}-3-[5-(2,2,2-trifluoro-ethoxy)-pyridin-3-yl]-propionic acid The title compound was synthesized from 3-{5-[2-(5,6,7,8-tetrahydro[1,8]naphthyridin-2-yl)-ethoxy]-indol-1-yl}-3-[5-(2,2,2-trifluoro-ethoxy)-pyridin-3-yl]-propionic acid ethyl ester using the procedure described in Example 18, step (g), in 56% yield. $^1$H NMR (DMSO-d6) δ 8.27 (s, 1H), 8.25 (s, 1H), 7.70 (d, 1H, J=3.3 Hz), 7.58 (m, 1H), 7.48 (d, 1H, J=9.0 Hz), 7.03 (d, 1H, J=7.2 Hz), 7.00 (d, 1H, J=2.6 Hz), 6.69 (dd, 1H, J=2.3, 6.5 Hz), 6.37 (d, 1H, J=3.0 Hz), 6.34 (d, 1H, J=7.2 Hz), 6.31 (bs, 1H), 5.98 (m, 1H), 4.82 (q, 2H, J=8.8 Hz), 4.17 (t, 2H, J=6.7 Hz), 3.55 (m, 2H), 3.21 (m, 2H), 2.85 (t, 2H, J=6.7 Hz), 2.58 (t, 2H, J=6.2 Hz), 1.73 (m, 2H). $^{19}$F NMR (DMSO-d$_6$) δ −73.05 (t, 3F, J=8.8 Hz). Mass Spectrum (LCMS, ESI) calculated for C$_{28}$H$_{28}$F$_3$N$_4$O$_4$: 541.2 (M+1); found: 541.3.

EXAMPLE 53

3-(5-Ethoxy-pyridin-3-yl)-3-{5-[2-(5,6,7,8-tetrahydro-[1,8]naphthyridin-2-yl)-ethoxy]-indol-1-yl}-propionic acid

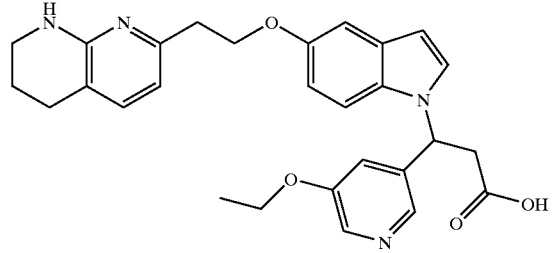

a) 3-Bromo-5-ethoxy-pyridine

The title compound was synthesized from 3,5-dibromopyridine and ethanol using the procedure described in Example 53, step (a) in 60% yield. $^1$H NMR (CDCl$_3$) δ 8.27 (bs, 1H), 8.23 (bs, 1H), 7.33 (m, 1H), 4.06 (q, 2H, J=7.0 Hz), 1.43 (t, 3H, J=7.0 Hz).

b) 3-Ethoxy-5-triethoxyprop-1-ynyl-pyridine

The title compound was synthesized from 3-bromo-5-ethoxy-pyridine and 3,3,3-triethoxypropyne using the procedure described in Example 43, step (e), in 37% yield. $^1$H NMR (CDCl$_3$) δ 8.27 (bs, 1H), 8.24 (bs, 1H), 7.21 (m, 1H), 4.02 (q, 2H, J=7.0 Hz), 3.72 (q, 6H, J=7.0 Hz), 1.39 (t, 3H, J=7.0 Hz), 1.23 (t, 9H, J=7.0 Hz).

c) (5-Ethoxy-pyridin-3-yl)-propynoic acid ethyl ester

The title compound was synthesized from 3-ethoxy-5-triethoxyprop-1-ynyl-pyridine using the procedure described in Example 43, step (f), in 96% yield. $^1$H NMR (CDCl$_3$) δ 8.40 (d, 1H, J=1.4 Hz), 8.35 (d, 1H, J=2.8 Hz), 7.33 (m, 1H), 4.32 (q, 2H, J=7.0 Hz), 4.08 (q, 2H, J=7.0 Hz), 1.46 (t, 3H, J=7.0), 1.38 (t, 3H, J=7.0 Hz).

d) 7-(2-{1-[2-Ethoxycarbonyl-1-(5-ethoxy-pyridin-3-yl)-vinyl-1H-indol-5-yloxy}-ethyl)-3,4-dihydro-2H-[1,8]naphthyridine-1-carboxylic acid tert-butyl ester The title compound was synthesized from (5-ethoxy-pyridin-3-yl)-propynoic acid ethyl ester and 7-[2-(1H-indol-5-yloxy)-ethyl]-3,4-dihydro-2H-[1,8]naphthyridine-1-carboxylic acid tert-butyl ester using the procedure described in Example 16, step (d1), in 70% yield. Mass Spectrum (LCMS, ESI) calculated for C$_{35}$H$_{40}$N$_4$O$_6$: 513.2 (M-Boc+H); found: 513.3 (-Boc).

e) 7-(2-{1-[2-Ethoxycarbonyl-1-(5-ethoxy-pyridin-3-yl)-ethyl]-1H-indol-5-yloxy}-ethyl)-3,4-dihydro-2H-[1,8]naphthyridine-1-carboxylic acid tert-butyl ester The title compound was synthesized from 7-(2-{1-[2-ethoxycarbonyl-1-(5-ethoxy-pyridin-3-yl)-vinyl-1H-indol-5-yloxy}-ethyl)-3,4-dihydro-2H-[1,8]naphthyridine-1-carboxylic acid tert-butyl ester using the procedure described in Example 18, step (e), in 60% yield. $^1$H NMR (CDCl$_3$) δ 8.19 (bs, 1H), 8.18 (bs, 1H), 7.31 (d, 1H, J=7.8 Hz), 7.19 (m, 2H), 7.10 (d, 1H, J=2.2 Hz), 6.95 (d, 1H, J=7.6 Hz), 6.84 (m, 2H), 6.47 (d, 1H, J=7.4 Hz), 6.03 (t, 1H, J=7.4 Hz), 4.38 (t, 2H, J=7.0 Hz), 4.07 (q, 2H, J=7.2 Hz), 3.95 (q, 2H, 7.0 Hz), 3.76 (m, 2H), 3.30 (t, 2H, J=8.3 Hz), 3.21 (t, 2H, J=7.0 Hz), 2.72 (t, 2H, J=8.3 Hz), 1.92 (m, 2H), 1.52 (s, 9H), 1.36 (t, 3H, J=7.0 Hz), 1.12 (t, 3H, J=7.2 Hz).

f) 3-(5-Ethoxy-pyridin-3-yl)-3-{5-[2-(5,6,7,8-tetrahydro-[1,8]naphthyridin-2-yl)-ethoxy-indol-1-yl}-propionic acid ethyl ester The title compound was synthesized from 7-(2-{1-[2-ethoxycarbonyl-1-(5-ethoxy-pyridin-3-yl)-ethyl]-1H-indol- 5-yloxy}-ethyl)-3,4-dihydro-2H-[1,8]naphthyridine-1-carboxylic acid tert-butyl ester using the procedure described in Example 16, step (f), in 71% yield. $^1$H NMR (CDCl$_3$) δ 8.19 (bs, 1H), 8.16 (bs, 1H), 7.19 (m, 3H), 7.08 (d, 1H, J=2.3 Hz), 6.87 (t, 1H, J=2.0 Hz), 6.81 (dd, 1H, J=2.3, 6.5 Hz), 6.51 (d, 1H, J=7.4 Hz), 6.47 (1H, J=3.3 Hz), 6.05 (bs, 1H), 6.02 (t, 1H, J=7.7 Hz), 4.29 (t, 2H, J=6.5 Hz), 4.06 (q, 2H, J=7.2 Hz), 3.95 (q, 2H, J=7.0 Hz), 3.43 (m, 2H), 3.29 (t, 2H, J=8.3 Hz), 3.08(t, 2H, J=6.5 Hz), 2.71 (t, 2H, J=6.3 Hz), 1.91 (m, 2H), 1.36 (t, 3H, J=7.0 Hz), 1.13 (t, 3H, J=7.2 Hz).

g) 3-(5-Ethoxy-pyridin-3-yl)-3-{5-[2-(5,6,7,8-tetrahydro-[1,8]naphthyridin-2-yl)-ethoxy-indol-1-yl}-propionic acid The title compound was synthesized from 3-(5-ethoxy-pyridin-3-yl)-3-{5-[2-(5,6,7,8-tetrahydro-[1,8]naphthyridin-2-yl)-ethoxy-indol-1-yl}-propionic acid ethyl ester using the procedure described in Example 18, step (g), in 69% yield. $^1$H NMR (DMSO-d$_6$) δ 8.18 (bs, 1H), 8.13 (bs, 1H), 7.73 (d, 1H, J=3.0 Hz), 7.48 (d, 1H, J=9.0 Hz), 7.35 (s, 1H), 7.13 (m, 1H), 7.02 (d, 1H, J=2.3 Hz), 6.71 (dd, 1H, J=2.0, 7.0 Hz), 6.53 (bs, 1H), 6.41 (m, 2H), 5.99 (t, 1H, J=7.0 Hz), 4.20 (t, 2H, J=7.0 Hz), 4.05 (m, 2H), 3.49 (m, 4H), 2.90 (t, 2H, J=6.0 Hz), 2.62 (t, 2H, J=6.0 Hz), 1.75 (m, 2H), 1.29 (t, 3H, J=7.0 Hz). Mass Spectrum (LCMS, ESI) calculated for C$_{28}$H$_{31}$N$_4$O$_4$: 487.2 (M+1); found: 487.3.

EXAMPLE 54

3-Pyridin-4-yl-3-{5-[2-(5,6,7,8-tetrahydro-[1,8]naphthyridin-2-yl)-ethoxy]-indol-1-yl}-propionic acid

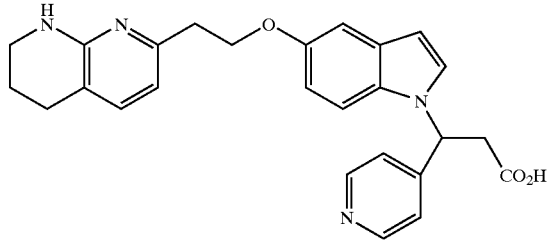

a) Pyridin-4-yl-propynoic acid ethyl ester

The title compound is prepared from commercially available material 3-oxo-3-pyridin-4-yl-propionic acid ethyl ester using the procedure described in Example 32, step (b), in 74% yield. $^1$H NMR (CDCl$_3$) δ 8.69 (m, 2H), 7.43 (m, 2H), 4.32 (q, 2H), 1.45 (t, 3H).

b) 7-{2-[1-(2-Ethoxycarbonyl-1-pyridin-4-yl-vinyl)-1H-indol-5-yloxy]-ethyl}-3,4-dihydro-2H-[1,8]naphthyridine-1-carboxylic acid tert-butyl ester The title compound is prepared from pyridin-4-yl-propynoic acid ethyl ester and 7-[2-(1H-Indol-5-yloxy)-ethyl]-3,4-dihydro-2H-[1,8]naphthyridine-1-carboxylic acid tert-butyl ester using the procedure described in Example 17, step (a), in 64% yield as an E/Z mixture. The mixture is used for the next reaction without further separation.

c) 7-{2-[1-(2-Ethoxycarbonyl-1-pyridin-4-yl-ethyl)-1H-indol-5-yloxy]-ethyl}-3,4-dihydro-2H-[1,8]naphthyridine-1-carboxylic acid tert-butyl ester The title compound is synthesized from 7-{2-[1-(2-Ethoxycarbonyl-1-pyridin-4-yl-vinyl)-1H-indol-5-yloxy]-ethyl}-3,4-dihydro-2H-[1,8]naphthyridine-1-carboxylic acid tert-butyl ester using the procedure described in Example 18, step (e), in 43% yield. $^1$H NMR (CDCl$_3$) δ 8.53 (d, 2H), 7.35 (m, 1H), 7.28 (m, 1H), 7.13 (m, 2H), 7.02 (d, 2H), 6.96 (m, 1H), 6.84 (m, 1H), 6.50 (m, 1H), 6.00 (t, 1H), 4.40 (t, 2H), 4.10 (q, 2H), 3.77 (t, 2H), 3.32(m, 2H), 3.25 (m, 2H), 2.75 (m, 2H), 1.92 (m, 2H), 1.52 (s, 9H), 1.15 (t, 3H). Mass Spectrum (LCMS, ESI) calculated for C$_{33}$H$_{39}$N$_4$O$_5$ 571.29 (M+H); found 471.4 (M-Boc+H, 100%).

d) 3-Pyridin-4-yl-3-{5-[2-(5,6,7,8-tetrahydro-[1,8]naphthyridin-2-yl)-ethoxy]-indol-1-yl}-propionic acid ethyl ester The title compound is synthesized from 7-{2-[1-(2-Ethoxycarbonyl-1-pyridin-4-yl-ethyl)-1H-indol-5-yloxy]-ethyl}-3,4-dihydro-2H-[1,8]naphthyridine-1-carboxylic acid tert-butyl ester using the procedure described in Example 16, step (e), in 36% yield. $^1$H NMR (CDCl$_3$) δ 8.52 (d, 2H), 7.16 (d, 1H), 7.10 (m, 2H), 7.00 (d, 1H), 6.83 (m, 1H), 6.48 (m, 2H), 6.00 (m, 1H), 4.30 (m, 2H), 4.12 (m, 2H), 3.40 (m, 2H), 3.28 (m, 2H), 3.05 (m, 2H), 2.70 (m, 2H), 1.90 (m, 2H), 1.20 (t, 3H). Mass Spectrum (LCMS, ESI) calculated for C$_{28}$H$_{31}$N$_4$O$_3$ 471.24 (M+H); found 471.3.

e) 3-Pyridin-4-yl-3-{5-[2-(5,6,7,8-tetrahydro-[1,8]naphthyridin-2-yl)-ethoxy]-indol-1-yl}-propionic acid The title compound is synthesized from 3-pyridin-4-yl-3-{5-[2-(5,6,7,8-tetrahydro-[1,8]naphthyridin-2-yl)-ethoxy]-indol-1-yl}-propionic acid ethyl ester using the procedure described in Example 16, step (f), in 66% yield. $^1$H NMR (CDCl$_3$) δ 8.44 (br, 2H), 7.38 (m, 1H), 7.20 (d, 1H), 7.18 (d, 1H), 7.15 (m, 1H), 7.02 (m, 1H), 6.65 (dd, 1H), 6.49 (m, 1H), 6.35 (m, 1H), 6.10 (m, 1H), 3.70 (m, 4H), 3.38 (m, 2H), 3.20 (m, 2H), 2.67 (m, 2H), 1.85 (m, 2H). Mass Spectrum (LCMS, ESI) calculated for C$_{26}$H$_{27}$N$_4$O$_3$ 443.21 (M+H); found 443.2.

EXAMPLE 55

3-Pyridin-2-yl-3-{5-[2-(5,6,7,8-tetrahydro-[1,8]naphthyridin-2-yl)-ethoxy]-indol-1-yl}-acrylic acid

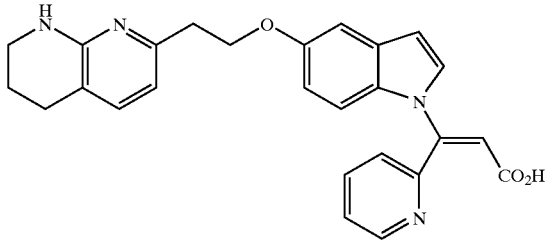

a) 3-Pyridin-2-yl-3-{5-[2-(5,6,7,8-tetrahydro-[1,8]naphthyridin-2-yl)-ethoxy]-indol-1-yl}-acrylic acid ethyl ester The title compound is prepared from 7-{2-[1-(2-Ethoxycarbonyl-1-pyridin-2-yl-vinyl)-1H-indol-5-yloxy]-ethyl}-3,4-dihydro-2H-[1,8]naphthyridine-1-carboxylic acid tert-butyl ester using the procedure described in Example 16, step (e), in 74% yield. $^1$H NMR (CDCl$_3$) δ 8.50 (d, 1H), 8.0 (s, 1H), 7.77 (t, 1H), 7.45 (m, 1H), 7.10 (d, 2H), 7.00 (d, 1H), 6.90 (d, 1H), 6.78 (dd, 1H), 6.60 (m, 1H), 6.50 (d, 1H), 6.30 (s, 1H), 4.90 (br, 1H), 4.30 (t, d, 2H), 4.13 (m, 2H), 3.40 (m, 2H), 3.10 (t, 2H), 2.70 (t, 2H), 1.90 (m, 2H), 1.15 (t, 3H).

b) 3-Pyridin-2-yl-3-{5-[2-(5,6,7,8-tetrahydro-[1,8]naphthyridin-2-yl)-ethoxy]-indol-1-yl}-acrylic acid The title compound is prepared from 3-pyridin-2-yl-3-{5-[2-(5,6,7,8-tetrahydro-[1,8]naphthyridin-2-yl)-ethoxy]-indol-1-yl}-acrylic acid ethyl ester using the procedure described in Example 16, step (f), in 54% yield. $^1$H NMR (CDCl$_3$) δ 8.9 (br, 1H), 8.6 (m, 1H), 7.60 (m, 1H), 7.25 (m, 2H), 7.20 (d, 1H), 7.08 (m, 2H), 6.98 (m, 1H), 6.72 (m, 1H), 6.50 (m, 2H), 6.42 (d, 1H), 4.20 (m, 2H), 3.40 (m, 2H), 2.95

(m, 2H), 2.70 (m, 2H), 1.90 (2H). Mass Spectrum (LCMS, ESI) calculated for $C_{26}H_{24}N_4O_3$ 440.27 (M+H); found 441.3.

EXAMPLE 56

Preparation of 6-(2-hydroxy-ethyl)-2,3-dihydro-pyrido[3,2-b][1,4]oxazine-4-carboxylic acid tert-butyl ester

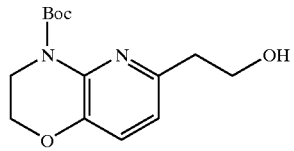

a) 2-Amino-6-methyl-pyridin-3-ol

A mixture of 6-methyl-2-nitro-pyridin-3-ol (18.5 g, 0.120 mmol), 10% palladium on activated carbon (1.35 g), and ethyl acetate (240 mL) was hydrogenated for 3 days. The mixture was filtered through Celite and washed with methanol/ethylacetate (5%). The filtrate and washing were combined and concentrated to give the title compound (14.7 g, 99% yield) as a pale brown solid. $^1$H NMR (DMSO-$d_6$) δ 9.19 (bs, 1H), 6.73 (d, 1H, J=7.6 Hz), 6.12 (d, 1H, J=7.6 Hz), 5.36 (bs, 2H), 2.15 (s, 3H).

b) 6-Methyl-4H-pyrido[3,2-b][1,4]oxazin-3-one L. Savelon, et. al, Bioorganic & Medicinal Chemistry, 6, 133, (1998).

To a suspension of 2-amino-6-methyl-pyridin-3-ol (18.3 g, 148 mmol), sodium bicarbonate (30 g, 354 mmol), $H_2O$ (100 mL), and 2-butanone (100 mL) in an ice-water bath was added a solution of chloroacetyl chloride (13.3 mL. 167 mmol) in 2-butanone (30 mL) over 1.5 h, controlling the temperature below 10° C. After the addition was complete, the ice-water bath was removed and the mixture was stirred at ambient temperature for 30 minutes, followed by refluxing for 1.5 h. The solvents were evaporated, and the resulting solid was washed with $H_2O$ (3 times), and dried under high vacuum overnight, giving the title compound (19.2 g, 79% yield) as a pale yellow solid. $^1$H NMR (CDCl$_3$) δ 10.45 (bs, 1H), 7.17 (d, 1H, J=8.1 Hz), 6.78 (d, 1H, J=8.1 Hz), 4.62 (s, 2H), 2.52 (s, 3H). Mass spectrum (LCMS, ESI) calculated for $C_8H_9N_2O_2$ 165.1 (M+1); found 165.1.

c) 6-Methyl-3,4-dihydro-2H-pyrido[3,2-b][1,4]oxazine

A flask was charged with lithium aluminum hydride (607 mg, 16.0 mmol) was placed in an ice-water bath under an argon atmosphere. THF (13 mL) was added slowly. To this suspension was added slowly a solution of 6-methyl-4H-pyrido[3,2-b][1,4]oxazin-3-one (1.05 g, 6.40 mmol) in THF (13 mL). After the addition was completed, additional THF (9 mL) was added, and the reaction was stirred in the ice-water bath for 30 minutes. Ice-water bath was removed, the mixture was stirred at ambient temperature for 3 h. The mixture was cooled with an ice-water bath, and $H_2O$ (0.86 mL) was added slowly, followed by cooled aqueous NaOH solution (0.64 mL, 10%). The ice-water bath was removed, additional $H_2O$ (1.8 mL) was added. After stirring for 30 minutes, Celite and $Na_2SO_4$ were added. The mixture was filtered through Celite, and the Celite was washed with EtOAc. The filtrate and the washing were combined, dried over $Na_2SO_4$, and concentrated to give the title compound (0.96 g, quantitative yield) as a while solid. $^1$H NMR (CDCl$_3$) δ 6.85 (d, 1H, J=8.0 Hz), 6.35 (d, 1H, J=8.0 Hz), 6.08 (bs, 1H), 4.19–4.16 (m, 2H), 3.54–3.52 (m, 2H), 2.31 (s, 3H).

d) 6-Methyl-2,3-dihydro-pyrido[3,2-b][1,4]oxazine-4-carboxylic acid tert-butyl ester A mixture of 6-methyl-3,4-dihydro-2h-pyrido[3,2-b][1,4]oxazine (0.89 g, 5.93 mmol) and di-tert-butyl dicarbonate was heated and stirred at 60° C. for 48 h, and then allowed to cooled to ambient temperature to give crude product. Recrystallization of the crude product from hexane gave the title compound (1.18 g, 80% yield) as a white solid. This crude product was used in next step reaction without further purification.

e) 6-tert-Butoxycarbonylmethyl-2,3-dihydro-pyrido[3,2-b][1,4]oxazine-4-carboxylic acid tert-butylester To a solution of diisopropylamine (1.23 ml, 8.80 mmol) in thf (8.0 ml) at −78° C. was added n-butyllithium (3.26 ml, 2.5 m in hexanes) and stirred for 20 min. To the above solution was added a solution of 6-tert-butoxycarbonylmethyl-2,3-dihydro-pyrido[3,2-b][1,4]oxazine-4-carboxylic acid tert-butylester (1.1 g, 4.40 mmol) in thf (15 ml) over a period of 30 min. After the addition completed, the mixture was stirred for 40 min. Diethylcarbonate (0.85 ml, 7.04 mmol) was added at once and stirred for 15 min. Dry ice-acetone bath was removed. The mixture was stirred in an ice water bath for 1 h. Saturated NH$_4$Cl was added. The mixture was diluted with ethyl acetate. The organic layer was separated, washed with h$_2$o, brine, dried over na$_2$so$_4$, concentrated, and flash chromatographed on silica gel, eluting with ethyl acetate/hexane (5, 10, 15, 25, 30%) to give the title compound (755 mg, 49% yield) as a yellow oil. $^1$H NMR (CDCl$_3$) δ 7.13 (d, 1H, j=8.2 Hz), 6.97 (d, 1H, j=8.2 Hz), 4.23 (t, 2H, j=4.4 Hz), 3.89 (t, 2H, j=4.5 Hz), 3.65 (s, 2H), 1.54 (s, 9H), 1.45 (s, 9H).

f) 2-(3,4-dihydro-2h-pyrido[3,2-b][1,4]oxazin-6-yl)-ethanol

To a solution of 6-tert-butoxycarbonylmethyl-2,3-dihydro-pyrido[3,2-b][1,4]oxazine-4-carboxylic acid tert-butyl ester (350 mg, 1mmol) in THF (4.0 ml) was added a solution of lithium borohydride (0.6 ml, 2.0 m in thf). The mixture was refluxed overnight, then cooled in an ice-bath. Aqueous solution of naoh (0.36 ml, 5%) was added. The ice-bath was removed. Additional h$_2$o (0.36 ml) was added and the mixture stirred for 10 min. Celite and na$_2$so$_4$ were added. The mixture was filtered through celite, and the celite washed with etoac. The filtrate and washing were combined, dried over na$_2$so$_4$, concentrated, and flash chromatographed on silica gel, eluting with meoh/dcm (1, 2, 3, 4%) to give the product (171 mg, 94% yield) as a yellow oil. $^1$H NMR (CDCl$_3$) δ 6.90 (d, 1H, J=7.8 Hz), 6.39 (d, 1H, J=7.7 Hz), 4.85 (bs, 1H), 4.20 (t, 2H, J=4.4 Hz), 3.91 (t, 2H, J=5.5 Hz), 3.69–3.52 (m, 2H), 2.78 (t, 2H, J=5.6 Hz).

EXAMPLE 57

In Vitro Inhibition of Purified Enzymes

Fibrinogen-IIb-IIIa assay

The assay is based on the method of Dennis (Dennis, M. S., et al., *Proteins* 15: 312–321 (1993)). Costar 9018 flat-bottom 96-well ELISA plates were coated overnight at 4° C. with 100 μL/well of 10 μg/mL human fibrinogen (Calbiochem 341578) in 20 mM Tris-HCl pH 7.5, 150 mM NaCl, 2 mM CaCl$_2$, 0.02% NaN$_3$ (TAC buffer), and blocked for 1 hr at 37° C. with 150 μL/well of TAC buffer containing 0.05% Tween 20 and 1% bovine serum albumin (TACTB buffer). After washing 3 times with 200 μL/well of 10 mM Na$_2$HPO$_4$ pH 7.5, 150 mM NaCl, 0.01% Tween 20 (PBST buffer), controls or test compound (0.027–20.0 μM) were mixed with 40 μg/mL human GPIIbIIIa (Enzyme Research Laboratories) in TACTB buffer, and 100 μL/well of these solutions were incubated for 1 hr at 37° C. The plate was then washed 5 times with PBST buffer, and 100 μL/well of a monoclonal anti-GPIIbIIIa antibody in TACTB buffer (1 μg/mL, Enzyme Research Laboratories MabGP2b3a) was incubated at 37° C. for 1 hr. After washing (5 times with PBST buffer), 100 μL/well of goat anti-mouse IgG conjugated to horseradish peroxidase (Kirkegaard & Perry 14-23-06) was incubated at 37° C. for 1 hr (25 ng/mL in PBST buffer), followed by a 6-fold PBST buffer wash. The plate was developed by adding 100 μL/well of 0.67 mg o-phenylenediamine dihydrochloride per mL of 0.012% $H_2O_2$, 22 mM sodium citrate, 50 mM sodium phosphate, pH 5.0 at room temperature. The reaction was stopped with 50 μL/well of 2M $H_2SO_4$, and the absorbence at 492 nm was recorded. Percent (%) inhibition was calculated from the average of three separate determinations relative to buffer controls (no test compound added), and a four parameter fit (Marquardt, D. W., *J. Soc. Indust. Appl. Math.* 11:431–441 (1963)) was used to estimate the half maximal inhibition concentration ($IC_{50}$).

$\alpha_v\beta_3$-Vitronectin Assay

The assay was based on the method of Niiya (Niiya, K., et al., *Blood* 70:475–483 (1987)). Costar 9018 flat-bottom 96-well ELISA plates were coated overnight at room temperature with 100 μL/well of 0.4 μg/mL human $\alpha_v\beta_3$ (Chemicon CC1019) in TS buffer (20 mM Tris-HCl pH 7.5, 150 mM NaCl, 1 mM $CaCl_2$, 1 mM $MgCl_2$, 1 mM $MnCl_2$). All subsequent steps were performed at room temperature. Plates were blocked for 2 hr with 150 μL/well of TS buffer containing 1% BSA (TSB buffer), and washed 3 times with 200 μL/well of PBST buffer. Controls or test compound (0.0001–20.0 μM) were mixed with 1 μg/mL of human vitronectin (Chemicon CC080) that had been biotinylated in-house with sulfo-NHS-LC-LC-biotin (Pierce 21338, 20:1 molar ratio), and 100 μL/well of these solutions (in TSB buffer) were incubated for 2 hr. The plate was then washed 5 times with PBST buffer, and 100 μL/well of 0.25 μg/mL NeutrAvidin-horseradish peroxidase conjugate (Pierce 31001) in TSB buffer was incubated for 1 hr. Following a 5-fold PBST buffer wash, the plate was developed and results were calculated as described for the fibrinogen-IIbIIIa assay. $IC_{50}$ values for inhibition of the $\alpha_v\beta_3$-vitronectin interaction by other compounds of the invention are presented in Table I.

TABLE 1

In Vitro Activity of New $\alpha_v\beta_3$ Antagonists

| Example # | $IC_{50}$ (nM) |
| --- | --- |
| 1 | 500 |
| 4 | 670 |
| 5 | 50 |
| 7 | 500 |
| 14 | 4.00 |
| 15 | 6.00 |
| 38 | 0.24 |

$\alpha_v\beta_5$-Vitronectin Assay

The assay is similar to the $\alpha_v\beta_3$-vitronectin assay. Costar 9018 flat-botom 96-well ELISA plates were coated overnight at room temperature with 100 μL/well of 1 μg/mL human $\alpha_v\beta_5$ (Chemicon CC1025) in TS buffer. All subsequent steps were preformed at room temperature. Plates were blocked for 2 hr at 30° C. with 150 μL/well of TSB buffer, and washed 3 times with 200 μL/well of PBST butter. Controls or test compound (0.0001–20 μM) were mixed with 1 μg/mL of human vitronectin (Chemicon CC080) that had been biotinylated in-house with sulfo-NHS-LC-LC-biotin (Pierce 21338, 20:1 molar ratio), and 100 μL/well of these solutions (in TSB buffer) were incubated for 2 hr. The plate was then washed 5 times with PBST buffer, and 100 μL/well of 0.25 μg/mL. NeutraAvidin-horseradish peroxidase conjugate (Pierce 31001) in TSB buffer was incubated at 30° C. for 1 hr. Following a 5-fold PBST buffer wash, the plate was developed and results were calculated as described for the fibrinogen-IIbIIIa assay.

EXAMPLE 58

Tablet Preparation

Tablets containing 25.0, 50.0, and 100.0 mg, respectively, of the compound of Example 1 ("active compound") are prepared as illustrated below:

| TABLET FOR DOSES CONTAINING FROM 25–100 MG OF THE ACTIVE COMPOUND | | | |
| --- | --- | --- | --- |
| | Amount-mg | | |
| Active compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 59

Intravenous Solution Preparation

An intravenous dosage form of the compound of Example 1 ("active compound") is prepared as follows:

| | |
| --- | --- |
| Active compound | 0.5–10.0 mg |
| Sodium citrate | 5–50 mg |
| Citric acid | 1–15 mg |
| Sodium chloride | 1–8 mg |
| Water for injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula IV:

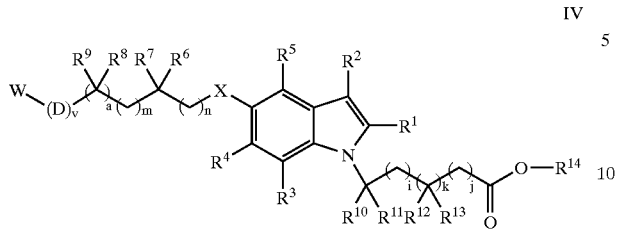

IV wherein:

$R^1$, $R^2$, $R^3$, $R^4$ and $R^5$ independently represent hydrogen, halogen, akyl, aryl, aralkyl, heteroaryl or heteroarylalkyl;

$R^6$, $R^7$, $R^8$ and $R^9$ independently represent hydrogen, alkyl, hydroxyalkyl, aminoalkyl, monoalkylaminoalkyl, dialkylaminoalkyl, carboxyalkyl, aryl or aralkyl;

or $R^6$ and $R^7$ are taken together to form —(CH$_2$)$_p$—, where p is 2–8, while $R^8$ and $R^9$ are defined as above; or $R^8$ and $R^9$ are taken together to form —(CH$_2$)$_q$—, where q is 2–8, while $R^6$ and $R^7$ are defined as above; or $R^6$ and $R^8$ are taken together to form —(CH$_2$)$_r$—, while r is zero (a bond), 1 or 2, while $R^7$ and $R^9$ are defined as above;

X represents oxygen, sulfur, —CH$_2$—, —NH—, —(C=O)NH— or —NH(C=O)—;

n is from 0 to 4;

m is from 0 to 4;

a is 0 or 1;

D represents oxygen;

v is 0 or 1;

$R^{10}$, $R^{11}$, $R^{12}$ and $R^{13}$ independently represent: hydrogen; hydroxy; alkyl; alkoxy; cycloalkyl; aryl, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkylalcoxyaryl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; alkanoyl; heteroaryl having 5–14 ring members, optionally substituted with one or more of halogen, hydroxy, cyano, alkyl, aryl, alkoxy, haloalkyl, arylalkyl, arylalkoxy, aryloxy, alkylsulfonyl, alkylsulfinyl, alkylalkoxyaryl, monoalkylamino, dialkylamino, aminoalkyl, monoalkylaminoalkyl, dialkylaminoalkyl, alkanoyl; or

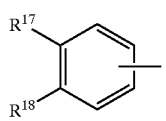

wherein $R^{17}$ and $R^{18}$ together form —CH$_2$CH$_2$—O—, —O—CH$_2$CH$_2$—, —O—CH$_2$—O— or —O—CH$_2$CH$_2$—O—; or $R^{10}$ and $R^{12}$ are taken together to form —(CH$_2$)$_s$—, wherein s is 0 (a bond) or 1 to 4, while $R^{11}$ and $R^{13}$ are as defined as above; or $R^{10}$ and $R^{12}$ are taken together to form a double bond when i is 0 and k is 1, while $R^{11}$ and $R^{13}$ are as defined above; or $R^{10}$ and $R^{11}$ are taken together to form —(CH$_2$)$_t$—, wherein t is 2 to 8, while $R^{12}$ and $R^{13}$ are as defined as above, or $R^{12}$ and $R^{13}$ are taken together to form —(CH$_2$)$_u$— wherein u is 2 to 8, while $R^{10}$ and $R^{11}$ are as defined as above;

i is from 0 to 4;

j is from 0 to 4;

k is 0 or 1;

$R^{14}$ is hydrogen, alkyl, aryl, aralkyl, dialkylaminoalkyl, 1-morpholinoalkyl, 1-piperidinylalkyl, pyridinylalkyl, alkoxy(alkoxy) alkoxyalkyl, or (alkoxycarbonyl)oxyethyl;

W is:

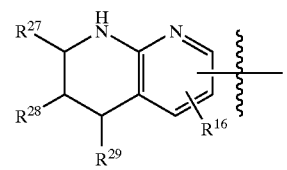

wherein:

$R^{16}$ is hydrogen, alkyl, haloalkyl or halogen; and $R^{27}$, $R^{28}$, and $R^{29}$ are independently hydrogen, halogen, alkyl, alkoxy or aryl.

2. The compound of claim 1, wherein $R^{14}$ is a prodrug, selected from the group consisting of: alkyl, aryl, aralkyl, dialkylaminoalkyl, 1-morpholinoalkyl, 1-piperidinylalkyl, pyridinylalkyl, alkoxy(alkoxy) alkoxyalkyl, or (alkoxycarbonyl)oxyethyl.

3. The compound of claim 1, wherein:

$R^1$, $R^2$, $R^3$, $R^4$ and $R^5$ independently represent hydrogen, halogen, (C$_{1-8}$)alkyl, (C$_{6-10}$)aryl, (C$_{6-10}$)ar(C$_{1-8}$)alkyl, 5–14 member heteroaryl, or 5–14 member heteroaryl (C$_{1-8}$)alkyl;

$R^6$, $R^7$, $R^8$ and $R^9$ independently represent hydrogen, (C$_{1-8}$)alkyl, hydroxy(C$_{1-8}$)alkyl, amino(C$_{1-8}$)alkyl, mono(C$_{1-8}$)alkylamino(C$_{1-8}$)alkyl, di(C$_{1-8}$)alkylamino (C$_{1-8}$)alkyl, carboxy(C$_{1-8}$)alkyl, (C$_{6-10}$)aryl or (C$_{6-10}$)ar(C$_{1-8}$)alkyl;

or $R^6$ and $R^7$ are taken together to form —(CH$_2$)$_p$—, where p is 2–8, while $R^8$ and $R^9$ are defined as above; or $R^8$ and $R^9$ are taken together to form —(CH$_2$)$_q$—, where q is 2–8, while $R^6$ and $R^7$ are defined as above; or $R^6$ and $R^8$ are taken together to form —(CH$_2$)$_r$—, while r is zero (a bond), 1 or 2, while $R^7$ and $R^9$ are defined as above;

X represents oxygen, sulfur, —CH$_2$—, —NH—, —(C=O)NH— or —NH(C=O)—;

n is from 0 to 4;

m is from 0 to 4;

a is from 0 or 1;

D represents oxygen;

v is from 0 or 1;

$R^{10}$, $R^{11}$, $R^{12}$ and $R^{13}$ independently represent: hydrogen; hydroxy; (C$_{1-8}$)alkyl; (C$_{1-8}$)alkoxy; (C$_{3-8}$)cycloalkyl; (C$_{6-10}$)aryl, optionally substituted with one or more of halogen, hydroxy, cyano, (C$_{1-8}$)alkyl, (C$_{6-10}$)aryl, (C$_{1-8}$)alkoxy, halo(C$_{1-8}$)alkyl, (C$_{6-10}$)aryl(C$_{1-8}$)alkyl, (C$_{6-10}$)aryl(C$_{1-8}$)alkoxy, (C$_{6-10}$)aryloxy, (C$_{1-8}$) alkylsulfonyl, (C$_{1-8}$)alkylsulfinyl, (C$_{1-8}$)alkoxy(C$_{6-10}$) aryl(C$_{1-8}$)alkyl, mono(C$_{1-8}$)alkylamino, di(C$_{1-8}$) alkylamino, amino(C$_{1-8}$)alkyl, mono(C$_{1-8}$)alkylamino ($C_{1-8}$)alkyl, di($C_{1-8}$)alkylamino($C_{1-8}$)alkyl, ($C_{1-8}$) alkanoyl; mono($C_{1-8}$)alkylamino; di($C_{1-8}$)alkylamino; amino($C_{1-8}$)alkyl; mono($C_{1-8}$)alkylamino($C_{1-8}$)alkyl; di($C_{1-8}$)alkylamino($C_{1-8}$)alkyl; ($C_{1-8}$)alkanoyl; heteroaryl having 5–14 ring members, optionally substituted with one or more of halogen, hydroxy, cyano, ($C_{1-8}$)alkyl, ($C_{6-10}$)aryl, ($C_{1-8}$)alkoxy, halo($C_{1-8}$)alkyl, ($C_{6-10}$)aryl($C_{1-8}$)alkyl, ($C_{6-10}$)aryl($C_{1-8}$)alkoxy, ($C_{6-10}$)aryloxy, ($C_{1-8}$)alkylsulfonyl, ($C_{1-8}$)alkylsulfinyl, ($C_{1-8}$)alkoxy($C_{6-10}$)aryl($C_{1-8}$)alkyl, mono($C_{1-8}$)alkylamino, di($C_{1-8}$)alkylamino, amino($C_{1-8}$)alkyl, mono($C_{1-8}$)alkylamino($C_{1-8}$)alkyl, di($C_{1-8}$)alkylamino($C_{1-8}$)alkyl, ($C_{1-8}$)alkanoyl; or

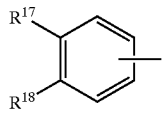

wherein $R^{17}$ and $R^{18}$ together form —CH$_2$CH$_2$—O—, —O—CH$_2$CH$_2$—, —O—CH$_2$—O— or —O—CH$_2$CH$_2$—O—; or $R^{10}$ and $R^{12}$ are taken together to form —(CH$_2$)$_s$—, wherein s is 0 (a bond) or 1 to 4, while $R^{11}$ and $R^{13}$ are as defined as above; or $R^{10}$ and $R^{12}$ are taken together to form a double bond when i is 0 and k is 1, while $R^{11}$ and $R^{13}$ are as defined above; or $R^{10}$ and $R^{11}$ are taken together to form —(CH$_2$)$_t$—, wherein t is 2 to 8, while $R^{12}$ and $R^{13}$ are as defined as above, or $R^{12}$ and $R^{13}$ are taken together to form —(CH$_2$)$_u$— wherein u is 2 to 8, while $R^{10}$ and $R^{11}$ are as defined as above; or i is from 0 to 4;
j is from 0 to 4; and
k is 0 or 1;
$R^{14}$ is hydrogen or a functionality that acts as a prodrug;
W is:

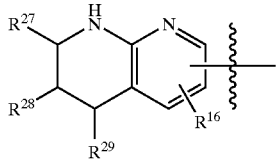

wherein:
$R^{16}$ is hydrogen, ($C_{1-8}$)alkyl, halo($C_{1-8}$)alkyl or halogen; $R^{27}$, $R^{28}$, and $R^{29}$ are independendently hydrogen, halogen, ($C_{1-8}$)alkyl, ($C_{1-8}$)alkoxy, or ($C_{6-10}$)aryl.

4. The compound of claim 1, wherein $R^1$ and $R^2$ independently represent hydrogen, halogen, ($C_{1-6}$)alkyl, ($C_{6-10}$)aryl, ($C_{6-10}$)ar($C_{1-6}$)alkyl, 5–14 member heteroaryl, or 5–14 member heteroaryl($C_{1-8}$)alkyl.

5. The compound of claim 4, wherein $R^1$ and $R^2$ independently represent hydrogen, methyl, ethyl, propyl, butyl, phenyl, benzyl or phenylethyl.

6. The compound of claim 5, wherein $R^1$ and $R^2$ independently represent hydrogen, methyl, ethyl or propyl.

7. The compound of claim 1, wherein $R^3$, $R^4$ and $R^5$ independently represent hydrogen, ($C_{1-6}$)alkyl, ($C_{6-10}$)aryl, or ($C_{6-10}$)ar($C_{1-6}$)alkyl.

8. The compound of claim 7, wherein $R^3$, $R^4$ and $R^5$ are hydrogen or ($C_{1-8}$)alkyl.

9. The compound of claim 1, wherein $R^6$, $R^7$, $R^8$ and $R^9$ independently represent hydrogen, halogen or ($C_{1-6}$)alkyl.

10. The compound of claim 1, wherein X is oxygen, —CH$_2$— or —(C=O)NH—.

11. The compound of claim 10, wherein X is oxygen or —CH$_2$—.

12. The compound of claim 1, wherein W is:

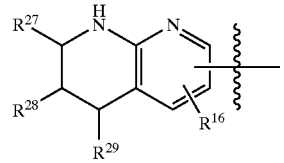

wherein:
$R^{16}$ is hydrogen, ($C_{1-8}$)alkyl, halo($C_{1-8}$)alkyl or halogen; and
$R^{27}$, $R^{28}$, and $R^{29}$ are hydrogen, halogen, ($C_{1-8}$)alkyl, ($C_{1-8}$)alkoxy, or ($C_{6-10}$)aryl.

13. The compound of claim 1, wherein W is

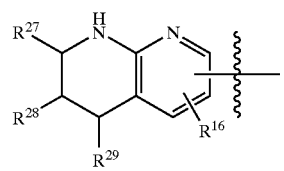

wherein:
$R^{16}$ is hydrogen, ($C_{1-8}$)alkyl, halo($C_{1-8}$)alkyl or halogen; and
$R^{27}$, $R^{28}$, and $R^{29}$ are hydrogen, halogen, ($C_{1-8}$)alkyl, ($C_{1-8}$)alkoxy, or ($C_{6-10}$)aryl.

14. The compound of claim 13, wherein W is

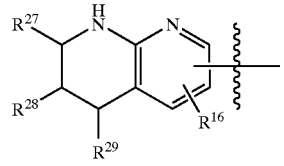

15. The compound of claim 1, wherein $R^{10}$, $R^{11}$, $R^{12}$ and $R^{13}$ independently represent: hydrogen; hydroxy, ($C_{1-12}$)alkyl; ($C_{3-6}$)cycloalkyl; or ($C_{6-10}$)aryl, optionally substituted with one or more of halogen, hydroxy, cyano, ($C_{1-8}$)alkyl, ($C_{6-10}$)aryl, ($C_{1-8}$)alkoxy, halo($C_{1-8}$)alkyl, ($C_{6-10}$)aryl($C_{1-8}$)alkyl, ($C_{6-10}$)aryl($C_{1-8}$)alkoxy, or ($C_{6-10}$)aryloxy.

16. The compound of claim 1, wherein $R^{10}$, $R^{11}$, $R^{12}$ and $R^{13}$ independently represent a heteroaryl having 5–14 ring members, optionally substituted with one or more of halogen, hydroxy, cyano, ($C_{1-8}$)alkyl, ($C_{1-8}$)alkoxy($C_{6-10}$)aryl, ($C_{1-8}$)alkoxy, halo($C_{1-8}$)alkyl, ($C_{6-10}$)aryl($C_{1-8}$)alkyl, ($C_{6-10}$)aryl($C_{1-8}$)alkoxy, ($C_{6-10}$)aryloxy, ($C_{1-8}$)alkylsulfonyl, ($C_{1-8}$)alkylsulfinyl, ($C_{1-8}$)alkylamino, ($C_{1-8}$)alkylamino($C_{1-8}$)alkyl, di($C_{1-8}$)alkylamino, di($C_{1-8}$)alkylamino($C_{1-8}$)alkyl, or carboxy($C_{1-8}$)alkyl; or

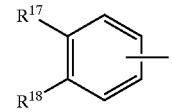

wherein $R^{17}$ and $R^{18}$ together form —CH$_2$CH$_2$—O—, —O—CH$_2$CH$_2$—, —O—CH$_2$—O— or —O—CH$_2$CH$_2$—O—.

17. The compound of claim 1, wherein $R^{12}$ and $R^{13}$ are independently thiazolyl, benzofuranyl,

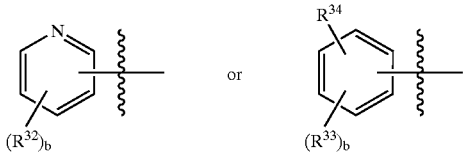 or 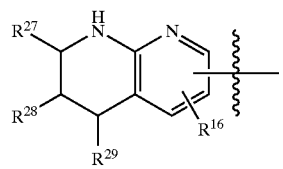

wherein:

b is from 0 to 4;

$R^{32}$ is halogen, $(C_{1-6})$alkyl, halo$(C_{1-6})$alkyl, $(C_{1-6})$alkoxy, $(C_{1-6})$alkoxy$(C_{1-6})$alkyl or halo$(C_{1-6})$alkoxy;

$R^{33}$ is halogen; and $R^{34}$ is $(C_{1-6})$alkyl, hydroxy or $(C_{1-6})$alkoxy, or two of $R^{32}$, or two of $R^{33}$, or one of $R^{33}$ and $R^{34}$, when attached to adjacent carbon atoms, may together form a ring, wherein the ring formed is an aliphatic, aryl or heteroaryl ring, each of which may be optionally substituted by one or more of halogen, hydroxy, cyano, alkyl, aryl, alkoxy, haloalkyl, arylalkyl, arylalkoxy, aryloxy, alkylsulfonyl, alkylsulfinyl, alkoxyarylalkyl, monoalkylamino, dialkylamino, aminoalkyl, monoalkylaminoalkyl, dialkylaminoalkyl, alkanoyl; monoalkylamino; dialkylamino; aminoalkyl; monoalkylaminoalkyl; dialkylaminoalkyl; aminoalkyl.

18. The compound of claim 1, wherein $R^{10}$ and $R^{12}$ are taken together to form a double bond where i is 0 and k is 1, and $R^{11}$ and $R^{13}$ are each hydrogen.

19. The compound of claim 1, wherein $R^{10}$ is an optionally substituted aryl or an optionally substituted heteroaryl.

20. The compound of claim 1, wherein i and j are each 0.

21. The compound of claim 1, wherein k is 1.

22. The compound of claim 1, wherein $R^{14}$ is hydrogen.

23. The compound of claim 1, wherein i and j are each zero; k is one; $R^{10}$, $R^{11}$ and $R^{12}$ are each hydrogen; and $R^{13}$ is hydrogen, $(C_{1-6})$alkyl, $(C_{6-10})$aryl or $(C_{6-10})$ar$(C_{1-4})$alkyl.

24. The compound of claim 1, wherein:

$R^1$ is hydrogen or $(C_{1-4})$alkyl;

$R^2$, $R^3$, $R^4$, and $R^5$ are hydrogen or $(C_{1-4})$alkyl;

$R^6$, $R^7$, $R^8$ and $R^9$ are hydrogen or $(C_{1-4})$alkyl;

X is oxygen or —$CH_2$—;

n is 0 or 1;

m is 0 or 1;

$R^{10}$, $R^{11}$, $R^{12}$ and $R^{13}$ independently represent hydrogen, $(C_{1-6})$alkyl or $(C_{6-10})$ar$(C_{1-6})$alkyl; or one of the combination $R^{10}$ and $R^{11}$, $R^{12}$ and $R^{13}$ or $R^{10}$ and $R^{12}$ are taken together to form —$(CH_2)_s$—, wherein s is 1 or 2 while the remaining of $R^{10}$–$R^{13}$ are as defined above;

i is 0 or 1;

j is 0 or 1;

k is 0 or 1;

$R^{14}$ is hydrogen, $C_{1-6}$ alkyl or benzyl;

W is:

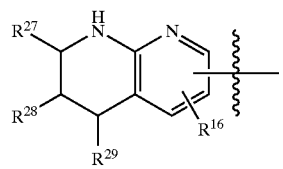

wherein:

$R^{16}$ is hydrogen, $(C_{1-8})$alkyl, halo$(C_{1-8})$alkyl or halogen; and $R^{27}$, $R^{28}$, and $R^{29}$ are hydrogen, halogen, $(C_{1-8})$alkyl, $(C_{1-8})$alkoxy, or $(C_{6-10})$aryl.

25. The compound of claim 24, wherein $R^1$, $R^2$, $R^3$, $R^4$, $R^5$, $R^6$, $R^7$, $R^8$, $R^9$, $R^{11}$, $R^{12}$, $R^{13}$ and $R^{14}$ are hydrogen.

26. The compound of claim 1, wherein $R^{10}$ and $R^{11}$ are taken together to form —$(CH_2)_t$—, where t is 2 to 5 and $R^{12}$ and $R^{13}$ are each hydrogen.

27. The compound of claim 1, wherein $R^{12}$ and $R^{13}$ are taken together to form —$(CH_2)_u$—, where u is 2 to 5 and $R^{10}$ and $R^{11}$ are each hydrogen.

28. The compound of claim 1, wherein $R^{10}$ and $R^{12}$ are taken together to form —$(CH_2)_s$— where s is zero or 1 to 4, and $R^{11}$ and $R^{13}$ are each hydrogen.

29. The compound of claim 1, wherein:

X is —(C=O)NH—;

n, m, a and v are each 0; and $R^6$, $R^7$, $R^{12}$ and $R^{13}$ are hydrogen.

30. The compound of claim 1, wherein:

X is oxygen;

n and m are each 0;

a and v are each 1;

D is oxygen;

$R^6$, $R^7$, $R^8$ and $R^9$ are hydrogen.

31. The compound of claim 1, wherein:

X is oxygen;

n, m and v are each 0;

a is 1; and $R^6$, $R^7$, $R^{12}$ and $R^{13}$ are hydrogen.

32. The compound of claim 1, wherein:

X is —$CH_2$—;

n, m and v are each 0;

a is 1; and $R^6$, $R^7$, $R^{12}$ and $R^{13}$ are hydrogen.

33. The compound of claim 1, wherein v is 0.

34. The compound of claim 1, wherein $R^1$ is hydrogen or —$CH_3$;

$R^2$, $R^3$, $R^4$, $R^5$, $R^6$, $R^7$, $R^8$ and $R^9$ are hydrogen;

X is oxygen or —$CH_2$—;

n is 0 or 1;

m is 0 or 1;

$R^{10}$, $R^{11}$, $R^{12}$ and $R^{13}$ independently represent hydrogen, $(C_1$–$C_6)$alkyl or $(C_{6-10})$ar$(C_{1-6})$alkyl; or one of the combination $R^{10}$ and $R^{11}$, $R^{12}$ and $R^{13}$ or $R^{10}$ and $R^{12}$ are taken together to form —$(CH_2)_s$—, wherein s is 1 while the remaining of $R^{10}$–$R^{13}$ are defined above;

i is 0 or 1;
j is 0 or 1;
k is 0 or 1;
$R^{14}$ is hydrogen or alkyl;
W is:

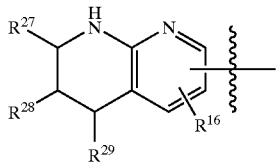

wherein:
$R^{16}$ is hydrogen, $(C_{1-8})$alkyl, halo$(C_{1-8})$alkyl or halogen; and $R^{27}$, $R^{28}$, and $R^{29}$ are hydrogen, halogen, $(C_{1-8})$alkyl, $(C_{1-8})$alkoxy, or $(C_{6-10})$aryl.

35. The compound of claim 1, wherein:
v, m, n, i and j are 0;
a is 1;
$R^1$, $R^2$, $R^3$, $R^4$, $R^5$, $R^6$, $R^7$, $R^8$, $R^9$, $R^{11}$, $R^{12}$, $R^{13}$ and $R^{14}$ are each hydrogen; and
$R^{10}$ is pyridinyl.

36. The compound of claim 1, wherein:
v, m, n, i and j are 0;
a is 1;
$R^1$, $R^2$, $R^3$, $R^4$, $R^5$, $R^6$, $R^7$, $R^8$, $R^9$, $R^{11}$, $R^{12}$, $R^{13}$ and $R^{14}$ are each hydrogen; and
$R^{10}$ is quinolinyl.

37. The compound of claim 1, wherein:
v, m, n, i and j are 0;
a is 1;
$R^1$, $R^2$, $R^3$, $R^4$, $R^5$, $R^6$, $R^7$, $R^8$, $R^9$, $R^{11}$, $R^{12}$, $R^{13}$ and $R^{14}$ are each hydrogen; and
$R^{10}$ is methoxyphenyl.

38. The compound of claim 1, which is one of:
3-[5-(2-5,6,7,8-tetrahydro-[1,8]naphthyridin-2-yl-acetylamino)-indol-1-yl]-hexanoic acid;
3-{5-[2-(5,6,7,8-tetrahydro-[1,8]naphthyridin-2-yl)-ethoxy]-indol-1-yl}-hexanoic acid;
3-{5-[2-(5,6,7,8-tetrahydro-[1,8]naphthyridin-2-yl)-ethoxy]-indol-1-yl}-propionic acid;
3-phenyl-3-{5-[2-(5,6,7,8-tetrahydro-[1,8]naphthyridin-2-yl)-ethoxy]-indol-1-yl}-propionic acid;
3-phenyl-3-{5-[2-(5,6,7,8-tetrahydro-[1,8]naphthyridin-2-yl)-ethoxy]-indol-1-yl}-propionic acid;
3-(3-benzyloxy-phenyl)-3-{5-[2-(5,6,7,8-tetrahydro-[1,8]naphthyridin-2-yl)-ethoxy]-indol-1-yl}-propionic acid;
3-{5-[2-(5,6,7,8-tetrahydro-[1,8]naphthyridin-2-yl)-ethoxy]-indol-1-yl}-3-p-tolyl-propionic acid;
3-{5-[2-(5,6,7,8-tetrahydro-[1,8]naphthyridin-2-yl)-ethoxy]-indol-1-yl}-3-m-tolyl-propionic acid;
3-{5-[2-(5,6,7,8-tetrahydro-[1,8]naphthyridin-2-yl)-ethoxy]-indol-1-yl}-3-o-tolyl-propionic acid;
3-biphenyl-4-yl-3-{5-[2-(5,6,7,8-tetrahydro-[1,8]naphthyridin-2-yl)-ethoxy]-indol-1yl}-propionic acid;
3-(3,5-dichloro-phenyl)-3-{5-[2-(5,6,7,8-tetrahydro-[1,8]naphthyridin-2-yl)-ethoxy]-indol-1-yl}-propionic acid;
3-(3,5-difluoro-phenyl)-3-{5-[2-(5,6,7,8-tetrahydro-[1,8]naphthyridin-2-yl)-ethoxy]-indol-1-yl}-propionic acid;
3-(3-cyano-phenyl)-3-{5-[2-(5,6,7,8-tetrahydro-[1,8]naphthyridin-2-yl)-ethoxy]-indol-1-yl}-propionic acid;
3-(4-cyano-phenyl)-3-{5-[2-(5,6,7,8-tetrahydro-[1,8]naphthyridin-2-yl)-ethoxy]-indol-1-yl}-propionic acid;
3-(2-methoxy-phenyl)-3-{5-[2-(5,6,7,8-tetrahydro-[1,8]naphthyridin-2-yl)-ethoxy]-indol-1-yl}-propionic acid;
3-(3-methoxy-phenyl)-3-{5-[2-(5,6,7,8-tetrahydro-[1,8]naphthyridin-2-yl)-ethoxy]-indol-1-yl}-propionic acid;
3-(4-methoxy-phenyl)-3-{5-[2-(5,6,7,8-tetrahydro-[1,8]naphthyridin-2-yl)-ethoxy]-indol-1-yl}-propionic acid;
3-quinolin-3-yl-3-{5-[2-(5,6,7,8-tetrahydro-[1,8]naphthyridin-2-yl)-ethoxy]-indol-1-yl}-propionic acid;
3-(3-chloro-phenyl)-3-{5-[2-(5,6,7,8-tetrahydro-[1,8]naphthyridin-2-yl)-ethoxy]-indol-1-yl}-propionic acid;
3-naphthalen-2-yl-3-{5-[2-(5,6,7,8-Tetrahydro-[1,8]naphthyridin-2-yl)-ethoxy]-indol-1-yl}-propionic acid;
3-(2-chloro-phenyl)-3-{5-[2-(5,6,7,8-tetrahydro-[1,8]naphthyridin-2-yl)-ethoxy]-indol-1-yl}-propionic acid;
3-naphthalen-1-yl-3-{5-[2-(5,6,7,8-Tetrahydro-[1,8]naphthyridin-2-yl)-ethoxy]-indol-1-yl}-propionic acid;
3-(4-fluoro-phenyl)-3-{5-[2-(5,6,7,8-tetrahydro-[1,8]naphthyridin-2-yl)-ethoxy]-indol-1-yl}-propionic acid;
3-{5-[2-(5,6,7,8-tetrahydro-[1,8]naphthyridin-2-yl)-ethoxy]-indol-1-yl}-3-(3-trifluoromethyl-phenyl)-propionic acid;
3-{5-[2-(5,6,7,8-tetrahydro-[1,8]naphthyridin-2-yl)-ethoxy]-indol-1-yl}-3-(4-trifluoromethyl-phenyl)-propionic acid;
3-pyridin-3-yl-3-{5-[2-(5,6,7,8-tetrahydro-[1,8]naphthyridin-2-yl)-ethoxy]-indol-1-yl}-propionic acid;
3-pyridin-2-yl-3-{5-[2-(5,6,7,8-tetrahydro-[1,8]naphthyridin-2-yl)-ethoxy]-indol-1-yl}-propionic acid;
3-pyridin-4-yl-3-{5-[2-(5,6,7,8-tetrahydro-[1,8]naphthyridin-2-yl)-ethoxy]-indol-1-yl}-acrylic acid;
3-(2,3-dihydro-benzofuran-5-yl)-3-{5-[2-(5,6,7,8-tetrahydro-[1,8]naphthyridin-2-yl)-ethoxy]-indol-1-yl}-propionic acid;
3-benzo[1,3]dioxol-5-yl-3-{5-[2-(5,6,7,8-tetrahydro-[1,8]naphthyridin-2-yl)-ethoxy]-indol-1-yl}-propionic acid;
3-(5-methanesulfonyl-pyridin-3-yl)-3-{5-[2-(5,6,7,8-tetrahydro-[1,8]naphthyridin-2-yl)-ethyoxy]-indol-1-yl}-propionic acid;
3-{5-[2-(2-methyl-5,6,7,8-tetrahydro-[1,8]naphthyridin-3-yl)-ethyl]-indol-1-yl}-propionic acid;
3-{5-[3-(5,6,7,8-tetrahydro-[1,8]naphthyridin-2-yl)-propyl]-indol-1-yl}-propionic acid;
3-{5-[3-(5,6,7,8-tetrahydro-[1,8]naphthyridin-2-yl)-propyl]-indol-1-yl}-hexanoic acid;
3-phenyl-3-{5-[3-(5,6,7,8-tetrahydro-[1,8]naphthyridin-2-yl)-propyl]-indol-1-yl}-propionic acid;
3-{5-[2-(5,6,7,8-tetrahydro-[1,8]naphthyridin-2-yl)-ethoxy]-indol-1-yl}-3-[5-(2,2,2-trifluoro-ethoxy)-pyridin-3-yl]-propionic acid;
3-(5-ethoxy-pyridin-3-yl)-3-{5-[2-(5,6,7,8-tetrahydro-[1,8]naphthyridin-2-yl)-ethoxy]-indol-1-yl}-propionic acid;
3-pyridin-4-yl-3-{5-[2-(5,6,7,8-tetrahydro-[1,8]naphthyridin-2-yl)-ethoxy]-indol-1-yl}-propionic acid;
3-pyridin-2-yl-3-{5-[2-(5,6,7,8-tetrahydro-[1,8]naphthyridin-2-yl)-ethoxy]-indol-1-yl}-acrylic acid;

or a pharmaceutically acceptable salt, hydrate, solvate or prodrug thereof.

39. The compound of claim 1, which is one of:

3-(3-methoxy-phenyl)-3-{5-[2-(5,6,7,8-tetrahydro-[1,8]naphthyridin-2-yl)-ethoxy]-indol-1-yl}-propionic acid;

3-quinolin-3-yl-3-{5-[2-(5,6,7,8-tetrahydro-[1,8]naphthyridin-2-yl)-ethoxy]-indol-1-yl}-propionic acid;

3-pyridin-3-yl-3-{5-[2-(5,6,7,8-tetrahydro-[1,8]naphthyridin-2-yl)-ethoxy]-indol-1-yl}-propionic acid;

3-pyridin-2-yl-3-{5-[2-(5,6,7,8-tetrahydro-[1,8]naphthyridin-2-yl)-ethoxy]-indol-1-yl}-propionic acid;

or a pharmaceutically acceptable salt, hydrate, solvate or prodrug thereof.

40. A pharmaceutical composition comprising a compound of claim 1 and a pharmaceutically acceptable carrier or diluent.

41. A method of treating a pathological condition selected from the group consisting of osteoporosis, macular degeneration, diabetic retinopathy, rheumatoid arthritis and sickle cell anemia, in a mammal in need of such treatment, comprising administering to said mammal an effective amount of a compound of claim 1.

42. The method of claim 41, wherein said condition is osteoporosis.

43. The method of claim 41, wherein said condition is macular degeneration.

44. The method of claim 41, wherein said condition is diabetic retinopathy.

45. The method of claim 41, wherein said condition is rheumatoid arthritis.

46. The method of claim 41, wherein said condition is sickle cell anemia.

47. A process for preparing a substituted indole compound of claim 1, comprising:

reacting a compound of Formula V:

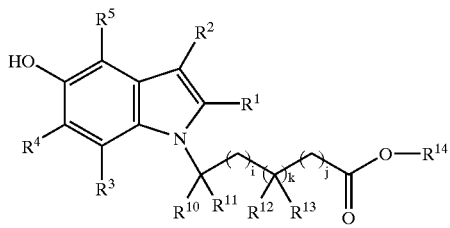

V or a salt, hydrate or solvate thereof, wherein $R^1$, $R^2$, $R^3$, $R^4$, $R^5$, $R^{10}$, $R^{11}$, $R^{12}$, $R^{13}$, $R^{14}$, i an j are as defined in claim 1, with the compound of Formula VI or Formula X:

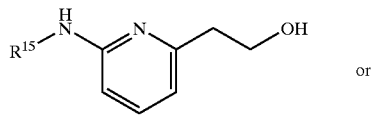

VI or

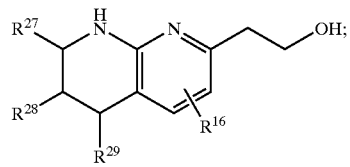

X or a salt, hydrate or solvate thereof, wherein $R^{15}$, $R^{16}$, $R^{27}$, $R^{28}$ and $R^{29}$ are as defined in claim 1, to form a substituted indole compound of claim 1.

48. A method for treating a central nervous system (CNS) related disorder selected from the group consisting of neuronal loss associated with ischemia, CNS trauma, hypoglycemia or surgery, schizophrenia, anxiety, convulsions, chronic pain, psychosis, and opiate tolerance, in a mammal in need of such treatment, comprising administering to said mammal an effective amount of a compound of claim 1.

49. The method according to claim 48, wherein said CNS related disorder is ischemia.

50. The method according to claim 48, wherein said CNS related disorder is CNS trauma.

51. The method according to claim 48, wherein said CNS related disorder is hypoglycemia.

52. The method according to claim 48, wherein said CNS related disorder is the result of surgery.

53. The method according to claim 48, wherein said CNS related disorder is schizophrenia.

54. The method according to claim 41, wherein the activity of α4 integrin is inhibited.

55. The method according to claim 48, wherein the activity of α4 integrin is inhibited.

56. The compound according to claim 17, wherein $R^{12}$ and $R^{13}$ are independently selected from:

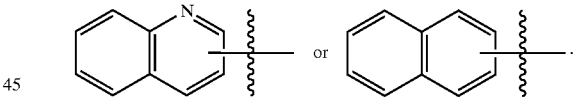

* * * * *